(12) United States Patent
Cadavid et al.

(10) Patent No.: US 10,435,467 B2
(45) Date of Patent: Oct. 8, 2019

(54) LINGO-1 ANTAGONISTS AND USES FOR TREATMENT OF DEMYELINATING DISORDERS

(71) Applicant: Biogen MA Inc., Cambridge, MA (US)

(72) Inventors: Diego Cadavid, Concord, MA (US); Sha Mi, Belmont, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 15/541,944

(22) PCT Filed: Jan. 8, 2016

(86) PCT No.: PCT/US2016/012619
§ 371 (c)(1),
(2) Date: Jul. 6, 2017

(87) PCT Pub. No.: WO2016/112270
PCT Pub. Date: Jul. 14, 2016

(65) Prior Publication Data
US 2018/0148505 A1 May 31, 2018

Related U.S. Application Data

(60) Provisional application No. 62/147,783, filed on Apr. 15, 2015, provisional application No. 62/101,336, filed on Jan. 8, 2015.

(51) Int. Cl.
| | | |
|---|---|---|
| A61K 38/00 | (2006.01) | |
| C07K 16/28 | (2006.01) | |
| A61K 38/21 | (2006.01) | |
| A61K 39/395 | (2006.01) | |
| A61K 45/06 | (2006.01) | |
| C07K 14/705 | (2006.01) | |
| A61K 39/00 | (2006.01) | |

(52) U.S. Cl.
CPC ........ *C07K 16/2803* (2013.01); *A61K 38/215* (2013.01); *A61K 39/3955* (2013.01); *A61K 45/06* (2013.01); *A61K 2039/505* (2013.01); *A61K 2039/54* (2013.01); *A61K 2039/545* (2013.01); *C07K 2317/21* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,399,216 A | 8/1983 | Axel et al. |
| 4,444,887 A | 4/1984 | Hoffman |
| 4,510,245 A | 4/1985 | Cousens et al. |
| 4,634,665 A | 1/1987 | Axel et al. |
| 4,694,778 A | 9/1987 | Learn et al. |
| 4,716,111 A | 12/1987 | Osband et al. |
| 4,816,397 A | 3/1989 | Boss et al. |
| 4,816,567 A | 3/1989 | Cabilly et al. |
| 4,946,778 A | 8/1990 | Ladner et al. |
| 4,968,615 A | 11/1990 | Koszinowski et al. |
| 4,987,071 A | 1/1991 | Cech et al. |
| 5,093,246 A | 3/1992 | Cech et al. |
| 5,116,742 A | 5/1992 | Cech et al. |
| 5,122,464 A | 6/1992 | Wilson et al. |
| 5,168,062 A | 12/1992 | Stinski |
| 5,179,017 A | 1/1993 | Axel et al. |
| 5,180,820 A | 1/1993 | Barde et al. |
| 5,223,409 A | 6/1993 | Ladner et al. |
| 5,225,539 A | 7/1993 | Winter |
| 5,252,714 A | 10/1993 | Harris et al. |
| 5,258,498 A | 11/1993 | Huston et al. |
| 5,314,995 A | 5/1994 | Fell, Jr. et al. |
| 5,403,484 A | 4/1995 | Ladner et al. |
| 5,413,923 A | 5/1995 | Kucherlapati et al. |
| 5,427,908 A | 6/1995 | Dower et al. |
| 5,428,130 A | 6/1995 | Capon et al. |
| 5,468,872 A | 11/1995 | Glicksman et al. |
| 5,516,637 A | 5/1996 | Huang et al. |
| 5,530,101 A | 6/1996 | Queen et al. |
| 5,532,351 A | 7/1996 | Stefansson |
| 5,545,806 A | 8/1996 | Lonberg et al. |
| 5,565,332 A | 10/1996 | Hoogenboom et al. |
| 5,565,335 A | 10/1996 | Capon et al. |
| 5,569,825 A | 10/1996 | Lonberg et al. |
| 5,571,698 A | 11/1996 | Ladner et al. |
| 5,574,009 A | 11/1996 | Cohen et al. |
| 5,580,717 A | 12/1996 | Dower et al. |
| 5,585,089 A | 12/1996 | Queen et al. |
| 5,589,369 A | 12/1996 | Seidman et al. |
| 5,605,690 A | 2/1997 | Jacobs et al. |

(Continued)

FOREIGN PATENT DOCUMENTS

| | | |
|---|---|---|
| EP | 0 125 023 | 11/1984 |
| EP | 0 171 496 | 2/1986 |

(Continued)

OTHER PUBLICATIONS

Conway et al., Combination therapy in multiple sclerosis, Mar. 2010, The Lancet .com/neurology vol. 9:299-308 (Year: 2010).*
[No Author Listed] "Opicinumab (anti-Lingo)," MS Trust, Nov. 2017, [retrieved on Mar. 21, 2018], retrieved from https://www.mstrust.org.uk/a-z/opicinumab-anti-lingo-1-biib033, 3 pages.
Biogen Report Top-Line Results from Phase 2 Study of Opicinumab (Anti-LINGO-1) in Multiple Sclerosis, Jun. 7, 2016, Business Wire, A Berkshire Hathaway Company, [retrieved Apr. 18, 2017], Retrieved from the Internet: http://www.businesswire.com/news/home/20160607005718/en, 3 pages.
Adams and Weiner, "Monoclonal antibody therapy of cancer," Nat. Biotechnol. 23:1147-1157 (Sep. 2005), 11 pages.

(Continued)

*Primary Examiner* — John D Ulm
(74) *Attorney, Agent, or Firm* — Fish & Richardson P.C.

(57) ABSTRACT

Methods, compositions and kits comprising an anti-LINGO antibody molecule are described herein useful for detecting and/or treating a CNS demyelinating disease.

25 Claims, 24 Drawing Sheets
Specification includes a Sequence Listing.

(56) References Cited

U.S. PATENT DOCUMENTS

| | | |
|---|---|---|
| 5,625,126 A | 4/1997 | Lonberg et al. |
| 5,633,425 A | 5/1997 | Lonberg et al. |
| 5,658,570 A | 8/1997 | Newman et al. |
| 5,658,727 A | 8/1997 | Barbas et al. |
| 5,661,016 A | 8/1997 | Lonberg et al. |
| 5,693,761 A | 12/1997 | Queen et al. |
| 5,693,762 A | 12/1997 | Queen et al. |
| 5,693,780 A | 12/1997 | Newman et al. |
| 5,698,426 A | 12/1997 | Huse |
| 5,707,829 A | 1/1998 | Jacobs et al. |
| 5,725,859 A | 3/1998 | Omer |
| 5,733,743 A | 3/1998 | Johnson et al. |
| 5,736,137 A | 4/1998 | Anderson et al. |
| 5,750,753 A | 5/1998 | Kimae et al. |
| 5,756,096 A | 5/1998 | Newman et al. |
| 5,770,577 A | 6/1998 | Kinstler et al. |
| 5,772,997 A | 6/1998 | Hudziak et al. |
| 5,780,225 A | 7/1998 | Wigler et al. |
| 5,807,715 A | 9/1998 | Morrison et al. |
| 5,811,524 A | 9/1998 | Brams et al. |
| 5,814,318 A | 9/1998 | Lonberg et al. |
| 5,821,047 A | 10/1998 | Garrard et al. |
| 5,837,821 A | 11/1998 | Wu |
| 5,840,299 A | 11/1998 | Bendig et al. |
| 5,888,507 A | 3/1999 | Burkly |
| 5,892,019 A | 4/1999 | Schlom et al. |
| 5,910,574 A | 6/1999 | Presta et al. |
| 5,914,237 A | 6/1999 | Godowski et al. |
| 5,939,598 A | 8/1999 | Kucherlapati et al. |
| 5,969,108 A | 10/1999 | McCafferty et al. |
| 6,025,145 A | 2/2000 | Godowski et al. |
| 6,034,119 A | 3/2000 | Ono et al. |
| 6,054,561 A | 4/2000 | Ring |
| 6,075,181 A | 6/2000 | Kucherlapati et al. |
| 6,150,584 A | 11/2000 | Kucherlapati et al. |
| 6,159,730 A | 12/2000 | Reff |
| 6,180,370 B1 | 1/2001 | Queen et al. |
| 6,190,887 B1 | 2/2001 | Boyce et al. |
| 6,193,980 B1 | 2/2001 | Efstathiou et al. |
| 6,280,964 B1 | 8/2001 | Kavanaugh et al. |
| 6,333,169 B1 | 12/2001 | Hudziak et al. |
| 6,338,953 B1 | 1/2002 | Boyce et al. |
| 6,387,371 B1 | 5/2002 | Hudziak et al. |
| 6,399,063 B1 | 6/2002 | Hudziak et al. |
| 6,413,777 B1 | 7/2002 | Reff et al. |
| 6,420,140 B1 | 7/2002 | Hori et al. |
| 6,455,277 B1 | 9/2002 | Fox et al. |
| 6,458,592 B1 | 10/2002 | Jakobovits et al. |
| 6,593,290 B1 | 7/2003 | Gao |
| 6,602,503 B1 | 8/2003 | Lobb et al. |
| 6,610,500 B1 | 8/2003 | Saragovi et al. |
| 6,656,465 B2 | 12/2003 | Clary et al. |
| 6,680,209 B1 | 1/2004 | Buechler et al. |
| 6,686,451 B1 | 2/2004 | Desnoyers et al. |
| 6,696,290 B2 | 2/2004 | Fitzpatrick et al. |
| 6,723,701 B2 | 4/2004 | Boone et al. |
| 6,800,607 B2 | 10/2004 | Igarashi et al. |
| 6,881,719 B2 | 4/2005 | Saragovi et al. |
| 6,919,426 B2 | 7/2005 | Boone et al. |
| 6,927,204 B2 | 8/2005 | Gao |
| 6,949,245 B1 | 9/2005 | Sliwkowski |
| 6,974,689 B1 | 12/2005 | Ashkenazi et al. |
| 6,987,088 B2 | 1/2006 | Dennis |
| 7,034,132 B2 | 4/2006 | Anderson et al. |
| 7,098,302 B2 | 8/2006 | Krag et al. |
| 7,205,387 B2 | 4/2007 | Wang et al. |
| 7,223,558 B2 | 5/2007 | Wu et al. |
| 7,693,698 B2 | 4/2010 | Mosyak et al. |
| 7,718,776 B2 | 5/2010 | Boyle et al. |
| 7,750,122 B2 | 7/2010 | Cho et al. |
| 7,785,829 B2 | 8/2010 | Mi et al. |
| 7,816,497 B2 | 10/2010 | Ambati |
| 7,846,438 B2 | 12/2010 | Mi et al. |
| 8,058,406 B2 | 11/2011 | Mi et al. |
| 8,128,926 B2 | 3/2012 | Mi et al. |
| 8,153,580 B2 | 4/2012 | Mi et al. |
| 8,299,221 B2 | 10/2012 | Walmsley et al. |
| 8,309,517 B2 | 11/2012 | Barker et al. |
| 8,425,910 B2 | 4/2013 | Mi et al. |
| 8,460,657 B2 | 6/2013 | Nykjaer et al. |
| 8,486,893 B2 | 7/2013 | Mi et al. |
| 8,551,476 B2 | 10/2013 | Mi et al. |
| 8,609,407 B2 | 12/2013 | Mi et al. |
| 8,642,040 B2 | 2/2014 | Mi et al. |
| 8,765,662 B2 | 7/2014 | Mi et al. |
| 8,932,821 B2 | 1/2015 | Mi et al. |
| 9,066,984 B2 | 6/2015 | Mi et al. |
| 9,068,992 B2 | 6/2015 | Mi et al. |
| 9,523,093 B2 | 12/2016 | Davidson et al. |
| 9,717,453 B2 | 8/2017 | Cadavid et al. |
| 9,745,375 B2 | 8/2017 | Mi et al. |
| 9,796,780 B2 | 10/2017 | Mi et al. |
| 2002/0004587 A1 | 1/2002 | Miller et al. |
| 2002/0077295 A1 | 6/2002 | Strittmatter |
| 2002/0123057 A1 | 9/2002 | Zauderer et al. |
| 2002/0182671 A1 | 12/2002 | Lal et al. |
| 2003/0032589 A1 | 2/2003 | Bartke et al. |
| 2003/0113326 A1 | 6/2003 | He et al. |
| 2003/0143204 A1 | 7/2003 | Lewis et al. |
| 2003/0157641 A1 | 8/2003 | Reff et al. |
| 2003/0162734 A1 | 8/2003 | Miller et al. |
| 2003/0166282 A1 | 9/2003 | Brown et al. |
| 2003/0195163 A1 | 10/2003 | Wu et al. |
| 2003/0216558 A1 | 11/2003 | Morris et al. |
| 2003/0224432 A1 | 12/2003 | Myers et al. |
| 2004/0005579 A1 | 1/2004 | Birse et al. |
| 2004/0009480 A1 | 1/2004 | Anderson et al. |
| 2004/0038278 A1 | 2/2004 | Tzertzinis et al. |
| 2004/0067490 A1 | 4/2004 | Zhong et al. |
| 2004/0086884 A1 | 5/2004 | Beach et al. |
| 2004/0167380 A1 | 8/2004 | Simon |
| 2004/0186044 A1 | 9/2004 | Cosgaya et al. |
| 2004/0253605 A1 | 12/2004 | McCarthy et al. |
| 2005/0123990 A1 | 6/2005 | Lal et al. |
| 2005/0153396 A1 | 7/2005 | Baker et al. |
| 2005/0214288 A1 | 9/2005 | Bell et al. |
| 2005/0215770 A1 | 9/2005 | Bell et al. |
| 2005/0271655 A1 | 12/2005 | Lee et al. |
| 2006/0009288 A1 | 1/2006 | deVos et al. |
| 2006/0009388 A1 | 1/2006 | Mi et al. |
| 2006/0034840 A1 | 2/2006 | Agus et al. |
| 2006/0058223 A1 | 3/2006 | Mi et al. |
| 2006/0063200 A1 | 3/2006 | Anderson et al. |
| 2006/0067935 A1 | 3/2006 | Ambati |
| 2006/0088523 A1 | 4/2006 | Andya et al. |
| 2007/0031418 A1 | 2/2007 | Tabares et al. |
| 2007/0059304 A1 | 3/2007 | Cho et al. |
| 2007/0059793 A1 | 3/2007 | Mi et al. |
| 2007/0060526 A1 | 3/2007 | Longo et al. |
| 2007/0071675 A1 | 3/2007 | Wu et al. |
| 2007/0083334 A1 | 4/2007 | Mintz et al. |
| 2007/0105122 A1 | 5/2007 | Ota et al. |
| 2007/0178088 A1 | 8/2007 | Wu et al. |
| 2007/0186296 A1 | 8/2007 | Gao et al. |
| 2007/0213290 A1 | 9/2007 | Kingsman et al. |
| 2007/0274918 A1 | 11/2007 | Mosyak et al. |
| 2009/0017039 A1 | 1/2009 | Mi et al. |
| 2009/0175846 A1 | 7/2009 | Mi et al. |
| 2009/0175872 A1 | 7/2009 | Mi et al. |
| 2009/0246189 A1 | 10/2009 | Mi et al. |
| 2009/0252748 A1 | 10/2009 | Mi et al. |
| 2010/0015131 A1 | 1/2010 | Mi et al. |
| 2010/0074907 A1 | 3/2010 | Mi et al. |
| 2010/0086997 A1 | 4/2010 | Lin et al. |
| 2010/0131432 A1 | 5/2010 | Kennedy et al. |
| 2010/0143362 A1 | 6/2010 | Walmsley et al. |
| 2010/0183317 A1 | 7/2010 | Harima |
| 2010/0204304 A1 | 8/2010 | Mi et al. |
| 2010/0297121 A1 | 11/2010 | Mi et al. |
| 2011/0123553 A1 | 5/2011 | Mi et al. |
| 2011/0311542 A1 | 12/2011 | Mi et al. |
| 2012/0014960 A1 | 1/2012 | Mi et al. |
| 2012/0190070 A1 | 7/2012 | Mi et al. |
| 2012/0230979 A1 | 9/2012 | Mi et al. |

(56) References Cited

U.S. PATENT DOCUMENTS

| | | |
|---|---|---|
| 2013/0071400 A1 | 3/2013 | Walmsley et al. |
| 2013/0273558 A1 | 10/2013 | Mi et al. |
| 2013/0287693 A1 | 10/2013 | Mi et al. |
| 2013/0287796 A1 | 10/2013 | Mi et al. |
| 2013/0323786 A1 | 12/2013 | Mi et al. |
| 2013/0336991 A1 | 12/2013 | Mi et al. |
| 2014/0037639 A1 | 2/2014 | Cortes-Cros et al. |
| 2014/0199315 A1 | 7/2014 | Mi et al. |
| 2015/0110741 A1 | 4/2015 | Cadavid et al. |
| 2015/0118241 A1 | 4/2015 | Me et al. |
| 2015/0177240 A1 | 6/2015 | Mi et al. |
| 2015/0220693 A1 | 8/2015 | Cadavid et al. |
| 2015/0238602 A1 | 8/2015 | Cadavid et al. |
| 2015/0315273 A1 | 11/2015 | Mi et al. |
| 2016/0002329 A1 | 1/2016 | Mi et al. |
| 2016/0083468 A1 | 3/2016 | Mi et al. |
| 2016/0213745 A1 | 7/2016 | Mi et al. |
| 2016/0354465 A1 | 12/2016 | Mi |
| 2016/0368984 A1 | 12/2016 | Mi et al. |
| 2017/0037126 A1 | 2/2017 | Mi et al. |
| 2018/0111994 A1 | 4/2018 | Mi et al. |
| 2019/0038744 A1 | 2/2019 | Cadavid et al. |
| 2019/0060398 A1 | 2/2019 | Mi et al. |

FOREIGN PATENT DOCUMENTS

| | | |
|---|---|---|
| EP | 0 173 494 | 3/1986 |
| EP | 0 184 187 | 6/1986 |
| EP | 0 154 316 | 9/1989 |
| EP | 0 401 384 | 12/1990 |
| EP | 0 256 055 | 8/1991 |
| EP | 0 323 997 | 4/1993 |
| EP | 0 396 387 | 12/1993 |
| EP | 0 368 684 | 3/1994 |
| EP | 0 239 400 | 8/1994 |
| EP | 0 338 841 | 3/1995 |
| EP | 0 958 831 | 11/1999 |
| EP | 1 074 617 | 2/2001 |
| EP | 0 058 481 | 5/2003 |
| EP | 0 592 106 | 11/2004 |
| EP | 0 519 596 | 2/2005 |
| EP | 1 574 520 | 9/2005 |
| GB | 2188638 | 10/1987 |
| JP | 9-502730 | 3/1997 |
| JP | 2000-501416 | 2/2000 |
| JP | 2000-514420 | 10/2000 |
| KR | 2013 0007974 | 1/2013 |
| WO | WO 1986/001533 | 3/1986 |
| WO | WO 1986/005807 | 10/1986 |
| WO | WO 1987/002671 | 5/1987 |
| WO | WO 1988/009810 | 12/1988 |
| WO | WO 1989/001036 | 2/1989 |
| WO | WO 1989/010134 | 11/1989 |
| WO | WO 1989/012624 | 12/1989 |
| WO | WO 1990/002809 | 3/1990 |
| WO | WO 1990/011364 | 10/1990 |
| WO | WO 1991/009967 | 7/1991 |
| WO | WO 1991/010737 | 7/1991 |
| WO | WO 1991/010741 | 7/1991 |
| WO | WO 1991/000906 | 10/1991 |
| WO | WO 1991/014438 | 10/1991 |
| WO | WO 1991/017271 | 11/1991 |
| WO | WO 1992/001047 | 1/1992 |
| WO | WO 1992/003917 | 3/1992 |
| WO | WO 1992/003918 | 3/1992 |
| WO | WO 1992/008495 | 5/1992 |
| WO | WO 1992/009690 | 6/1992 |
| WO | WO 1992/015679 | 9/1992 |
| WO | WO 1992/018619 | 10/1992 |
| WO | WO 1992/020791 | 11/1992 |
| WO | WO 1992/022324 | 12/1992 |
| WO | WO 1993/001288 | 1/1993 |
| WO | WO 1993/011236 | 6/1993 |
| WO | WO 1994/004678 | 3/1994 |
| WO | WO 1994/009817 | 5/1994 |
| WO | WO 1995/007911 | 3/1995 |
| WO | WO 1995/015982 | 6/1995 |
| WO | WO 1995/020401 | 8/1995 |
| WO | WO 1995/021193 | 8/1995 |
| WO | WO 1996/033735 | 10/1996 |
| WO | WO 1996/034096 | 10/1996 |
| WO | WO 1997/000271 | 1/1997 |
| WO | WO 1997/004847 | 11/1997 |
| WO | WO 1997/049406 | 12/1997 |
| WO | WO 1998/016654 | 4/1998 |
| WO | WO 1998/024893 | 6/1998 |
| WO | WO 1998/046645 | 10/1998 |
| WO | WO 1998/050433 | 11/1998 |
| WO | WO 1998/052976 | 11/1998 |
| WO | WO 1999/006427 | 2/1999 |
| WO | WO 1999/014328 | 3/1999 |
| WO | WO 1999/048908 | 9/1999 |
| WO | WO 2000/015796 | 3/2000 |
| WO | WO 2000/031235 | 6/2000 |
| WO | WO 2000/034317 | 6/2000 |
| WO | WO 2000/058473 | 10/2000 |
| WO | WO 2001/004311 | 1/2001 |
| WO | WO 2001/012662 | 2/2001 |
| WO | WO 2001/033042 | 5/2001 |
| WO | WO 2001/040306 | 6/2001 |
| WO | WO 2001/040466 | 6/2001 |
| WO | WO 2001/051520 | 7/2001 |
| WO | WO 2001/055317 | 8/2001 |
| WO | WO 2001/055320 | 8/2001 |
| WO | WO 2001/055333 | 8/2001 |
| WO | WO 2001/057262 | 8/2001 |
| WO | WO 2001/059063 | 8/2001 |
| WO | WO 2002/001047 | 1/2002 |
| WO | WO 2002/014368 | 2/2002 |
| WO | WO 2002/022802 | 3/2002 |
| WO | WO 2002/029058 | 4/2002 |
| WO | WO 2002/029059 | 4/2002 |
| WO | WO 2002/060955 | 8/2002 |
| WO | WO 2002/068579 | 9/2002 |
| WO | WO 2002/096948 | 12/2002 |
| WO | WO 2002/099116 | 12/2002 |
| WO | WO 2003/008583 | 1/2003 |
| WO | WO 2003/014161 | 2/2003 |
| WO | WO 2003/023008 | 3/2003 |
| WO | WO 2003/031462 | 4/2003 |
| WO | WO 2003/035833 | 5/2003 |
| WO | WO 03/050238 | 7/2003 |
| WO | WO 2003/054152 | 7/2003 |
| WO | WO 2003/061559 | 7/2003 |
| WO | WO 2003/083047 | 10/2003 |
| WO | WO 2004/014311 | 2/2004 |
| WO | WO 2004/020404 | 3/2004 |
| WO | WO 2004/022718 | 3/2004 |
| WO | WO 2004/050016 | 6/2004 |
| WO | WO 2004/085648 | 10/2004 |
| WO | WO 2005/016955 | 2/2005 |
| WO | WO 2005/018572 | 3/2005 |
| WO | WO 2005/021579 | 3/2005 |
| WO | WO 2005/035584 | 4/2005 |
| WO | WO 2005/063819 | 7/2005 |
| WO | WO 2005/079566 | 9/2005 |
| WO | WO 2006/002437 | 1/2006 |
| WO | WO 2006/060787 | 6/2006 |
| WO | WO 2006/119013 | 11/2006 |
| WO | WO 2006/133533 | 12/2006 |
| WO | WO 2006/136006 | 12/2006 |
| WO | WO 2007/008547 | 1/2007 |
| WO | WO 2007/050866 | 5/2007 |
| WO | WO 2007/056161 | 5/2007 |
| WO | WO 2007/064882 | 6/2007 |
| WO | WO 2007/092370 | 8/2007 |
| WO | WO 2007/098283 | 8/2007 |
| WO | WO 2008/013782 | 1/2008 |
| WO | WO 2008/058736 | 5/2008 |
| WO | WO 2008/086006 | 7/2008 |
| WO | WO 2009/048605 | 4/2009 |
| WO | WO 2009/061500 | 5/2009 |
| WO | WO 2009/111886 | 9/2009 |
| WO | WO 2010/003101 | 1/2010 |

(56) References Cited

FOREIGN PATENT DOCUMENTS

| WO | WO 2010/003108 | 1/2010 |
|---|---|---|
| WO | WO 2010/005570 | 1/2010 |
| WO | WO 2011/121257 | 10/2011 |
| WO | WO 2011/133799 | 10/2011 |
| WO | WO 2012/109108 | 8/2012 |
| WO | WO 2013/173364 | 11/2013 |
| WO | WO 2014/028299 | 2/2014 |
| WO | WO 2014/058875 | 4/2014 |
| WO | WO 2016/112270 | 7/2016 |

OTHER PUBLICATIONS

Almagro and Fransson, "Humanization of antibodies," Frontiers in Bioscience, 13:1619-1633 (2008), 15 pages.
Altschul et al., "Basic local alignment search tool" J. Mol. Biol. 215:403-10 (Oct. 1990), 8 pages.
Altschul et al., "Gapped BLAST and PSI-BLAST: a new generation of protein database search programs" Nucleic Acids Res. 25:3389-3402 (Sep. 1997), 14 pages.
Archer et al., "The natural history of acute painful neuropathy in diabetes mellitus," J Neurol., 46:491-499 (1983), 10 pages.
Balcer et al., "Evaluating loss of visual function in multiple sclerosis as measured by low-contrast letter acuity," Neurogology 74(13):816-23 (Apr. 2010), 8 pages.
Barbacid, "The Trk Family of Neurotrophin Receptors," J Neurobiol., 25(11):1386-1403 (1994), 18 pages.
Barbas, et al., "Assembly of combinatorial antibody libraries on phage surfaces: the gene III site" PNAS 88:7978-7982 (Sep. 1991), 5 pages.
Barrette et al., "Expression profile of receptors for myelin-associated inhibitors of axonal regeneration in the intact and injured mouse central nervous system" Mol Cell Neurosci 34:519-38 (Apr. 2007), 20 pages.
Basso and Fisher, "The Basso Mouse Scale for Locomotion (BMS) is a more Sensitive Indication of Recovery than the BBB Scale in Mice with Spinal Cord Injury", J Rehab Res Develop., 40(6):26, Supplement 3, abstract P21 (2003), 1 page.
Basso et al., "Basso Mouse Scale for Locomotion Detects Differences in Recovery after Spinal Cord Injury in Five Common Mouse Strains," J Neurotrauma, 23:635-659 (2006), 30 pages.
Battaglia et al., "Protective role of group-II metabotropic glutamate receptors against nigro-striatal degeneration induced by I-methyl-4-phenyl-1,2,3,6-tetrahydropyridine in mice," Neuropharmacol. 45:155-166 (2003), 12 pages.
Baulida and Carpenter, "Heregulin Degradation in the Absence of Rapid Receptor-Mediated Internalization," Exp. Cell Res. 232:167-172 (1997), 6 pages.
Baulida et al., "All ErbB Receptors Other Than the Epidermal Growth Factor Receptor Are Endocytosis Impaired," J. Biol. Chem., 271:5251-5257 (1996), 7 pages.
Baumann and Pham-Dinh, "Biology of Oligodendrocyte and Myelin in the Mammalian Central Nervous System," J. Physioi. Rev., 81:871-927 (2001), 57 pages.
Beck et al., "A randomized, controlled trial of corticosteroids in the treatment of acute optic neuritis. The Optic Neuritis Study Group," N Engl J Med, 1992, 326:581-8.
Behan, et al., "The sad plight of multiple sclerosis research (low on fact, high on fiction): critical data to support it being a neurocristopathy," Inflammopharmacology 18:265-290 (Dec. 2010), 26 pages.
Beidler et al., "Cloning and high level expression of a chimeric antibody with specificity for human carcinoembryonic antigen" J. Immunol. 141:4053-4060 (Dec. 1988), 8 pages.
Better et al., "*Escherichia coli* secretion of an active chimeric antibody fragment" Science 240:1041-1043 (May 1988), 3 pages.
Binder et al., "Selective Inhibition of Kindling Development by Intraventricular Administration of TrkB Receptor Body," J Neurosci., 19(4):1424-1436 (1999), 13 pages.
Bird et al., "Single-chain antigen-binding proteins" Science 242:423-426 (1988), 4 pages.

Bitsch et al., "Acute axonal injury in multiple sclerosis. Correlation with demyelination and inflammation" Brain 123:1174-1183 (2000), 10 pages.
Bjartmar et al., "Axonal and neuronal degeneration in multiple sclerosis: mechanisms and functional consequences" Curr Opin Neurol 14:271-278 (2001), 8 pages.
Bjartmar et al., "Axonal pathology in myelin disorders" J Neurocytol 28:383-395 (1999), 13 pages.
Blum, "A null mutation in TGF-a leads to a reduction in midbrain dopaminergic neurons in the substantia nigra," Nat. Neurosci., 1:374-377 (1998), 4 pages.
Bock, M., et al., "Impairment of contrast visual acuity as a functional correlate of retinal nerve fibre layer thinning and total macular volume reduction in multiple sclerosis" Br J Ophthalmol. 96(1):62-7 (2012), 6 pages.
Boeshore et al., "rtTrkB Isofonns with Distinct Neurotrophin Specificities Are Expressed in Predominantly Nonoverlapping Populations of Avian Dorsal Root Ganglion Neurons," II J Neurosci., 19(12):4739-4747 (1999), 9 pages.
Brazil et al., "PKB Binding Proteins: Getting in on the Akt," Cell 111:293-303, (2002), 13 pages.
Brittis and Flanagan, "Nogo Domains and a Nogo Receptor: Implications for Axon Regeneration," Neuron 30:11-14 (2001), 4 pages.
Bruggeman et al., "Desinger Mice: The Production of Human Antibody Repertoires in Transgenic Animals," Year Immunol 7:33-40 (1993), 8 pages.
Bruggeman et al., "Human antibody production in transgenic mice: expression from 100 kb of the human IgH locus" Eur J Immunol 21:1323-1326 (1991), 4 pages.
Brummell et al. "Probing the combining site of an anti-carbohydrate antibody by saturation-mutagenesis: role of the heavy-chain CDR3 residues," Biochem., 32:1180-1187 (1993), 8 pages.
Brundin et al., "The rotating 6-hydroxydopamine-lesioned mouse as a model for assessing functional effects of neuronal grafting," Brain Res., 366:346-349 (1986), 4 pages.
Buffo et al., "Application of Neutralizing Antibodies against NI-35/250 Myelin-Associated Neurite Growth Inhibitory Proteins to the Adult Rat Cerebellum Induces Sprouting of Uninjured Purkinje Cell Axons," J Neurosci., 20(6):2275-2286 (2000), 12 pages.
Burks et al., "In vitro scanning saturation mutagenesis of an antibody binding pocket," PNAS 94:412-417 (1997), 6 pages.
Cadavid et al., "Efficacy Analysis of the Anti-LINGO-1 Monoclonal Antibody BIIB033 in acute Optic Neuritis: the RENEW Trial (P7.202)," Neurology, 84(14):Suppl. P7.202 (Apr. 2015).
Cadavid et al., "Evidence of remyelination with the anti-LINGO-1 monoclonal antibody BIIB033 after acute optic neuritis," Neurology, 85(4).
Carim-Todd et al., "LRRN6A/LERN1 (leucine-rich repeat neuronal protein 1), a novel gene with enriched expression in limbic system and neocortex," Eur. J. Neurosci., 18:3167-3182 (2003), 16 pages.
Casset et al., "A peptide mimetic of an anti-CD4 monoclonal antibody by rational design," BBRC, 307:198-205 (2003), 8 pages.
Cattaneo et al., "Functional Blockade of Tyrosine Kinase A in a Rat Basal Forebrain by a Novel Antagonistic Anti-Receptor Monoclonal Antibody," J Neuroscience, 19(22):9687-9697 (1999), 11 pages.
Cellerino et al., "Reduced Size of Retinal Ganglion Cell Axons and Hypomyelination in Mice Lacking Brain-Derived Neurotrophic Factor," Mol Cell Neurosci., 9:397-408 (1997), 14 pages.
Ceni and Barker et al., "Getting RIP'd Stunts your Growth," Neuron, 46:839-844 (2005), 2 pages.
Chakrabarti et al., "Critical Role for Kalirin in Nerve Growth Factor Signaling through TrkA," Mol Cell Biol., 25(12):5106-5118 (2005), 13 pages.
Chan et al., "NGF Controls Axonal Receptivity to Myelination by Schwann Cells or Oligodendrocytes," Neuron, 43:183-191 (2004), 9 pages.
Chang et al., "Remyelinating Oligodendrocytes in Chronic Lesions of Multiple Sclerosis," N. Engl. J. Med., 346:165-173 (2002), 9 pages.
Chao et al., "Neurotrophin signaling in health and disease," Clinical Sci., 110:167-173 (2006), 7 pages.

(56) References Cited

OTHER PUBLICATIONS

Chard et al., "Progressive grey matter atrophy in clinically early relapsing-remitting multiple sclerosis," Multiple Sclerosis, 10:387-391 (2004), 5pages.
Chen et al., "A Chemical-Genetic Approach to Studying Neurotrophin Signaling," Neuron, 46:13-21 (2005), 9 pages.
Chen et al., "AMIGO and friends: An emerging family of brain-enriched, neuronal growth modulating, type 1 transmembrane proteins with leucine-rich repeats (LRR) and cell adhesion molecule motifs," Brain Res. Rev., 51:265-74 (Jan. 2006), 10 pages.
Chen et al., "Nogo-A is a Myelin-Associated Neurite Outgrowth Inhibitor and an Antigen for Monoclonal Antibody IN-1," Nature, 403:434-439 (2000), 6 pages.
Chen et al., "Selection and analysis of an optimized anti-VEGF antibody: crystal structure of an affinity-matured Fab in complex with antigen," J. Mol. Biol., 293:865-881 (1999), 17 pages.
Cheng et al., "TrkB Gene Transfer Protects Retinal Ganglion Cells from Axotomy-Induced Death In Vivo," J Neuroscience, 22(10):3977-3986 (2002), 10 pages.
Cheung et al., "Regulation of caspase activation in axotomized retinal ganglion cells," Mol Cell Neurosci., 25:383-393 (2004), 13 pages.
Chiabrando et al., "Low-Density Lipoprotein Receptor-Related Protein Mediates in PC12 Cell Cultures the Inhibition of Nerve Growth Factor-Promoted Neurite Outgrowth by Pregnancy Zone Protein and $\alpha_2$-Macroglobulin," J Neurosci Res., 70:57-64 (2002), 10 pages.
Chinta and Anderson, "Dopaminergic neurons," IJBCB, 37:942-946 (2005), 5 pages.
Chothia, C., et al., "Canonical structures for the hypervariable regions of immunoglobulins" J. Mol. Biol. 196:901-917 (1987), 18 pages.
Citri et al., "The deaf and the dumb: The biology of ErbB-2 and ErbB-3," Exp. Cell Res., 284:54-65 (2003), 12 pages.
Clackson et al., "Making antibody fragments using phage display libraries" Nature 352:624-628 (1991), 5 pages.
Cockett et al., "High level expression of tissue inhibitor of metalloproteinases in Chinese hamster ovary cells using glutamine synthetase gene amplification" Bioltechnology 8: 662-667 (1990), 6 pages.
Cohen et al., "Nonchromosomal Antibiotic Resistance in Bacteria: Genetic Transformation of *Escherichia coli* by R-Factor DNA," Proc. Natl. Acad. Sci. USA, 69:2110-2114 (1972), 5 pages.
Colcher, D., et a., "Single-chain antibodies in pancreatic cancer" Ann NY Acad Sci 880:263-80 (1999), 18 pages.
Cole et al., "The National Eye Institute Visual Function Questionnaire: experience of the ONTT. Optic Neuritis Treatment Trial," Invest Ophthalmol Vis Sci, 2000, 41(5):1017-1021.
Colello and Pott, "Signals that Initiate Myelination in the Developing Mammalian Nervous System," Mol Neurobiol., 15(1):83-100 (1997), 19 pages.
Coleman and Perry, "Axon pathology in neurological disease: a neglected therapeutic target," Trends in Neurosci., 25:532-537 (2002), 6 pages.
Colman, "Effects of amino acid sequence changes on antibody-antigen interactions," Research in Immunol. 145:33-36 (1994), 4 pages.
Croxford et al., "Mouse models for multiple sclerosis: historical facts and future implications," Biochimica et Biphysica Acta (BBA)-Molecular Basis of Disease, 1812.2 (2011):177-183.
Csordas et al,. "Sustained Down-regulation of the Epidermal Growth Factor Receptor by Decorin," J. Biol. Chem., 275:32879-32887 (2000), 9 pages.
Cui et al., "Expression of trkA, trkB, and trkC in Injured and Regenerating Retinal Ganglion Cells of Adult Rats," Investigative Ophthalmology & Visual Science, 43(6):1954-1964 (2002), 11 pages.
Damle and Frost, "Antibody-targeted chemotherapy with immunoconjugates of calicheamicin," Curro Opin. Pharmacal., 3:386-390 (2003), 5 pages.

Daugherty and Mrsny, "Formulation and delivery issues for monoclonal antibody therapeutics," Adv Drug Delivery Rev, 58:686-706 (2006), 21 pages.
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J Immunol, 169:3076-3084 (2002), 11 pages.
Declaration of Robert B. Pepinsky filed in U.S. Appl. No. 11/165,576 dated Feb. 5, 2009, 5 pages.
Declaration of Robert H. Miller filed in U.S. Appl. No. 11/165,576 dated May 8, 2008, 20 pages.
Declaration of Sha Mi filed in U.S. Appl. No. 11/165,576 dated May 8, 2008, 5 pages.
Dey et al., "CSK negatively regulates nerve growth factor induced neural differentiation and augments AKT kinase activity," Exp. Cell Res., 307(1):1-14 (2005), 16 pages.
Domeniconi and Filbin, "Overcoming inhibitors in myelin to promote axonal regeneration," J Neurological Sci., 233:43-47 (Jun. 2005), 7 pages.
Domeniconi et al., "Myelin-Associated Glycoprotein Interacts with the Nog066 Receptor to Inhibit Neurite Outgrowth," Neuron, 35:283-290 (2002), 8 pages.
Dotti et al., "Human cytotoxic T lymphocytes with reduced sensitivity to Fas-induced apoptosis," Blood, 105:4677-4684 (2005), 8 pages.
Dousset et al. "Lysolecithin-Induced Demyelination in Primates: Preliminary In Vivo Study with MR and Magnetization Transfer," Am J Neuroradiol., 16:225-231 (Feb. 1995), 15 pages.
Dreyfus and Black, "Multiple Approaches to Brain Culture," Cell Culture, 2:3-16 (1990), 19 pages.
Dubessy et al., "Biotherapies in multiple sclerosis: a step toward remyelination and neuroprotection?," Revue Neurologique Dec., 170(12):770-778 (Dec. 2014).
E. Meyers; W. Miller, "Optimal alignments in linear space," Computer applications in the Biosciences: CABIOS 4:11-17 (1989), 13 pages.
Eby et al., "TAJ, a Novel Member of the Tumor Necrosis Factor Receptor Family, Activates the c-Jun N-terminal Kinase Pathway and Mediates Caspase-independent Cell Death," J. Biol. Chem., 275:15336-15342 (2000), 7 pages.
Eggert et al., "Different Effects of TrkA Expression in Neuroblastoma Cell Lines With or Without MYCN Amplification," Med Pediatr. Oncol., 35(6):623-627 (2000), 7 pages.
Engesser-Cesar et al., "Voluntary Wheel Running Improves Recovery from a Moderate Spinal Cord Injury," J Neurotrauma, 22:157-171 (Jan. 2005), 17 pages.
Esposito et al., "The Cytoplasmic and Transmembrane Domains of the p75 and Trk a Receptors regulate high affinity binding to nerve growth factor," J Biol Chem., 276(35):32687-32695 (2001).
Estaquier et al., "Fas-mediated apoptosis of CD4+ and CD8+ T cells from human immunodeficiency virus-infected persons: differential in vitro preventive effect of cytokines and protease antagonists," Blood, 87:4959-4966 (1996), pages.
Extended European Search Report for EP App. Ser. No. 15160028.5, dated Apr. 24, 2015, 6 pages.
Extended European Search Report in European Application No. 15183027.0, dated Nov. 19, 2015, 10 pages.
Fendly et al., "The Extracellular Domain of HER2/neu is a Potential Immunogen for Active Specific Immunotherapy of Breast Cancer," J. Biol. Resp. Mod., 9:449-455 (1990), 7 pages.
Ferguson et al., "Axonal damage in acute multiple sclerosis lesions" Brain 120:393-399 (1997), 7 pages.
Ferraro et al., "Molecular Targets to Promote Central Nervous System Regeneration," Current Neurovascular Res., 1:61-75 (2004), 15 pages.
Fisniku et al., "Gray Matter Atrophy Is Related to Long-Term Disability in Multiple Sclerosis," Annals of Neurology, 64(3):247-254 (2008), 8 pages.
Foecking et al., "Powerful and versatile enhancer-promoter unit for mammalian expression vectors" Gene 45:101 (1986), 5 pages.

(56) References Cited

OTHER PUBLICATIONS

Foote and Winter, "Antibody Framework Residues Affecting the Conformation of the Hypervariable Loops," J Mol Bio., 224:487-499 (1992), 13 pages.
Fournier et al., "Identification of a Receptor Mediating Nogo-66 Inhibition of Axonal Regeneration," Nature, 409:341-346 (2001), 6 pages.
Fournier et al., "Truncated soluble Nogo receptor binds Nogo-66 and blocks inhibition of axon growth by myelin," J. Neuroscience, 22(20):8876-8883 (Oct. 15, 2002), 8 pages.
Fu et al., "Blocking LINGO-1 Function Promotes Retinal Ganglion Cell Survival Following Ocular Hypertension and Optic Nerve Transection," Invest. Ophthal Vis. Sci., 49:975-985 (Mar. 2008), 11 pages.
Fu et al., "Combination Brain-Derived Neurotrophic Factor and LINGO-I Fusion Protein Promote Long-Term Survival to Retinal Ganglion Cells after Ocular Hypertension," Neurosci Res. Abs. 65(1):S171 (2009), 1 page.
Fu et al., "Combined Effect of Brain-derived Neurotrophic Factor and Lingo-1 Fusion Protein on Long-Term Survival of Retinal Ganglion Cells in Chronic Glaucoma," Neurosci., 162:375-382 (2009), 8 pages.
Fu et al., "LINGO-I Exerts Neuroprotection in a Rat Glaucoma Model," Invest. Ophthalmol Vis. Sci., 46:157 (2005), 1 page.
Fu et al., "LINGO-1 negatively regulates TrkB phosphorylation after ocular hypertension," Eur J Neuroscience, 31:1091-1097 (2010), 7 pages.
Fuchs et al., "Targeting Recombinant Antibodies to the Surface of *Escherichia coli:* Fusion to a Peptidoglycan Associated Lipoprotein" Biotechnology 9:1370-1372 (1991), 4 pages.
Fuxe and Ungerstedt, "Antiparkinsonian Drugs and Dopaminergic Neostriatal Mechanisms: Studies in Rats with Unilateral 6-Hydroxydoparnine (=6-OH-DA)-Induced Degeneration of the Nigro-Neostriatal DA Pathway and Quantitative Recording of Rotational Behaviour," Pharmac. Ther., B:41-47 (1976), 9 pages.
Gallo et al., "The trkA Receptor Mediates Growth Cone Turning toward a Localized Source Nerve Growth Factor," J Neurosci., 17(14):5445-5454 (1997), 10 pages.
Galvin et al, "Axon pathology in Parkinson's disease and Lewy body dementia hippocampus contains α-, β-, γ-synuclein," Proc. Natl Acad. Sci. USA, 96:13450-13455 (1999), 6 pages.
Garrard et al., "Fab assembly and enrichment in a monovalent phage display system" Biotechnology 9:1373-1377 (1991), 5 pages.
Geiger and Peeper, "The Neurotrophic Receptor TrkB in Anoikis Resistance and Metastasis: A Perspective," Cancer Res., 65(16):7033-7036 (2005), 4 pages.
Ghiglione et al., "The Transmembrane Molecule Kekkon 1 Acts in a Feedback Loop to Negatively Regulate the Activity of the *Drosophila* EGF Receptor during Oogenesis," Cell, 96:847-856 (1999), 10 pages.
Gill et al., "Addendum: Direct brain infusion of glial cell line-derived neurotrophic factor in Parkinson disease," Nat. Med., 12:479 (Apr. 2006), 1 page.
Gill et al., "Direct brain infusion of glial cell line-derived neurotrophic factor in Parkinson disease," Nat. Med., 9:589-595 (2003), 8 pages.
Gille et al., "Oxidative Stress to Dopaminergic Neurons as Models of Parkinson's Disease," Ann. N.y. Acad. Sci., 1018:533-540 (Jun. 2004), 8 pages.
Gram, et al., "In vitro selection and affinity maturation of antibodies from a naive combinatorial immunoglobulin library" PNAS 89:3576-3580 (1992), 5 pages.
Grandpre et al., "Identification of the Nogo Inhibitor of Axon Regeneration as a Reticulon Protein," Nature, 403:439-444 (2000), 6 pages.
Grandpre et al., "Nogo-66 receptor antagonist peptide promotes axonal regeneration," Nature, 417:547-551 (May 30, 2002), 5 pages.
Green, L.L. et al., "Antigen-specific human monoclonal antibodies from mice engineered with human Ig heavy and light chain YACs" A1. Nature Genet. 7:13-21 (1994), 9 pages.
Griffths et al., "Human anti-self antibodies with high specificity from phage display libraries" Embo Biol 12:725-734 (1993), 10 pages.
Grimbergen et al., "Postural instability in Parkinson's disease: the adrenergic hypothesis and the locus coeruleus," Expert Rev. Neurother., 9(2):279-290 (2009), 12 pages.
Grimpe et al., "The Critical Role of Basement Membrane-Independent Laminin γ1 Chain During Axon Regeneration in the CNS," J. Neurosci., 22:3144-3160 (2002), 17 pages.
Gur et al., "LRIG1 restricts growth factor signaling by enhancing receptor ubiquitylation and degradation," EMBO J., 23:3270-3281 (Aug. 2004), 12 pages.
Ha et al., "Membrane Rafts Play a Crucial Role in Receptor Activator of Nuclear Factor KB Signaling and Osteoclast Function," J. Biol. Chem., 278:18573-18580 (2003), 8 pages.
Haines and Rigby, "Expression of Lingo/LERN gene family during mouse embryogenesis," Gene Expression Patterns, 8:79-86 (2008), 8 pages.
Haniu et al., "Interactions between Brain-derived Neurotropic Factor and the TRKB Receptor," J Biol. Chem., 272(40):25296-25303 (1997), 8 pages.
Hartmann et al., "Truncated TrkB receptor-induced outgrowth of dendritic filopodia involves the p75 neurotrophin receptor," J Cell Sci., 117:5803-5814 (2004), 12 pages.
Harwerth et al., "Monoclonal Antibodies against the Extracellular Domain of the erbB-2 Receptor Function as Partial Ligand Agonists," J. Biol. Chem., 267: 15160-15167 (1992), 8 pages.
Hauser et al., "The Neurobiology of Multiple Sclerosis: Genes, Inflammation and Neurodegeneration" Neuron, 52(1):61-76 (2006), 16 pages.
Hawkins et al., "Selection of phage antibodies by binding affinity. Mimicking affinity maturation" J Mol Biol 226:889-896 (1992), 8 pages.
Hay et al., "Bacteriophage cloning and *Escherichia coli* expression of a human IgM Fab" Hum Antibody Hybridomas 3:81-85 (1992), 5 pages.
Hefti et al., "Novel class of pain drugs based on antagonism of NGF," Trends Pharmacol Sci., 27(2):85-91 (2006), 8 pages.
Hoet et al., "Generation of high-affinity human antibodies by combining donor-derived and synthetic complementarity-determining-region diversity," Nat. Biotechnol., 23:344-348 (Mar. 2005), 5 pages.
Hoke et al., "Glial Cell Line-Derived Neurotrophic Factor Alters Axon Schwann Cell Units and Promotes Myelination in Unmyelinated Nerve Fibers," J Neurosci., 23(2):561-567 (2003), 7 pages.
Holm et al., "Functional mapping and single chain construction of the anti-cytokeratin 8 monoclonal antibody TSI," Mol. Immunol., 44:1075-1084 (2007), 10 pages.
Hoogenboom et al., "Multi-subunit proteins on the surface of filamentous phage: methodologies for displaying antibody (Fab) heavy and light chains" Nuc Acid Res 19:4133-4137 (1991), 5 pages.
Howland et al., "Focal loss of glutamate transporter EAAT2 in a transgenic rat model of SOD1 mutant-mediated amyotrophic lateral sclerosis (ALS)," Pro Natl Acad Sci USA, 99:1604-1609 (2002), 6 pages.
Huang and Reichardt, "TRK Receptors Roles in Neuronal Signal Transduction," Annu Rev Biochem., 72:609-642 (2003), 36 pages.
Huang and Reichardt, "Neurotrophins: Roles in Neuronal Development and Function," Annu. Rev. Neurosci., 24:677-736 (2001), 64 pages.
Huang et al., "Glial Membranes at the Node of Ranvier Prevent Neurite Outgrowth," Science, 310:1813-7 (Dec. 2005), 5 pages.
Hunt et al., "Nogo receptor mRNA expression in intact and regenerating CNS neurons," Molecular Cellular Neurosci., 20:537-552 (2002), 16 pages.
Huse et al., "Generation of a large combinatorial library of the immunoglobulin repertoire in phage lambda" Science 246:1275-1281 (1989), 7 pages.
Huston et al., "Protein engineering of antibody binding sites: recovery of specific activity in an anti-digoxin single-chain Fv analogue produced in *Escherichia coli*" Proc. Natl. Acad. Sci. USA 85:5879-5883 (1988), 5 pages.

(56) References Cited

OTHER PUBLICATIONS

Ibanez et al., "An extended surface of binding to Trk tyrosine kinase receptors in NGF and BDNF allows the engineering of a multi-functional pan-neurotrophin," EMBO J, 12(6):2281-2293 (1993), 13 pages.
Inoue et al., "Inhibition of the leucine-rich repeat protein LINGO-1 enhances survival, structure, and function of dopaminergic neurons in Parkinson's disease models", Proc Nat Acad Sci, 104(36):14430-14435 (Sep. 4, 2007), 6 pages.
International Preliminary Report on Patentability dated Apr. 14, 2015, in International Application No. PCT/US2013/06387, 13 pages.
International Preliminary Report on Patentability for International Application No. PCT/US2013/040988, dated Nov. 27, 2014, 9 pages.
International Preliminary Report on Patentability dated Apr. 13, 2010, in International Application No. PCT/US2008/011633, 7 pages.
International Preliminary Report on Patentability dated Apr. 29, 2008, in International Application No. PCT/US2006/041966, 7 pages.
International Preliminary Report on Patentability dated Dec. 28, 2006, in International Application No. PCT/US2005/22881, 5 pages.
International Preliminary Report on Patentability dated Feb. 24, 2009 in International Application No. PCT/US2006/026271, 8 pages.
International Preliminary Report on Patentability dated Jan. 11, 2011, in International Application No. PCT/US2009/003999, 11 pages.
International Preliminary Report on Patentability dated Jan. 27, 2009, in International Application No. PCT/US2007/016589, 6 pages.
International Preliminary Report on Patentability dated Jul. 14, 2009, in International Application No. PCT/US2008/000316, 6 pages.
International Preliminary Report on Patentability dated Jun. 4, 2008, in International Application No. PCT/US2006/045993, 8 pages.
International Preliminary Report on Patentability dated May 11, 2010, in International Application No. PCT/US2008/012620, 8 pages.
International Preliminary Report on Patentability dated May 6, 2008, in International Application No. PCT/US2006/042990, 5 pages.
International Preliminary Report on Patentability dated Sep. 23, 2005, in International Application No. PCT/US2004/008323, 8 pages.
International Search Report and Written Opinion for International Application No. PCT/US2008/11633, dated Feb. 18, 2009, 8 pages.
International Search Report and Written Opinion for International Application No. PCT/US2008/12620, dated Feb. 26, 2009, 10 pages.
International Search Report and Written Opinion in International Application No. PCT/US2013/063873, dated Jul. 4, 2014, 20 pages.
International Search Report and Written Opinion in International Application No. PCT/US2005/022881, dated Oct. 31, 2006, 7 pages.
International Search Report and Written Opinion in International Application No. PCT/US2006/041966, dated Jul. 9, 2007, 9 pages.
International Search Report and Written Opinion in International Application No. PCT/US2006/26271, dated Jan. 27, 2009, 21 pages.
International Search Report and Written Opinion in International Application No. PCT/US2007/016589, dated Oct. 2, 2008, 8 pages.
International Search Report and Written Opinion in International Application No. PCT/US2016/012619, dated Jun. 22, 2016, 23 pages.
International Search Report for International Application No. PCT/US2004/008323, dated Oct. 15, 2004, 5 pages.
International Search Report for International Application No. PCT/US2006/42990, dated Apr. 18, 2007, 3 pages.
International Search Report for International Application No. PCT/US2009/003999, dated Mar. 8, 2010, 9 pages.
International Search Report for International Patent Application No. PCT/US2006/45993 dated Sep. 28, 2007, 7 pages.
International Search Report in International Application No. PCT/US2013/040988, dated Nov. 1, 2013, 5 pages.
International Search Report dated Sep. 16, 2008, in International Application No. PCT/US2008/00316, 4 pages.
Invitation to Pay Additional Fees from International Application No. PCT/US2016/012619, dated Apr. 15, 2016.
Irvine et al., "Remyelination protects axons from demyelination-associated axon degeneration," Brain, 131(6):1464-1477 (Jan. 2008).
Isacson, "Problems and Solutions for Circuits and Synapses in Parkinson's Disease," Neuron, 43:165-168 (Jul. 2004), 4 pages.
Jasmin; Ohara, "Remyelination within the CNS: do schwann cells pave the way for oligodendrocytes?" Neuroscientists 8(3):198-203 (2003), 6 pages.
Jellinger et al., "Pathology of Parkinson's Disease, Changes other than the Nigrostriatal Pathway," Molecular Chem Neuropathol., 14:153-197 (1991), 47 pages.
Ji et al., "Assessment of functional recovery and axonal sprouting in oligodendrocyte-myelin glycoprotein (OMgp) null mice after spinal cord injury" Mol Cell Neurosci. 39:258-67 (2008), 22 pages.
Ji et al., "CNTF promotes survival of retinal ganglion cells after induction of ocular hypertension in rats: the possible involvement of STAT3 pathway," Eur J Neuroscience, 19:265-272 (2004), 11 pages.
Ji et al., "Cyclic AMP controls BDNF-induced TrkB phosphorylation and dendritic pine formation in mature hippocampal neurons," Nature Neuroscience, 8(2):164-172 (2005), 10 pages.
Ji et al., "LINGO-1 antagonist promotes functional recovery and axonal sprouting after spinal cord injury" Mol Cell Neurosci. 33(3):11-20 (2006), 10 pages.
Jones et al., "NG2 Is a Major Chondroitin Sulfate Proteoglycan Produced after Spinal Cord Injury and Is Expressed by Macrophages and Oligodendrocyte Progenitors," J. Neurosci., 22:2792-2803 (2002), 12 pages.
Jonnala and Buccafusco, "Inhibition of nerve growth factor signaling by peroxynitrite," J Neurosci. Res., 63(1):27-34 (2001), 11 pages.
Kaplan and Miller, "Neurotrophin signal transduction in the nervous system," Current Opinion in Neurobiology, 10:381-391, (2000), 13 pages.
Kasper et al, "Structural Basis of Cell-Cell Adhesion by NCAM," Nat. Struct. Biol., 7:389-393 (2000), 5 pages.
Kernie and Parada, "The Molecular Basis for Understanding Neurotrophins and Their Relevance to Neurologic Disease," Arch Neurol., 57(5):654-657 (2000), 4 pages.
Kim et al., "The Role of ErbB2 Signaling in the Onset of Terminal Differentiation of Oligodendrocytes In Vivo," J. Neurosci., 23:5561-5571 (2003), 11 pages.
Kimpinski, "The Anti-P75 Antibody, MC192, and Brain-Derived Neurotrophic Factor Inhibit Nerve Growth Factor-Dependent Neurite Growth from Adult Sensory Neurons," Neurosci., 93(1):253-263 (1999), 11 pages.
Klapper et al., "A subclass of tumor-inhibitory monoclonal antibodies to ErbB-2/HER2 blocks crosstalk with growth factor receptors," Oncogene, 14:2099-2109 (1997), 11 pages.
Kleitman et al., "Tissue Culture Methods for the Study of Myelination," Culture Nerve Cells, Banker and Goslin, eds., pp. 337-377, MIT Press, Cambridge, Massachusetts, United States (1991), 43 pages.
Knappik et al., "Fully Synthetic Human Combinatorial Antibody Libraries (HuCAL) Based on Modular Consensus Frameworks and CDRs Randomized with Trinucleotides," J. Mol. Biol., 296:57-86 (2000), 30 pages.
Kobayashi et al., "Tryptophan H33 plays an important role in pyrimidine (6-4) pyrimidone photoproduct binding by a high-affinity antibody," Protein Engineering, 12:879-884 (1999), 6 pages.
Kohler, "Immunoglobulin chain loss in hybridoma lines" Proc. Natl. Acad. Sci. USA 77:2197 (1980), 3 pages.
Kolodny, "Dysmyelinating and demyelinating conditions in infancy," Curro Opin. Neurol. Neurosurg., 6:379-386 (1993), 8 pages.

(56) References Cited

OTHER PUBLICATIONS

Kornek et al, "Multiple sclerosis and chronic autoimmune encephalomyelitis: a comparative quantitative study of axonal injury in active, inactive, and remyelinated lesions," Am J Pathol., 2000, 157: 267-276.
Kornilova et al., "Lysosomal Targeting of Epidermal Growth Factor Receptors via a Kinase-dependent Pathway Is Mediated by the Receptor Carboxyl-terminal Residues 1022-1123," J. Biol. Chem., 271:30340-30346 (1996), 7 pages.
Kotliarov et al., "Correlation Analysis between Single-Nucleotide Polymorphism and Expression Arrays in Gliomas Identifies Potentially Relevant Target Genes," Cancer Res., 69:1596-1603 (Feb. 2009), 8 pages.
Kottis et al., "Oligodendrocyte-myelin glycoprotein (OMgp) is an inhibitor of neurite outgrowth," J Neurochem., vol. 82, pp. 1566-1569 (2002), 4 pages.
Kurtze, "Clinical Definition for Multiple Sclerosis Treatment Trials," Ann. Neurol. 36:573-79 (1994), 7 pages.
Laederich et al., "The Leucine-rich Repeat Protein LRIG1 is a Negative Regulator of ErbB Family Receptor Tyrosine Kinases," J. Biol. Chem., 279:47050-47056 (Nov. 2004), 8 pages.
Laederich et al., "The Leucine-rich Repeat Protein LRIG1 is a Negative Regulator of ErbB Family Receptor Tyrosine Kinases," J. Biol. Chem., 279:52806 (Dec. 2004), 8 pages.
Ledford, "Drug that boosts nerve signals offers hope for multiple sclerosis," Nature, 520:417 (Apr. 2015).
Lee and Chao, "Activation of Trk neurotrophin receptors in the absence of neurotrophins," Proc. Natl. Acad. Sci., 98(6):3555-3560 (2001), 6 pages.
Lee et al., "LINGO-1 regulates oligodendrocyte differentiation by inhibiting ErbB2 translocation and activation in lipid rafts," Mol Cellular Neurosci., 60:36-42 (2014), 7 pages.
Lee et al., "NGF Regulates the Expression of Axonal LINGO-1 to Inhibit Oligodendrocyte Differentiation and Myelination," J Neurosci., 27(1):220-225 (2007), 6 pages.
Lehmann et al., "Inactivation of Rho Signaling Pathway Promotes CNS Axon Regeneration," J Neurosci., 19(17):7537-7547 (1999), 11 pages.
Lehner et al., "How to use RNA interference," Briefings in Functional Genomics 1 and Proteomics, 3(1):68-83 (Apr. 2004), 16 pages.
Lemke, "Myelin and Myelination," in an Introduction to Molecular Neurobiol, Z. Hall, ed., pp. 281-309 (1992), 36 pages.
Li et al., "Blockade of Nogo-66, Myelin-Associated Glycoprotein, and Oligodendrocyte Myelin Glycoprotein by Soluble Nogo-66 Receptor Promotes Axonal Sprouting and Recovery after Spinal Injury," J. Neurosci., 24:10511-10520 (Nov. 2004), 10 pages.
Li et al., "Huntingtin Aggregate-Associated Axonal Degeneration is an Early Pathological Even in Huntington's Disease Mice," J Neurosci., 21:8473-8481 (2001), 9 pages.
Li et al., "Melanopsin-Expressing Retinal Ganglion Cells Are More Injury-Resistant in a Chronic Ocular Hypertension Model," Investigative Ophthalmology & Visual Science 47(7):2951-2958 (2006), 8 pages.
Li et al., "Neutralization of Myelin-Associated NOGO-A by a NOGO Receptor-FC Fusion Protein," Society for Neuroscience Abstracts 333.2 (2002), 1 pages.
Li et al., "Nogo-66 receptor antagonist peptide promotes axonal regeneration and functional recovery after spinal cord injury," Society for Neuroscience Abstract Viewer and Itinerary Planner, Abstract No. 203.4 (2002), 2 pages.
Li et al., "Neutralization of NGR1 may be Sufficient to Promote Rat DRG Neurite Outgrowth in the Presence of CNS Myelin," Society for Neuroscience Meeting Abstracts, Program 678.3, 1 page (Oct. 2003).
Liang et al., "Signaling from Integrins to Fyn to Rho Family GTPases Regulates Morphologic Differentiation of Oligodendrocytes," J. Neurosci., 24:7140-7149 (Aug. 2004), 10 pages.
Lin et al., "Netrin-1 and slit-2 regulate and direct neurite growth of ventral midbrain dopaminergic neurons," Molec. Cell. Neurosci., 28:547-555 (Mar. 2005), 9 pages.
Liu et al., "Chimeric mouse-human IgG1 antibody that can mediate lysis of cancer cells" PNAS 84:3439-3443 (1987), 5 pages.
Liu et al., "Enhancement of Schwann cell myelin formation by K252a in the trembler-J mouse dorsal root ganglion explant culture" J Neurosci. Res., 79(3):310-317 (2005), 9 pages.
Liu et al., "Extracellular regulators of axonal growth in the adult central nervous system," Phil. Trans. R. Soc. B, 361:1593-1610 (Sep. 2006), 18 pages.
Liu et al., "Production of a mouse-human chimeric monoclonal antibody to CD20 with potent Fc-dependent biologic activity" J. Immunol. 139:3521-3526 (1987), 6 pages.
Llorens et al., "Developmental analysis of Lingo-1/Lern1 protein expression in the mouse brain: interaction of its intracellular domain with Myt1l" Dev Neurobiol 68:521-41 (2008), 21 pages.
Llovera et al., "Trk is a calmodulin-binding protein: implications for receptor processing," J Neurochem., 88:422-433 (2004), 14 pages.
Lobuglio et al., "Phase I clinical trial of CO17-1A monoclonal antibody" Hybridoma 5:S117-123 (1986), 7 pages.
Longberg, N., et al. "Antigen-specific human antibodies from mice comprising four distinct genetic modifications" Nature 368:856-859 (1994), 4 pages.
Lowy et al., "Isolation of transforming DNA: cloning the hamster aprt gene" Cell 22:817 (1980), 7 pages.
Lv et al., "Passive immunization with LINGO-1 polyclonal antiserum afforded neuroprotection and promoted functional recovery in a rat model of spinal cord injury" Neuroimmunomodulation 17:270-8 (2010), 9 pages.
Ma et al., "Ligand-Dependent Recruitment of the ErbB4 Signaling Complex into Neuronal Lipid Rafts," J. Neurosci., 23:3164-3175 (2003), 12 pages.
Macay, "Real-Time Rapid Acuity Assessment Using VEPs: Development and Validation of the Step VEP Technique," Am Invest Ophthalmol Vis Sci. 49(1): 438-41 (2008), 4 pages.
MacCallum et al., "Antibody-antigen interactions: contact analysis and binding sit topography," J. Mol. Biol., 262:732-745 (1996), 14 pages.
Magy et al, "Transient exposure to FGF2 enhances myelination in embryonic brain cell cocultures," Exp. Neurol., 181:17-24 (2003), 8 pages.
Mangione et al., "Psychometric properties of the National Eye Institute Visual Function Questionnaire (NEI-VFQ). NEI-VFQ Field Test Investigators," Arch Ophthalmol. 5 (1988) 116(11):1496-1504.
Markus et al., "Raf and Akt Mediate Distinct Aspects of Sensory Axon Growth," Neuron, 35:65-76 (2002), 14 pages.
Marmigere et al., "The Runx1/AML1 transcription factor selectively regulates development and survival of TrkA nociceptive sensory neurons," Nat. Neurosci., 9(2):180-187 (2006), 8 pages.
Marsh et al., "SHP-1 negatively regulates neuronal survival by functioning as a TrkA phosphatase," J Cell Biol., 163(5):999-1010 (2003), 14 pages.
Martin et al., "Gene Therapy with Brain-Derived Neurotrophic Factor As a Protection: Retinal Ganglion Cells in a Rat Glaucoma Model," Investigative Ophthalmology & Visual Science, 44(10):4357-4365 (2003), 9 pages.
McDonald and Chao, "Structural Determinants of Neurotrophin Action," J Biol. Chem., 270(34):19669-19672 (1995), 4 pages.
McKerracher et al., "Identification of Myelin-Associated Glycoprotein as a Major Myelin-Derived Inhibitor of Neurite Growth," Neuron, 13:805-811 (1994), 7 pages.
Merrick et al., "Selective Destruction of Stable Microtubules and Axons by Inhibitors of Protein Serine/Threonine Phosphatases in Cultured Human Neurons (NT2N Cells)," J Neurosci., 17:5726-5737 (1997), 12 pages.
Messier et al., "New Techniques in Stereotaxic Surgery and Anesthesia in the Mouse," Pharmacol. Biochem. Behav., 63:313-318 (1999), 8 pages.
Meyer-Franke et al., "Characterization of the Signaling Interactions That Promote the Survival and Growth of Developing Retinal Ganglion Cells in Culture," Neuron, 15(4):805-819 (1995), 17 pages.

(56) References Cited

OTHER PUBLICATIONS

Mi et al., "A Novel CNS-Specific Protein Promotes Axonal Elongation by Modulating RHOA Signaling," Society for Neuroscience Abstracts, Abstract No. 891.5, Soc Neurosci., (2003), 1 page.
Mi et al., "Blocking LINGO-1 as a therapy to promote CNS repair: From concept to the clinic," CNS Drugs, 27(7):493-503, Jul. 2013, 11 pages.
Mi et al., "LINGO-1 and its role in CNS repair," Int'l J Biochem Cell Biol., 40:1971-1978 (2008), 8 pages.
Mi et al., "LINGO-1 antagonist promotes spinal cord remyelination and axonal integrity in MOG-induced experimental autoimmune encephalomyelitis," Nat. Med., 13:1228-1233 (Oct. 2007), 6 pages.
Mi et al., "LINGO-1 is a component of the Nogo-66 receptor/p75 signaling complex," Nat. Neurosci., 7:221-8 (Mar. 2004), 8 pages.
Mi et al., "LINGO-1 negatively regulates myelination by oligodendrocytes," Nat. Neurosci., 8:745-51 (May 2005), 7 pages.
Mi et al., "Promotion of Central Nervous System Remyelination by Induced Differentiation of Oligodendrocyte Precursor Cells," Ann Neurol., 65:304-315 (2009), 12 pages.
Mi et al., "Synctin is a captive retroviral envelope protein involved in human placental morphogenesis," Nature, 403:785-789 (2000), 7 pages.
Michailov et al., "Axonal Neuregulin-1 Regulates Myelin Sheath Thickness," Sci., 304:700-703 (2004), 4 pages.
Mikol and Stefansson, "A Phosphatidylinositol-Linked Peanut Agglutinin-Binding Glycoprotein in Central Nervous System Myelin and on Oligodendrocytes," J. Cell. Biol., 106:1273-1279 (1988), 7 pages.
Mikol et al., "The oligodendrocyte-myelin glycoprotein belongs to a distinct family of proteins and contains the HNK-1 carbohydrate," J Cell Biol., 110:471-479 (1990), 9 pages.
Miller et al., "Increased Neurite Outgrowth Induced by Inhibition of Protein Tyrosine Kinase Activity in PC12 Pheochromocytoma Cells," J Neurochem., 60(6):2134-2144 (1993), 13 pages.
Morell et al., "Gene Expression in Brain during Cuprizone-Induced Demyelination and Remyelination," Molec. Cell. Neurosci., 12:220-227 (1998), 10 pages.
Morgan; Anderson, "Human gene therapy" Ann. Rev. Biochem. 62:191-217 (1993), 27 pages.
Morrison, S. L., "Transfectomas provide novel chimeric antibodies" Science 229:1202-1207 (1985), 6 pages.
Mukhopadhyay et al., "A Novel Role for Myelin-Associated Glycoprotein as an Inhibitor of Axonal Regeneration," Neuron, 13:757-767 (1994), 11 pages.
Mullard, "An audience with Doug Williams," Nature Reviews Drug Discovery, 13(1):880-881 (Dec. 2014).
Mulligan, "The basic science of gene therapy" Science 260:926-932 (1993), 8 pages.
Mulligan; Berg, "Selection for animal cells that express the *Escherichia coli* gene coding for xanthine-guanine phosphoribosyltransferase," Proc. Natl. Sci. USA 78:2072 (1981), 5 pages.
Murdoch, et al., "Spotlight on Subcutaneous Recombinant Interferon-beta-1a (Rebif) in Relapsing-Remitting Multiple Sclerosis" Biodrugs 19(5)323-325 (2005), 3 pages.
Nagy et al., "Fully human, HLA-DR-specific monoclonal antibodies efficiently induce programmed death of malignant lymphoid cells," Nat. Med., 8:801-807 (2002), 7 pages.
Nagy et al., "Lipid rafts and the local density of ErbB proteins influence the biological role of homo- and heteroassociations of ErbB2," J. Cell Sci., 115:4251-4262 (2002), 12 pages.
NCBI Entrez, Accession No. AY324320, (first available May 4, 2004; last updated May 4, 2004), 2 pages.
NCBI Entrez, Accession No. AY324322, (first available May 4, 2004; last updated May 4, 2004), 2 pages.
NCBI Entrez, Accession No. AY324323, (first available May 4, 2004; last updated May 4, 2004), 2 pages.
NCBI Entrez, Accession No. BC011057, (first available Jul. 30, 2001; last updated Feb. 8, 2007), 3 pages.
NCBI Entrez, Accession No. BC068558, (first available Apr. 6, 2004; last updated Feb. 8, 2007), 4 pages.
NCBI Entrez, Accession No. DR000281, (first available May 17, 2005; last updated May 17, 2005), 2 pages.
NCBI Entrez, Accession No. NM_032808, (first available May 31, 2001; last updated Feb. 11, 2008), 4 pages.
NCBI Entrez, Accession No. NM_152570, (first available Sep. 6, 2002; last updated Feb. 11, 2008), 4 pages.
Needleman; Wunsch, "A general method applicable to the search for similarities in the amino acid sequence of two proteins" J. Mol. Biol. 48:444-453 (1970), 11 pages.
Nilsson et al., "Neurotrophin-7: a novel member of the neurotrophin family from the zebrafish," FEES Letters, 424:285-2901 (1998), 8 pages.
Nishimura et al., "Recombinant human-mouse chimeric monoclonal antibody specific for common acute lymphocytic leukemia antigen" Canc. Res. 47:999-1005 (1987), 8 pages.
Nusser et al., "Nerve Growth Factor Signals through TrkA, Phosphatidylinositol 3-Kinase, and Rac1 to Inactivate RhoA during the Initiation of Neuronal Differentiation ofPC12 Cells," J. Biol Chem., 277(39):35840-35846 (2002), 8 pages.
Oh et al., "Emerging injectable therapies for multiple sclerosis," Lancet Neurol., 12:1115-1126 (Oct. 2013).
O'Hare et al., "Transformation of mouse fibroblasts to methotrexate resistance by a recombinant plasmid expressing a prokaryotic dihydrofolate reductase" Proc. Natl. Acad. Aci. USA 78:1527 (1981), 5 pages.
Oi et al., "Chimeric antibodies" Biotechniques 4:214 (1986), 9 pages.
Okafuji et al., "Expression pattern of LINGO-1 in the developing nervous system of the chick embryo," Gene Expr. Patterns, 6:57-62 (Jul. 2005), 6 pages.
O'Leary and Hughes, "Design of Potent Peptide Mimetics of Brain-derived Neurotrophic Factor," J Biol. Chem., 278(28):25738-25744 (2003), 7 pages.
Orlandi et al., "Cloning immunoglobulin variable domains for expression by the polymerase chain reaction," Proc. Natl. Acad. Sci. USA, 86:3833-3837 (1989), 5 pages.
Osada et al., "Assignment of 118 novel cDNAs of cynomolgus monkey brain to human chromosomes," Gene, 275:31-37 (2001), 7 pages.
Padlan et al., "Structure of an antibody-antigen complex: crystal structure of the HyHEL-10 Fab-lysozyme complex," PNAS, 86:5938-5942 (1989), 5 pages.
Park et al., "A TNF Receptor Family Member, TROY, is a Coreceptor with Nogo Receptor in Mediating the Inhibitory Activity of Myelin Inhibitors," Erratum in Neuron, 3:815 (Mar. 2005), 1 page.
Park et al., "A TNF Receptor Family Member, TROY, is a Coreceptor with Nogo Receptor in Mediating the Inhibitory Activity of Myelin Inhibitors," Neuron, 3:345-351 (Feb. 2005), 7 pages.
Park et al., "The erbB2 gene is required for the development of terminally differentiated spinal cord oligodendrocytes," J. Cell Biol., 154:1245-1258 (2001), 14 pages.
Park et al., "Transcriptional regulation of artemin is related to neurite outgrowth and actin polymerization in mature DRG neurons,"Neurosci Letter 404:61-6 (2006), 6 pages.
Parran et al., "Methylmercury decreases NGF-induced TrkA autophosphorylation and neurite outgrowth in PC12 cells," Developmental Brain Res., 141:71-81 (2003), 13 pages.
Paul ed. Fundamental Immunology, Third Edition. Raven Press, New York, pp. 292-295, under the heading "Fv Structure and Diversity in Three Dimensions," (1993), 6 pages.
Pease et al., "Obstructed Axonal Transport of BDNF and Its Receptor TrkB in Experimental Glaucoma," Invest Ophthalmol Vis Sci., 41(3):764-74 (2000), 11 pages.
Pepinsky et al., "Exposure Levels of Anti-LINGO-1 Li81 Antibody in the Central Nervous System and Dose-Efficacy Relationships in Rat Spinal Cord Remyelination Models after Systemic Administration," J. Pharmacal. Exp. Ther., 339(2):519-529 (2011), 11 pages.
Pepinsky et al., "Structure of the LINGO-1 Anti-LINGO-1 Li81 Antibody Complex Provides Insights into the Biology of LINGO-1 and the Mechanism of Action of the Antibody Therapy," Journal of Pharmacology and Experimental Therapeutics, 350(1):110-123 (Apr. 2014).

(56) References Cited

OTHER PUBLICATIONS

Persengiev and Kilpatrick, "Nerve growth factor induced differentiation of neuronal cells requires gene methylation," NeuroReport, 8:227-231 (1996), 7 pages.
Pesavento, "Blocking the NGF-TrkA Interaction Rescues the Developmental Loss of LTP in the Rat Visual Cortex: Role of the Cholinergic System," Neuron, 25:165-75 (2000), 13 pages.
Peterson et al., "VCAM-1-positive microglia target oligodendrocytes at the border of multiple sclerosis lesions" J Neuropathol Exp Neurol 61:539-546 (2002), 8 pages.
Philo et al., "Interactions of Neurotrophin-3 (NT-3), Brian-derived Neurotrophic Factor (BDNF), and the NT-3•BDNF Heterodimer with the Extracellular Domains of the TrkB and TrkC Receptors," J Biol. Chem., 269(45):27840-27846 (1994), 7 pages.
Pinkas-Kramarski et al., "Neu Differentiation Factor/Neuregulin Isoforms Activate Distinct Receptor Combinations," J Biol. Chem., 271:19029-19032 (1996), 4 pages.
Plant et al., "Purified Adult Ensheathing Glia Fail to Myelinate Axons under Culture Conditions that Enable Schwann Cells to Form Myelin," J Neurosci., 22:6083-6091 (2002), 9 pages.
Pollack and Harper, "Small Molecule Trk Receptor Agonists and Other Neurotrophic Factor Mimetics," Current Drug Targets—CNS & Neurological Disorders, 1:59-80 (2002), 22 pages.
Presta et al., "Engineering of therapeutic antibodies to minimize immunogenicity and optimize function," Advanced Drug Delivery Reviews, Elsevier, Aug. 2006, 58(5-6):640-656, 17 pages.
Proudfoot, "Transcriptional interference and termination between duplicated alpha-globin gene constructs suggests a novel mechanism for gene regulation" Nature 322:562-565 (1986), 4 pages.
Qian et al., "Novel Agonist Monoclonal Antibodies Activate TrkB Receptors and Demonstrate Potent Neurotrophic Activities," J Neurosci., 26(37):9394-403 (2006), 10 pages.
Qiu and Goldberg, "Nrdp1/FLRF is a ubiquitin ligase promoting ubiquitination and degradation of the epidermal growth factor receptor family member, ErbB3," Proc. Natl. Acad. Sci. USA, 99:14843-14848 (2002), 10 pages.
Rader, "TNF Receptor-IgG Fc, rDNA," in Biopharmaceutical Products in the US. and European Markets, 5th ed., pp. 610-619 (Jul. 2006), 11 pages.
Rakhit et al., "Nerve Growth Factor Stimulation of p42/p44 Mitogen-Activated Proteu: Kinase in PC12 Cells: Role of $G_{i/o}$, G Protein-Coupled Receptor Kinase 2, β-Arrestin I, and Endocytic Processing," Mol. Pharmacol., 60(1):63-70 (2001), 8 pages.
Ransohoff, R.M., "Animal models of multiple sclerosis: the good, the bad and the bottom line," Nature Neuroscience 15(8):1074-1077 (2012), 4 pages.
Rauchenberger et al., "Human Combinatorial Fab Library Yielding Specific and Functional Antibodies against the Human Fibroblast Growth Factor Receptor 3," J. Biol. Chem., 278:38194-38205 (2003), 12 pages.
Reichert et al., "Monoclonal antibody successes in the clinic," Nat. Biotech., 23:1073-1078 (Sep. 2005), 6 pages.
Reiter, Y., "Antibody engineering of recombinant Fv immunotoxins for improved targeting of cancer: disulfide-stabilized Fv immunotoxins" Clin Cancer Res 2:245-52 (1996), 9 pages.
Ridgway, A.A.G., "Mammalian Expression Vector" Butterworths 470-472 (1988), 26 pages.
Robinson "Gene therapy—proceeding from laboratory to clinic," TIB TECH 11(5):155 (1993), 1 page.
Robinson, "The experimental autoimmune encephalomyelitis (EAE) model of MS: utility for understanding disease pathophysiology and treatment," Handbook of clinical neurology, 122(2014):173.
Rosado et al., "Transforming growth factor-/31 regulation of growth zone chondrocytes is mediated by multiple interacting pathways," Biochim. Biophys Acta., 1590:1-15 (2002), 15 pages.
Roux et al., "K252a and CEP1347 are Neuroprotective Compounds that inhibit mixed-linage Kinase-3 and Induce Activation of Akt and ERK," J Biol. Chem., 277(51):49473-49480 (2002), 8 pages.

Rubinson et al., "A lentivirus-based system to functionally silence genes in primary mammalian cells, stem cells and transgenic mice by RNA interference," Nat. Genet., 33:401-406 (2003), 6 pages.
Rudikoff et al., "Single amino acid substitution altering antigen-binding specificity," PNAS, 79:1979-1983 (1982), 5 pages.
Rudinger, "Characteristics of the amino acids as components of a peptide hormone sequence," in Peptide Hormones, (ed. J.A. Parsons) University Park Press, Baltimore, pp. 1-7 (1976), 9 pages.
Rudzinski et al., "Changes in Retinal Expression of Neurotrophins and Neurotrophin Receptors Induced by Ocular Hypertension," J Neurobiol., 58(3):341-354 (2004), 15 pages.
Rueda et al. "The Endocannabinoid Anandamide Inhibits Neuronal Progenitor Cell Differentiation through Attenuation of the Rap1/B-Raf/ERK Pathway," J. Biol Chem., 277(48):46645-46650 (2002), 7 pages.
Ruiz et al., "Treatment with trkC agonist antibodies delays disease progression in neuromuscular degeneration (nmd) mice," Hum. Mol. Genet., 14(13):1825-1837 (2005), 13 pages.
Rutishauser and Jessell, "Cell Adhesion Molecules in Vertebrate Neural Development," Physiol. Rev., 68:819-857 (1988), 39 pages.
Saha et al., "Ganglioside mediate the interaction between Nogo receptor 1 and LINGO-1," Biochem Biophysical Res Comm., 413:92-97 (2011), 6 pages.
Saleh et al., "A phase II trial of murine monoclonal antibody 17-1A and interferon-gamma: clinical and immunological data" Cancer Immunol. Immunother. 32:185-190 (1990), 6 pages.
Santerre et al., "Expression of prokaryotic genes for hygromycin B and G418 resistance as dominant-selection markers in mouse L cells" Gene 30:147 (1984), 10 pages.
Saragovi and Burgess, "Small Molecule and protein-based neurotrophic ligands: agonists and antagonists as therapeutic agents," Exp. Opin. Ther. Patents, 9(6):737-751 (1999), 15 pages.
Schiemann et al., "An Essential Role for BAFF in the Normal Development of B Cells Through a BCMA-Independent Pathway", Science, 293:2111-2114 (2001), 6 pages.
Schmucker et al., "erbB3 is Dispensable for Oligodendrocyte Development In Vitro and In Vivo," Glia, 44:67-75 (2003), 9 pages.
Schori et al., "Vaccination for protection of retinal ganglion cells against death from glutamate cytotoxicity and ocular hypertension: Implications for glaucoma," Proc. Natl. Acad. Sci., 98(6):3398-403 (2001), 6 pages.
Schwab et al., "Inhibitors of Neurite Growth", Annual Review of Neuroscience, 16:565-595 (1993), 33 pages.
Sha Mi et al., "LINGO-1 antagonist promotes spinal cord remyelination and axonal integrity in MOG-induced experimental autoimmune encephalomyelitis," Nature Medicine, 13(10):1228-1233 (Sep. 2007).
Sha Mi et al., "Promotion of central nervous systems remyelination by induced differentiation of oligodendrocyte precursor cells", Annals of Neurology 65(3):304-315 (2009), 12 pages. XP055098017, ISSN: 0364-5134, DOI: 10.1002/ana.21581.
Shah et al., "Role of EGF Receptor Transactivation in Phosphoinositide 3-Kinase-Dependent Activation of MAP Kinase by GPCRs," J. Cell. Physiol., 206:47-57 (Jan. 2006), 11 pages.
Shao et al., "TAJ/TROY, an Orphan TNF Receptor Family Member, Binds Nogo-66 Receptor 1 and Regulates Axonal Regeneration," Neuron, 45:353-9 (Feb. 2005), 7 pages.
Shaw et al., "Mouse/human chimeric antibodies to a tumor-associated antigen: biologic activity of the four human IgG subclasses" J. Natl Cancer Inst. 80:1553-1559 (1988), 7 pages.
Shelton et al., "Human trks: Molecular Cloning, Tissue Distribution, and Expression of Extracellular Domain Immunoadhesins," J Neurosci., 15(1-2):477-491 (1995), 15 pages.
Stankoff et al., "Ciliary Neurotrophic Factor (CNTF) Enhances Myelin Formation: A Novel Role for CNTF and CNTF-Related Molecules," J Neurosci., 22(21):9221-9227 (2002), 7 pages.
Stolt et al., "Terminal differentiation of myelin-forming oligodendrocytes depends on the transcription factor Sox 10," Genes & Dev., 16:165-170 (2002), 6 pages.
Streltsov, "Structure of a shark IgNAR antibody variable domain and modeling of an early-developmental isotype" Protein Sci. 14:2901-2909 (2005), 9 pages.

(56) References Cited

OTHER PUBLICATIONS

Strohmaier et al., "A splice variant of the neurotrophin receptor trkB with increased specificity for brain-derived neurotrophic factor," EMBO J., 15(13):3332-7 (1996), 6 pages.
Sun et al., "Chimeric antibody with human constant regions and mouse variable regions directed against carcinoma-associated antigen 17-1A" PNAS 84:214-218 (1987), 5 pages.
Supplementary European Search Report for EP Application No. 06 83 6888, search completed on Dec. 11, 2009, 8 pages.
Supplementary European Search Report for European Application No. 06 83 8776, dated Nov. 10, 2009, 4 pages.
Supplementary European Search Report for European Application No. 08 84 8257, dated Jan. 18, 2013, 4 pages.
Supplementary European Search Report for European Application No. EP 05 76 4255, The Hague, Netherlands, dated Nov. 5, 2009, 3 pages.
Supplementary European Search Report for European Application No. EP 08 83 7617, European Patent Office, Germany, dated Apr. 19, 2012, 4 pages.
Supplementary European Search Report for European Application No. EP 13 79 0850, dated Jan. 13, 2016, 14 pages.
Supplementary Partial European Search Report for European Application No. EP 06836566, completed on Jun. 26, 2009, Munich, Germany, 7 pages.
Sussman, "For MS Patients, No Additive Benefit Found in Combining Gladtiramer Acetate and Interferon Beta-1A," News From The AAN Annual Meeting, Neurology 122 (2014): 173.
Sussman et al., "The ErbB4 Neurogulin Receptor Mediates Suppression of Oligodendrocyte Maturation," J. Neurosci., 25:5757-5762 (Jun. 2005), 6 pages.
t Hart et al., "Modelling of multiple sclerosis: lessons learned in a non-human primate," The Lancet Neurology 3(10):588-597 (2004), 10 pages.
Takatori et al., "Local Anesthetics Suppress Nerve Growth Factor-Mediated Neurite Outgrowth by Inhibition of Tyrosine Kinase Activity of TrkA," Anesth. Analg., 102:462-467 (2006), 8 pages.
Tanpakushitu Kakusan Kouso (Protein, Nucleic Acid, Enzyme), 1998, 43(2):159-167 (with English abstract), 10 pages.
Taupin et al., "Identification of agonistic and antagonistic antibodies against gp 190, the Leukemia Inhibitory Factor Receptor, reveals distinct roles for its cytokine-binding domains," J Biol. Chem., 376(51):47975-47981 (Dec. 21, 2001), 7 pages.
Taveggia et al. "Neuregulin-1 Type III Determines the Ensheathment Fate of Axons," Neuron, 47:681-694 (2005), 16 pages.
Tezel et al., "Immunohistochemical Assessment of the Glial Mitogen-Activated Protein Kinase Activation in Glaucoma," investigative Ophthalmology & Visual Science, 44(7):3025-3033 (2003), 9 pages.
Tolstoshev, "Gene therapy, concepts, current trials and future directions" Ann. Rev. Pharmacol. Toxicol. 32:573-596 (1993), 24 pages.
Tong et al., "Intracellular Calcium Levels Influence Apoptosis in Mature Sensory Neurons after Trophic Factor Deprivation," Exp. Neurol., 138:45-52 (1996), 10 pages.
Torkildsen et al., "The cuprizone model for demyelination," Acta Neurol Scand Suppl., 188:72-76 (2008), 5 pages.
Trapp et al., "Axonal pathology in multiple sclerosis: relationship to neurologic disability," Curr Opin. Neurol., 12:295-302 (1999), 8 pages.
Trapp et al., "Axonal transection in the lesions of multiple sclerosis" N Engl J Med 338:278-285 (1998), 8 pages.
Trapp et al., "Pathogenesis of tissue injury in MS lesions," J. Neuroimmunol., 98:49-56 (1999), 8 pages.
Trifunovski et al. "Neuronal activity-induced regulation of LINGO-1," Neuroreport, 15:2397-2400 (Oct. 2004), 4 pages.
Tuaillon et al., "Human immunoglobulin heavy-chain minilocus recombination in transgenic mice: gene-segment use in mu and gamma transcripts" PNAS 90:3720-3724 (1993), 5 pages.
Tzahar et al., "Bivalence of EGF-like ligands drives the ErbB signaling network," EMBO J., 16:4938-4950 (1997), 13 pages.
Urfer et al., "High Resolution Mapping of the Binding Site of TrkA for Nerve Growth Factor and TrkC for Neurotrophin-3 on the Second Immunoglobulin-like Domain of the Trk Receptors," J. Biol. Chem., 273(10):5829-5840 (1998), 17 pages.
Vajdos et al., "Comprehensive functional maps of the antigen-binding site of an anti-ErbB2 antibody obtained with shotgun scanning mutagenesis," J. Mol. Biol., 320: 415-428 (2002), 14 pages.
Vartanian et al., "Failure of spinal cord oligodendrocyte development in mice lacking neuregulin," Proc. Natl. Acad. Sci. USA, 96:731-735 (1999), 5 pages.
Verhoeyan et al., "Reshaping human antibodies: grafting an antilysozyme activity" Science 239:1534 (1988), 3 pages.
Vick et al., "Role of adult oligodendrocytes in remyelination after neural injury" J. Neurotrauma 9(1):593-103 (1992), 11 pages.
Viskochil et al., "The Gene Encoding the Oligodendrocyte-Myelin Glycoprotein is Embedded within the Neurofibromatosis Type 1 Gene", Molecular and Cellular Biology, 11:906-912 (1991), 9 pages.
Vourc'h et al., "Oligodendrocyte myelin glycoprotein (OMgp) evolution, structure and function," Br Res Rev., 45:115-124 (2004), 12 pages.
Vourc'h et al., "Oligodendrocyte myelin glycoprotein growth inhibition function requires its conserved leucine-rich repeat domain, not its glycosylphosphatidyl-inositol anchor," J Neurochem., 85:889-897 (2003), 9 pages.
Vourc'h et al., "The Oligodendrocyte-Myelin Glycoprotein Gene in Highly Expressed During the Late Stages of Myelination in the Rat Central Nervous System", Developmental Brain Research, 144:159-168 (2003), 12 pages.
Wang et al., "Oligodendrocyte-Myelin Glycoprotein is a Nogo Receptor Ligand That Inhibits Neurite Outgrowth," Nature, 417:941-944 (2002), 4 pages.
Werkerle et al., "Animal models of multiple sclerosis" Drug Discovery Today: Disease Models 3(4):359-367 (2006), 9 pages.
West et al., "Parkinson's disease-associated mutations in leucine-rich repeat kinase 2 augment kinase activity," PNAS, 102:16842-16847 (2005), 6 pages.
Wigler et al., "Transfer of purified herpes virus thymidine kinase gene to cultured mouse cells" Cell 11:223 (1977), 10 pages.
Wigler et al., "Transformation of mammalian cells with an amplifiable dominant-acting gene" Natl. Acad. Sci. USA 77:3567 (1980), 4 pages.
Wikipedia 2013; File: Spinal cord tracts. At Wikipedia.org/wiki/File:Spinal_cord_tracts_-_English.svg, 4 pages.
Williams and Doherty, "Evidence for and against a Pivotal Role of PI 3-Kinase in a Neuronal Cell Survival Pathway," Molec. Cell. Neurosci., 13:272-280 (1999), 9 pages.
Williams et al., "Overcoming the Inhibitors of Myelin with a Novel Neurotrophin Strategy," J Biol Chem., 280(7):5862-5869 (2006), 8 pages.
Woldemussie et al., "Neuroprotection of Retinal Ganglion Cells by Brimonidine in Rats with Laser-Induced Chronic Ocular Hypertension," Investigative Ophthalmology & Visual Sci., 42(12):2849-2855 (2001), 7 pages.
Wood et al., "The synthesis and in vivo assembly of functional antibodies in yeast" Nature 314:446-449 (1985), 4 pages.
Woronowicz et al., "Trypanosome trans-sialidase targets TrkA tyrosine kinase receptor and induces receptor internalization and activation," Glycobiology, 14(11):987-998 (2004), 14 pages.
Wu et al., "Humanization of a murine monoclonal antibody by simultaneous optimization of framework and CDR residues," J. Mol. Biol., 294: 151-162 (1999), 12 pages.
Wu et al., "MR diffusion changes correlate with ultra-structurally defined axonal degeneration in murine optic nerve" NeuroImage 37:1138-1147 (2007), 10 pages.
Wu; Wu, "Delivery systems for gene therapy" Biotherapy 3:87-95 (1991), 9 pages.
Xu et al., "Chaperone-dependent E3 ubiquitin ligase CHIP mediates a degradative pathway for c-ErbB2/Neu," Proc. Natl. Acad. Sci. USA, 99:12847-12852 (2002), 6 pages.
Yamada and Nabeshima, "Brain-Derived Neurotrophic Factor/TrkB Signaling in Memory Processes," J Pharmacal. Sci., 91:267-270 (2003), 4 pages.

(56) References Cited

OTHER PUBLICATIONS

Yamashita et al., "Multiple signals regulate axon regeneration through the Nogo receptor complex" Mol Neurobiol 32:105-11 (2005), 7 pages.
Yang et al., "A novel azulenyl nitron antioxidant protects against MPTP and 3-nitropropionic acid neurotoxicities," Exp. Neural., 191:86-93 (Jan. 2005), 8 pages.
Yu et al., "Segregation of Nogo66 receptors into lipid rafts in rat brain and inhibition of Nogo66 signaling by cholesterol depletion," FEBS Lett., 577:87-92 (Nov. 2004), 6 pages.
Zaccaro et al., "Selective Small Molecule Peptidomimetic Ligands of TrkC and TrkA Receptors Afford Discrete or Complete Neurotropic Activities," Chem. & Biol., 12:1015-1028 (2005), 14 pages.
Zhao et al., "Inactivation of Glycogen Synthase Kinase-3β and Up-regulation of LINGO-1 are Involved in LINGO-1 Antagonist Regulated Survival of Cerebellar Granular Neurons," Cell Mol Neurobiol. 28:737-35 (2008), 9 pages.
Zhou et al., "ErbB2 Degradation Mediated by the Co-chaperone Protein CHIP," J. Biol. Chem., 278:13829-13837 (2003), pages.
"Wikipedia: The Free Encyclopedia" [online], "Progressive supranuclear palsy," first available Jan. 26, 2005, [retrieved on Mar. 9, 2016], Retrieved from the Internet: URL<https://en.wikipedia.org/w/index.php?title=Progressive_supranuclear_palsy&oldid=704724726>, 7 pages.
Abulrob et al., "The blood-brain barrier transmigrating single domain antibody: mechanisms of transport and antigenic epitopes in human brain endothelial cells," Journal of Neurochemistry, Wiley Interscience, 2005, 95(4):1201-1214.
Arduini et al., "Expression, purification, and characterization of rat interferon-beta, and preparation of an N-terminally PEGylated form with improved pharmacokinetic parameters," Protein Expression and Purification, 2004, 34(2):229-242.
Baker et al., "N-Terminally PEGylated Human lnterferon-beta-1a with Improved Pharmacokinetic Properties and in Vivo Efficacy in a Melanoma Angiogenesis Model," Bioconjugate Chem, 2006, 17(1):179-188.
Baker, et al., "PEGylated Interferon Beta-1a: Meeting an Unmet Medical Need in the Treatment of Relapsing Multiple Sclerosis," J of Interferon and Cytokine Res, 2010, 30(10):777-785.
Barten et al., "New approaches in the management of multiple sclerosis," Drug Design, Development and Therapy, 2010, 4:343-366.
Benedict el al., "Repeated assessment of neuropsychological deficits in multiple sclerosis using the Symbol Digit Modalities Test and the MS Neuropsychological Screening Questionnaire," Mult. Scler., 2008, 14(7):940-946.
Benedict et al., "An attempt at memory retraining in severe amnesia: An experimental single-case study," Neuropsychological Rehabilitation: An International Journal, 1993, 3(1):37-51.
Benedict et al., "Neocortical Atrophy, Third Ventricular Width, and Cognitive Dysfunction in Multiple Sclerosis," Arch Neurol., 2006, 63:1301-1306.
Benedict et al., "Preliminary standardization of a new visuospatial memory test with six alternate forms," The Clinical Neuropsychologist, 1995, 9(1):11-16.
Benedict et al., "Reliability and equivalence of alternate forms for the Symbol Digit Modalities Test: implications for multiple sclerosis clinical trials," Multiple Sclerosis Journal, 2012, 18(9):1320-1325.
Benedict et al., "Revision of the Brief Visuospatial Memory Test: Studies of normal performance, reliability, and validity," Psychological Assessment, 1996, 8(2):145-153.
Benedict et al., "Screening for multiple sclerosis cognitive impairment using a self-administered 15-item questionnaire," Multiple Sclerosis, 2003, 9(1):95-101.
Benedict et al., "Validity of the minimal assessment of cognitive function in multiple sclerosis. (MACFIMS)," Journal of International Neuropsychological Society, 2006, 12(4):549-558.
Benedict et al., "Diffusion-weighted imaging predicts cognitive impairment in multiple sclerosis," Mult. Scler., 2007, 13:722-730.
Benedict et al., "Effects of using same- versus alternate-form memory tests during short-interval repeated assessments in multiple sclerosis," Journal of International Neuropsychological Society, 2005, 11(6):727-736.
Benedict et al., "Minimal Neuropsychological Assessment of MS Patients: A Consensus Approach," The Clinical Neuropsychologist, 2002, 16(3):381-397.
Bethoux et al., "Evaluating Walking in Patients with Multiple Sclerosis", International Journal of MS Care, 2011, 13(1):4-14.
Boringa et al., "The Brief Repeatable Battery of Neuropsychological Tests: normative values allow application in multiple sclerosis clinical practice," Multiple Sclerosis, 2007, 7:263-267.
Bornstein et al., "A Pilot Trial of COP 1 in Exacerbating-Remitting Multiple Sclerosis," The New England Journal of Medicine, 1987, 317(7):408-414.
Buschke et al., "Evaluating storage, retention, and retrieval in disordered memory and learning," Neurology, 1974, 24:1019-1025.
Cadavid et al., "BIIB033, Anti-LINGO-1 Antibody, for Treatment of Relapsing Forms of Multiple Sclerosis: Baseline Data of the Phase 2 SYNERGY Trial (p. 7. 204)," Neurology, 2015, p. 7.204.
Cadavid et al., "Clinical consequences of MRI activity in treated multiple sclerosis," Multiple Sclerosis Journal, 2011, 17(9):1113-1121.
Cadavid et al., "Safety and efficacy of opicinumab in acute optic neuritis (RENEW): a randomised, placebo-controlled, phase 2 trial," The Lancet Neurology, 2017, 16:189-199.
Chiaravalloti et al., "Cognitive impairment in multiple sclerosis," The Lancet Neurology, 2008, 7(12):1139-1151.
Christodoulou et al., "Cognitive performance and MR markers of cerebral injury in cognitively impaired MS patients," Neurology, 2003, 60(11):1793-1798.
ClinicalTrials.gov [online], "BIIB033 In Acute Optic Neuritis (AON)," Last Update Jun. 30, 2016, [retrieved on Apr. 5, 2019], retrieved from: URL<https://clinicaltrials.gov/ct2/show/NCT01721161?term=215ON201&rank=2,> 8 pages.
ClinicalTrials.gov [online], "Long-Term Assessment of Remyelinating Therapy (RENEWED)," Last Update Mar. 6, 2019, [retrieved on Apr. 5, 2019], retrieved from: URL<https://clinicaltrials.gov/ct2/show/NCT02657915?term=215ON201&rank=1>, 8 pages.
Cohen et al., "Benefit of interferon β-1a on MSFC progression in secondary progressive MS," Neurology, 2002, 59(5):679-687.
Deloire et al., "Cognitive impairment as marker of diffuse brain abnormalities in early relapsing remitting multiple sclerosis," J Neurol Neurosurg Psychiatry, 2005, 76:519-526.
Deluca et al., "Is Speed of Processing or Working Memory the Primary Information Processing Deficit in Multiple Sclerosis," Journal of Clinical and Experimental Neuropsychology, 2004, 26(4):550-562.
Drake et al., "Psychometrics and normative data for the Multiple Sclerosis Functional Composite: replacing the PASAT with the Symbol Digit Modalities Test," Mult. Scler., 2010 16(2):228-237.
Duda et al., "Glatiramer acetate (Copaxone®) induces degenerate, Th2-polarized immune responses in patients with multiple sclerosis," J. Clin. Invest., 2000, 105:967-976.
Ebers et al., "Disability as an outcome in MS clinical trials," Neurology, 2008, 71(9):624-631.
Fischer et al., "What Do We Really Know About Cognitive Dysfunction, Affective Disorders, and Stress in Multiple Sclerosis? A Practitioner's Guide," Neurorehabilitation and Neural Repair, 1994, 8(3):151-164.
Fischer et al., "Neuropsychological effects of interferon β-1a in relapsing multiple sclerosis" Annals of Neurology, 2000, 48(6):885-892.
Frohman et al., "The utility of MRI in suspected MS. Report of the Therapeutics and Technology Assessment Subcommittee of the American Academy of Neurology," Neurology, 2003, 61(5):602-611.
Gaspari M et al., "Refining an Automatic EDSS Scoring Expert System for Routine Clinical Use in Multiple Sclerosis", IEEE Transactions on Information Technology in Biomedicine, IEEE Service Center, 2009, 13(4):501-511.

(56) References Cited

OTHER PUBLICATIONS

Gijbels et al., "Comparison of the 2- and 6-minute walk test in multiple sclerosis," Multiple Sclerosis Journal, 2011, 17(10):1269-1272.
Gilewski et al., "The Memory Functioning Questionnaire for Assessment of Memory Complaints in Adulthood and Old Age," Psychology and Aging, 1990, 5(4):482-490.
Gronwall et al., "Paced Auditory Serial-Addition Task: A Measure of Recovery from Concussion," Perceptual and Motor Skills, 1977, 44(2): 367-373.
Hannay et al., "Selective reminding test: An examination of the equivalence of four forms," Journal of Clinical and Experimental Neuropsychology, 1985, 7(3):251-263.
Hawker et al., "Rituximab in patients with primary progressive multiple sclerosis: Results of a randomized double-blind placebo-controlled multicenter trial," Annals of Neurology, 2009, 66(4):460-471.
Heesen et al., "Correlates of cognitive dysfunction in multiple sclerosis," Brain, Behavior, and Immunity, 2010, 24(7):1148-1155.
Hemler et al., "Characterization of the Cell Surface Heterodimer VLA-4 and Related Peptides," The Journal of Biological Chemistry, 1987, 262(24):11478-11485.
Hobart et al., "The Multiple Sclerosis Impact Scale (MSIS-29): A new patient-based outcome measure," Brain, 2001, 124:962-973.
Hobart et al., "The SF-36 in multiple sclerosis: why basic assumptions must be tested," J Neural Neurosurg. Psychiatry, 2001, 71:363-370.
Holland et al., "Talking the talk on walking the walk: a 12-item generic walking scale suitable for neurological conditions?," Journal of Neurology, 2006, 253(12):1594-1602.
Hoogervorst et al., "Multiple Sclerosis Impact Scale (MSIS-29): relation to established measures of impairment and disability," Multiple Sclerosis, 2004, 10:569-574.
Hoogervorst et al., "The patient's perception of a (reliable) change in the Multiple Sclerosis Functional Composite," Multiple Sclerosis, 2004, 10:55-60.
Houtchens et al., "Thalamic atrophy and cognition in multiple sclerosis," Neurology, 2007, 69(12):1213-1223.
International Preliminary Report on Patentability in application No. PCT/US2013/054128, dated Feb. 17, 2015, 11 pages.
International Preliminary Report on Patentability dated Jan. 27, 2009, in International Application No. PCT/US2017/041757, 8 pages.
International Preliminary Report on Patentability with Written Opinion for PCT/US2013/037329, dated Oct. 21, 2014.
International Search Report and Written Opinion in International Application No. PCT/US2017/041757, dated Sep. 25, 2017, 12 pages.
International Search Report for corresponding PCT Application No. PCT/US2013/054128 dated May 12, 2013, 5 pages.
International Search Report for PCT/US2013/037329, dated Jul. 23, 2013.
Issekutz et al., "Effect of a new monoclonal antibody, TA-2, that inhibits lymphocyte adherence to cytokine stimulated endothelium in the rat," J Immunol., 1991, 147(1):109-116.
Jankovic, "Multiple System Atrophy (MSA)," Baylor College of Medicine, publicly available Jan. 2011, [retrieved on Mar. 9, 2016], Retrieved from the Internet: URL<https://www.bcm.edu/healthcare/care-centers/parkinsons/conditions/multiple-system-atrophy>, 5 pages.
Jönsson et at., "Cognitive impairment in newly diagnosed multiple sclerosis patients: A 4-year follow-up study," Journal of Neurological Sciences, 2006, 245(1-2):77-85.
Kaufman et al., "The significant change for the Timed 25-Foot Walk in the Multiple Sclerosis Functional Composite," Multiple Sclerosis, 2000, 6:286-290.
Klistorner et al., "Assessment of Opicinumab in Acute Optic Neuritis Using Multifocal Visual Evoked Potential," CNS Drugs, 2018, 32:1159-1171.

Kragt et al., "Clinical impact of 20% worsening on Timed 25-foot Walk and 9-hole Peg Test in multiple sclerosis," Multiple Sclerosis, 2006, 12(5):594-598.
Kragt et al., "How similar are commonly combined criteria for EDSS progression in multiple sclerosis," Multiple Sclerosis, 2006, 12:782-786.
Kragt et al., "Responsiveness and predictive value of EDSS and MSFC in primary progressive MS," Neurology, 2008, 70(13 pt 2):1084-1091.
Kurtzke et al., "Rating neurologic impairment in multiple sclerosis: An expanded disability status scale (EDSS)," Neurology, 1983, 33:1444-1452.
Kurtzke, "Clinical Definition for Multiple Sclerosis Treatment Trials," Ann Neural, 1994, 36:S73-S79.
Langdon et al., "Recommendations for a Brief International Cognitive Assessment for Multiple Sclerosis (BICAMS)," Mult. Scler. Journal, 2012, 18(6):891-898.
Lee et al., "Spotlight on fumarates," International MS Journal, 2008, 15(1):12-18.
Luliano et al., "Multiple Sclerosis: Relapses and Timing of Remissions," European Neurology, 2008, 59:44-48.
Lyon-Caen et al., "Cognitive Function in Recent-Onset Demyelinating Diseases," Arch. Neurol., (1986), 43(11):1138-1141.
McDonald et al., "Are magnetic resonance findings predictive of clinical outcome in therapeutic trials in multiple sclerosis? The dilemma of interferon-β," Annals of Neurolology, 1994, 36(1):14-18.
McDonald et al., "Recommended Diagnostic Criteria for Multiple Sclerosis: Guidelines from the International Panel on the Diagnosis of Multiple Sclerosis," Ann. Neurol., 2001, 50:121-127.
Mellion et al., "Additional Efficacy Analyses from the Phase 2b SYNERGY Study Investigating the Anti-LINGO-1 Monoclonal Antibody Opicinumab for Treatment of Disabling Multiple Sclerosis (p. 5. 337)," Neurology, 2017, p. 5.337.
Mellion et al., "Efficacy results from the phase 2b SYNERGY study: Treatment of disabling multiple sclerosis with the anti-LINGO-1 monoclonal antibody opicinumab (s33. 004)," Neurology, 2017, S33.004.
Morrow et al., "Erratum to: Effects of acute relapses on neuropsychological status in multiple sclerosis patients," J Neurol., 2011, 258(9):1609.
Nicholas et al., "Development of oral immunomodulatory agents in the management of multiple sclerosis," Drug Design, Development and Therapy, (2011), 5:255-274.
Nociti et al., "Somatosensory evoked potentials reflect the upper limb motor performance in multiple sclerosis," J Neural Sci., 2008, 273(1-2):99-102.
Noseworthy, "Clinical Scoring Methods for Multiple Sclerosis," Annals of Neurology, (1994), 36(1):S80-S85.
Padua et al., Letter to the Editor, Reply to "Motor assessment of upper extremity function and its relation with fatigue, cognitive function and quality of life in multiple sclerosis patients," J Neurol. Sci., 2007, 253(1-2):106.
Paltamaa et al., "Measuring Deterioration in International Classification of Functioning Domains of People With Multiple Sclerosis Who Are Ambulatory," Physical Therapy, 2008, 88(2):176-190.
Pardridge et al., "Human insulin receptor monoclonal antibody undergoes high affinity binding to human brain capillaries in vitro and rapid transcytosis through the blood-brain barrier in vivo in the primate," Pharmaceutical Research, Springer New York LLC, 12(6):807-816 (Jan. 1995).
Pardridge, "Selective Transport of an Anti-transferrin Receptor Antibody through the Blood-Brain Barrier in Vivo," Journal of Pharmacology and Experimental Therapeutics, 259(1):66-70 (Jan. 1991).
Parmenter et al, "The utility of regression-based norms in interpreting the minimal assessment of cognitive function in multiple sclerosis (MACFIMS)," Journal of International Neuropsychological Society, 2010, 16(1):6-16.
Parmenter et al., "Screening for cognitive impairment in multiple sclerosis using the Symbol Digit Modalities Test," Multiple Sclerosis, 2007, 13:52-57.

(56) References Cited

OTHER PUBLICATIONS

Paty et al., "Interferon beta-1b is effective in relapsing-remitting multiple sclerosis. II. MRI analysis results of a multicenter, randomized, double-blind, placebo-controlled trial" Neurology, 1993, 43:662-667.
Penta et al., "ABILHAND: A Rasch-Built Measure of Manual Ability," Arch. Phys. Med. Rehabil., (1998), 79:1038-1042.
Pepinsky et al., "Improved Pharmacokinetic Properties of a Polyethylene Glycol-Modified Form of Interferon-B-1a with Preserved in Vitro Bioactivity" The Journal of Pharmacology and Experimental Therapeutics, 2001, 297(3):1059-1066.
Peyser. et al., "Cognitive Function in Patients with multiple Sclerosis" Arch Neurol, 1980, 37(9):577-579.
Polman et al., "Diagnostic Criteria for Multiple Sclerosis: 2010 Revisions to the McDonald Criteria," Ann. Neurol., 2011, 69(2):292-302.
Polman et al., "The Multiple Sclerosis Functional Composite—A clinically meaningful measure of disability", Neurology, vol. 74(17 Supplement_3) Supplement 3, New Frontiers in Multiple Sclerosis: Impact of Disease-1 Modifying Therapies on Nontraditional Measures of Disease Activity, Apr. 27, 2010, pp. S8-S17, XP055071466, Retrieved from the Internet: <URL:http://patients.aan.com/resources/neurologynow/index.cfm?event=home.articlePDF&id=ovid.com:/bib/ovftdb/00006114-201004273-00003>.
Polman et al., "The Multiple Sclerosis Functional Composite—A clinically meaningful measure of disability," Neurology, 2010, 74(3):S8-S15.
Poser et al., "New Diagnostic: Criteria for Multiple Sclerosis: Guidelines for Research Protocols" Annals of Neurology, 1983, 13(3):227-231.
Prakash et al., "Cognitive impairments in relapsing-remitting multiple sclerosis: a meta-analysis" Mult. Scler., 2008, 14:1250-1261.
Pulido et al., "Functional Evidence for Three Distinct and Independently Inhabitable Adhesion Activities Mediated by the Human Integrin VLA-4," The Journal of Biological Chemistry, 1991, 266(16):10241-10245.
Rao et al., "Cognitive dysfunction in multiple sclerosis: II. Impact on employment and social functioning," Neurology, 1991, 41(5):692-696.
Rao et al., "Cognitive dysfunction in multiple sclerosis: I. Frequency, patterns, and prediction," Neurology, 1991, 41(5):685-691.
Rao, "Neuropsychology of multiple sclerosis," Current Opinion in Neurology, 1995, 8(3):216-220.
Ravnborg et al., "Responsiveness of the Multiple Sclerosis Impairment Scale in comparison with the Expanded Disability Status Scale," Multiple Sclerosis, 2005, 11:81-84.
Sánchez-Madrid et al., "VLA-3: A novel polypeptide association within the VLA molecular complex: cell distribution and biochemical characterization," European Journal of Immunology 1986, 16(11):1343-1349.
Schumacher et al., "Problems of Experimental Trials of Therapy in Multiple Sclerosis: Report by the Panel on the Evaluation of Experimental Trials of Therapy in Multiple Sclerosis," Annals of the New York Academy of Sciences, 1965, 122(1):552-568.
Schwid et al., "Quantitative assessment of sustained-release 4-aminopyridine for symptomatic treatment of multiple sclerosis," Neurology, 1997, 48(4):817-821.
Sipe et al., "A neurologic rating scale (NRS) for use in multiple sclerosis," Neurology, 1984, 34(10):1368-1372.
Stankiewicz et al., "Brain MRI Lesion Load at 1.5T and 3T versus Clinical Status in Multiple Sclerosis," J Neuroimaging, 2011, 21:e50-e56.
Strober et al., "Sensitivity of conventional memory tests in multiple sclerosis: comparing the Rao Brief Repeatable Neuropsychological Battery and the Minimal Assessment of Cognitive Function in MS," Mult. Scler., 2009, 15(9):1077-1084.
Su et al., "LINGO-2 polymorphism and the risk of parkinson's disease in Taiwan," Parkinsonism & related disorders, 2012, 18(5):609-611.
Tekok-Kilic el al., "Independent contributions of cortical gray matter atrophy and ventricle enlargement for predicting neuropsychological impairment in multiple sclerosis," J NeuroImage, 2007, 36:1294-1300.
Thornton et al., Memory Impairment in Multiple Sclerosis: A Quantitative Review, Neuropsychology, 1997, 11(3):357-366.
Tombaugh, T.N., "A comprehensive review of the Paced Auditory Serial Addition Test (PASAT)," Archives of Clinical Neuropsychology, 21:53-76.
Tran et al., "Randomized phase I trials of the safety/tolerability of anti-LINGO-1 monoclonal antibody BIIB033," Neurology-Neuroimmunology Neuroinflammation, 2014, 1(2):e18.
Wallin et al., "Cognitive dysfunction in multiple sclerosis; Assessment, imaging and risk factors," Journal of Rehabilitation Research and Development, 2006, 43(1):63-72.
Weiner et al., "Treatment of multiple sclerosis with cyclophosphamide: critical review of clinical and immunologic effects," Multiple Sclerosis, 2002, 8(2):142-154.
Wingerchuk et al., "Clinical Outcome Measures and Rating Scales in Multiple Sclerosis Trials," Mayo Clinical Proceedings, 1997, 72(11):1070-1079.
Wishart et al., "Neuropsychological Aspects of Multiple Sclerosis: A Quantitative Review," Journal of Clinical and Experimental Neuropsychology, 1997, 19(6):810-824.
Written Opinion of the International Searching Authority for PCT/US2013/054128, dated May 12, 2013, 10 pages.
Written Opinion of the International Searching Authority for PCT/US2013/037329, dated Jul. 23, 2013, 8 pages.
Wu et al., "Lingo2 variants associated with essential tremor and Parkinson's disease," Human genetics, 2011, 129(6):611-615.
Xia et al., "Recombinant Human Adenovirus: Targeting to the Human Transferrin Receptor Improves Gene Transfer to Brain Microcapillary Endothelium," Journal of Virology, 74(23):11359-11366 (Dec. 2000).
Yozbatiran et al., "Motor assessment of upper extremity function and its relation with fatigue, cognitive function and quality of life in multiple sclerosis patients," J. Neurol. Sci., 2006, 246:117-122.
Neurotherapeutics "Abstracts from the ASENT 14th Annual Meeting", American Society for Experimental NeuroTherapeutics, May 2012, 9:673-683.
Baker et al., "Critical Appraisal of Animal Models of Multiple Sclerosis", Multiple Sclerosis Journal, 2011, 17(6):347-657.
Cadavid et al., "Efficacy and safety of opicinumab in relapsing multiple sclerosis: results from SYNERGY, a randomized, placebo-controlled, phase 2 trial", The Lancet Neurology, Supplementary Appendix, 2019, 33 pages.
Cadavid et al., "Safety and Efficacy of Opicinumab in patients with relapsing multiple sclerosis (SYNERGY): a randomized, placebo-controlled, phase 2 trial", Lancet Neurology, 2019, 12 pages.
Green "Lessons from an unsuccessful therapeutic trial", The Lancet Neurology, 2019, 2 pages.
Sheikh et al., "Predictors of an Opicinumab Treatment Effect and Identification of an Efficacy Subpopulation: A Post hoc Analysis of the SYNERGY Study," Poster Presented at American Academy of Neurology, Apr. 2018, p. 3.408, 1 page.
Sheikh et al., "Predictors of an Opicinumab Treatment Effect and Identification of an Efficacy Subpopulation: A Post hoc Analysis of the SYNERGY Study," Poster Presented at 7th Joint ECTRIMS-ACTRIMS Meeting, Paris, France, Oct. 2017, p. 718, 1 page.

\* cited by examiner

| Histological Analysis | Placebo | Anti-LINGO | P value= |
|---|---|---|---|
| Optic Nerve Area ($\mu m^2$) | 85609.22 ±SEM 2914.48 | 84982.89 ±SEM 3811.65 | 0.77 |
| Average Central Axon Area ($\mu m^2$) | 0.265±SEM 0.01 | 0.30 ±SEM 0.01 | 0.07 |
| Peripheral Axon Area ($\mu m^2$) | 0.320 ±SEM 0.01 | 0.324 ±SEM 0.01 | 0.80 |
| Total Central Axon Count | 18320.26 ±SEM 838.26 | 17421.41 ±SEM 1247.90 | 0.56 |
| Total Peripheral Axon Count | 21907.52 ±SEM 961.03 | 22134.15 ±SEM 1407.20 | 0.90 |
| Total Central Axoplasmal Area ($\mu m^2$) | 4841.63 ±SEM 267.344 | 5100.95 ±SEM 457.50 | 0.63 |
| Total Peripheral Axoplasmal Area ($\mu m^2$) | 7066.74 ±SEM 456.16 | 7279.08 ±SEM 601.27 | 0.78 |

FIG. 6

AE = adverse event.

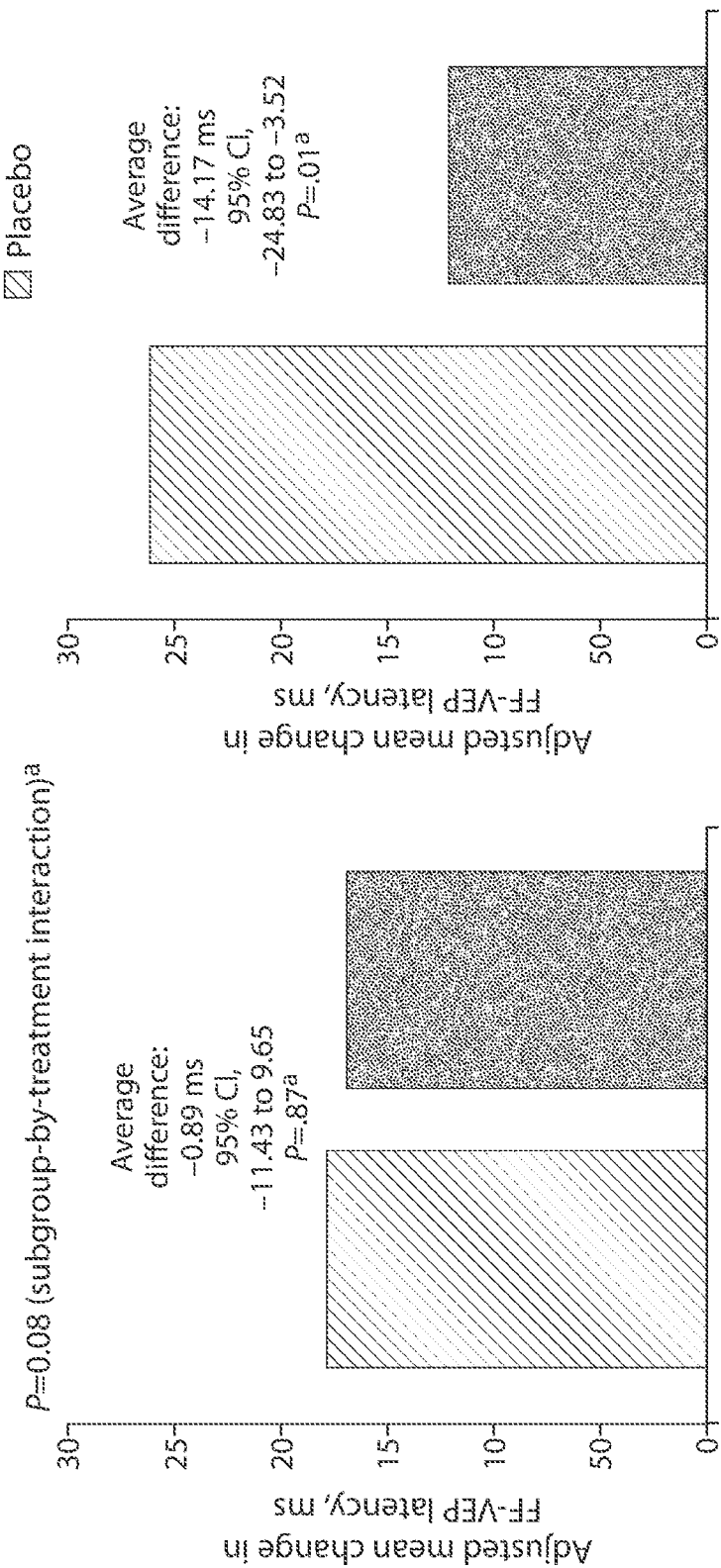

CI = confidence interval.

LINGO-1 ANTAGONISTS AND USES FOR TREATMENT OF DEMYELINATING DISORDERS

RELATED APPLICATIONS

This application is the U.S. National Phase Application under 35 U.S.C. § 371 of International Application No. PCT/US2016/012619 filed Jan. 8, 2016, which claims the benefit of U.S. Provisional Application No. 62/101,336, filed Jan. 8, 2015, and U.S. Provisional Application 62/147,783, filed Apr. 15, 2015, the contents of each of the aforesaid applications are incorporated herein by reference in their entirety.

BACKGROUND OF THE INVENTION

Multiple sclerosis (MS) is an inflammatory disease of the brain and spinal cord characterized by recurrent foci of inflammation that lead to destruction of the myelin sheath. In many areas, nerve fibers are also damaged. Inflammatory activity in MS patients tends to be highest in the initial phase of disease.

Emerging data demonstrate that irreversible axonal loss occurs early in the course of MS. Transected axons fail to regenerate in the central nervous system (CNS); and therefore, early treatment aimed at suppressing MS lesion formation is of importance. As early as disease onset, axons are transected in lesions with active inflammation (Trapp et al. (1998) *N Engl J Med* 338: 278-285; Bjartmar et al. (2001) *Curr Opin Neurol* 14: 271-278; Ferguson et al. (1997) *Brain* 120: 393-399). The degree of demyelination is related to the degree of inflammation and the exposure of demyelinated axons to the inflammatory environment, as well as non-inflammatory mediators (Trapp et al. (1998) *N Engl J Med* 338: 278-285; Kornek et al. (2000) *Am J Pathol* 157: 267-276; Bitsch et al. (2000) *Brain* 123: 1174-1183). There is also destruction of oligodendrocytes and impaired remyelination in demyelinating lesions (Peterson et al. (2002) *J Neuropathol Exp Neurol* 61: 539-546; Chang et al. (2002) *N Engl J Med* 346: 165-173). A loss of oligodendrocytes leads to a reduction in the capacity to re-myelinate and may also result in the loss of trophic factors that support neurons and axons (Bjartmar et al. (1999) *J Neurocytol* 28: 383-395).

Optic neuritis, e.g., acute optic neuritis (AON), is characterized by inflammatory white matter lesions in the optic nerve. It is often associated with MS and is one the most common initial manifestations of the disease. AON causes structural and functional optic nerve damage (e.g., neuroaxonal injury and demyelination) that can result in permanent visual impairment for some patients (Cole, S. R. et al. *Invest Ophtalmol Vis Sci* (2000) 41(5):1017-1021; Mi, S. et al. *CNS Drugs* 2013: 27(7):493-503; Mangione C M et al. *Arch Ophthalmol.* (1988) 116(11):1496-1504). The current treatment for acute optic neuritis is high dose steroids which provides mostly symptomatic relief and fails to enhance CNS remyelination or provide neuroaxonal protection (Beck R W et al. *N Engl J Med* 1992 326:581-8).

Currently approved therapies for MS are primarily immunomodulatory, and typically do not have direct effects on CNS repair. Although some degree of axonal remyelination by oligodendrocytes takes place early during the course of MS, typically, in younger patients, the ability to repair the CNS eventually fails, leading to irreversible tissue injury and an increase in disease-related disabilities. Thus, there is a need for additional therapies that enhance remyelination and neuroaxonal protection in CNS demyelinating diseases, such as MS and optic neuritis.

SUMMARY OF THE INVENTION

The present invention provides, at least in part, methods and compositions for treating or preventing CNS disorders, e.g., CNS demyelinating disorders, using a reparative agent (e.g., a LINGO-1 antagonist). In certain embodiments, the methods and compositions described herein include a reparative agent (e.g., a LINGO-1 antagonist) as a monotherapy, or in combination with an immunomodulatory agent. In certain embodiments, the reparative agent is administered at a selected time interval such as to enhance one or more of: myelination, re-myelination, differentiated oligodendrocyte numbers, or neuroaxonal protection in a subject, e.g., a human (e.g., a human MS patient). In certain embodiments, the reparative agent (e.g., a LINGO-1 antagonist) can be used to treat multiple sclerosis (MS) or an inflammatory condition of the optic nerve, e.g., optic neuritis (e.g., acute optic neuritis (AON). Thus, methods, compositions and kits described herein can be useful for treating a CNS disorder, e.g., a CNS demyelinating disease.

In one aspect, the invention features a method of treating a CNS disorder, e.g., a CNS demyelinating disease (e.g., MS or an inflammatory condition of the optic nerve, e.g., optic neuritis (e.g., AON), in a subject (e.g., a subject in need of treatment). The method includes administering to the subject a reparative agent (e.g., a LINGO-1 antagonist), in an amount sufficient to reduce one or more symptoms associated with the disorder, thereby treating the disorder.

In one embodiment, the CNS demyelinating disorder treated or prevented is MS. In another embodiment, the CNS demyelinating disorder treated or prevented is optic neuritis, e.g., AON.

In certain embodiments, the reparative agent (e.g., a LINGO-1 antagonist) is administered at a selected time interval chosen from one, two, or all of:

(i) prior to the onset or relapse of one or more symptoms of the CNS demyelinating disease;

(ii) within 7 days after the onset or relapse of one or more symptoms of the CNS demyelinating disease (e.g., to enhance neuroprotection); or (iii) within 30 days after the onset or relapse of one or more symptoms of the CNS demyelinating disease (e.g., to enhance remyelination).

In certain embodiments, administration of the anti-LINGO-1 antibody molecule, as a monotherapy or a combination therapy, results in one or more of:

(i) reducing, delaying or preventing one or more symptoms associated with the CNS demyelinating disease;

(ii) reducing, delaying or preventing a relapse, or the worsening of the CNS demyelinating disease;

(iii) reducing, delaying or preventing the development of a new lesion in the subject; and/or (iv) reversing or preventing structural and/or functional CNS damage in the subject.

In certain embodiments, the one or more symptoms associated with the CNS demyelinating disease can be chosen from one, two, three, four, five, six, seven, eight, nine, ten or more (all) of visual loss, edema, inflammation, damage or demyelination of the myelin sheath covering the optic nerve and axons, loss of retinal fiber layer, loss of retinal ganglion cell layer, visual field defect, motion perception defect, color desaturation, decreased color vision, ocular pain, decreased visual acuity (e.g., as measured by low contract letter acuity or high contrast visual acuity), Uhthoff's symptom, swollen optic disc, or relative afferent papillary defect.

In certain embodiments, administration of the anti-LINGO-1 antibody molecule, as a monotherapy or a combination therapy, results in one or more of: reducing one or more symptoms associated with the disease, e.g., MS; and/or reducing, retarding or preventing a relapse, or the worsening of a disability, in the subject.

In certain embodiments described herein, Applicants have discovered that administration, e.g., acute administration, of the reparative agent as a monotherapy or a combination therapy can reduce neuronal/axonal damage after an acute lesion, and/or more effectively reduces demyelination or increases remyelination. Accordingly, in certain embodiments, the method disclosed herein is used to treat or prevent an acute lesion of a CNS demyelinating disorder (e.g., an acute MS lesion, an MS relapse, or an optic nerve lesion (e.g., AON)). In certain embodiments, the reparative agent is an antibody molecule against LINGO-1 and is administered acutely, as a monotherapy or a combination therapy, e.g., within 30, 28, 25, 24, 20, 18, 15, 12, 10, 5, 2, or 1 day after the onset or relapse of one or more symptoms of the CNS demyelinating disease (e.g., less than 4, 3, 2, 1 week after an acute lesion (e.g., any lesion in MS, an MS relapse or AON)). In one embodiment, the acute administration is less than 2 weeks or 1 week after the acute lesion (e.g., less than 13, 12, 11, 10, 9, 8, 7, 6, 5, 4, 3, 2, 1 day, or hours after the acute lesion). In such embodiments, the antibody molecule is administered, as a monotherapy or a combination therapy, at about 1, 3, 10, 30, 60, 100 or 150 mg/kg, e.g., once every one, two, three, four, five, eight, or 12 weeks by injection (e.g., intravenous (IV), subcutaneous (SC), or intramuscular administration (IM)). In one embodiment, the anti-LINGO-1 antibody molecule is administered at about 3 mg/kg via IV infusion or SC injection once every 4 weeks. In one embodiment, the anti-LINGO-1 antibody molecule is administered at about 10 mg/kg via IV infusion or SC injection once every 4 weeks. In one embodiment, the anti-LINGO-1 antibody molecule is administered at about 30 mg/kg via IV infusion or SC injection once every 4 weeks. In one embodiment, the anti-LINGO-1 antibody molecule is administered at about 100 mg/kg via IV infusion or SC injection once every 4 weeks.

Without being bound by theory, Applicants further believe that chronic or prophylactic administration of the reparative agent as a monotherapy or as a combination therapy can preserve neuronal function and/or neuronal tissue, and/or prevent or delay a disability in a subject, e.g., an MS or AON subject as described herein. In certain embodiments, chronic or prophylactic administration of the reparative agent may prevent the onset or delay the progressive form of the disease, e.g., MS, for example, by reducing one or more of axonal/neuronal degeneration and/or axonal loss. In some embodiments, the method disclosed herein can include an administration of the anti-LINGO antibody molecule that is initiated before the onset or relapse of one or more symptoms of MS, or the inflammatory condition of the optic nerve, e.g., optic neuritis, e.g., AON, in one or both eyes of the subject. In other embodiments, the method disclosed herein includes administration of the anti-LINGO antibody molecule during primary progressive MS, e.g., when progression of MS begins without a preceding relapse.

In one embodiment, administration of the antibody molecule against LINGO-1 is chronic and/or prophylactic. In certain embodiments, the anti-LINGO-1 antibody molecule is administered prophylactically and/or administration continues for a prolonged period of time, e.g., administration continues until the incremental beneficial effects of the treatment are reduced or not detectable (e.g., as detected by one or more of: remyelination, reduction in neuronal damage, reduction of disability, or increased neurological function). In such embodiments, the antibody molecule is administered, as a monotherapy or a combination therapy, at about 0.3, 1.0, 3.0, 10, 30, 60, or 100 mg/kg, e.g., once every one, two, three, four, five, six, seven, eight, nine, ten, eleven, twelve, thirteen, fourteen or fifteen weeks by injection (e.g., intravenous, subcutaneous, or intramuscular administration). In one embodiment, the anti-LINGO-1 antibody molecule is administered by intravenous or subcutaneous injection at about 1 to 100 mg/kg (typically, at about 3 mg/kg, about 10 mg/kg, about 30 mg/kg, about 50 mg/kg or about 100 mg/kg), once every one, two, three, four or five weeks.

In other embodiments, the method disclosed herein is used to treat or prevent disease initiation or disease progression in a subject, e.g., a subject with AON or MS, e.g., a subject with a relapsing form of MS (RRMS) or a subject with primary progressive MS (PPMS), or secondary progressive MS (SPMS)). In certain embodiments, the reparative agent is an antibody molecule against LINGO-1 and is administered chronically or prophylactically, as a monotherapy or a combination therapy.

In one embodiment, administration, e.g., chronic or prophylactic administration, of the agent occurs after a lesion (e.g., an MS or AON lesion), in an area that has not suffered detectable neuronal damage. In one embodiment, the treatment occurs in an area prior to irreversible neuronal damage. For example, the subject can have an AON diseased eye and does not show a detectable symptom in the other eye (referred to herein as the "fellow eye" or "normal eye"). In certain embodiment, the subject can be treated with the reparative agent (e.g., a LINGO-1 antagonist), as a monotherapy or in combination, as a way of preventing or delaying the onset of the nerve disorder or condition in the normal eye or elsewhere in the brain or spinal cord (anywhere in the central nervous system or CNS). Without wishing to be bound by theory, treatment of a normal fellow eye after diagnosis of acute optic neuritis in a first eye may delay or prevent one or more symptoms of neuritis in the normal fellow eye or subsequent lesions or damage and/or loss of axons in the visual pathway and elsewhere in the CNS.

In certain embodiments, administration of the reparative agent (e.g., a LINGO-1 antagonist, e.g., anti-LINGO antibody molecule) to the subject prevents or delays the onset of the optic nerve disorder, e.g., acute optic neuritis, in either or both eyes.

In certain embodiments, administration of the reparative agent (e.g., a LINGO-1 antagonist, e.g., anti-LINGO antibody molecule) to the subject delays or prevents the onset or relapse of an MS symptom.

In yet other embodiments, administration of the reparative agent (e.g., a LINGO-1 antagonist, e.g., anti-LINGO antibody molecule) to the subject delays one or more symptoms of MS or the optic nerve disorder by at least a day, a week, a month, a year or longer.

In another embodiment, the subject is identified as having (e.g., diagnosed with) the optic nerve disorder or condition, e.g., acute optic neuritis, in one or both eyes, but does not show an MS symptom (e.g., is a subject not diagnosed with MS or a subject that has MS but does not suffer from a relapse or is not showing disease progression). In one embodiment, prophylactic or chronic treatment of said subject with the optic nerve disorder or condition, e.g., acute optic neuritis, delays or prevents the onset or relapse of an MS symptom. In one embodiment, administration of the reparative agent (e.g., a LINGO-1 antagonist, e.g., anti-LINGO antibody molecule) (e.g., prophylactic or chronic treatment) of said subject with the optic nerve disorder or condition, e.g., acute optic neuritis, delays or prevents the onset and/or relapse of PPMS or SPMS.

In certain embodiments, the methods described herein further include identifying a subject to be treated with the anti-LINGO-1 antibody molecule, by detecting one or both of optic nerve damage or optic nerve function for one or both eyes. In some embodiments, detection of at least a minimal level of optic nerve damage in one eye or both eyes, and/or a delay in optic nerve conductance in said one eye or both eyes identifies the subject as a subject to be treated. For example, the step of measuring optic nerve damage can include a measure of visual evoked potential (VEP) amplitude, e.g., full field VEP (FF-VEP) amplitude and/or multi-field VEP (mfVEP) amplitude. In some embodiments, administration of an anti-LINGO antibody as described herein improves recovery of latency by mfVEP, and/or prevents an mfVEP amplitude loss in the non-AON visual path:

In certain embodiments, one or more of the following is indicative of the minimal level of optic nerve damage in the eye, e.g., as determined by mfVEP amplitude changes.
  (i) an mfVEP amplitude of not more than 40 nanovolts lower than a reference value, e.g., a control amplitude,
  (ii) an mfVEP amplitude of not more than 20% lower than a reference value, e.g., control amplitude, or
  (iii) an mfVEP amplitude of 180 nanovolts or higher.

In certain embodiments, the control amplitude is the average VEP amplitude, e.g., FF-VEP amplitude and/or mfVEP amplitude, of a normal eye, e.g., an eye of a subject not having an optic nerve disorder, e.g., AON.

In other embodiments, the step of measuring optic nerve conductance comprises a measure of VEP latency, e.g., FF-VEP latency or mfVEP latency measured in milliseconds. In some embodiments, one or more of the following is indicative of a delay in optic nerve conductance in the eye as determined by FF-VEP:
  (i) a VEP latency that is at least 3 milliseconds higher than a reference value, e.g., a control latency,
  (ii) a VEP latency that is at least 3% higher (e.g., 3%, 5%, 8%, 10%, 12% or higher) than a reference value, e.g., a control latency, or
  (iii) an FF-VEP latency that is 110 milliseconds or higher,
  (iv) an mfVEP latency that is 155 milliseconds or higher.

In certain embodiments, the control latency is the average VEP latency, e.g., FF-VEP latency or mfVEP latency, of a normal eye, e.g., an eye of a subject not having an optic nerve disorder, e.g., AON, or the non-affected or fellow eye from within the same subject if only one eye is affected.

Additional embodiments, features or improvements of any of the methods, compositions and kits disclosed herein include one or more of the following:

CNS Disorders and CNS Demyelinating Diseases

The CNS disorder (e.g., the CNS demyelinating disease) can be any condition, disease, disorder or injury associated with one or more of: demyelination, dysmyelination, axonal injury, loss of axonal area or axial diffusivity, or loss of neuronal synapsis/connectivity, and/or dysfunction or death of an oligodendrocyte or a neuronal cell. In certain embodiments, the CNS disorder affects the nervous system by causing damage to the myelin sheath of axons. In other embodiments, the CNS disorder includes Nogo receptor-1 (NgR1−) mediated inhibition of axonal extension or neurite extension, e.g., in the brain and spinal cord. In other embodiments, the CNS disorder has one or more inflammatory components. Exemplary CNS disorders include, but are not limited to, CNS demyelinating diseases, CNS injury, Amyotrophic lateral sclerosis (ALS), Huntington's disease, Alzheimer's disease, Parkinson's disease, diabetic neuropathy, idiopathic inflammatory demyelinating disease, multiple sclerosis (MS), optic neuritis (e.g., acute optic neuritis), transverse myelitis, neuromyelitis optica (NMO), vitamin B12 deficiency, progressive multifocal leukoencephalopathy (PML), encephalomyelitis (EPL), acute disseminated encephalomyelitis (ADEM), central pontine myelolysis (CPM), Wallerian Degeneration, adrenoleukodystrophy, Alexander's disease, Pelizaeus Merzbacher disease (PMZ), leukodystrophies, traumatic glaucoma, periventricular leukomalatia (PVL), essential tremor, white matter stroke, stroke, or radiation or toxic induced white matter injury. A CNS demyelinating disease can be chosen from one or more of the aforesaid disorders. In one embodiment, the CNS demyelinating disease is multiple sclerosis. In other embodiments, the CNS demyelinating disease is optic neuritis, e.g., acute optic neuritis.

Optic Neuritis

In certain embodiments, a method of treating or preventing an inflammatory condition or disorder of the optic nerve, e.g., optic neuritis (e.g., acute optic neuritis (AON)), in a subject (e.g., a subject in need of treatment) is disclosed. The method includes administering to the subject a reparative agent (e.g., a LINGO-1 antagonist), as a monotherapy or in combination with a second agent (e.g., an immunomodulatory agent as described herein) in an amount sufficient to reduce one or more manifestations associated with the optic nerve condition or disorder, thereby treating or preventing the optic nerve condition or disorder.

In certain embodiments, said treatment includes: reducing one or more symptoms associated with the optic nerve condition or disorder; reducing, retarding or preventing a relapse, or the worsening of the optic nerve condition or disorder; and/or inhibiting or retarding the development of a new lesion in the subject. In other embodiments, said prevention includes delaying or ameliorating one or more symptoms or severity of the optic nerve disorder or condition. In one embodiment, one or more symptoms associated with the optic nerve disorder or condition (e.g., acute optic neuritis) includes one, two, three, four, five or more of visual loss, VEP latency delay (e.g., time for a signal to travel from the retina to the visual cortex), edema, inflammation, damage or demyelination of the myelin sheath covering the optic nerve and axons, loss of retinal fiber layer, or loss of retinal ganglion cell layer.

In certain embodiments, the treatment or prevention results in a recovery of VEP latency delay. In one embodiment, the recovery of the visual evoked potential (VEP) latency, e.g., full-field VEP (FF-VEP) or multifocal VEP (mfVEP), is partial or complete (e.g., at least 10%, 20%, 30%, 40%, 50%, 60%, 70%, 80%, 90% or 100% that of the unaffected fellow eye or the reference normal control VEP latency).

In certain embodiments, the treatment or prevention delays one or more symptoms of the optic nerve disorder or condition, e.g., acute optic neuritis, by at least a day, a week, a month, 3 months, 6 months, a year or longer.

In one embodiment, the treatment or prevention is initiated before the onset or relapse of one or more symptoms of the nerve disorder or condition, e.g., acute optic neuritis. In one embodiment, the status of a subject with AON is measured by determining the visual evoked potential latency and amplitude.

Subjects

For any of the methods, compositions and kits disclosed herein, the subject treated, is a subject (e.g., a human) having, or at risk of having, a CNS disorder or a CNS demyelinating disease, e.g., as described herein.

In certain embodiments, the subject is a human, e.g., a human adult. In one embodiment, the subject is a human about 30 years old or older, e.g., at least 30, 35, 40, 45, 50, 55, 60 years old or older.

In one embodiment, the subject (e.g., the human) has, or is at risk of having, MS. In one embodiment, the human subject has one or more symptoms associated with MS ("an MS symptom"). The subject with MS can be at any stage of treatment. In certain embodiments, the subject with MS is chosen from a human having one or more of: Benign MS, RRMS (e.g., quiescent RRMS, active RRMS), primary progressive MS (PPMS), or secondary progressive MS (SPMS), active SPMS, clinically isolated syndrome (CIS), or clinically defined MS (CDMS). In one embodiment, the subject has a relapsing form of MS. In one embodiment, the subject has RRMS or SPMS. In one embodiment, the subject with MS has SPMS. In one embodiment, the subject with MS has RRMS. In other embodiments, the subject has one or more MS-like symptoms, such as those having clinically isolated syndrome (CIS) or clinically defined MS (CDMS). In other embodiments, the subject has one or more MS relapses (e.g. acute optic neuritis, transverse myelitis, brainstem syndrome, internuclear ophthalmoplegia).

In other embodiments, the subject does not yet have a symptom associated with MS, but is at risk for developing the disease. In one embodiment, the subject is asymptomatic at the time of treatment, e.g., initial treatment. In some embodiments, the subject is not diagnosed with MS, or is diagnosed with MS but does not suffer from a relapse.

In one embodiment, the subject has a relapsing form of MS (e.g., RRMS or relapsing SPMS). In one embodiment, the subject has RRMS and has one or more ongoing clinical exacerbations and/or subclinical activity, e.g., as shown by gadolinium (Gd) enhancement or development of new and/or enlarged T2/FLAIR lesions on magnetic resonance imaging (e.g., brain or spinal cord MRI). In another embodiment, the subject has SPMS and has one or more ongoing clinical exacerbations and/or subclinical activity, e.g., as shown by gadolinium (Gd) enhancement or development of new and/or enlarged T2/FLAIR lesions on magnetic resonance imaging (e.g., brain or spinal cord MRI). In one embodiment, the subject has an active form of MS, e.g., an active RRMS. In other embodiments, the MS subject has at least one newly developed lesion. In other embodiment, the MS subject has at least one pre-existing lesion. In one embodiment, the subject has RRMS, and has one or more newly developed or pre-existing lesions, or a combination thereof. In other embodiments, the subject has a baseline EDSS score of 1.5 to 7.

In one embodiment, the subject is an MS patient (e.g., a patient with RRMS or SPMS) prior to administration of an MS therapy (a monotherapy or a combination therapy of the agents described herein). In one embodiment, the subject is a newly diagnosed or an undiagnosed RRMS or SPMS patient. In another embodiment, a subject has a radiologically isolated syndrome or clinically isolated syndrome. In yet another embodiment, a subject has an asymptomatic finding (e.g., does not present with MS symptoms, but has an MS associated finding noted on testing). In another embodiment, the subject is an MS patient (e.g., an RRMS patient) after administration of an MS therapy described herein (a monotherapy or a combination therapy of the agents described herein). In other embodiments, the subject is an MS patient after administration of the MS therapy for one, two weeks, one month, two months, three months, four months, six months, one year or more.

In other embodiments, the subject does not have a symptom associated with AON in one or both eyes. In one embodiment, the subject is not diagnosed with the optic nerve disorder or condition, e.g., acute optic neuritis, in one or both eyes (e.g., has normal eyes).

In one embodiment, the subject is diagnosed with the optic nerve disorder or condition, e.g., acute optic neuritis, in one or both eyes, referred to herein as the "diseased eye(s)." In one embodiment, the subject has a diseased eye and does not show a detectable symptom in the other eye (referred to herein as the "fellow eye" or "normal eye"). In one embodiment, the subject is diagnosed with the optic nerve disorder, e.g., AON, in one or both eyes, but does not show an MS symptom. In certain embodiment, the subject can be treated with the reparative agent (e.g., a LINGO-1 antagonist), as a monotherapy or in combination, as a way of preventing or delaying the onset of the nerve disorder or condition in the normal eye. Without wishing to be bound by theory, treatment of a normal fellow eye after diagnosis of acute optic neuritis in a first eye may delay or prevent one or more symptoms of neuritis in the normal fellow eye or elsewhere in the brain. In certain embodiments, the treatment or prevention delays one or more symptoms of the optic nerve disorder or condition, e.g., acute optic neuritis, and/or MS by at least a day, a week, a month, a year or longer.

Thus, in one embodiment, administration of the anti-LINGO-1 antibody molecule to the subject treats the diseased eye. In related embodiments, administration of the anti-LINGO-1 antibody molecule delays or prevents the onset of MS or the optic nerve disorder, e.g., AON, in the normal fellow eye, or elsewhere in the CNS.

In other embodiment, the subject is diagnosed with the optic nerve disorder or condition, e.g., acute optic neuritis, in one or both eyes, but does not show other MS symptoms (e.g., is a subject not diagnosed with MS or a subject that has MS but does not suffer from a relapse or is not progressing). In one embodiment, treatment of said subject with the optic nerve disorder or condition, e.g., acute optic neuritis, delays or prevents the onset or relapse of an MS symptom. In certain embodiments, the treatment or prevention delays one or more MS symptoms by at least a day, a week, a month, a year or longer.

In one embodiment, the reparative agent administered is a LINGO-1 antagonist (e.g., an anti-LINGO antibody as described herein), as a monotherapy. In one embodiment, the reparative agent is an anti-LINGO-1 antibody which is administered as a monotherapy in an amount ranging from about 0.3, 1.0, 3.0, 10, 30, 60, or 100 mg/kg. For example, between about 3 to 100 mg/kg, 10 to 300 mg/kg, 20 to 250 mg/kg, 50 to 200 mg/kg, 75 to 150 mg/kg, 90 to 120 mg/kg, or about 100 mg/kg.

In other embodiments, the reparative agent administered is a LINGO-1 antagonist (e.g., an anti-LINGO antibody as described herein) in combination with a second agent (e.g., an immunomodulatory agent as described herein). In one embodiment, the reparative agent is an anti-LINGO antibody which is administered as a combination therapy in an amount ranging from about 0.3, 1.0, 3.0, 10, 30, 60, or 100 mg/kg. For example, between about 3 to 100 mg/kg, 10 to 300 mg/kg, 20 to 250 mg/kg, 50 to 200 mg/kg, 75 to 150 mg/kg, 90 to 120 mg/kg, or about 100 mg/kg. In one embodiment, the immunomodulatory agent is administered according to the standard of care for that agent. In another embodiment, administration of the LINGO-antagonist allows for administration of a reduced amount of the immunomodulatory agent.

Reparative Agents

In certain embodiments, the reparative agent causes one or more of: enhances myelination or re-myelination, enhances neuroaxonal protection, increases axonal extension, increases neuronal sprouting, and/or increases differentiated oligodendrocyte numbers (e.g., by increasing one or more of: survival or differentiation of oligodendrocytes), e.g., in a subject (e.g., a subject in need thereof). The method includes administering to the subject a reparative agent (e.g., a LINGO-1 antagonist), as a monotherapy or in combination with an immunomodulatory agent, in an amount sufficient to enhance one or more of: myelination, re-myelination, oligodendrocyte numbers, or neuroaxonal protection.

In one embodiment, the reparative agent is an antagonist of LRR and Ig domain-containing, Nogo receptor-interacting protein ("LINGO," e.g., LINGO-1). LINGO-1, previously called Sp35, is a cell surface glycoprotein that is selectively expressed in the adult CNS in neurons and oligodendrocytes, where it is believed to function as a negative regulator of oligodendrocyte differentiation, myelination, and remyelination. Thus, antagonism of LINGO-1 can enhance myelination or re-myelination of axons, e.g., by oligodendrocytes, and enhance neuroaxonal protection in the CNS. LINGO-1 has been described in International Applications PCT/US2006/026271, filed Jul. 7, 2006, PCT/US2004/008323, filed Mar. 17, 2004, PCT/US2005/022881, filed Jun. 24, 2005 and PCT/US2008/000316, filed Jan. 9, 2008, each of which is incorporated by reference in its entirety herein.

In one embodiment, the reparative agent, e.g., the LINGO-1 antagonist, inhibits or reduces the expression or activity of LINGO-1, e.g., human LINGO-1.

In one embodiment, the reparative agent, e.g., the LINGO-1 antagonist, inhibits or reduces the formation and/or activity of a complex (e.g., a functional signaling complex) of the NgR1, pp 75, and LINGO-1; and/or NgR1, TAJ (TROY), and LINGO-1. In another embodiment, the reparative agent, e.g., the LINGO-1 antagonist, inhibits or reduces LINGO-1 binding to NgR1.

In one embodiment, the reparative agent, e.g., the antagonist of LINGO-1, is an antibody molecule. In one embodiment, the antibody molecule reduces the formation and/or activity of a complex (e.g., a functional signaling complex) of the NgR1, pp 75, and LINGO-1; and/or NgR1, TAJ (TROY), and LINGO-1. In one embodiment, the antibody molecule binds to at least one of the components of the complex (e.g., at least one of NgR1, p75, and LINGO-1; and/or NgR1, TAJ (TROY), and LINGO-1), and inhibits or reduces the functional signaling.

In one embodiment, the antibody molecule binds to LINGO, e.g., human LINGO. In another embodiment, the antibody molecule binds to LINGO-1, e.g., human LINGO-1. The antibody molecule can be a monoclonal or single specificity antibody, or an antigen-binding fragment thereof (e.g., an Fab, F(ab')$_2$, Fv, a single chain Fv fragment, a single domain antibody, a diabody (dAb), a bivalent or bispecific antibody or fragment thereof, a single domain variant thereof) that binds to LINGO-1, e.g., a mammalian (e.g., human LINGO-1 (or a functional variant thereof)). In one embodiment, the antibody molecule is a monoclonal antibody against LINGO-1, e.g., human LINGO-1. Typically, the antibody molecule is a human, a humanized, a CDR-grafted, a chimeric, a camelid, or an in vitro generated antibody to human LINGO-1 (or functional fragment thereof, e.g., an antibody fragment as described herein). Typically, the antibody inhibits, reduces or neutralizes one or more activities of LINGO-1 (e.g., one or more biological activities of LINGO-1 as described herein).

The antibody molecule can be full-length (e.g., can include at least one, and typically two, complete heavy chains, and at least one, and typically two, complete light chains) or can include an antigen-binding fragment (e.g., a Fab, an F(ab')$_2$, an Fv, a single chain Fv fragment, or a single domain antibody or fragment thereof). In yet other embodiments, the antibody molecule has a heavy chain constant region chosen from, e.g., the heavy chain constant region of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The framework region or constant region of the antibody molecule can be altered, e.g., mutated, to modify the properties of the antibody (e.g., to increase or decrease one or more of: Fc receptor binding, antibody glycosylation, the number of cysteine residues, effector cell function, and/or complement function). In one embodiment, the framework or constant region of the antibody molecule is altered, e.g., mutated, to decrease one or more of: Fc receptor binding, antibody glycosylation, the number of cysteine residues, effector cell function, and/or complement function. In one embodiment, the framework region of the antibody molecule is modified to reduce antibody glycosylation, effector cell and/or complement function. In one embodiment, the antibody molecule includes an aglycosyl framework.

In another embodiment, the antibody molecule binds to LINGO-1, e.g., human LINGO-1, and is an immunoglobulin G subclass 1 (IgG1). In certain embodiments, the antibody molecule is modified to reduce effector cell and complement function compared to wild-type IgG1. In one embodiment, the antibody molecule includes an aglycosyl (IgG1) framework.

In certain embodiments, the antibody molecule specifically binds to the same, or substantially the same, LINGO-1 epitope as the reference monoclonal antibody Li62 or Li81, described in U.S. Pat. Nos. 8,058,406 and 8,128,926, both of which are incorporated by reference in their entirety herein. In an embodiment, the antibody molecule comprises, consists essentially of, or consists of, an immunoglobulin heavy chain variable region (VH) wherein the CDR1, CDR2 and CDR3 regions are selected from the amino acid sequences shown in Table 3, or an amino acid sequence substantially identical thereto (e.g., an amino acid sequence at least 80%, 85%, 90% or 95% identical to the amino acid sequences shown in Table 3; or at least 80%, 85%, 90, 95% or 100% identical to the VH CDR1, CDR2 and CDR3 regions of the immunoglobulin heavy chain of Li62 or Li81).

In some embodiments, the antibody molecule includes a VH that comprises, consists essentially of, or consists of, the amino acid sequence of SEQ ID NO: 4 or SEQ ID NO:8 or any one of SEQ ID NOs: 17 to 49, or an amino acid sequence substantially identical thereto (e.g., an amino acid sequence at least 80%, 85%, 90% or 95% identical thereto).

In one embodiment, the antibody molecule includes a VH wherein the VH CDR1, CDR2, and CDR3 comprise, consist essentially of, or consist of, the amino acids of SEQ ID NOs:

6, 7, and 8, respectively, or an amino acid sequence substantially identical thereto (e.g., an amino acid sequence at least 80%, 85%, 90% or 95% identical thereto).

In one embodiment, the antibody molecule includes a VH wherein the VH CDR1, CDR2, and CDR3 comprise, consist essentially of, or consist of, the amino acids of SEQ ID NOs: 2, 3, and 30, respectively, or an amino acid sequence substantially identical thereto (e.g., an amino acid sequence at least 80%, 85%, 90% or 95% identical thereto).

In other embodiments, the antibody molecule includes an immunoglobulin light chain variable region (VL) wherein the CDR1, CDR2 and CDR3 regions are selected from the polypeptide sequences shown in Table 4, or an amino acid sequence substantially identical thereto (e.g., an amino acid sequence at least 80%, 85%, 90% or 95% identical to the amino acid sequences shown in Table 4; or at least 80%, 85%, 90%, 95% or 100% identical to the VL CDR1, CDR2 and CDR3 regions of the immunoglobulin light chain of Li62 or Li81).

In one embodiment, the antibody molecule includes a VL wherein the VL CDR1, CDR2, and CDR3 comprise, consist essentially of, or consist of, the amino acids of SEQ ID NOs: 14, 15, and 16, respectively, or an amino acid sequence substantially identical thereto (e.g., an amino acid sequence at least 80%, 85%, 90% or 95% identical thereto).

In one embodiment, the antibody molecule includes a VL wherein the VL CDR1, CDR2, and CDR3 comprise, consist essentially of, or consist of, the amino acids of SEQ ID NOs: 10, 11, and 12, respectively, or an amino acid sequence substantially identical thereto (e.g., an amino acid sequence at least 80%, 85%, 90% or 95% identical thereto).

In one embodiment, the antibody molecule includes a VH wherein the VH CDR1, CDR2, and CDR3 comprise, consist essentially of, or consist of, the amino acids of SEQ ID NOs: 6, 7, and 8, respectively; and a VL wherein the VL CDR1, CDR2, and CDR3 comprise, consist essentially of, or consist of, the amino acids of SEQ ID NOs: 14, 15, and 16, respectively; or an amino acid sequence substantially identical thereto (e.g., an amino acid sequence at least 80%, 85%, 90% or 95% identical thereto).

In one embodiment, the antibody molecule includes a VH wherein the VH CDR1, CDR2, and CDR3 comprise, consist essentially of, or consist of, the amino acids of SEQ ID NOs: 2, 3, and 30, respectively; and a VL wherein the VL CDR1, CDR2, and CDR3 comprise, consist essentially of, or consist of, the amino acids of SEQ ID NOs: 10, 11, and 12, respectively; or an amino acid sequence substantially identical thereto (e.g., an amino acid sequence at least 80%, 85%, 90% or 95% identical thereto).

In other embodiments, the antibody molecule includes a VH selected from the group consisting of SEQ ID NOs: 1, 5, and 53-85, or an amino acid sequence substantially identical thereto (e.g., an amino acid sequence at least 80%, 85%, 90% or 95% identical to said SEQ ID NOs: 1, 5 and 53-85).

In one embodiment, the antibody molecule includes a VH that comprises, consists essentially of, or consists of, the amino acid sequence of SEQ ID NO: 5 or an amino acid sequence substantially identical thereto (e.g., an amino acid sequence at least 80%, 85%, 90% or 95% identical to said SEQ ID NO: 5).

In one embodiment, the antibody molecule includes a VH that comprises, consists essentially of, or consists of, the amino acid sequence of SEQ ID NO:66, or an amino acid sequence substantially identical thereto (e.g., an amino acid sequence at least 80%, 85%, 90% or 95% identical to said SEQ ID NO: 66).

In yet other embodiments, the antibody molecule includes a VL selected from the group consisting of SEQ ID NOs: 9 and 13, as shown in Table 4, or an amino acid sequence substantially identical thereto (e.g., an amino acid sequence at least 80%, 85%, 90% or 95% identical to said SEQ ID NOs: 9 and 13, as shown in Table 4).

In one embodiment, the antibody molecule includes a VL that comprises, consists essentially of, or consists of, the amino acid sequence of SEQ ID NO:13, or an amino acid sequence substantially identical thereto (e.g., an amino acid sequence at least 80%, 85%, 90% or 95% identical to said SEQ ID NO: 13).

In one embodiment, the antibody molecule includes a VL that comprises, consists essentially of, or consists of, the amino acid sequence of SEQ ID NO:9, or an amino acid sequence substantially identical thereto (e.g., an amino acid sequence at least 80%, 85%, 90% or 95% identical to said SEQ ID NO: 9).

In one embodiment, the antibody molecule includes a VH that comprises, consists essentially of, or consists of, the amino acid sequence of SEQ ID NO:5, or an amino acid sequence substantially identical thereto (e.g., an amino acid sequence at least 80%, 85%, 90% or 95% identical to said SEQ ID NO: 5); and a VL that comprises, consists essentially of, or consists of, the amino acid sequence of SEQ ID NO: 13, or an amino acid sequence substantially identical thereto (e.g., an amino acid sequence at least 80%, 85%, 90% or 95% identical to said SEQ ID NO: 13).

In one embodiment, the antibody molecule includes a VH that comprises, consists essentially of, or consists of, the amino acid sequence of SEQ ID NO:66, or an amino acid sequence substantially identical thereto (e.g., an amino acid sequence at least 80%, 85%, 90% or 95% identical to said SEQ ID NO: 66); and a VL that comprises, consists essentially of, or consists of, the amino acid sequence of SEQ ID NO: 9, or an amino acid sequence substantially identical thereto (e.g., an amino acid sequence at least 80%, 85%, 90% or 95% identical to said SEQ ID NO: 9).

In another embodiment, the antibody molecule includes a heavy chain as shown below, that comprises, consists essentially of, or consists of, the amino acid sequence of SEQ ID NO: 275, or a sequence substantially identical thereto (e.g., an amino acid sequence at least 80%, 85%, 90% or 95% identical thereto), as follows:

```
                                        (SEQ ID NO: 275)
EVQLLESGGG LVQPGGSLRL SCAASGFTFS AYEMKWVRQA

PGKGLEWVSV IGPSGGFTFY ADSVKGRFTI SRDNSKNTLY

LQMNSLRAED TAVYYCATEG DNDAFDIWGQ GTTVTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKKVEPKS CDKTHTCPPC PAPELLGGPS

VFLFPPKPKD TLMISRTPEV TCVVVDVSHE DPEVKFNWYV

DGVEVHNAKT KPREEQYNSA YRVVSVLTVL HQDWLNGKEY

KCKVSNKALP APIEKTISKA KGQPREPQVY TLPPSRDELT

KNQVSLTCLV KGFYPSDIAV EWESNGQPEN NYKTTPPVLD

SDGSFFLYSK LTVDKSRWQQ GNVFSCSVMH EALHNHYTQK

SLSLSPG.
```

In other embodiments, the antibody molecule comprises, consists essentially of, or consists of, a light chain as shown below, comprising the amino acid sequence of SEQ ID NO: 276, or a sequence substantially identical thereto (e.g., an amino acid sequence at least 80%, 85%, 90% or 95% identical thereto), as follows:

```
                                           (SEQ ID NO: 276)
DIQMTQSPAT LSLSPGERAT LSCRASQSVS SYLAWYQQKP

GQAPRLLIYD ASNRATGIPA RFSGSGSGTD FTLTISSLEP

EDFAVYYCQQ RSNWPMYTFG QGTKLEIKRT VAAPSVFIFP

PSDEQLKSGT ASVVCLLNNF YPREAKVQWK VDNALQSGNS

QESVTEQDSK DSTYSLSSTL TLSKADYEKH KVYACEVTHQ

GLSSPVTKSF NRGEC.
```

In one embodiment, the antibody molecule is the anti-LINGO-1 antibody, opicinumab (also referred to herein as "BIIB033"). In one embodiment, the anti-LINGO-1 antibody molecule comprises (i) a heavy chain comprising, consisting essentially of, or consisting of, the amino acid sequence of SEQ ID NO: 275, and (ii) a light chain comprising, consisting essentially of, or consisting of, the amino acid sequence of SEQ ID NO: 276.

In another embodiment, the reparative agent, e.g., the antagonist of LINGO-1, is a soluble LINGO molecule, e.g., a LINGO-1 molecule (e.g., a fragment of LINGO-1), or a soluble form of a component of the LINGO-1 complex (e.g., a soluble form of NgR1, p75, or TAJ (TROY)).

A soluble form of LINGO or a complex component can be used alone or functionally linked (e.g., by chemical coupling, genetic or polypeptide fusion, non-covalent association or otherwise) to a second moiety, e.g., an immunoglobulin Fc domain, serum albumin, pegylation, a GST, Lex-A, an MBP polypeptide sequence, or an antibody (e.g., a bispecific or a multispecific antibody). The fusion proteins may additionally include a linker sequence joining the first moiety, e.g., the soluble form of LINGO-1 or the complex component, to the second moiety. In other embodiments, additional amino acid sequences can be added to the N- or C-terminus of the fusion protein to facilitate expression, steric flexibility, detection and/or isolation or purification. For example, a soluble form of LINGO-1 or a complex component can be fused to a heavy chain constant region of the various isotypes, including: IgG1, IgG2, IgG3, IgG4, IgM, IgA1, IgA2, IgD, and IgE. Typically, the fusion protein can include the extracellular domain of LINGO or the complex component (or a sequence homologous thereto), and, e.g., fused to, a human immunoglobulin Fc chain, e.g., a human IgG (e.g., a human IgG1 or a human IgG2, or a mutated form thereof). The Fc sequence can be mutated at one or more amino acids to reduce effector cell function, Fc receptor binding and/or complement activity.

In another embodiment, one or more reparative agents are added in combination. For example, a LINGO-1 antagonist can be added in combination with another remyelinating agent.

Immunomodulatory Agents

The methods, kits and compositions described herein can include one or more immunomodulatory agents. In certain embodiments, the immunomodulatory agent is chosen from one or more of:

an IFN-β1 molecule;
a polymer of glutamic acid, lysine, alanine and tyrosine, e.g., glatiramer (e.g., Copaxone®);
an antibody or fragment thereof against alpha-4 integrin, e.g., natalizumab (e.g., Tysabri®);
an anthracenedione molecule, e.g., mitoxantrone (e.g., Novantrone®);
a fingolimod, e.g., FTY720 (e.g., Gilenya®);
a dimethyl fumarate, e.g., an oral dimethyl fumarate (e.g., Tecfidera®);
an antibody to the alpha subunit of the IL-2 receptor of T cells (CD25), e.g., daclizumab;
an antibody against CD52, e.g., alemtuzumab (e.g., CAMPATH);
an inhibitor of a dihydroorotate dehydrogenase, e.g., leflunomide or an active metabolite thereof, e.g., teriflunomide (e.g., AUBAGIO);
an antibody to CD20, e.g., rituximab, or ocrelizumab;
a Sphingosine 1-phosphate (S1P) modulating agent, e.g., as described in WO 2012/109108; or
a corticosteroid.

In one embodiment, the immunomodulatory agent is an IFN-β1 molecule. The IFN-β1 molecule can be chosen from one or more of an IFN-β1a or IFN-β1b polypeptide, a variant, a homologue, a fragment or a pegylated variant thereof.

In one embodiment, the IFN-β1 molecule includes an IFNβ agent chosen from an IFN-β1a molecule, an IFN-β1b molecule, or a pegylated variant of an IFN-β1a molecule or an IFN-β1b molecule.

In one embodiment, the IFNβ1 molecule is an IFN-β1a agent (e.g., Avonex®, Rebif®). In another embodiment, the IFNβ1 molecule is an INF-β1b agent (e.g., Betaseron®, Betaferon® or Extavia®).

In one embodiment, the immunomodulatory agent is a polymer of glutamic acid, lysine, alanine and tyrosine, e.g., glatiramer (e.g., Copaxone®).

In one embodiment, the immunomodulatory agent is an antibody or fragment thereof against alpha-4 integrin (e.g., natalizumab (e.g., Tysabri®)).

In yet other embodiments, the immunomodulatory agent is an anthracenedione molecule (e.g., mitoxantrone (e.g., Novantrone®)).

In yet another embodiment, the immunomodulatory agent is a fingolimod (e.g., FTY720; e.g., Gilenya®).

In one embodiment, the immunomodulatory agent is a dimethyl fumarate (e.g., an oral dimethyl fumarate (e.g., BG-12)).

In other embodiments, the immunomodulatory agent is an antibody to the alpha subunit of the IL-2 receptor of T cells (CD25) (e.g., Daclizumab).

In other embodiments, the immunomodulatory agent is an antibody to CD20, e.g., ocrelizumab.

In other embodiments, the immunomodulatory agent is a corticosteroid, e.g., methylprednisolone (e.g., high dose corticosteroid, e.g., methylprednisolone).

In certain embodiments, the method further includes the use of one or more symptom management therapies, such as antidepressants, analgesics, anti-tremor agents, among others.

Any combination of the reparative agent (e.g., one or more reparative agents described herein, e.g., a LINGO-1 antagonist) and an immunomodulatory agent (e.g., one or more immunomodulatory agents described herein) can be used in the methods, kits and compositions described herein. For example, the reparative agent can be combined with a polymer of glutamic acid, lysine, alanine and tyrosine, e.g., glatiramer. In other embodiments, the reparative agent can be combined with an antibody or fragment thereof against alpha-4 integrin, e.g., natalizumab. In yet another embodiment, the reparative agent can be combined with an anthracenedione molecule, e.g., mitoxantrone. In yet another embodiment, the reparative agent can be combined with a fingolimod, e.g., FTY720. In yet another embodiment, the reparative agent can be combined with a dimethyl fumarate, e.g., an oral dimethyl fumarate. In other embodiments, the reparative agent can be combined with an antibody to the alpha subunit of the IL-2 receptor of T cells (CD25), e.g., daclizumab. In yet another embodiment, the reparative agent can be combined with an antibody against CD52, e.g., alemtuzumab. In yet another embodiment, the reparative agent can be combined with an inhibitor of a dihydroorotate dehydrogenase, e.g., teriflunomide. In another embodiment, the reparative agent can be combined with an antibody to CD20, e.g., ocrelizumab. In another embodiment, the reparative agent can be combined with a corticosteroid, e.g., methylprednisolone. In one embodiment, the reparative agent can be combined with a S1P modulating agent.

In other embodiment, the reparative agent is combined with two, three, four or more immunomodulatory agents, e.g., two, three, four or more of the immunomodulatory agents described herein. In one exemplary embodiment, a combination of a LINGO antagonist, an IFN-β1 molecule and a corticosteroid is used. In other embodiments, a combination of a LINGO antagonist, an IFN-β1 molecule and a polymer of glutamic acid, lysine, alanine and tyrosine, e.g., glatiramer, is used. In yet other embodiments, a combination of a LINGO antagonist, an IFN-β1 molecule and an antibody or fragment thereof against alpha-4 integrin, e.g., natalizumab, is used.

In certain embodiment of the methods, kits and compositions described herein, the reparative agent is an antibody molecule against LINGO-1, e.g., an anti-LINGO antibody as described herein, and the immunosuppressive agent is an IFN-β1 molecule, e.g., an IFN-β1 molecule as described herein.

Monotherapy and Combination Therapy; Timing of Administration

The reparative agent can be administered as a monotherapy or a combination therapy. The combinations of reparative agent (e.g., LINGO-1 antagonist) and the immunomodulatory agent described herein can be administered in any order, e.g., concurrently or sequentially as described herein. In one embodiment, the reparative agent and the immunomodulatory agent are administered concurrently. In another embodiment, the reparative agent and the immunomodulatory agent are administered sequentially. For example, the administration of the reparative agent and the immunomodulatory agent can overlap, at least in part or completely, with each other.

In certain embodiments, initiation of the administration of the immunomodulatory agent and the reparative agent occurs at the same time. In other embodiments, the immunomodulatory agent is administered before initiating treatment with the reparative agent. In yet other embodiments, the reparative agent is administered before initiating treatment with the immunomodulatory agent. In another embodiment, the administration of the immunomodulatory agent continues after cessation of administration of the reparative agent. In other embodiments, administration of the reparative agent continues after cessation of administration of the immunomodulatory agent. In other embodiments, administration of the reparative agent continues intermittently (e.g., for 2 or 3 months every 3 or 6 or 12 months, or for 3-6 months every 1-2 years) while the immunomodulatory agent is given continuously. In other embodiments, administration of the immunomodulatory agent continues intermittently (e.g., for 2 or 3 months every 3 or 6 or 12 months, or for 3-6 months every 1-2 years), while the reparative agent is given continuously, e.g., as background therapy.

In certain embodiments, the reparative agent is an antibody molecule against LINGO-1 and is administered, as a monotherapy or a combination therapy, intravenously, subcutaneously or intramuscularly. In one embodiment, the antibody molecule is administered intravenously. In such embodiments, the antibody molecule is administered, as a monotherapy or a combination therapy, at about 0.3, 1.0, 3.0, 10, 30, 60, or 100 mg/kg. For example, between about 1 to 150 mg/kg, e.g., 3 to 100 mg/kg (typically, at about 3 mg/kg, about 10 mg/kg, about 30 mg/kg, about 50 mg/kg or about 100 mg/kg). In some embodiments, the antibody molecule is administered once every one, two, three, four or five weeks by IV infusion. In one embodiment, the anti-LINGO-1 antibody molecule is administered at about 100 mg/kg via IV infusion or SC injection once every 4 weeks. In one embodiment, the administration of the anti-LINGO-1 antibody molecule is acute, e.g., it is administered less than 2 weeks after an acute MS lesion (e.g., any lesion in MS, a relapse or AON). In one embodiment, the acute administration is less than 2 weeks or 1 week after the acute MS lesion (e.g., less than 13, 12, 11, 10, 9, 8, 7, 6, 5, 4, 3, 2, 1 day, or hours after the acute MS lesion). In one embodiment, administration is chronic, e.g., is administered prophylactically and/or administration continues for a prolonged period of time, e.g., administration continues until the beneficial effects of the treatment (e.g., as detected by remyelination or reduction in neuronal damage) are reduces or not detectable.

In certain embodiments, the immunomodulatory agent is an IFN-β1 molecule is administered intravenously, subcutaneously or intramuscularly. For example, the IFN-β1 molecule can be administered at one or more of:

(i) at 20-45 microgram (e.g., 30 microgram), e.g., once a week via intramuscular injection;

(ii) at 20-30 microgram (e.g., 22 microgram), e.g., three times a week, or at 40-50 micrograms (e.g., 44 micrograms), e.g., once a week, via subcutaneous injection; or (iii) in an amount of between 10 and 50 µg intramuscularly, e.g., three times a week, or every five to ten days, e.g., once a week; or (iv) in an amount between 200 and 600 m (e.g., between 250 and 500 µg), e.g., every other day, via subcutaneous injection. In one embodiment, the IFN-β1 molecule is an interferon β-1b (Betaseron®/Betaferon®, or Extavia®).

In other embodiments, the reparative agent is an antibody molecule against LINGO-1 and is administered once every four weeks by IV infusion or SC injection dosed at about 3 mg/kg, about 10 mg/kg, about 30 mg/kg, 50 mg/kg or about 100 mg/kg; and the immunomodulatory agent the IFN-β1 is administered at one or more of:

(i) at 20-45 microgram (e.g., 30 microgram), e.g., once a week via intramuscular injection;

(ii) at 20-30 microgram (e.g., 22 microgram), e.g., three times a week, or at 40-50 micrograms (e.g., 44 micrograms), e.g., once a week, via subcutaneous injection; or (iii) in an amount of between 10 and 50 µg intramuscularly, e.g., three times a week, or every five to ten days, e.g., once a week.

Subject Monitoring

Alternatively, or in combination, with the methods disclosed herein, a method of evaluating, diagnosing, and/or monitoring the progression of, a CNS disorder or a CNS demyelinating disease is disclosed. The method includes evaluating a subject (e.g., a patient, a patient group or a patient population), having the CNS disorder or CNS demyelinating disease, or at risk of developing the disorder. In one embodiment, the subject is evaluated using (i) a neurological examination (e.g., EDSS); and/or (ii) an assessment of physical function. For example, an assessment of physical function can include an assessment of ambulatory function (e.g., short distance and/or longer distance ambulatory function), alone or in combination with an assessment of upper and/or lower extremity function.

In certain embodiments, the subject is evaluated by one or more of:

performing a neurological examination;

acquiring the subject's status on the Expanded Disability Status Scale (EDSS);

acquiring the subject's status on the Multiple Sclerosis Functional Composite (MSFC);

detecting the subject's lesion status, e.g., as assessed using an MRI;

acquiring a measure of upper and/or lower extremity function;

acquiring a measure of ambulatory function (e.g., short distance ambulatory function) (e.g., Timed Walk of 25 Feet (T25FW)); or long distance ambulatory function (e.g. the 6 minute walk test (6MW);

acquiring a measure of cognitive function (e.g., an MS-COG or BICAMS or SDMT); or acquiring an assessment of visual function.

In one embodiment, the measure of upper extremity function is acquired using a 9 Hole Peg Test (9HP).

In other embodiments, the measure of short distance ambulatory function is acquired using a Timed Walk of 25 Feet (T25FW).

In other embodiments, the measure of long distance ambulatory function is acquired using a 6 minute walk test (6MW).

In certain embodiments, an increase by at least 10%, 15%, 20%, 25% or higher in a measure of extremity and/or ambulatory function is indicative of disease progression, e.g., a steady worsening of symptoms and/or disability, in the subject; and a decrease of at least 10%, 15%, 20%, 25% or more in a measure of extremity and/or ambulatory function as described above is indicative of an improved outcome (e.g., a decrease in disease progression or an improved condition) in the subject.

In certain embodiments, the subject is evaluated using a neurological examination, e.g., EDSS. In some embodiments, the EDSS includes an assessment of neurological function, an assessment of ambulatory function, or both. In one embodiment, an EDSS score is calculated based on a combination of one or more scores for the EDSS functional systems (FS) (e.g., one, two, three, four, five, six, or all seven individual scores for the EDSS FS chosen from visual, brainstem, cerebellar, motor, sensory, bladder/bowel or cognitive systems). In other embodiments, the EDSS includes a score for ambulation. In one embodiment, the EDSS includes a determination of a subject's ambulation that includes an assessment of one or more (or all) of: Unrestricted ambulation, e.g., without aid or rest for a predetermined distance (e.g., a distance greater or equal to 500, 300, 200, or 100 meters, or less than 200 or 100 meters); unilateral assistance; bilateral assistance; essentially or fully restricted to a wheelchair; or essentially or fully restricted to a bed.

In one embodiment, the assessment of visual function is acquired by one or more of: e.g., visual acuity (e.g., low-contrast letter acuity (LCLA) or high contrast visual acuity), Visual Function Questionnaire (VFQ), a 10-Item Neuro-Ophthalmic Supplement (NOS-10). Functional Acuity Contrast Testing (FACT), VEPs, such as FF-VEP or mfVEP (described e.g., in MacKay, AM (2008) *Invest Ophthalmol Vis Sci.* 49(1):438-41), optical coherence tomography (OCT), some of which are described in, e.g., Balcer et al. (2010) *Neurology* 74 Suppl 3:S16-23; Bock, M. et al. (2012) *Br J Ophthalmol.* 96(1):62-7).

In yet other embodiments, the measure of cognitive function comprises an evaluation of a learning test, a memory test and/or an attention/processing speed test. For example, the measure of cognitive function can include an evaluation of one or more of auditory memory, verbal learning and/or remembering visual information (e.g., Selective Reminding Test (SRT)); tests for evaluating auditory/verbal memory (e.g., California Verbal Learning Test Second Edition (CVLT2)), the Rey Auditory Verbal Learning Test (RAVLT); tests for evaluating visual/spatial memory (e.g., Brief Visuospatial Memory Test Revised (BVMTR)); processing speed cognitive tests, e.g., Paced Auditory Serial Addition Test (PASAT), Symbol Digit Modalities Test (SDMT); MSNQ-information, MSNQ-subject, and/or SF-36. In one embodiment, the measure of cognitive function is performed using a composite of MS cognitive endpoint that comprises SDMT, PASAT-3 and −3, SRT-Total Learned (SRT-TL), SRT Delayed Recall (SRT-DR), and BVMTR Delayed Recall (BVMTR-DR) (e.g., MS-COG as described in Cadavid et al., 29$^{th}$ Congress European Committee for Treatment and Research in MS (ECTRIMS), 2-5 Oct. 2013).

In certain embodiments, the subject's lesion status is evaluated using magnetic resonance imaging. In one embodiment, the magnetic resonance imaging comprises magnetization transfer ration and/or diffusion tensor imaging.

In certain embodiments, an improvement in the subject is defined by one or more of:

a. ≥1.0 point decrease in EDSS from a baseline score of ≤6.0;

b. ≥15% improvement from baseline in T25FW;

c. ≥15% improvement from baseline in SHPT; or d. ≥10% (e.g., 10%, 12%, 20%, 30%) improvement from baseline in PASAT or SDMT.

In other embodiments, the method further includes one or more of the following:

(i) identifying the subject as being in need of a therapy, e.g., a therapy as described herein;

(ii) identifying the subject as having an increased or a decreased response to a therapy, e.g., a therapy as described herein;

(iii) identifying the subject as being stable, as showing an improvement in function or abilities (e.g., as being a disease non-progressor), or showing a decline in function or abilities (e.g., as being a disease progressor);

(iv) diagnosing, and/or prognosing the subject.

The steps in the methods described herein (e.g., administration of the reparative agent and immunomodulatory agent ("administration step"), and subject monitoring and/or evaluating ("evaluating step") can be performed in any order. In one embodiment, the administration step occurs prior to the evaluating step. In another embodiment, the evaluating step occurs prior to the administration step.

In another aspect, the invention features a method of evaluating, e.g., diagnosing, a subject at risk of developing, a CNS demyelinating disorder (e.g., multiple sclerosis or optic neuritis, or both). The method includes acquiring a measure (e.g., detecting or measuring), one or both of optic nerve damage or optic nerve conductance for one or both eyes of the subject, wherein the presence of optic nerve damage and/or a delay in optic nerve conductance in one or both eyes indicates that the subject is at risk for developing the CNS demyelinating disorder.

In one embodiment, the subject has not been diagnosed with multiple sclerosis according to one or more of:

performing a neurological examination;

acquiring the subject's status on the Expanded Disability Status Scale (EDSS);

acquiring the subject's status on the Multiple Sclerosis Functional Composite (MSFC);

detecting the subject's lesion status;

acquiring a measure of upper and/or lower extremity function;

acquiring a measure of short distance ambulatory function;

acquiring a measure of long distance ambulatory function; or acquiring a measure of cognitive function.

In certain embodiments, the step of acquiring the measure of optic nerve damage comprises measuring visual evoked potential (VEP) amplitude, e.g., full field VEP (FF-VEP) amplitude and/or multi-field VEP (mfVEP) amplitude. In one embodiment, an mfVEP amplitude that is (i) at least 40 nanovolts lower than a control amplitude, (ii) at least 20% lower than a control amplitude, or (iii) less than or equal to 180 nanovolts, indicates the presence of optic nerve damage in the eye(s) of the subject. The control amplitude can be the average VEP amplitude, e.g., FF-VEP amplitude and/or mfVEP amplitude, of a normal eye, e.g., an eye of a subject not having an optic nerve disorder or condition, e.g., acute optic neuritis.

In other embodiments, the step of of acquiring the measure of optic nerve conductance comprises measuring VEP latency, e.g., FF-VEP latency or mfVEP latency. In some embodiments, a VEP latency (i) that is at least 3 milliseconds higher than a control latency, or (ii) that is at least 3% higher than a control latency; or (iii) an FF-VEP latency that is 110 milliseconds or higher, or (iv) an mfVEP latency that is 155 milliseconds or higher, indicates a delay in optic nerve conductance in the eye. In yet other embodiments, the control latency is the average VEP latency, e.g., FF-VEP latency or mfVEP latency, of a normal eye, e.g., an eye of a subject not having an optic nerve disorder or condition, e.g., acute optic neuritis.

Kits and Compositions

In another aspect, the invention features a kit that includes a reparative agent (e.g., a LINGO-1 antagonist, e.g., an anti-LINGO-1 antibody molecule as described herein). Optionally, the kit is labeled and/or contains instructions for use in treating or preventing a CNS disorder, e.g., a CNS demyelinating disease as described herein. In one embodiment, the LINGO-1 antagonist is instructed to be administered at one, two or all of the following:

(i) prior to the onset or relapse of one or more symptoms of the CNS demyelinating disease;

(ii) within 7 days after the onset or relapse of one or more symptoms of the CNS demyelinating disease (e.g., to enhance neuroprotection); or (iii) within 30 days after the onset or relapse of one or more symptoms of the CNS demyelinating disease (e.g., to enhance remyelination).

In one embodiment, the kit further comprises a second agent, e.g., a second agent as described herein (e.g., an IFN-β1 molecule) to be administered in combination with the LINGO-1 antagonist.

In yet another aspect, the invention features a composition (e.g., a packaged composition) that includes a reparative agent (e.g., a LINGO-1 antagonist, e.g., an anti-LINGO-1 antibody molecule as described herein). Optionally, the composition is labeled and/or contains instructions for use of the reparative agent in treating or preventing a CNS disorder, e.g., a CNS demyelinating disease. In one embodiment, the LINGO-1 antagonist is instructed to be administered at one, two or all of the following:

(i) prior to the onset or relapse of one or more symptoms of the CNS demyelinating disease;

(ii) within 7 days after the onset or relapse of one or more symptoms of the CNS demyelinating disease (e.g., to enhance neuroprotection); or (iii) within 30 days after the onset or relapse of one or more symptoms of the CNS demyelinating disease (e.g., to enhance remyelination).

In one embodiment, the composition further comprises a second agent, e.g., a second agent as described herein (e.g., an IFN-β1 molecule) to be administered in combination with the LINGO-1 antagonist.

The LINGO-1 antagonist and/or the immunomodulatory agent of the compositions, kits and packaged compositions described herein can be in a form suitable for any route of administration, e.g., peripheral administration (e.g., intravenous, subcutaneous, intramuscular, intravitreal, intrathecal, or oral administration). The route of administration can be the same or different depending on the composition used. In one embodiment, the packaged pharmaceutical composition includes a LINGO-1 antagonist (e.g., an antibody against LINGO-1) in a form or preparation suitable for intravenous administration. In another embodiment, the packaged pharmaceutical composition includes an immunomodulatory agent (e.g., an interferon) in a form or preparation suitable for intramuscular administration. One or more agents can be included in the packaged pharmaceutical composition.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

BRIEF DESCRIPTION OF THE FIGURES

FIG. 3A is an image of a T2 weighted localizer scan. FIG. 3B is an image of a diffusion weighted image perpendicular to the optic nerve. FIG. 3C is an image of a diffusion weighted scan parallel to the optic nerve. FIG. 3D is an image of a diffusion weighted image perpendicular to the optic nerve. FIG. 3E is an enlargement of the optic nerve image of FIG. 3B. FIG. 3F is an enlargement of the optic nerve image of FIG. 3D.

FIG. 6 depicts the measurement of axonal loss in the optic nerve in EAE mice treated with vehicle or anti-LINGO-1 antibody or healthy mice. FIG. 6 includes measurements of optic nerve area ($\mu m^2$), average central axon area ($\mu m^2$), total central axon count, total peripheral axon count, total central axo-plasmal area ($\mu m^2$), and total peripheral axoplasmal area ($\mu m^2$).

FIGS. 16A and 16B are bar graphs showing the adjusted mean change in optic nerve conduction latency (measured by FF-VEP) in the affected eye compared with the unaffected fellow eye at baseline in the PP populations in the RENEW trial in subjects <33 years old (A) and in subjects ≥33 years old (B). The left bar of each set of bars refers to the placebo group, and the right bar of each set of bars refers to the anti-LINGO-1 group.

DETAILED DESCRIPTION OF THE INVENTION

Figure 1:
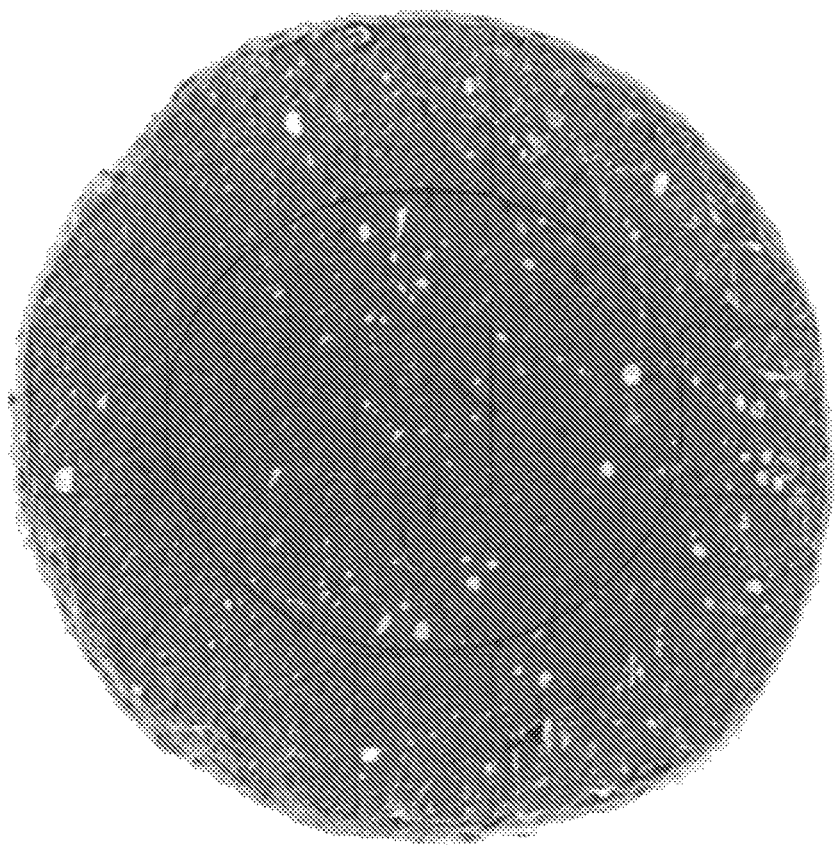
FIG. 1 depicts the region of interest (ROI) selection for the quantification of optic nerve axonal density in the mouse model of experimental autoimmune encephalomyelitis (EAE).

The invention is based, at least in part, on the discovery that a reparative agent (an anti-LINGO-1 antibody) is capable of increasing the remyelination of an optic nerve in patients after an onset (e.g., a first attack) of acute optic neuritis (AON), as well as preventing (e.g., delaying) the onset of new disease in the visual pathways served by both the normal (unaffected) and the affected eye. In addition, by utilizing methods such as VEP (e.g., FF-VEP and mfVEP) to measure the function of the visual pathway including the optic nerve (e.g., measure the latency and amplitude of the VEP), a beneficial effect of the reparative agent on remyelination was detected. As described in the appended examples, a protective effect of the anti-LINGO-1 treatment was seen for the amplitude of the mfVEP in both the affected and the fellow eye visual pathways over 32 weeks, which was highly statistically significant at 32 weeks for the fellow eye mfVEP amplitude.

Also, methods to measure latency and amplitude of an optic nerve, such as VEP (e.g., FF-VEP and mfVEP, and in particular, mfVEP) provide a way to diagnose patients at risk of developing MS earlier than using previously described methods. Methods such as VEP also provide a way to diagnose/identify patients at risk of developing AON, e.g., one or both eyes, earlier than using previously described methods. Further, methods such as VEP provide a way to identify subjects that would most likely respond positively (e.g., have improved neuronal function) to a reparative agent described herein, e.g., anti-LINGO-1. Thus, without being bound by theory, the methods described herein provide an early intervention to treat and/or prevent AON as well as MS, e.g., by preserving myelination or causing remyelination of damaged areas early in the disease.

In embodiments, the methods described herein treat and/or prevent AON and/or MS in a subject before neuronal (e.g., axonal) damage, e.g., optic nerve damage in the subject. In embodiments, the methods described herein treat and/or prevent AON and/or MS in a subject before neuronal (e.g., axonal) damage and after demyelination of one or more nerves (e.g., an optic nerve) in the subject. In yet other embodiments, the methods described herein prevent AON and/or MS in a subject before neuronal (e.g., axonal damage and before demyelination of one or more nerves (e.g., an optic nerve) in the subject, e.g., the subject has one eye affected by AON (with demyelination of the optic nerve) and one fellow normal eye that is asymptomatic (without demyelination of the optic nerve).

Accordingly, in some embodiments, provided herein are methods comprising chronic and/or prophylactic administration of the reparative agent as a monotherapy or a combination therapy that can preserve neuronal function and/or neuronal tissue and/or prevent (e.g., delay) a disability in a subject, e.g., an MS or AON subject as described herein. In certain embodiments, chronic or prophylactic administration of the reparative agent may prevent the onset or delay the progressive form of the disease, e.g., AON or MS, for example, by reducing axonal/neuronal degeneration and/or demyelination.

Inflammatory demyelinating CNS diseases, such as MS, are a common cause of non-traumatic neurological disability in young adults. Currently approved therapies for MS are primarily immunomodulatory, and do not have detectable direct effects on CNS repair. For example, the current standard of care for patients with relapsing MS includes the use of immunomodulatory drugs to reduce the frequency and severity of relapses and the accumulation of relapse-related physical disability, and to provide various symptomatic treatment as needed such as for depression, bladder dysfunction, or walking impairment. Several immunomodulatory drugs are currently available for relapsing MS, including, but not limited to, different preparations of interferon β (interferon β-1a given intramuscularly [IM] [Avonex] or subcutaneously [SC] [Rebif®], interferon β-1b [Betaseron/Betaferon®/Extavia®]), glatiramer acetate (Copaxone®), natalizumab (Tysabri®), and fingolimod (Gilenya®). Short courses of corticosteroids are occasionally given with mixed success. Chemotherapeutic agents, such as mitoxantrone and cyclophosphamide, are occasionally used in cases of severe relapsing MS. Although some degree of axonal remyelination by oligodendrocytes takes place early during the course of MS, the ability to endogenously repair the CNS often fails, leading to irreversible tissue injury and an increase in disease-related disability.

Several preclinical studies have demonstrated a role for LINGO-1 antagonism in enhancing CNS remyelination and neuroaxonal protection in animal models of toxic injury (Cuprizone) (Mi et al. (2009) *Ann Neurology,* 65: 304-15), chemical injury (lysophosphatidylcholine [LPC]), and inflammatory demyelination (myelin oligodendrocyte glycoprotein-experimental autoimmune encephalomyelitis [MOG-EAE]) [Mi et al. (2007) *Nat Med,* 13: 1228-33); and of toxic (1-methyl-4-phenyl-1,2,3,6-tetrahydropyridine [MPTP]) neuronal injury (Inoue et al. (2007) *Proc Natl Acad Sci,* 104: 14430-5), traumatic/hypertensive optic nerve injury (Fu et al. (2008) *Invest Opthalmol Vis Sci.* 49: 975-85) and spinal cord injury (Ji et al. (2006) *Mol Cell Neurosci,* 33: 311-20; Ji et al. (2008) *Mol Cell Neurosci,* 39: 258-67; Lv et al. (2010) *Neuroimmunomodulat,* 17: 270-8). Thus, antagonizing LINGO-1 with an anti-LINGO-1 antibody can enhance remyelination and neuroaxonal protection in the CNS. An anti-LINGO-1 antibody can reach the CNS in sufficient concentrations to block LINGO-1 in both axons and oligodendroyctes after peripheral administration. This in turn, can enhance remyelination via differentiation of oligodendrocyte precursor cells (OPC) normally present in the brain of MS patients.

Binding of an anti-LINGO-1 antibody to LINGO-1 in axons and neurons can also provide neuroaxonal protection via blockade of signaling by myelin debris on the Nogo66 receptor-1(NgR1)/p75/LINGO-1 receptor complex in the CNS. It has been proposed that the failure of axonal repair/neurite regeneration in MS can be due, at least in part, to signaling of myelin debris on the NgR1/p75/LINGO-1 complex and the NgR1/TROY/LINGO-1 complex in damaged axons (Mi et al. (2004) *Nat Neurosci,* 7: 221-8). Signaling on the NgR1 receptor complex may interfere not only with axonal regeneration (Yamashita et al. (2005) *Mol Neurobiol,* 32: 105-11), but also with neuronal survival following neuroaxonal injury (Mi et al. (2004) *Nat Neurosci,* 7: 221-8; Fu et al. (2008) *Invest Opthalmol Vis Sci,* 49: 975-85; Zhao et al. (2008) *Cell Mol Neurobiol,* 28: 727-35).

Without wishing to be bound by theory, it is believed that newly developed lesions may be easier to repair and remyelinate due, at least in part, to the greater preservation of axons and lesser interference from glial scar (Jasmin and Ohara (2002) Neuroscientists 8(3):198-203; Vick et al. (1992) *J. Neurotrauma* 9 Suppl 1:S93-103). However, reparative effects of LINGO-1 antagonists on pre-existing lesions can also occur. For example, the efficacy of an anti-LINGO-1 antibody treatment in pre-existing lesions is supported by (1) the finding that OPCs are found in chronically demyelinated MS lesions, (2) animal studies that show the ability of chronically demyelinated brain lesions to be remyelinated, and (3) studies showing the enhancement of remyelination by LINGO-1 blockade in established demyelinated lesions (e.g., in the Cuprizone model).

Thus, antagonism of LINGO-1 with an anti-LINGO-1 antibody can enhance remyelination and neuroaxonal protection (thus, preventing axonal degeneration) in CNS demyelinating diseases, such as MS and acute optic neuritis, leading to improved CNS repair with corresponding beneficial effects on neurological function and disability. Since an anti-LINGO-1 antibody does not have detectable immunomodulatory effects on the inflammatory component of MS pathogenesis, concurrent administration with an immunomodulatory agent is desirable. Therefore, combination treatments of an immunomodulatory agent, e.g., IFN-β agent, e.g., Avonex®; with a reparative agent, e.g., anti-LINGO-1 antibody, are disclosed.

The present invention provides, at least in part, methods, composition and kits for enhancing one or more of: myelination, re-myelination, oligodendrocyte numbers, or neuroaxonal protection in a subject, e.g., a human (e.g., a human MS patient), while ameliorating an inflammatory condition in the subject. Such methods, compositions and kits described herein are useful for treating a CNS disorder, e.g., a CNS demyelinating disease. Accordingly, methods, composition and kits include a reparative agent (e.g., a LINGO-1 antagonist) and an immunomodulatory agent, in combination, as described herein.

In other embodiments, the reparative agent (e.g., a LINGO-1 antagonist) can be used to treat an inflammatory condition of the optic nerve, e.g., optic neuritis (e.g., acute optic neuritis (AON). Thus methods and compositions comprising a reparative agent for treating an inflammatory condition of the optic nerve, e.g., optic neuritis (e.g., AON) are also disclosed.

The term "reparative agent" as used herein includes any agent that causes one or more of: enhances myelination, re-myelination, enhances neuroaxonal protection, increases axonal extension, increases neuronal sprouting, and/or promotes oligodendrocyte numbers (e.g., by increasing one or more of: survival or differentiation of oligodendrocytes), without having a substantial (e.g., a detectable) immunomodulatory effect. In one embodiment, the reparative agent is a LINGO-1 antagonist, e.g., a LINGO-1 antagonist as described herein.

Various aspects of the invention are described in further detail in the following subsections.

Definitions

As used herein, each of the following terms has the meaning associated with it in this section.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

The terms "proteins" and "polypeptides" are used interchangeably herein.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

"Acquire" or "acquiring" as the terms are used herein, refer to obtaining possession of, determining, or evaluating, a desired result, e.g., a value, e.g., a numerical value, by "directly acquiring" or "indirectly acquiring" the result. "Directly acquiring" means performing a process (e.g., performing a test, e.g., a measure of upper and/or lower extremity function, and/or ambulatory function) to obtain the result, e.g., the value. "Indirectly acquiring" refers to receiving the result, e.g., the value, from another party or source (e.g., a third party clinician or health professional that directly acquired the value).

A "CNS disorder" (e.g., a "CNS demyelinating disease") can be any disease, disorder or injury associated with one or more of: demyelination, dysmyelination, axonal injury, and/or dysfunction or death of an oligodendrocyte or a neuronal cell, or loss of neuronal synapsis/connectivity. In certain embodiments, the CNS disorder affects the nervous system by causing damage to the myelin sheath of axons. In other embodiments, the CNS disorder includes Nogo receptor-1 (NgR1−) mediated inhibition of axonal extension or neurite extension, e.g., in the brain and spinal cord. In other embodiments, the CNS disorder has one or more inflammatory components. In one embodiment, the CNS disorder (e.g., the CNS demyelinating disease) is multiple sclerosis. In one embodiment, the CNS disorder (e.g., the CNS demyelinating disease) is an optic nerve condition or disorder, e.g., optic neuritis, e.g., acute optic neuritis.

The CNS disorder (e.g., the CNS demyelinating disease) is "treated," "inhibited" or "reduced," if at least one symptom of the disease or disorder is reduced, alleviated, terminated, slowed, or prevented. Treatment or prevention need not be 100%, and in some embodiments a reduction or delay in at least one symptom of the disease or disorder by at least 50%, 60%, 70%, 80%, 90%, 95%, or 99% is sufficient to be considered within these terms.

In embodiments, the CNS disorder is "prevented" if at least one symptom of the disease or disorder is delayed, e.g., by about 4 weeks, 8 weeks, 12 weeks, 24 weeks, 36 weeks, 48 weeks, 1 year, 2 years, 3 years, 4 years, 5 years, 6 years, 7 years, 8 years, 9 years, 10 years, or more. In embodiments, the CNS disorder is prevented if initial onset (e.g., first occurrence of a symptom) of the disorder is delayed, e.g., by about 4 weeks, 8 weeks, 12 weeks, 24 weeks, 36 weeks, 48 weeks, 1 year, 2 years, 3 years, 4 years, 5 years, 6 years, 7 years, 8 years, 9 years, 10 years, or more.

As used herein, in some embodiments, an optic nerve condition or disorder, e.g., optic neuritis, e.g., acute optic neuritis, is "prevented" if at least one symptom of the optic nerve condition or disorder is delayed in one or both eyes, e.g., by about 4 weeks, 8 weeks, 12 weeks, 24 weeks, 36 weeks, 48 weeks, 1 year, 2 years, 3 years, 4 years, 5 years, 6 years, 7 years, 8 years, 9 years, 10 years, or more. In embodiments, an optic nerve condition or disorder, e.g., optic neuritis, e.g., acute optic neuritis, is "prevented" if initial onset (e.g., first occurrence of a symptom) of the optic nerve condition or disorder is delayed in one or both eyes, e.g., by about 4 weeks, 8 weeks, 12 weeks, 24 weeks, 36 weeks, 48 weeks, 1 year, 2 years, 3 years, 4 years, 5 years, 6 years, 7 years, 8 years, 9 years, 10 years, or more, i.e., if function is preserved for a period of time. In an example, optic neuritis is prevented in a normal fellow eye that does not show symptoms of optic neuritis if at least one symptom of the optic neuritis is delayed in the normal fellow eye, e.g., by about 4 weeks, 8 weeks, 12 weeks, 24 weeks, 36 weeks, 48 weeks, 1 year, 2 years, 3 years, 4 years, 5 years, 6 years, 7 years, 8 years, 9 years, 10 years, or more. In an example, optic neuritis is prevented in a normal fellow eye that does not show symptoms of optic neuritis if initial onset (e.g., first occurrence of a symptom) of the optic neuritis is delayed in the normal fellow eye, e.g., by about 4 weeks, 8 weeks, 12 weeks, 24 weeks, 36 weeks, 48 weeks, 1 year, 2 years, 3 years, 4 years, 5 years, 6 years, 7 years, 8 years, 9 years, 10 years, or more.

As used herein, an optic nerve condition or disorder, e.g., optic neuritis, e.g., acute optic neuritis, is "treated," "inhibited," or "reduced," if recurrence or relapse of the disease is reduced, retarded, slowed, delayed, or prevented. Exemplary clinical symptoms of acute optic neuritis that can be used to aid in determining disease status in a subject can include, e.g., visual loss, edema, inflammation, damage or demyelination of the myelin sheath covering the optic nerve and axons, loss of retinal fiber layer, loss of retinal ganglion cell layer, visual field defect, color desaturation, decreased color vision, ocular pain, decreased visual acuity, Uhthoff's symptom, swollen optic disc, or relative afferent papillary defect. In embodiments, clinical outcomes can be used to aid in determining disease status in a subject, e.g., optic nerve damage (e.g., as measured by full field visual evoked potential amplitude or multi-focal visual evoked potential), optic nerve latency (e.g., as measured by full field visual evoked potential or multi-focal visual evoked potential), thickness of retinal layers such as retinal nerve fiber layer or retinal ganglion cell layer (e.g., as measured by spectral domain optical coherence tomography), visual function (e.g., as measured by visual acuity, e.g., low contrast or high contrast letter acuity), or visual quality of life (e.g., as measured by a patient reported outcome test, e.g., a NIH-NEI visual functional questionnaire or a neuro-ophthalmic supplement, NOS-10).

As used herein, "normal" eye (e.g., a "normal fellow eye") is an eye in a subject that does not show one or more symptoms of an optic nerve condition or disorder, e.g., optic neuritis, e.g., acute optic neuritis.

As used herein, multiple sclerosis is "treated," "inhibited," or "reduced," if recurrence or relapse of the disease is reduced, slowed, delayed, or prevented. Exemplary clinical symptoms of multiple sclerosis that can be used to aid in determining the disease status in a subject can include e.g., tingling, numbness, muscle weakness, loss of balance, blurred or double vision, slurred speech, sudden onset paralysis, lack of coordination, cognitive difficulties, fatigue, heat sensitivity, spasticity, dizziness, tremors, gait abnormalities, speech/swallowing difficulties, and extent of lesions assessed by imaging techniques, e.g., MRI. Clinical signs of MS are routinely classified and standardized, e.g., using an EDSS rating system based on neurological examination and long distance ambulation. For the lower end of the scale (1-5.5) a decrease of one full step indicates an effective MS treatment (Kurtzke, Ann. Neurol. 36:573-79, 1994), while an increase of one full step will indicate the progression or worsening of the disease (e.g., exacerbation). For the higher end of the scale (5-7), a half a point typically indicates improvement (a reduction) or worsening (an increase).

As used herein, the "Expanded Disability Status Scale" or "EDSS" is intended to have its customary meaning in the medical practice. EDSS is a rating system that is frequently used for classifying and standardizing MS. The accepted scores range from 0 (normal) to 10 (death due to MS). Typically patients having an EDSS score of about 4-6 will have moderate disability (e.g., limited ability to walk), whereas patients having an EDSS score of about 7 or 8 will have severe disability (e.g., will require a wheelchair). More specifically, EDSS scores in the range of 1-3 refer to an MS patient who is fully ambulatory, but has some signs in one or more functional systems; EDSS scores in the range higher than 3 to 4.5 show moderate to relatively severe disability; an EDSS score of 5 to 5.5 refers to a disability impairing or precluding full daily activities; EDSS scores of 6 to 6.5 refer to an MS patient requiring intermittent to constant, or unilateral to bilateral constant assistance (cane, crutch or brace) to walk; EDSS scores of 7 to 7.5 means that the MS patient is unable to walk beyond five meters even with aid, and is essentially restricted to a wheelchair; EDSS scores of 8 to 8.5 refer to patients that are restricted to bed; and EDSS scores of 9 to 10 mean that the MS patient is confined to bed, and progressively is unable to communicate effectively or eat and swallow, until death due to MS.

As used herein, a "disease progression" includes a measure (e.g., one or more measures) of a worsening of one or more symptoms and/or disability in a subject. In certain embodiments, disease progression is evaluated as a steady worsening of one or more symptoms and/or disability over time, as opposed to a relapse, which is relatively short in duration. In certain embodiments, the disease progression is evaluated in a subject with a relapsing form of MS (e.g., RRMS) or a progressive form of MS (e.g., a subject with primary or secondary progressive multiple sclerosis (PPMS or SPMS, respectively), or a subject with progressive-relapsing MS (PRMS)).

In certain embodiments, the disease progression is evaluated in a subject with an optic nerve condition or disorder, e.g., optic neuritis, e.g., acute optic neuritis, e.g., in one or both eyes. In some embodiments, the evaluation of disease progression includes a measure of a clinical symptom or outcome of acute optic neuritis described herein.

In other embodiments, the evaluation of disease progression includes a measure of upper extremity function (e.g., a 9HP assessment). Alternatively or in combination, disease progression includes a measure of lower extremity function. Alternatively or in combination, disease progression includes a measure of ambulatory function, e.g., short distance ambulatory function (e.g., T25FW). Alternatively or in combination, disease progression includes a measure of ambulatory function, e.g., longer distance ambulatory function (e.g., a 6-minute walk test). In one embodiment, the disease progression includes a measure of ambulatory function other than EDSS ambulatory function. In one embodiment, disease progression includes a measure of upper extremity function (e.g., a 9HP assessment) and a measure of ambulatory function, e.g., short distance ambulatory function (e.g., T25FW). In one embodiment, disease progression includes a measure of upper extremity function (e.g., a 9HP assessment) and a measure of lower extremity function. In one embodiment, disease progression includes a measure of upper extremity function (e.g., a 9HP assessment), a measure of lower extremity function, and a measure of ambulatory function, e.g., short distance ambulatory function (e.g., T25FW) and/or longer distance ambulatory function (e.g., a timed (e.g., 6-minute) walk test (e.g., 6MWT)). In one embodiment, one, two or the combination of the T25FW, 6MWT and 9HP assessments can be used to acquire a disease progression value. The measure of ambulatory function (e.g., short distance ambulatory function (e.g., T25FW) or longer distance ambulatory function (e.g., a timed (e.g., 6-minute) walk test (e.g., 6MWT)) and/or measure of upper extremity function (e.g., a 9HP assessment) can further be used in combination with the EDSS to evaluate MS, e.g., progressive forms of MS.

In one embodiment, a progressor is a subject who possesses a disease progression value reflecting at least one, two or all of the following criteria:

a. confirmed progression in T25FW: Time taken for 25-foot walk increased by at least 15% or 20% of the baseline walk, confirmed at a second time point at least 3, 4, 5, or 6 months apart;

b. confirmed progression in a timed (e.g., 6-minute) walk test (e.g., 6MWT): Time taken for walk increased by at least 10%, 15% or 20% of the baseline walk, confirmed at a second time point at least 3, 4, 5, or 6 months apart;

c. confirmed progression in 9HP: Time taken for 9-hole peg increased by at least 15% or 20% of the time taken at baseline, confirmed at a second time point at least 3, 4, 5, or 6 months apart. The progression in 9HP can occur on either hand, but will have to be confirmed on the same hand; and/or d. confirmed progression in EDSS:

(i) EDSS total score increase from baseline by at least 1 point, if the change in EDSS total score is determined (or primarily determined) by evaluating a change in neurological function (e.g., one or more changes in neurological systems); and/or (ii) EDSS total score increased from baseline by at least 0.5 point if the change in EDSS total score is determined (or primarily determined) by a change in ambulatory function, if either or both of (i) or (ii) is/are confirmed on a second examination at least 3, 4, 5 or 6 months apart (typically, at least 6 months apart).

Baseline values for the aforementioned tests (e.g., T25FW, 6MWT, EDSS, or 9HP) can be determined using the best baseline value or the average baseline value.

"Baseline," as used herein, refers to a value or measurement prior to administration of a therapy, e.g., a therapy described herein. In embodiments, "baseline" with respect to a "fellow eye" refers to a value or measurement of the eye of a subject other than the affected eye (e.g., affected by an optic nerve condition or disorder, e.g., optic neuritis), prior to administration of a therapy, e.g., a therapy described herein.

"Responsiveness," to "respond" to a treatment, and other forms of this term, as used herein, refer to the reaction of a subject to treatment with a therapy as described. As an example, an MS subject responds to therapy if at least one symptom of multiple sclerosis (e.g., disease worsening) in the subject is reduced or retarded by about 10%, 20%, 30%, 40%, 50%, 60%, 70%, 80%, 90% or more. In another example, an MS subject responds to a therapy, if at least one symptom of multiple sclerosis in the subject is reduced by about 5%, 10%, 20%, 30%, 40%, 50% or more as determined by any appropriate measure, e.g., one or more of: a measure of upper or lower extremity function, a measure of ambulatory function, or an assessment of Expanded Disability Status Scale (EDSS). In another example, an MS subject responds to treatment with a therapy, if the subject has an increased time to progression. Several methods can be used to determine if a patient responds to a treatment including the assessments described herein, as set forth herein.

In certain embodiments, an improvement in the subject is defined by one or more of:

a. ≥1.0 point decrease in EDSS from a baseline score of ≤6.0;

b. ≥15% improvement from baseline in T25FW;

c. ≥15% improvement from baseline in SHPT; or d. ≥10% (e.g., 10%, 12%, 20%, 30%) improvement from baseline in PASAT or SDMT.

As an example, a subject with optic neuritis (e.g., acute optic neuritis) responds to treatment with a therapy if at least one symptom of optic neuritis in the subject is reduced or retarded by about 10%, 20%, 30%, 40%, 50%, 60%, 70%, 80%, 90% or more. In an example, a subject with acute optic neuritis responds to a therapy if at least one symptom of acute optic neuritis in the subject is reduced by about 5%, 10%, 20%, 30%, 40%, 50% or more as determined by any appropriate measure, e.g., one or more of: a measure of optic nerve damage, a measure of optic nerve latency, a measure of thickness of retinal layer, a measure of visual function, or a measure of visual quality of life.

A "non-responder" or "progressor" refers to a subject, e.g., an MS patient or optic neuritis (e.g., acute optic neuritis) patient, if in response to a therapy (e.g., a therapy described herein), at least one symptom or disability of e.g., multiple sclerosis or optic neuritis (e.g., acute optic neuritis), in the subject is reduced by less than about 5%, as determined by any appropriate measure, e.g., one or more of: a measure of upper or lower extremity function, a measure of ambulatory function, a measure of cognitive function, an assessment of Expanded Disability Status Scale (EDSS), a measure of optic nerve damage, a measure of optic nerve latency, a measure of thickness of retinal layer, a measure of visual function, or a measure of visual quality of life.

The methods, compositions and kits disclosed herein encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to a sequence described herein are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%. 91%, 92%, 93%, 94%, 95%, 96%, 97%, 98% or 99% identity to a sequence described herein are termed substantially identical.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS*, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to BMP-10/BMP-10 receptor nucleic acid (SEQ ID NO:1) molecules of the invention. BLAST protein searches can be performed with the XBLAST program, score=50, wordlength=3 to obtain amino acid sequences homologous to BMP-10/BMP-10 receptor (SEQ ID NO:1) protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

Also included are fragments, derivatives, analogs, or variants of the polypeptides, and any combination thereof. The terms "fragment," "variant," "derivative" and "analog" include any polypeptides which retain at least some of the properties of the corresponding native polypeptide. Fragments of polypeptides include proteolytic fragments, as well as deletion fragments. Variants of polypeptides include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions.

The term "functional variant" refers polypeptides that have a substantially identical amino acid sequence to the naturally-occurring sequence, or are encoded by a substantially identical nucleotide sequence, and are capable of having one or more activities of the naturally-occurring sequence.

Derivatives of polypeptides are polypeptides which have been altered so as to exhibit additional features not found on the native polypeptide. Examples include fusion proteins.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Various aspects of the invention are described in further detail below. Additional definitions are set out throughout the specification.

Reparative Agents

Methods, composition and kits described herein include a combination of a reparative agent (e.g., a LINGO-1 antagonist) and an immunomodulatory agent. In one embodiment, the reparative agent is an antagonist of LRR and Ig domain-containing, Nogo receptor-interacting protein ("LINGO," e.g., LINGO-1). For example, the LINGO-1 antagonist can inhibit or reduce the expression or activity of LINGO-1, e.g., human LINGO-1. In one embodiment, the LINGO-1 antagonist inhibits or reduces the formation and/or activity of a complex (e.g., a functional signaling complex) of the NgR1, p75, and LINGO-1; and/or NgR1, TAJ (TROY), and LINGO-1. In another embodiment, the LINGO-1 antagonist inhibits or reduces LINGO-1 binding to NgR1.

LINGO-1 and LINGO-1 Antagonists

LINGO-1, previously called Sp35, is a cell surface glycoprotein that is selectively expressed in the adult CNS in neurons and oligodendrocytes. LINGO-1 is a member of a protein family comprising 3 other paralogs: LINGO-2 (GI: 12309630, 61% protein identity), LINGO-3 (GI: 23342615, 56% identity) and LINGO-4 (GI: 21211752, 44% identity). LINGO-1 is highly conserved evolutionarily with human and mouse orthologues sharing 99.5% identity. By Northern blot analysis, LINGO-1 was found to be highly expressed in human brain and was not detectable in non-neural tissues (Barrette et al. (2007) *Mol Cell Neurosci*, 34: 519-38; Carim-Todd et al. (2003) *Eur Journal Neurosci*, 18: 3167-82; Llorens et al. (2008) *Dev Neurobiol*, 68: 521-41; Mi et al. (2004) *Nat Neurosci*, 7: 221-8; Okafuji et al. (2005) *Gene Expr Patterns*, 6: 57-62; Park et al. (2006) *Neurosci Lett*, 404: 61-6; Shao et al. (2005) *Neuron*, 45: 353-9). LINGO-1 has also been described in detail in International Applications PCT/US2006/026271, filed Jul. 7, 2006, PCT/US2004/008323, filed Mar. 17, 2004, PCT/US2005/022881, filed Jun. 24, 2005 and PCT/US2008/000316, filed Jan. 9, 2008, each of which is incorporated by reference in its entirety herein.

LINGO-1 is selectively expressed in both oligodendrocyte precursor cells (OPCs) and neurons. LINGO-1 functions as a negative regulator of oligodendrocyte differentiation myelination, and remyelination; preventing myelination of axons by oligodendrocytes (Lee et al. (2007) *J Neurosci,* 27: 220-5; Mi et al. (2005) *Nat Neurosci,* 8: 745-51; Mi et al. (2008) *Int Journal Biochem Cell Biol* 40(10):1971-8; Mi et al. (2009) *Ann Neurology,* 65: 304-15). Axonal and neuronal expression of LINGO-1 increases after injury (Ji et al. (2006) *Mol Cell Neurosci,* 33: 311-20). LINGO-1 expression prevents myelination of axons by oligodendrocytes. Several preclinical studies have demonstrated the potential for LINGO-1 antagonism to enhance CNS remyelination and neuroaxonal protection in animal models of toxic (Cuprizone) (Mi et al. (2009) *Ann Neurology,* 65: 304-15), chemical injury (lysophosphatidylcholine [LPC]), and inflammatory (myelin oligodendrocyte glycoprotein-experimental autoimmune encephalomyelitis [MOG-EAE]) [Mi et al. (2007) *Nat Med,* 13: 1228-33) demyelination; and of toxic (1-methyl-4-phenyl-1,2,3,6-tetrahydropyridine [MPTP]) neuronal injury (Inoue et al. (2007) *Proc Natl Acad Sci,* 104: 14430-5), traumatic/hypertensive optic nerve injury (Fu et al. (2008) *Invest Opthalmol Vis Sci,* 49: 975-85) and spinal cord injury (Ji et al. (2006) *Mol Cell Neurosci,* 33: 311-20; Ji et al. (2008) *Mol Cell Neurosci,* 39: 258-67; Lv et al. (2010) *Neuroimmunomodulat,* 17: 270-8). Remyelination and neuroaxonal protection can be provided via blockade of signaling by myelin debris and/or sulfated proteoglycans on the NgR1 receptor complex in the CNS caused by the inhibition of LINGO-1 in axons and oligodendroyctes. This in turn may enhance remyelination via differentiation of oligodendrocyte precursor cells (OPCs) normally present in the brain of MS patients. Thus, antagonism of LINGO-1 can enhance myelination or re-myelination of axons, e.g., by oligodendrocytes, and enhance neuroaxonal protection in the CNS, and for example, in CNS demyelinating diseases such as multiple sclerosis (MS) and acute optic neuritis, leading to improved CNS repair.

LINGO-1 is also known in the art by the names LRRN6, LRRN6A, FLJ14594, LERN1, MGC17422 and UNQ201. The human, full-length wild-type LINGO-1 polypeptide contains an LRR domain consisting of 14 leucine-rich repeats (including N- and C-terminal caps), an Ig domain, a transmembrane region, and a cytoplasmic domain. The cytoplasmic domain contains a canonical tyrosine phosphorylation site. In addition, the naturally occurring LINGO-1 protein contains a signal sequence, a short basic region between the LRR-C-terminal domain (LRRCT) and Ig domain, and a transmembrane region between the Ig domain and the cytoplasmic domain. The human LINGO-1 gene (SEQ ID NO:52) contains alternative translation start codons, so that six additional amino acids, i.e., MQVSKR (SEQ ID NO:87) may or may not be present at the N-terminus of the LINGO-1 signal sequence. Table 2 lists the LINGO-1 domains and other regions, according to amino acid residue number, based on the LINGO-1 amino acid sequence presented herein as SEQ ID NO: 51. The LINGO-1 polypeptide is characterized in more detail in PCT Publication No. WO 2004/085648, which is incorporated herein by reference in its entirety.

TABLE 2

LINGO-1 Domains

| Domain or Region | Beginning Residue | Ending Residue |
|---|---|---|
| Signal Sequence | 1 | 33 or 35 |
| LRRNT | 34 or 36 | 64 |

TABLE 2-continued

LINGO-1 Domains

| Domain or Region | Beginning Residue | Ending Residue |
|---|---|---|
| LRR | 66 | 89 |
| LRR | 90 | 113 |
| LRR | 114 | 137 |
| LRR | 138 | 161 |
| LRR | 162 | 185 |
| LRR | 186 | 209 |
| LRR | 210 | 233 |
| LRR | 234 | 257 |
| LRR | 258 | 281 |
| LRR | 282 | 305 |
| LRR | 306 | 329 |
| LRR | 330 | 353 |
| LRRCT | 363 | 414 or 416 |
| Basic | 415 or 417 | 424 |
| Ig | 419 | 493 |
| Connecting sequence | 494 | 551 |
| Transmembrane | 552 | 576 |
| Cytoplasmic | 577 | 614 |

Tissue distribution and developmental expression of LINGO-1 has been studied in humans and rats. LINGO-1 biology has been studied in an experimental animal (rat) model. Expression of rat LINGO-1 is localized to neurons and oligodendrocytes, as determined by northern blot and immuno-histochemical staining. Rat LINGO-1 mRNA expression level is regulated developmentally, peaking shortly after birth, i.e., ca. postnatal day one. In a rat spinal cord transection injury model, LINGO-1 is up-regulated at the injury site, as determined by RT-PCR. See Mi et al. *Nature Neurosci.* 7:221-228 (2004).

In the context of the amino acids comprising the various structural and functional domains of a LINGO-1 polypeptide, the term "about" includes the particularly recited value and values larger or smaller by several (e.g., 10, 9, 8, 7, 6, 5, 4, 3, 2, or 1) amino acids. Since the location of these domains as listed in Table 2 have been predicted by computer graphics, one of ordinary skill would appreciate that the amino acid residues constituting the domains may vary slightly (e.g., by about 1 to 15 residues) depending on the criteria used to define the domain.

Full-length, wild-type LINGO-1 binds to NgR1. See PCT Publication No. WO 2004/085648. LINGO-1 is expressed in oligodendrocytes and that the LINGO-1 protein is involved in the regulation of oligodendrocyte-mediated myelination of axons. See U.S. Patent Publication No. 2006/0009388 A1, which is incorporated herein by reference in its entirety.

The nucleotide sequence for the full-length LINGO-1 molecule is as follows:

(SEQ ID NO: 52)
ATGCTGGCGGGGGGCGTGAGGAGCATGCCCAGCCCCCTCCTGGCCTGCTG

GCAGCCCATCCTCCTGCTGGTGCTGGGCTCAGTGCTGTCAGGCTCGGCCA

CGGGCTGCCCGCCCCGCTGCGAGTGCTCCGCCCAGGACCGCGCTGTGCTG

TGCCACCGCAAGCGCTTTGTGGCAGTCCCCGAGGGCATCCCCACCGAGAC

GCGCCTGCTGGACCTAGGCAAGAACCGCATCAAAACGCTCAACCAGGACG

AGTTCGCCAGCTTCCCGCACCTGGAGGAGCTGGAGCTCAACGAGAACATC

GTGAGCGCCGTGGAGCCCGGCGCCTTCAACAACCTCTTCAACCTCCGGAC

GCTGGGTCTCCGCAGCAACCGCCTGAAGCTCATCCCGCTAGGCGTCTTCA

```
CTGGCCTCAGCAACCTGACCAAGCTGGACATCAGCGAGAACAAGATTGTT

ATCCTGCTGGACTACATGTTTCAGGACCTGTACAACCTCAAGTCACTGGA

GGTTGGCGACAATGACCTCGTCTACATCTCTCACCGCGCCTTCAGCGGCC

TCAACAGCCTGGAGCAGCTGACGCTGGAGAAATGCAACCTGACCTCCATC

CCCACCGAGGCGCTGTCCCACCTGCACGGCCTCATCGTCCTGAGGCTCCG

GCACCTCAACATCAATGCCATCCGGGACTACTCCTTCAAGAGGCTCTACC

GACTCAAGGTCTTGGAGATCTCCCACTGGCCCTACTTGGACACCATGACA

CCCAACTGCCTCTACGGCCTCAACCTGACGTCCCTGTCCATCACACACTG

CAATCTGACCGCTGTGCCCTACCTGGCCGTCCGCCACCTAGTCTATCTCC

GCTTCCTCAACCTCTCCTACAACCCCATCAGCACCATTGAGGGCTCCATG

TTGCATGAGCTGCTCCGGCTGCAGGAGATCCAGCTGGTGGGCGGGCAGCT

GGCCGTGGTGGAGCCCTATGCCTTCCGCGGCCTCAACTACCTGCGCGTGC

TCAATGTCTCTGGCAACCAGCTGACCACACTGGAGGAATCAGTCTTCCAC

TCGGTGGGCAACCTGGAGACACTCATCCTGGACTCCAACCCGCTGGCCTG

CGACTGTCGGCTCCTGTGGGTGTTCCGGCGCCGCTGGCGGCTCAACTTCA

ACCGGCAGCAGCCCACGTGCGCCACGCCCGAGTTTGTCCAGGGCAAGGAG

TTCAAGGACTTCCCTGATGTGCTACTGCCCAACTACTTCACCTGCCGCCG

CGCCCGCATCCGGGACCGCAAGGCCCAGCAGGTGTTTGTGGACGAGGGCC

ACACGGTGCAGTTTGTGTGCCGGGCCGATGGCGACCCGCCGCCCGCCATC

CTCTGGCTCTCACCCCGAAAGCACCTGGTCTCAGCCAAGAGCAATGGGCG

GCTCACAGTCTTCCCTGATGGCACGCTGGAGGTGCGCTACGCCCAGGTAC

AGGACAACGGCACGTACCTGTGCATCGCGGCCAACGCGGGCGGCAACGAC

TCCATGCCCGCCCACCTGCATGTGCGCAGCTACTCGCCCGACTGGCCCCA

TCAGCCCAACAAGACCTTCGCTTTCATCTCCAACCAGCCGGGCGAGGGAG

AGGCCAACAGCACCCGCGCCACTGTGCCTTTCCCCTTCGACATCAAGACC

CTCATCATCGCCACCACCATGGGCTTCATCTCTTTCCTGGGCGTCGTCCT

CTTCTGCCTGGTGCTGCTGTTTCTCTGGAGCCGGGGCAAGGGCAACACAA

AGCACAACATCGAGATCGAGTATGTGCCCCGAAAGTCGGACGCAGGCATC

AGCTCCGCCGACGCGCCCCGCAAGTTCAACATGAAGATGATATGA.
```

The polypeptide sequence for the full-length LINGO-1 polypeptide is as follows:

```
                                        (SEQ ID NO: 51)
MLAGGVRSMPSPLLACWQPILLLVLGSVLSGSATGCPPRCECSAQDRAVL

CHRKRFVAVPEGIPTETRLLDLGKNRIKTLNQDEFASFPHLEELELNENI

VSAVEPGAFNNLFNLRTLGLRSNRLKLIPLGVFTGLSNLTKLDISENKIV

ILLDYMFQDLYNLKSLEVGDNDLVYISHRAFSGLNSLEQLTLEKCNLTSI

PTEALSHLHGLIVLRLRHLNINAIRDYSFKRLYRLKVLEISHWPYLDTMT

PNCLYGLNLTSLSITHCNLTAVPYLAVRHLVYLRFLNLSYNPISTIEGSM

LHELLRLQEIQLVGGQLAVVEPYAFRGLNYLRVLNVSGNQLTTLEESVFH

SVGNLETLILDSNPLACDCRLLWVFRRRWRLNFNRQQPTCATPEFVQGKE

FKDFPDVLLPNYFTCRRARIRDRKAQQVFVDEGHTVQFVCRADGDPPPAI

LWLSPRKHLVSAKSNGRLTVFPDGTLEVRYAQVQDNGTYLCIAANAGGND

SMPAHLHVRSYSPDWPHQPNKTFAFISNQPGEGEANSTRATVPFPFDIKT

LIIATTMGFISFLGVVLFCLVLLFLWSRGKGNTKHNIEIEYVPRKSDAGI

SSADAPRKFNMKMI.
```

Anti-LINGO-1 Antibody Molecules

In certain embodiments the antibody molecule binds to LINGO, e.g., human LINGO. In another embodiment, the antibody molecule binds to LINGO-1, e.g., human LINGO-1. In one embodiment, the antibody molecule is isolated, purified or recombinant. By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

As used herein, the term "antibody molecule" refers to a protein comprising at least one immunoglobulin variable domain sequence. The term antibody molecule includes, for example, full-length antibodies, mature antibodies, fragments, e.g., antigen-binding fragments of an antibody, derivatives, analogs, or variants of the antibodies disclosed herein, and any combination thereof.

The terms "fragment," "variant," "derivative" and "analog" when referring to LINGO-1 antibody molecules or antibody polypeptides include any polypeptides which retain at least some of the antigen-binding properties of the corresponding native antibody or polypeptide. Fragments of polypeptides include proteolytic fragments, as well as deletion fragments, in addition to specific antibody fragments discussed elsewhere herein. Variants of LINGO-1 antibody and antibody polypeptides include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions. Derivatives of LINGO-1 antibody molecules and antibody polypeptides are polypeptides which have been altered so as to exhibit additional features not found on the native polypeptide. Examples include fusion proteins.

As used herein a "derivative" of a LINGO-1 antibody molecule or antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

For example, an antibody molecule can include a heavy (H) chain variable domain sequence (abbreviated herein as VH), and a light (L) chain variable domain sequence (abbreviated herein as VL). In another example, an antibody molecule includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The antibody molecules can be monoclonal or polyclonal. The antibody can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda.

Examples of antigen-binding fragments include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments are obtained using conventional techniques known to those with skill in the art, and the fragments are screened for utility in the same manner as are intact antibodies.

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. In one aspect of the invention, a single domain antibody can be derived from a variable region of the immunoglobulin found in fish, such as, for example, that which is derived from the immunoglobulin isotype known as Novel Antigen Receptor (NAR) found in the serum of shark. Methods of producing single domain antibodies derived from a variable region of NAR ("IgNARs") are described in WO 03/014161 and Streltsov (2005) *Protein Sci.* 14:2901-2909. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

The VH and VL regions can be subdivided into regions of hypervariability, termed "complementarity determining regions" (CDR), interspersed with regions that are more conserved, termed "framework regions" (FR). The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., *Protein Sequence and Structure Analysis of Antibody Variable Domains.* In: Antibody Engineering Lab Manual (Ed.: Duebel, S. and Kontermann, R., Springer-Verlag, Heidelberg). Generally, unless specifically indicated, the following definitions are used: AbM definition of CDR1 of the heavy chain variable domain and Kabat definitions for the other CDRs. In addition, embodiments of the invention described with respect to Kabat or AbM CDRs may also be implemented using Chothia hypervariable loops. Each VH and VL typically includes three CDRs and four FRs, arranged from amino-terminus to carboxy-terminus in the following order: FR1, CDR1, FR2, CDR2, FR3, CDR3, FR4.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding site" refers to the part of an antibody molecule that comprises determinants that form an interface that binds to LINGO-1, or an epitope thereof. With respect to proteins (or protein mimetics), the antigen-binding site typically includes one or more loops (of at least four amino acids or amino acid mimics) that form an interface that binds to LINGO-1. Typically, the antigen-binding site of an antibody molecule includes at least one or two CDRs, or more typically at least three, four, five or six CDRs.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.*, 32:180-190 (1990)) and also because of potential allergic reactions (see, e.g., LoBuglio et al., *Hybridoma*, 5:5117-5123 (1986)).

In certain embodiments, the antibody molecule can be a monoclonal or single specificity antibody, or an antigen-binding fragment thereof (e.g., an Fab, F(ab')$_2$, Fv, a single chain Fv fragment, a single domain antibody, a diabody (dAb), a bivalent or bispecific antibody or fragment thereof, a single domain variant thereof) that binds to LINGO-1, e.g., a mammalian (e.g., human LINGO-1 (or a functional variant thereof)). In one embodiment, the antibody molecule is a monoclonal antibody against LINGO-1, e.g., human LINGO-1. Typically, the antibody molecule is a human, humanized, a CDR-grafted, chimeric, camelid, or in vitro generated antibody to human LINGO-1 (or functional fragment thereof, e.g., an antibody fragment as described herein). Typically, the antibody inhibits, reduces or neutralizes one or more activities of LINGO-1 (e.g., one or more biological activities of LINGO-1 as described herein).

In certain embodiments, the antibody molecule specifically binds to the same, or substantially the same, LINGO-1 epitope as the reference monoclonal antibody Li62 or Li81, described in U.S. Pat. No. 8,058,406, incorporated by reference in its entirety herein. Exemplary anti-LINGO-1 antibody molecules are described in U.S. Pat. No. 8,058,406. In one embodiment, antibody molecule includes at least the antigen-binding domains of Li62, Li81. As used herein, the term "antigen binding domain" includes a site that specifically binds an epitope on an antigen (e.g., an epitope of LINGO-1). The antigen binding domain of an antibody typically includes at least a portion of an immunoglobulin heavy chain variable region and at least a portion of an immunoglobulin light chain variable region. The binding site formed by these variable regions determines the specificity of the antibody.

In other embodiments, the anti-LINGO-1 antibody molecule competitively inhibits Li62 or Li81 from binding to LINGO-1.

In certain embodiments, the anti-LINGO-1 antibody molecule specifically or preferentially binds to a particular LINGO-1 polypeptide fragment or domain. Such LINGO-1 polypeptide fragments include, but are not limited to, a LINGO-1 polypeptide comprising, consisting essentially of, or consisting of amino acids 34 to 532; 34 to 417; 34 to 425; 34 to 493; 66 to 532; 66 to 417; 66 to 426; 66 to 493; 66 to 532; 417 to 532; 417 to 425 (the LINGO-1 basic region); 417 to 493; 417 to 532; 419 to 493 (the LINGO-11 g region); or 425 to 532 of SEQ ID NO:51; or a LINGO-1 variant polypeptide at least 70%, 75%, 80%, 85%, 90%, or 95% identical to amino acids 34 to 532; 34 to 417; 34 to 425; 34 to 493; 66 to 532; 66 to 417; 66 to 426; 66 to 493; 66 to 532; 417 to 532; 417 to 425 (the LINGO-1 basic region); 417 to 493; 417 to 532; 419 to 493 (the LINGO-11 g region); or 425 to 532 of SEQ ID NO:51.

In certain embodiments, the anti-LINGO-1 antibody molecule specifically or preferentially binds to a LINGO-1 peptide fragment comprising, consisting essentially of, or consisting of one or more leucine-rich-repeats (LRR) of LINGO-1. Such fragments, include, for example, fragments comprising, consisting essentially of, or consisting of amino acids 66 to 89; 66 to 113; 66 to 137; 90 to 113; 114 to 137; 138 to 161; 162 to 185; 186 to 209; 210 to 233; 234 to 257; 258 to 281; 282 to 305; 306 to 329; or 330 to 353 of SEQ ID NO:51. Corresponding fragments of a variant LINGO-1 polypeptide at least 70%, 75%, 80%, 85%, 90%, or 95% identical to amino acids 66 to 89; 66 to 113; 90 to 113; 114 to 137; 138 to 161; 162 to 185; 186 to 209; 210 to 233; 234 to 257; 258 to 281; 282 to 305; 306 to 329; or 330 to 353 of SEQ ID NO:51 are also contemplated.

In certain embodiments, the anti-LINGO-1 antibody molecule specifically or preferentially binds to a fragment comprising, consisting essentially of, or consisting of one or more cysteine rich regions flanking the LRR of LINGO-1. Such fragments, include, for example, a fragment comprising, consisting essentially of, or consisting of amino acids 34 to 64 of SEQ ID NO:51 (the N-terminal LRR flanking region (LRRNT)), or a fragment comprising, consisting essentially of, or consisting of amino acids 363 to 416 of SEQ ID NO:51 (the C-terminal LRR flanking region (LRRCT)), amino acids Corresponding fragments of a variant LINGO-1 polypeptide at least 70%, 75%, 80%, 85%, 90%, or 95% identical to amino acids 34 to 64 and 363 to 416 of SEQ ID NO:51 are also contemplated.

In certain embodiments, the anti-LINGO-1 antibody molecule specifically or preferentially binds to a fragment comprising, consisting essentially of, or consisting of amino acids 41 to 525 of SEQ ID NO:51; 40 to 526 of SEQ ID NO:51; 39 to 527 of SEQ ID NO:51; 38 to 528 of SEQ ID NO:51; 37 to 529 of SEQ ID NO:51; 36 to 530 of SEQ ID NO:51; 35 to 531 of SEQ ID NO:51; 34 to 531 of SEQ ID NO:51; 46 to 520 of SEQ ID NO:51; 45 to 521 of SEQ ID NO:51; 44 to 522 of SEQ ID NO:51; 43 to 523 of SEQ ID NO:51; and 42 to 524 of SEQ ID NO:51.

In certain embodiments, the anti-LINGO-1 antibody molecule specifically or preferentially binds to a fragment comprising, consisting essentially of, or consisting of amino acids 1 to 33 of SEQ ID NO:51; 1 to 35 of SEQ ID NO:51; 34 to 64 of SEQ ID NO:51; 36 to 64 of SEQ ID NO:51; 66 to 89 of SEQ ID NO:51; 90 to 113 of SEQ ID NO:51; 114 to 137 of SEQ ID NO:51; 138 to 161 of SEQ ID NO:51; 162 to 185 of SEQ ID NO:51; 186 to 209 of SEQ ID NO:51; 210 to 233 of SEQ ID NO:51; 234 to 257 of SEQ ID NO:51; 258 to 281 of SEQ ID NO:51; 282 to 305 of SEQ ID NO:51; 306 to 329 of SEQ ID NO:51; 330 to 353 of SEQ ID NO:51; 363 to 416 of SEQ ID NO:51; 417 to 424 of SEQ ID NO:51; 419 to 493 of SEQ ID NO:51; and 494 to 551 of SEQ ID NO:51.

In certain embodiments, the anti-LINGO-1 antibody molecule specifically or preferentially binds to a fragment comprising, consisting essentially of, or consisting of amino acids 1 to 33 of SEQ ID NO:51; 1 to 35 of SEQ ID NO:51; 1 to 64 of SEQ ID NO:51; 1 to 89 of SEQ ID NO:51; 1 to 113 of SEQ ID NO:51; 1 to 137 of SEQ ID NO:51; 1 to 161 of SEQ ID NO:51; 1 to 185 of SEQ ID NO:51; 1 to 209 of SEQ ID NO:51; 1 to 233 of SEQ ID NO:51; 1 to 257 of SEQ ID NO:51; 1 to 281 of SEQ ID NO:51; 1 to 305 of SEQ ID NO:51; 1 to 329 of SEQ ID NO:51; 1 to 353 of SEQ ID NO:51; 1 to 416 of SEQ ID NO:51; 1 to 424 of SEQ ID NO:51; 1 to 493 of SEQ ID NO:51; 1 to 551 of SEQ ID NO:51; 1 to 531 of SEQ ID NO:51 and 1 to 532 of SEQ ID NO:51.

In certain embodiments, the anti-LINGO-1 antibody molecule specifically or preferentially binds to a fragment comprising, consisting essentially of, or consisting of amino acids 34 to 64 of SEQ ID NO:51; 34 to 89 of SEQ ID NO:51; 34 to 113 of SEQ ID NO:51; 34 to 137 of SEQ ID NO:51; 34 to 161 of SEQ ID NO:51; 34 to 185 of SEQ ID NO:51; 34 to 209 of SEQ ID NO:51; 34 to 233 of SEQ ID NO:51; 34 to 257 of SEQ ID NO:51; 34 to 281 of SEQ ID NO:51; 34 to 305 of SEQ ID NO:51; 34 to 329 of SEQ ID NO:51; 34 to 353 of SEQ ID NO:51; 34 to 416 of SEQ ID NO:51; 34 to 424 of SEQ ID NO:51; 34 to 493 of SEQ ID NO:51; and 34 to 551 of SEQ ID NO:51.

In certain embodiments, the anti-LINGO-1 antibody molecule specifically or preferentially binds to a fragment comprising, consisting essentially of, or consisting of amino acids 34 to 530 of SEQ ID NO:51; 34 to 531 of SEQ ID NO:51; 34 to 532 of SEQ ID NO:51; 34 to 533 of SEQ ID NO:51; 34 to 534 of SEQ ID NO:51; 34 to 535 of SEQ ID NO:51; 34 to 536 of SEQ ID NO:51; 34 to 537 of SEQ ID NO:51; 34 to 538 of SEQ ID NO:51; 34 to 539 of SEQ ID NO:51; 30 to 532 of SEQ ID NO:51; 31 to 532 of SEQ ID NO:51; 32 to 532 of SEQ ID NO:51; 33 to 532 of SEQ ID NO:51; 34 to 532 of SEQ ID NO:51; 35 to 532 of SEQ ID NO:51; 36 to 532 of SEQ ID NO:51; 30 to 531 of SEQ ID NO:51; 31 to 531 of SEQ ID NO:51; 32 to 531 of SEQ ID NO:51; 33 to 531 of SEQ ID NO:51; 34 to 531 of SEQ ID NO:51; 35 to 531 of SEQ ID NO:51; and 36 to 531 of SEQ ID NO:51.

In certain embodiments, the anti-LINGO-1 antibody molecule specifically or preferentially binds to a fragment comprising, consisting essentially of, or consisting of amino acids 36 to 64 of SEQ ID NO:51; 36 to 89 of SEQ ID NO:51; 36 to 113 of SEQ ID NO:51; 36 to 137 of SEQ ID NO:51; 36 to 161 of SEQ ID NO:51; 36 to 185 of SEQ ID NO:51; 36 to 209 of SEQ ID NO:51; 36 to 233 of SEQ ID NO:51; 36 to 257 of SEQ ID NO:51; 36 to 281 of SEQ ID NO:51; 36 to 305 of SEQ ID NO:51; 36 to 329 of SEQ ID NO:51; 36 to 353 of SEQ ID NO:51; 36 to 416 of SEQ ID NO:51; 36 to 424 of SEQ ID NO:51; 36 to 493 of SEQ ID NO:51; and 36 to 551 of SEQ ID NO:51.

In certain embodiments, the anti-LINGO-1 antibody molecule specifically or preferentially binds to a fragments comprising, consisting essentially of, or consisting of amino acids 36 to 530 of SEQ ID NO:51; 36 to 531 of SEQ ID NO:51; 36 to 532 of SEQ ID NO:51; 36 to 533 of SEQ ID NO:51; 36 to 534 of SEQ ID NO:51; 36 to 535 of SEQ ID NO:51; 36 to 536 of SEQ ID NO:51; 36 to 537 of SEQ ID NO:51; 36 to 538 of SEQ ID NO:51; and 36 to 539 of SEQ ID NO:51.

In certain embodiments, the anti-LINGO-1 antibody molecule specifically or preferentially binds to a fragment comprising, consisting essentially of, or consisting of amino acids 417 to 493 of SEQ ID NO:51; 417 to 494 of SEQ ID NO:51; 417 to 495 of SEQ ID NO:51; 417 to 496 of SEQ ID NO:51; 417 to 497 of SEQ ID NO:51; 417 to 498 of SEQ ID NO:51; 417 to 499 of SEQ ID NO:51; 417 to 500 of SEQ ID NO:51; 417 to 492 of SEQ ID NO:51; 417 to 491 of SEQ ID NO:51; 412 to 493 of SEQ ID NO:51; 413 to 493 of SEQ ID NO:51; 414 to 493 of SEQ ID NO:51; 415 to 493 of SEQ ID NO:51; 416 to 493 of SEQ ID NO:51; 411 to 493 of SEQ ID NO:51; 410 to 493 of SEQ ID NO:51; 410 to 494 of SEQ ID NO:51; 411 to 494 of SEQ ID NO:51; 412 to 494 of SEQ ID NO:51; 413 to 494 of SEQ ID NO:51; 414 to 494 of SEQ ID NO:51; 415 to 494 of SEQ ID NO:51; 416 to 494 of SEQ ID NO:51; 417 to 494 of SEQ ID NO:51; and 418 to 494 of SEQ ID NO:51.

In certain embodiments, the anti-LINGO-1 antibody molecule specifically or preferentially binds to a LINGO-1 polypeptide comprising, consisting essentially of, or consisting of peptides of the Ig domain of LINGO-1 or fragments, variants, or derivatives of such polypeptides. Specifically, polypeptides comprising, consisting essentially of, or consisting of the following polypeptide sequences: ITX$_1$X$_2$X$_3$ (SEQ ID NO:88), ACX$_1$X$_2$X$_3$ (SEQ ID NO:89), VCX$_1$X$_2$X$_3$ (SEQ ID NO:90) and SPX$_1$X$_2$X$_3$ (SEQ ID NO:91) where X$_1$ is lysine, arginine, histidine, glutamine, or asparagine, X$_2$ is lysine, arginine, histidine, glutamine, or asparagine and X$_3$ is lysine, arginine, histidine, glutamine, or asparagine. For example, LINGO-1 peptide fragments to which certain antibody molecules can bind include, those fragments comprising, consisting essentially of, or consisting of the following polypeptide sequences: SPRKH (SEQ ID NO:92), SPRKK (SEQ ID NO:93), SPRKR (SEQ ID NO:94), SPKKH (SEQ ID NO:95), SPHKH (SEQ ID NO:96), SPRRH (SEQ ID NO:97), SPRHH (SEQ ID NO:98), SPRRR (SEQ ID NO:99), SPHHH (SEQ ID NO:100) SPKKK (SEQ ID NO:101), LSPRKH (SEQ ID NO:102), LSPRKK (SEQ ID NO:103), LSPRKR (SEQ ID NO:104), LSPKKH (SEQ ID NO:105), LSPHKH (SEQ ID NO:106), LSPRRH (SEQ ID NO:107), LSPRHH (SEQ ID NO:108), LSPRRR (SEQ ID NO:109), LSPHHH (SEQ ID NO:110) LSPKKK (SEQ ID NO:111), WLSPRKH (SEQ ID NO:112), WLSPRKK (SEQ ID NO:113), WLSPRKR (SEQ ID NO:114), WLSPKKH (SEQ ID NO:115), WLSPHKH (SEQ ID NO:116), WLSPRRH (SEQ ID NO:117), WLSPRHH (SEQ ID NO:118), WLSPRRR (SEQ ID NO:119), WLSPHHH (SEQ ID NO:120) WLSPKKK (SEQ ID NO:121). These LINGO-1 polypeptides include the basic "RKH loop" (Arginine-Lysine-Histidine amino acids 456-458) in the Ig domain of LINGO-1. Additional LINGO-1 peptides which include a basic tripeptide are ITPKRR (SEQ ID NO:122), ACHHK (SEQ ID NO:123) and VCHHK (SEQ ID NO:124).

In certain embodiments, the anti-LINGO-1 antibody molecule specifically or preferentially binds to a LINGO-1 polypeptide comprising, consisting essentially of, or consisting of peptides of the Ig domain of LINGO-1 or fragments, variants, or derivatives of such polypeptides. Specifically, peptides comprising, consisting essentially of, or consisting of the following polypeptide sequences: X$_4$X$_5$RKH (SEQ ID NO:125), X$_4$X$_5$RRR (SEQ ID NO:126), X$_4$X$_5$KKK (SEQ ID NO:127), X$_4$X$_5$HHH (SEQ ID NO:128), X$_4$X$_5$RKK (SEQ ID NO:129), X$_4$X$_5$RKR (SEQ ID NO:130), X$_4$X$_5$KKH (SEQ ID NO:131), X$_4$X$_5$HKH (SEQ ID NO:132), X$_4$X$_5$RRH (SEQ ID NO:133) and X$_4$X$_5$RHH (SEQ ID NO:134) where X$_4$ is any amino acid and X$_5$ is any amino acid.

In certain embodiments, the anti-LINGO-1 antibody molecule specifically or preferentially binds to a LINGO-1 polypeptide comprising, consisting essentially of, or consisting of peptides of the Ig domain of LINGO-1 or fragments, variants, or derivatives of such polypeptides. Specifically, polypeptides comprising, consisting essentially of, or consisting of the following polypeptide sequences: ITX$_6$X$_7$X$_8$ (SEQ ID NO:135), ACX$_6$X$_7$X$_8$ (SEQ ID NO:136), VCX$_6$X$_7$X$_8$ (SEQ ID NO:137) and SPX$_6$X$_7$X$_8$ (SEQ ID NO:138) where X$_6$ is lysine, arginine, histidine, glutamine, or asparagine, X$_7$ is any amino acid and X$_8$ is lysine, arginine, histidine, glutamine, or asparagine. For example, a polypeptide comprising, consisting essentially of, or consisting of the following polypeptide sequence: SPRLH (SEQ ID NO:139).

In certain embodiments, the anti-LINGO-1 antibody molecule specifically or preferentially binds to a LINGO-1 polypeptide comprising, consisting essentially of, or consisting of peptides which contain amino acids 452-458 in the Ig domain of LINGO-1, or derivatives thereof, wherein amino acid 452 is a tryptophan or phenylalanine residue.

In certain embodiments, the anti-LINGO-1 antibody molecule specifically or preferentially binds to a LINGO-1 polypeptide comprising, consisting essentially of, or consisting of peptides of the basic domain of LINGO-1. Specifically, peptides comprising, consisting essentially of, or consisting of the following polypeptide sequences: RRARIRDRK (SEQ ID NO:140), KKVKVKEKR (SEQ ID NO:141), RRLRLRDRK (SEQ ID NO:142), RRGRGRDRK (SEQ ID NO:143) and RRIRARDRK (SEQ ID NO:144).

Additional exemplary soluble LINGO-1 polypeptides and methods and materials for obtaining these molecules for producing antibodies or antibody fragments of the present invention may be found, e.g., in International Patent Application No. PCT/US2004/008323, incorporated herein by reference in its entirety.

Methods of making antibodies are known in the art and described herein. Once antibodies to various fragments of, or to the full-length LINGO-1 without the signal sequence, have been produced, determining which amino acids, or epitope, of LINGO-1 to which the antibody or antigen binding fragment binds can be determined by epitope mapping protocols as described herein as well as methods known in the art (e.g. double antibody-sandwich ELISA as described in "Chapter 11—Immunology," Current Protocols in Molecular Biology, Ed. Ausubel et al., v0.2, John Wiley & Sons, Inc. (1996)). Additional epitope mapping protocols may be found in Morris, G. Epitope Mapping Protocols, New Jersey: Humana Press (1996), which are both incorporated herein by reference in their entireties. Epitope mapping can also be performed by commercially available means (i.e. ProtoPROBE, Inc. (Milwaukee, Wis.)).

Additionally, antibodies produced which bind to any portion of LINGO-1 can then be screened for their ability to act as an antagonist of LINGO-1 and thus promote neurite outgrowth, neuronal and oligodendrocyte survival, proliferation and differentiation, as well as enhance myelination. Antibodies can be screened for oligodendrocyte/neuronal survival for example by using the methods described herein such as in Examples 11 or 12 or as described in PCT/US2008/000316, filed Jan. 9, 2008, and PCT/US2006/026271, filed Jul. 7, 2006, which are incorporated herein by reference in their entireties. Additionally, antibodies can be screened for example by their ability to enhance myelination by using the methods described herein such as in Examples 2, 6, 9, 10, 11 or 13 or as described in PCT/US2008/000316 and/or PCT/US2006/026271. Finally, antibodies can be screened for their ability to promote oligodendrocyte proliferation and differentiation, as well as neurite outgrowth for example by using the methods described herein such as in Examples 4 or 5 or as described in PCT/US2008/000316 and/or PCT/US2006/026271. Other antagonist functions of antibodies of the present invention can be tested using other assays as described in the Examples of U.S. Pat. No. 8,058,406, incorporated by reference herein.

In certain embodiments, the anti-LINGO-1 antibody molecule specifically or preferentially binds to at least one epitope of LINGO-1, where the epitope comprises, consists essentially of, or consists of at least about four to five amino acids of SEQ ID NO:5, at least seven, at least nine, or between at least about 15 to about 30 amino acids of SEQ ID NO:5. The amino acids of a given epitope of SEQ ID NO:51 as described may be, but need not be contiguous or linear. In certain embodiments, the at least one epitope of LINGO-1 comprises, consists essentially of, or consists of a non-linear epitope formed by the extracellular domain of LINGO-1 as expressed on the surface of a cell or as a soluble fragment, e.g., fused to an IgG Fc region. Thus, in certain embodiments the at least one epitope of LINGO-1 comprises, consists essentially of, or consists of at least 4, at least 5, at least 6, at least 7, at least 8, at least 9, at least 10, at least 15, at least 20, at least 25, between about 15 to about 30, or at least 10, 15, 20, 25, 30, 35, 40, 45, 50, 55, 60, 65, 70, 75, 80, 85, 90, 95, or 100 contiguous or non-contiguous amino acids of SEQ ID NO:51, where the non-contiguous amino acids form an epitope through protein folding.

In other embodiments, the anti-LINGO-1 antibody molecule specifically or preferentially binds to at least one epitope of LINGO-1, where the epitope comprises, consists essentially of, or consists of, in addition to one, two, three, four, five, six or more contiguous or non-contiguous amino acids of SEQ ID NO:51 as described above, and an additional moiety which modifies the protein, e.g., a carbohydrate moiety may be included such that the LINGO-1 antibody binds with higher affinity to modified target protein than it does to an unmodified version of the protein. Alternatively, the LINGO-1 antibody does not bind the unmodified version of the target protein at all.

In certain embodiments, the anti-LINGO-1 antibody molecule specifically or preferentially binds to a LINGO-1 polypeptide or fragment thereof, or a LINGO-1 variant polypeptide, with an affinity characterized by a dissociation constant ($K_D$) which is less than the $K_D$ for said reference monoclonal antibody.

In certain embodiments, the anti-LINGO-1 antibody molecule specifically or preferentially binds to at least one epitope of LINGO-1 or fragment or variant described above, i.e., binds to such an epitope more readily than it would bind to an unrelated, or random epitope; binds preferentially to at least one epitope of LINGO-1 or fragment or variant described above, i.e., binds to such an epitope more readily than it would bind to a related, similar, homologous, or analogous epitope; competitively inhibits binding of a reference antibody which itself binds specifically or preferentially to a certain epitope of LINGO-1 or fragment or variant described above; or binds to at least one epitope of LINGO-1 or fragment or variant described above with an affinity characterized by a dissociation constant $K_D$ of less than about $5 \times 10^{-2}$ M, about $10^{-2}$ M, about $5 \times 10^{-3}$ M, about $10^{-3}$ M, about $5 \times 10^{-4}$ M, about $10^{-4}$ M, about $5 \times 10^{-5}$ M, about $10^{-5}$ M, about $5 \times 10^{-6}$ M, about $10^{-6}$ M, about $5 \times 10^{-7}$ M, about $10^{-7}$ M, about $5 \times 10^{-8}$ M, about $10^{-8}$ M, about $5 \times 10^{-9}$ M, about $10^{-9}$ M, about $5 \times 10^{-10}$ M, about $10^{-10 1}$ M, about $5 \times 10^{-11}$ M, about $10^{-11}$ M, about $5 \times 10^{-12}$ M, about $10^{-12}$ M, about $5 \times 10^{-13}$ M, about $10^{-13}$ M, about $5 \times 10^{-14}$ M, about $10^{-14}$ M, about $5 \times 10^{-15}$ M, about $10^{-15}$ M. In a particular aspect, the antibody or fragment thereof preferentially binds to a human LINGO-1 polypeptide or fragment thereof, relative to a murine LINGO-1 polypeptide or fragment thereof.

In other embodiments, the anti-LINGO-1 antibody molecule binds LINGO-1 polypeptides or fragments or variants thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. Alternatively, an antibody, or antigen-binding fragment, variant, or derivative thereof of the invention binds LINGO-1 polypeptides or fragments or variants thereof with an off rate (k(off)) of less than or equal to $5 \times 10^{-4}$ sec$^1$, $10^{-4}$ sec$^1$, $5 \times 10^{-5}$ sec$^1$, or $10^{-5}$ sec$^1$, $5 \times 10^{-6}$ sec$^1$, $10^{-6}$ sec$^1$, $5 \times 10^{-7}$ sec$^1$ or $10^{-7}$ sec$^1$.

In other embodiments, the anti-LINGO-1 antibody molecule binds LINGO-1 polypeptides or fragments or variants thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$, $5 \times 10^4$ M$^{-1}$ sec$^{-1}$. Alternatively, the antibody molecule binds LINGO-1 polypeptides or fragments or variants thereof with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, $5 \times 10^6$ M$^{-1}$ sec$^{-1}$, or $10^7$ M$^{-1}$ sec$^{-1}$, $5 \times 10^7$ M$^{-1}$ sec$^{-1}$.

In other embodiments, the LINGO-1 antibody molecule is an antagonist of LINGO-1 activity. In certain embodiments, for example, binding of an antagonist LINGO-1 antibody to LINGO-1, as expressed on neurons, blocks myelin-associated neurite outgrowth inhibition or neuronal cell death. In other embodiments, binding of the LINGO-1 antibody to LINGO-1, as expressed on oligodendrocytes, blocks inhibition of oligodendrocyte growth or differentiation, or blocks demyelination or dysmyelination of CNS neurons.

Modified forms of LINGO-1 antibody molecules can be made from whole precursor or parent antibodies using techniques known in the art. Exemplary techniques are discussed in more detail herein.

In certain embodiments, the antibody molecule can be recombinantly produced, e.g., produced by phage display or by combinatorial methods. Phage display and combinatorial methods for generating anti-LINGO-1 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the anti-LINGO-1 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. The non-human antibody can be a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An anti-LINGO-1 antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to LINGO-1 or a fragment thereof.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference. Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Humanized antibodies can have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The anti-LINGO-1 antibody can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-

52). The single chain antibody can be dimerized or multimerized to generate multivalent antibodies having specificities for different epitopes of the same target LINGO-1 protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement. In other embodiments the antibody does not; recruit effector cells; or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

LINGO-1 antibody molecules can comprise a constant region which mediates one or more effector functions. For example, binding of the C1 component of complement to an antibody constant region may activate the complement system. Activation of complement is important in the opsonisation and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (also referred to herein as antibody-dependent cell-mediated cytotoxicity, or ADCC), release of inflammatory mediators, placental transfer and control of immunoglobulin production.

In certain embodiments, the anti-LINGO-1 antibody molecule, in which at least a fraction of one or more of the constant region domains has been deleted or otherwise altered so as to provide desired biochemical characteristics such as reduced effector functions, the ability to non-covalently dimerize, increased ability to localize at the site of a tumor, reduced serum half-life, or increased serum half-life when compared with a whole, unaltered antibody of approximately the same immunogenicity. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted.

In certain LINGO-1 antibody molecules, the Fc portion may be mutated to decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, may easily be measured and quantified using well know immunological techniques without undue experimentation.

Exemplary Anti-LINGO-1 Antibody Molecules

In certain embodiments, the anti-LINGO-1 antibody molecules comprise, consist essentially of, or consist of an immunoglobulin heavy chain variable region (VH), where at least one of the CDRs of the heavy chain variable region, or at least two the CDRs of the heavy chain variable region are at least 80%, 85%, 90% or 95% identical to reference heavy chain CDR1, CDR2, or CDR3 amino acid sequences of Li62 or Li81 or variants thereof as described in Table 3. Alternatively, the CDR1, CDR2, and CDR3 regions of the VH are at least 80%, 85%, 90% or 95% identical to reference heavy chain CDR1, CDR2, and CDR3 amino acid sequences of Li62 or Li81 or variants thereof as described in Table 3. Thus, according to this embodiment a heavy chain variable region of the invention has CDR1, CDR2, or CDR3 polypeptide sequences related to the polypeptide sequences shown in Table 3. In certain embodiment, the anti-LINGO-1 antibody molecules comprise, consist essentially of, or consist of the VH polypeptide or a fragment thereof as described in Table 3, or an amino acid sequence at least 80%, 85%, 90% or 95% identical thereto.

TABLE 3

| | LINGO-1 Antibody VH Sequences | | | |
| --- | --- | --- | --- | --- |
| Antibody | VH SEQUENCE | VH CDR1 | VH CDR2 | VH CDR3 |
| Li62 | EVQLLESGGGLVQPGGSLRLSCAASGFTFSIYPMFWV RQAPGKGLEWVSWIGPSGGITKYADSVKGRFTISRD NSKNTLYLQMNSLRAEDTATYYCAREGHNDWYFDL WGRGTLVTVSS (SEQ ID NO: 1) | IYPMF (SEQ ID NO: 2) | WIGPSG GITKYA DSVKG (SEQ ID NO: 3) | EGHND WYFDL (SEQ ID NO: 4) |

TABLE 3-continued

LINGO-1 Antibody VH Sequences

| Antibody | VH SEQUENCE | VH CDR1 | VH CDR2 | VH CDR3 |
|---|---|---|---|---|
| Li62 variant B06 | EVQLLESGGGLVQPGGSLRLSCAASGFTFSIYPMFWVRQAPGKGLEWVSWIGPSGGITKYADSVKGRFTISRDNSKNTLYLQMNSLRAEDTATYYCAREGYYDWYFDQWGRGTLVTVSS (SEQ ID NO: 53) | IYPMF (SEQ ID NO: 2) | WIGPSGGITKYADSVKG (SEQ ID NO: 3) | EGYYDWYFDQ (SEQ ID NO: 17) |
| Li62 variant B12 | EVQLLESGGGLVQPGGSLRLSCAASGFTFSIYPMFWVRQAPGKGLEWVSWIGPSGGITKYADSVKGRFTISRDNSKNTLYLQMNSLRAEDTATYYCAREGQYDWYFDVWGRGTLVTVSS (SEQ ID NO: 54) | IYPMF (SEQ ID NO: 2) | WIGPSGGITKYADSVKG (SEQ ID NO: 3) | EGQYDWYFDV (SEQ ID NO: 18) |
| Li62 variant F06 | EVQLLESGGGLVQPGGSLRLSCAASGFTFSIYPMFWVRQAPGKGLEWVSWIGPSGGITKYADSVKGRFTISRDNSKNTLYLQMNSLRAEDTATYYCAREGDYDWYFDLWGRGTLVTVSS (SEQ ID NO: 55) | IYPMF (SEQ ID NO: 2) | WIGPSGGITKYADSVKG (SEQ ID NO: 3) | EGDYDWYFDL (SEQ ID NO: 19) |
| Li62 variant B01 | EVQLLESGGGLVQPGGSLRLSCAASGFTFSIYPMFWVRQAPGKGLEWVSWIGPSGGITKYADSVKGRFTISRDNSKNTLYLQMNSLRAEDTATYYCAREGQYDWYFELWGRGTLVTVSS (SEQ ID NO: 56) | IYPMF (SEQ ID NO: 2) | WIGPSGGITKYADSVKG (SEQ ID NO: 3) | EGQYDWYFEL (SEQ ID NO: 20) |
| Li62 variant D09 | EVQLLESGGGLVQPGGSLRLSCAASGFTFSIYPMFWVRQAPGKGLEWVSWIGPSGGITKYADSVKGRFTISRDNSKNTLYLQMNSLRAEDTATYYCAREADIDWFFDLWGRGTLVTVSS (SEQ ID NO: 57) | IYPMF (SEQ ID NO: 2) | WIGPSGGITKYADSVKG (SEQ ID NO: 3) | EADIDWFFDL (SEQ ID NO: 21) |
| Li62 variant D12 | EVQLLESGGGLVQPGGSLRLSCAASGFTFSIYPMFWVRQAPGKGLEWVSWIGPSGGITKYADSVKGRFTISRDNSKNTLYLQMNSLRAEDTATYYCAREGHYDWYFDLWGRGTLVTVSS (SEQ ID NO: 58) | IYPMF (SEQ ID NO: 2) | WIGPSGGITKYADSVKG (SEQ ID NO: 3) | EGHYDWYFDL (SEQ ID NO: 22) |
| Li62 variant F01 | EVQLLESGGGLVQPGGSLRLSCAASGFTFSIYPMFWVRQAPGKGLEWVSWIGPSGGITKYADSVKGRFTISRDNSKNTLYLQMNSLRAEDTATYYCAREGRYDWYFDPWGRGTLVTVSS (SEQ ID NO: 59) | IYPMF (SEQ ID NO: 2) | WIGPSGGITKYADSVKG (SEQ ID NO: 3) | EGRYDWYFDP (SEQ ID NO: 23) |
| Li62 variant F02 | EVQLLESGGGLVQPGGSLRLSCAASGFTFSIYPMFWVRQAPGKGLEWVSWIGPSGGITKYADSVKGRFTISRDNSKNTLYLQMNSLRAEDTATYYCAREGDYDWYFGLWGRGTLVTVSS (SEQ ID NO: 60) | IYPMF (SEQ ID NO: 2) | WIGPSGGITKYADSVKG (SEQ ID NO: 3) | EGDYDWYFGL (SEQ ID NO: 24) |
| Li62 variant F06 | EVQLLESGGGLVQPGGSLRLSCAASGFTFSIYPMFWVRQAPGKGLEWVSWIGPSGGITKYADSVKGRFTISRDNSKNTLYLQMNSLRAEDTATYYCAREGRYDWYFDLWGRGTLVTVSS (SEQ ID NO: 61) | IYPMF (SEQ ID NO: 2) | WIGPSGGITKYADSVKG (SEQ ID NO: 3) | EGRYDWYFDL (SEQ ID NO: 25) |
| Li62 variant F10 | EVQLLESGGGLVQPGGSLRLSCAASGFTFSIYPMFWVRQAPGKGLEWVSWIGPSGGITKYADSVKGRFTISRDNSKNTLYLQMNSLRAEDTATYYCARESHIDRYFDLWGRGTLVTVSS (SEQ ID NO: 62) | IYPMF (SEQ ID NO: 2) | WIGPSGGITKYADSVKG (SEQ ID NO: 3) | ESHIDRYFDL (SEQ ID NO: 26) |
| Li62 variant G08 | EVQLLESGGGLVQPGGSLRLSCAASGFTFSIYPMFWVRQAPGKGLEWVSWIGPSGGITKYADSVKGRFTISRDNSKNTLYLQMNSLRAEDTATYYCAREGQYDWYFDVWGRGTLVTVSS (SEQ ID NO: 63) | IYPMF (SEQ ID NO: 2) | WIGPSGGITKYADSVKG (SEQ ID NO: 3) | EGQYDWYFDV (SEQ ID NO: 27) |
| Li62 variant H08 | EVQLLESGGGLVQPGGSLRLSCAASGFTFSIYPMFWVRQAPGKGLEWVSWIGPSGGITKYADSVKGRFTISRDNSKNTLYLQMNSLRAEDTATYYCAREGHYNGYFDLWGRGTLVTVSS (SEQ ID NO: 64) | IYPMF (SEQ ID NO: 2) | WIGPSGGITKYADSVKG (SEQ ID NO: 3) | EGHYNGYFDL (SEQ ID NO: 28) |
| Li62 variant | EVQLLESGGGLVQPGGSLRLSCAASGFTFSIYPMFWVRQAPGKGLEWVSWIGPSGGITKYADSVKGRFTISRD | IYPMF (SEQ | WIGPSGGITKYA | EGYYDWYFDL |

TABLE 3-continued

LINGO-1 Antibody VH Sequences

| Antibody | VH SEQUENCE | VH CDR1 | VH CDR2 | VH CDR3 |
|---|---|---|---|---|
| C10 | NSKNTLYLQMNSLRAEDTATYYCAREGYYDWYFDL WGRGTLVTVSS (SEQ ID NO: 65) | ID NO: 2) | DSVKG (SEQ ID NO: 3) | (SEQ ID NO: 29) |
| Li62 variant C02 | EVQLLESGGGLVQPGGSLRLSCAASGFTFSIYPMFWV RQAPGKGLEWVSWIGPSGGITKYADSVKGRFTISRD NSKNTLYLQMNSLRAEDTATYYCAREGTYDWYLDL WGRGTLVTVSS (SEQ ID NO: 66) | IYPMF (SEQ ID NO: 2) | WIGPSG GITKYA DSVKG (SEQ ID NO: 3) | EGTYD WYLDL (SEQ ID NO: 30) |
| Li62 variant D05 | EVQLLESGGGLVQPGGSLRLSCAASGFTFSIYPMFWV RQAPGKGLEWVSWIGPSGGITKYADSVKGRFTISRD NSKNTLYLQMNSLRAEDTATYYCAREGYYDWYFEL WGRGTLVTVSS (SEQ ID NO: 67) | IYPMF (SEQ ID NO: 2) | WIGPSG GITKYA DSVKG (SEQ ID NO: 3) | EGYYD WYFEL (SEQ ID NO: 31) |
| Li62 variant F02 | EVQLLESGGGLVQPGGSLRLSCAASGFTFSIYPMFWV RQAPGKGLEWVSWIGPSGGITKYADSVKGRFTISRD NSKNTLYLQMNSLRAEDTATYYCAREGLIDWFFDQ WGRGTLVTVSS (SEQ ID NO: 68) | IYPMF (SEQ ID NO: 2) | WIGPSG GITKYA DSVKG (SEQ ID NO: 3) | EGLID WFFDQ (SEQ ID NO: 32) |
| Li62 variant C10 | EVQLLESGGGLVQPGGSLRLSCAASGFTFSIYPMFWV RQAPGKGLEWVSWIGPSGGITKYADSVKGRFTISRD NSKNTLYLQMNSLRAEDTATYYCAREGQFDWYFDL WGRGTLVTVSS (SEQ ID NO: 69) | IYPMF (SEQ ID NO: 2) | WIGPSG GITKYA DSVKG (SEQ ID NO: 3) | EGQFD WYFDL (SEQ ID NO: 33) |
| Li62 variant H08 | EVQLLESGGGLVQPGGSLRLSCAASGFTFSIYPMFWV RQAPGKGLEWVSWIGPSGGITKYADSVKGRFTISRD NSKNTLYLQMNSLRAEDTATYYCAREGTYDWYFDL WGRGTLVTVSS (SEQ ID NO: 70) | IYPMF (SEQ ID NO: 2) | WIGPSG GITKYA DSVKG (SEQ ID NO: 3) | EGTYD WYFDL (SEQ ID NO: 34) |
| Li81 | EVQLLESGGGLVQPGGSLRLSCAASGFTFSAYEMKW VRQAPGKGLEWVSVIGPSGGFTFYADSVKGRFTISRD NSKNTLYLQMNSLRAEDTAVYYCATEGDNDAFDIW GQGTTVTVSS (SEQ ID NO: 5) | AYEM K (SEQ ID NO: 6) | VIGPSG GFTFYA DSVKG (SEQ ID NO: 7) | EGDND AFDI (SEQ ID NO: 8) |
| Li81 variant F09 | EVQLLESGGGLVQPGGSLRLSCAASGFTFSAYEMKW VRQAPGKGLEWVSVIGPSGGFTFYADSVKGRFTISRD NSKNTLYLQMNSLRAEDTAVYYCATEGENDAFDVW GQGTTVTVSS (SEQ ID NO: 71) | AYEM K (SEQ ID NO: 6) | VIGPSG GFTFYA DSVKG (SEQ ID NO: 7) | EGEND AFDV (SEQ ID NO: 35) |
| Li81 variant G02 | EVQLLESGGGLVQPGGSLRLSCAASGFTFSAYEMKW VRQAPGKGLEWVSVIGPSGGFTFYADSVKGRFTISRD NSKNTLYLQMNSLRAEDTAVYYCATEGDNDAYDT WGQGTTVTVSS (SEQ ID NO: 72) | AYEM K (SEQ ID NO: 6) | VIGPSG GFTFYA DSVKG (SEQ ID NO: 7) | EGDND AYDT (SEQ ID NO: 36) |
| Li81 variant H03 | EVQLLESGGGLVQPGGSLRLSCAASGFTFSAYEMKW VRQAPGKGLEWVSVIGPSGGFTFYADSVKGRFTISRD NSKNTLYLQMNSLRAEDTAVYYCATEGTNDAFDIW GQGTTVTVSS (SEQ ID NO: 73) | AYEM K (SEQ ID NO: 6) | VIGPSG GFTFYA DSVKG (SEQ ID NO: 7) | EGTND AFDI (SEQ ID NO: 37) |
| Li81 variant A12 | EVQLLESGGGLVQPGGSLRLSCAASGFTFSAYEMKW VRQAPGKGLEWVSVIGPSGGFTFYADSVKGRFTISRD NSKNTLYLQMNSLRAEDTAVYYCATEGDNDAFDSW GQGTTVTVSS (SEQ ID NO: 74) | AYEM K (SEQ ID NO: 6) | VIGPSG GFTFYA DSVKG (SEQ ID NO: 7) | EGDND AFDS (SEQ ID NO: 38) |
| Li81 variant C02 | EVQLLESGGGLVQPGGSLRLSCAASGFTFSAYEMKW VRQAPGKGLEWVSVIGPSGGFTFYADSVKGRFTISRD NSKNTLYLQMNSLRAEDTAVYYCATEGDNDAFDTW GQGTTVTVSS (SEQ ID NO: 75) | AYEM K (SEQ ID NO: 6) | VIGPSG GFTFYA DSVKG (SEQ ID NO: 7) | EGDND AFDT (SEQ ID NO: 39) |
| Li81 variant C11 | EVQLLESGGGLVQPGGSLRLSCAASGFTFSAYEMKW VRQAPGKGLEWVSVIGPSGGFTFYADSVKGRFTISRD NSKNTLYLQMNSLRAEDTAVYYCATEGDNDAYDR WGQGTTVTVSS (SEQ ID NO: 76) | AYEM K (SEQ ID NO: 6) | VIGPSG GFTFYA DSVKG (SEQ ID NO: 7) | EGDND AYDR (SEQ ID NO: 40) |

TABLE 3-continued

LINGO-1 Antibody VH Sequences

| Antibody | VH SEQUENCE | VH CDR1 | VH CDR2 | VH CDR3 |
|---|---|---|---|---|
| Li81 variant D11 | EVQLLESGGGLVQPGGSLRLSCAASGFTFSAYEMKW VRQAPGKGLEWVSVIGPSGGFTFYADSVKGRFTISRD NSKNTLYLQMNSLRAEDTAVYYCATEGDNDVFDSW GQGTTVTVSS (SEQ ID NO: 77) | AYEMK (SEQ ID NO: 6) | VIGPSG GFTFYA DSVKG (SEQ ID NO: 7) | EGDND VFDS (SEQ ID NO: 41) |
| Li81 variant E05 | EVQLLESGGGLVQPGGSLRLSCAASGFTFSAYEMKW VRQAPGKGLEWVSVIGPSGGFTFYADSVKGRFTISRD NSKNTLYLQMNSLRAEDTAVYYCATEGDDDVFDM WGQGTTVTVSS (SEQ ID NO: 78) | AYEMK (SEQ ID NO: 6) | VIGPSG GFTFYA DSVKG (SEQ ID NO: 7) | EGDDD VFDM (SEQ ID NO: 42) |
| Li81 variant H04 | EVQLLESGGGLVQPGGSLRLSCAASGFTFSAYEMKW VRQAPGKGLEWVSVIGPSGGFTFYADSVKGRFTISRD NSKNTLYLQMNSLRAEDTAVYYCATEGYNDAFDFW GQGTTVTVSS (SEQ ID NO: 79) | AYEMK (SEQ ID NO: 6) | VIGPSG GFTFYA DSVKG (SEQ ID NO: 7) | EGYND AFDF (SEQ ID NO: 43) |
| Li81 variant B04 | EVQLLESGGGLVQPGGSLRLSCAASGFTFSAYEMKW VRQAPGKGLEWVSVIGPSGGFTFYADSVKGRFTISRD NSKNTLYLQMNSLRAEDTAVYYCATEGDDDAYDM WGQGTTVTVSS (SEQ ID NO: 80) | AYEMK (SEQ ID NO: 6) | VIGPSG GFTFYA DSVKG (SEQ ID NO: 7) | EGDDD AYDM (SEQ ID NO: 44) |
| Li81 variant A02 | EVQLLESGGGLVQPGGSLRLSCAASGFTFSAYEMKW VRQAPGKGLEWVSVIGPSGGFTFYADSVKGRFTISRD NSKNTLYLQMNSLRAEDTAVYYCATEQDYDTYDLW GQGTTVTVSS (SEQ ID NO: 81) | AYEMK (SEQ ID NO: 6) | VIGPSG GFTFYA DSVKG (SEQ ID NO: 7) | EQDYD TYDL (SEQ ID NO: 45) |
| Li81 variant B12 | EVQLLESGGGLVQPGGSLRLSCAASGFTFSAYEMKW VRQAPGKGLEWVSVIGPSGGFTFYADSVKGRFTISRD NSKNTLYLQMNSLRAEDTAVYYCATEGDDDAFDTW GQGTTVTVSS (SEQ ID NO: 82) | AYEMK (SEQ ID NO: 6) | VIGPSG GFTFYA DSVKG (SEQ ID NO: 7) | EGDDD AFDT (SEQ ID NO: 46) |
| Li81 variant H06 | EVQLLESGGGLVQPGGSLRLSCAASGFTFSAYEMKW VRQAPGKGLEWVSVIGPSGGFTFYADSVKGRFTISRD NSKNTLYLQMNSLRAEDTAVYYCATEADDDAFDIW GQGTTVTVSS (SEQ ID NO: 83) | AYEMK (SEQ ID NO: 6) | VIGPSG GFTFYA DSVKG (SEQ ID NO: 7) | EADDD AFDI (SEQ ID NO: 47) |
| Li81 variant H08 | EVQLLESGGGLVQPGGSLRLSCAASGFTFSAYEMKW VRQAPGKGLEWVSVIGPSGGFTFYADSVKGRFTISRD NSKNTLYLQMNSLRAEDTAVYYCATEGENDAFDM WGQGTTVTVSS (SEQ ID NO: 84) | AYEMK (SEQ ID NO: 6) | VIGPSG GFTFYA DSVKG (SEQ ID NO: 7) | EGEND AFDM (SEQ ID NO: 48) |
| Li81 variant E07 | EVQLLESGGGLVQPGGSLRLSCAASGFTFSAYEMKW VRQAPGKGLEWVSVIGPSGGFTFYADSVKGRFTISRD NSKNTLYLQMNSLRAEDTAVYYCATEGEYDTYDIW GQGTTVTVSS (SEQ ID NO: 85) | AYEMK (SEQ ID NO: 6) | VIGPSG GFTFYA DSVKG (SEQ ID NO: 7) | EGEYD TYDI (SEQ ID NO: 49) |

In another embodiment, the anti-LINGO-1 antibody molecule includes a polypeptide comprising, consisting essentially of, or consisting of an immunoglobulin heavy chain variable region (VH), wherein at least the CDR3 region is at least 80%, 85%, 90% or 95% identical to a reference CDR3 sequence selected from the group consisting of SEQ ID NOs: 4, 8 and 17-49. In further embodiments, the CDR3 region is identical to a reference CDR3 sequence selected from the group consisting of SEQ ID NOs: 4, 8 and 17-49. In still further embodiments, the anti-LINGO-1 antibody molecule includes a polypeptide comprising, consisting essentially of, or consisting of an immunoglobulin heavy chain variable region (VH), wherein, the CDR1 and CDR2 regions are at least 80%, 85%, 90%, 95% or 100% identical to the CDR1 and CDR2 amino acid sequences of SEQ ID NOs: 2 and 3, respectively, and the CDR3 region is at least 80%, 85%, 90%, 95% or 100% identical to a CDR3 amino acid sequence selected from the group consisting of SEQ ID NOs: 4 and 17-34. In other embodiments, the anti-LINGO-1 antibody molecule includes a polypeptide comprising, consisting essentially of, or consisting of an immunoglobulin heavy chain variable region (VH), wherein the CDR1 and CDR2 regions are at least 80%, 85%, 90%, 95% or 100% identical to the CDR1 and CDR2 amino acid sequences of SEQ ID NOs: 6 and 7, respectively, and the CDR3 region is at least 80%, 85%, 90%, 95% or 100% identical to a CDR3 amino acid sequence selected from the group consisting of SEQ ID NOs: 8 and 35-49.

In another embodiment, the anti-LINGO-1 antibody molecule includes a polypeptide comprising, consisting essentially of, or consisting of an immunoglobulin heavy chain variable region (VH) in which the CDR1, CDR2, and CDR3 regions have polypeptide sequences which are identical to the CDR1, CDR2, and CDR3 groups shown in Table 3. In certain embodiments, the anti-LINGO-1 antibody molecule includes the VH polypeptide specifically or preferentially binds to LINGO-1.

In a further embodiment, the anti-LINGO-1 antibody molecule includes a polypeptide comprising, consisting essentially of, or consisting of a VH polypeptide at least 80%, 85%, 90% 95% or 100% identical to a reference VH polypeptide sequence selected from SEQ ID NOs: 1, 5 and 53-85. In one particular embodiment, the VH polypeptide comprises a CDR3 amino acid sequence selected from the group consisting of SEQ ID NOs: 4, 8 and 17-49.

In certain embodiments, the anti-LINGO-1 antibody molecule includes a polypeptide comprising, consisting essentially of, or consisting of a VH polypeptide selected from the group consisting of SEQ ID NOs: 1, 5 and 53-85. In certain embodiments, an antibody or antigen-binding fragment comprising the VH polypeptide specifically or preferentially binds to LINGO-1.

In another aspect, the anti-LINGO-1 antibody molecule includes a VH comprising the amino acids of SEQ ID NO: 1 or SEQ ID NO: 5. In certain embodiments, an antibody or antigen-binding fragment comprising the VH that specifically or preferentially binds to LINGO-1. In certain embodiments, an antibody or antigen-binding fragment thereof comprising, consisting essentially of, or consisting of a VH that specifically or preferentially binds to the same epitope as Li62, Li81 or a variant thereof as described in Table 3 or will competitively inhibit such a monoclonal antibody from binding to LINGO-1.

In certain embodiments, the anti-LINGO-1 antibody molecule includes a polypeptide, comprising, consisting essentially of, or consisting of an immunoglobulin heavy chain which is identical to the polypeptide of SEQ ID NO:146 except for a replacement of one or more of the following amino acids: W50, P53, I57 and/or W104. In some embodiments, W50 is replaced with an H, F, L, M, G, I, or D residue. In some embodiments, P53 is replaced with an L, S, T, W, or G residue. In some embodiments, I57 is replaced with a G, M, N, H, L, F, W, Y, S, P, V or T residue. In some embodiments, W104 is replaced with a V, H, S, Q, M, L, T, or I residue.

In certain embodiments, the anti-LINGO-1 antibody molecule includes a polypeptide, comprising, consisting essentially of, or consisting of an immunoglobulin heavy chain variable region which is identical to the polypeptide of SEQ ID NO:5 except for a replacement of amino acid P53. In some embodiments, P53 is replaced with an L, S, T, W, or G residue.

In certain embodiments, the anti-LINGO-1 antibody molecule includes a polypeptide, comprising, consisting essentially of, or consisting of an immunoglobulin heavy chain variable region which is identical to the polypeptide of SEQ ID NO:1 except for a replacement of one or more of the following amino acids: W50, P53, I57 and/or W104. In some embodiments, W50 is replaced with an H, F, L, M, G, I, or D residue. In some embodiments, P53 is replaced with an L, S, T, W, or G residue. In some embodiments, I57 is replaced with a G, M, N, H, L, F, W, Y, S, P, V or T residue. In some embodiments, W104 is replaced with a V, H, S, Q, M, L, T, or I residue.

In certain embodiments, the anti-LINGO-1 antibody molecule includes a polypeptide, comprising, consisting essentially of, or consisting of an immunoglobulin heavy chain variable region which is identical to the polypeptide of SEQ ID NO:66 except for a replacement of one or more of the following amino acids: W50, P53, I57 and/or W104. In some embodiments, W50 is replaced with an H, F, L, M, G, I, or D residue. In some embodiments, P53 is replaced with an L, S, T, W, or G residue. In some embodiments, I57 is replaced with a G, M, N, H, L, F, W, Y, S, P, V or T residue. In some embodiments, W104 is replaced with a V, H, S, Q, M, L, T, or I residue.

In certain embodiments, the anti-LINGO-1 antibody molecule includes one or more of the VH polypeptides described above specifically or preferentially binds to the same epitope as Li62, Li81 or a variant thereof as described in Table 3, or can competitively inhibit such an antibody from binding to LINGO-1.

In another embodiment, the anti-LINGO-1 antibody molecule includes a polypeptide comprising, consisting essentially of, or consisting of an immunoglobulin light chain variable region (VL), where at least one of the CDRs of the light chain variable region or at least two of the CDRs of the light chain variable region are at least 80%, 85%, 90% or 95% identical to reference heavy chain CDR1, CDR2, or CDR3 amino acid sequences from monoclonal LINGO-1 antibodies disclosed herein. Alternatively, the CDR1, CDR2 and CDR3 regions of the VL are at least 80%, 85%, 90% or 95% identical to reference light chain CDR1, CDR2, and CDR3 amino acid sequences from monoclonal LINGO-1 antibodies disclosed herein. Thus, according to this embodiment a light chain variable region of the antibody molecule has CDR1, CDR2, and CDR3 polypeptide sequences related to the polypeptides shown in Table 4. In certain embodiments, the anti-LINGO-1 antibody molecule comprising the VL polypeptide specifically or preferentially binds to LINGO-1.

TABLE 4

LINGO-1 Antibody VL Sequences

| Antibody | VL SEQUENCE | VL CDR1 | VL CDR2 | VL CDR3 |
|---|---|---|---|---|
| Li62 | DIQMTQSPSFLSASVGDSVAITCRASQDISRYLAWYQQ RPGKAPKLLIYDASNLQTGVPSRFSGSGSGTDFTFTITS LQPEDFGTYYCQQYDTLHPSFGPGTTVDIK (SEQ ID NO: 9) | RASQD ISRYL A (SEQ ID NO: 10) | DASNL QT (SEQ ID NO: 11) | QQYDT LHPS (SEQ ID NO: 12) |
| Li81 | DIQMTQSPATLSLSPGERATLSCRASQSVSSYLAWYQ QKPGQAPRLLIYDASNRATGIPARFSGSGSGTDFTLTIS SLEPEDFAVYYCQQRSNWPMYTFGQGTKLEIK (SEQ | RASQS VSSYL A (SEQ | DASNR AT (SEQ ID NO: | QQRSN WPMY T (SEQ |

TABLE 4-continued

LINGO-1 Antibody VL Sequences

| Antibody | VL SEQUENCE | VL CDR1 | VL CDR2 | VL CDR3 |
|---|---|---|---|---|
| | ID NO: 13) | ID NO: 14) | 15) | ID NO: 16) |

In another embodiment, the anti-LINGO-1 antibody molecule includes a polypeptide comprising, consisting essentially of, or consisting of an immunoglobulin light chain variable region (VL) in which the CDR1, CDR2, and CDR3 regions have polypeptide sequences which are identical to the CDR1, CDR2, and CDR3 groups shown in Table 4. In certain embodiments, an antibody or antigen-binding fragment comprising the VL polypeptide specifically or preferentially binds to LINGO-1.

In a further embodiment, the anti-LINGO-1 antibody molecule includes a polypeptide comprising, consisting essentially of, or consisting of a VL polypeptide at least 80%, 85%, 90% or 95% identical to a reference VL polypeptide sequence selected from SEQ ID NO: 9 or SEQ ID NO: 13, shown in Table 4. In certain embodiments, the anti-LINGO-1 antibody molecule includes comprising the VL polypeptide specifically or preferentially binds to LINGO-1. In another aspect, the anti-LINGO-1 antibody molecule includes a polypeptide comprising, consisting essentially of, or consisting of a VL polypeptide selected from SEQ ID NO: 9 or SEQ ID NO: 13, shown in Table 4. In certain embodiments, the anti-LINGO-1 antibody molecule comprising the VL polypeptide specifically or preferentially binds to LINGO-1.

In certain embodiments, the anti-LINGO-1 antibody molecule includes a polypeptide consisting essentially of, or consisting of an immunoglobulin light chain which is identical to the polypeptide of SEQ ID NO:145 except for a replacement of amino acid W94. In some embodiments, W94 is replaced with an A, D, L, N, G, Q, V, or S residue.

In certain embodiments, the anti-LINGO-1 antibody molecule includes a polypeptide, comprising, consisting essentially of, or consisting of an immunoglobulin light chain variable region which is identical to the polypeptide of SEQ ID NO:5 except for a replacement of amino acid W94. In some embodiments, W94 is replaced with an A, D, L, N, G, Q, V, or S residue.

In certain embodiments, the anti-LINGO-1 antibody molecule includes a polypeptide comprising, consisting essentially of, one or more of the VL polypeptides described above specifically or preferentially binds to the same epitope as Li62 or Li81, or will competitively inhibit such a monoclonal antibody from binding to LINGO-1.

In other embodiments, the anti-LINGO-1 antibody molecule comprises, consists essentially of or consists of a VH polypeptide, as shown in Table 3, and a VL polypeptide, as shown in Table 4, selected from the group consisting of: i) SEQ ID NO: 1 or SEQ ID NOs: 53-70 and SEQ ID NO: 9; and iii) SEQ ID NO: 5 or SEQ ID NOs: 71-85 and SEQ ID NO: 13.

In some embodiments, the anti-LINGO-1 antibody molecule comprises, consists essentially of or consists of an antibody heavy chain as shown below in SEQ ID NO:86, or an amino acid sequence at least 80%, 85%, 90% or 95% identical thereto.

```
                                          (SEQ ID NO: 86)
EVQLLESGGGLVQPGGSLRLSCAASGFTFSAYEMKWVRQAPGKGLEWVSV

IGPSGGFTFYADISVKGRFTISRDNSKNTLYLQMNSLRAEDTAVYYCATE

GDNDAFDIWGQGTTVTVSSASTKGPISVFPLAPSSKSTSGGTAALGCLVK

DYFPEPVTVSWNSGALTSGVHTFPAVLQSSGLYSLSSVVTIVPSSSLGTQ

TYICNVNHKPSNTKVDKKVEPKSCDKTHTCPPCPAPELLGGPSVFLFPPK

PKDTLIMISRTPEVTCVVVDVSHEDPEVKFNWYVDGVEVHNAKTKPREEQ

YNSTYRVVSVLTVLHQDIWLNGKEYKCKVSNKALPAPIEKTISKAKGQPR

EPQVYTLPPSRDELTKNQVSLTCLVKGFYPSIDIAVEWESNGQPENNYKT

TPPVLDSDGSFFLYSKLTVDKSRWQQGNVFSCSVMHEALHNHYTIQKSLS

LSPG
```

In other embodiments, the anti-LINGO-1 antibody molecule comprises, consists essentially of or consists of an aglycosylated version of an antibody heavy chain. For example, an aglycosylated version of Li81 is described in PCT/US2008/000316, filed Jan. 9, 2008 and U.S. Pat. No. 8,128,926, which are incorporated herein by reference in its entirety. An aglycosylated version of the Li81 antibody was created by changing a single amino acid (T to A) in the Li81 heavy chain sequence. The sequence of an aglycosylated version of Li81 heavy chain (SEQ ID NO:50) is shown below. The single amino acid change is marked in bold and underlined:

```
                                          (SEQ ID NO: 50)
EVQLLESGGGLVQPGGSLRLSCAASGFTFSAYEMKWVRQAPGKGLEWVSV

IGPSGGFTFYADISVKGRFTISRDNSKNTLYLQMNSLRAEDTAVYYCATE

GDNDAFDIWGQGTTVTVSSASTKGPISVFPLAPSSKSTSGGTAALGCLVK

DYFPEPVTVSWNSGALTSGVHTFPAVLQSSGLYSLSSVVTIVPSSSLGTQ

TYICNVNHKPSNTKVDKKVEPKSCDKTHTCPPCPAPELLGGPSVFLFPPK

PKDTLIMISRTPEVTCVVVDVSHEDPEVKFNWYVDGVEVHNAKTKPREEQ

YNSAYRVVSVLTVLHQDIWLNGKEYKCKVSNKALPAPIEKTISKAKGQPR

EPQVYTLPPSRDELTKNQVSLTCLVKGFYPSIDIAVEWESNGQPENNYKT

TPPVLDSDGSFFLYSKLTVDKSRWQQGNVFSCSVMHEALHNHYTIQKSLS

LSPG.
```

The anti-LINGO-1 antibody molecule includes a heavy chain at least 80%, 85%, 90% or 95% identical to a reference polypeptide comprising the amino acids of SEQ ID NO:50 or 86. In certain embodiments, an antibody or antigen-binding fragment comprising the heavy chain specifically or preferentially binds to LINGO-1.

In one embodiment, the anti-LINGO-1 antibody molecule is a fully human anti-LINGO-1 monoclonal antibody engineered into an aglycosyl immunoglobulin G subclass 1 (IgG1) framework to reduce effector function (also referred to herein as anti-LINGO-1 Antibody 1. Histological and functional evaluations of LINGO-1 knock-out mice have been performed, and in vivo pharmacological activity of anti-LINGO-1 Antibody 1 has been demonstrated in several animal models of demyelination. Anti-LINGO-1 Antibody 1 has been characterized in vitro and in vivo based on the evaluation of binding characteristics, biological activity, and pharmacological activity. The results of these studies indicate that anti-LINGO-1 Antibody 1 has the following characteristics described in Table 1.

TABLE 1

Characteristics of Anti-LINGO-1 Antibody 1

Binds to LINGO-1 with similar high apparent affinity across human, monkey, rat and mouse.
Is selective for LINGO-1 and does not bind the other LINGO family members, LINGO-2, LINGO-3, or LINGO-4.
Enhances differentiation of primary rat, monkey, and human oligodendrocytes in vitro.
Enhances axonal myelination in an in vitro rat dorsal root ganglion/OPC co-culture bioassay.
Has reduced Fc (γ) and complement effector functions compared to wild-type IgG1.
Is efficacious in animal models using biochemical and functional readouts. Remyelination activity has been demonstrated in the rat LPC model following systemic administration from to 100 mg/kg.
Functional recovery in the rat MOG-EAE model has been demonstrated following weekly systemic administration of 3 and 10 mg/kg.
Is efficacious in animal models when given in the presence of interferon β.
Is efficacious in animal models when given in the presence of high dose corticosteroids.

In one embodiment, the antibody molecule includes a VH wherein the VH CDR1, CDR2, and CDR3 comprise the amino acids of SEQ ID NOs: 6, 7, and 8, respectively, or an amino acid sequence substantially identical thereto (e.g., an amino acid sequence at least 80%, 85%, 90% or 95% identical thereto).

In one embodiment, the antibody molecule includes a VH wherein the VH CDR1, CDR2, and CDR3 comprise the amino acids of SEQ ID NOs: 2, 3, and 30, respectively, or an amino acid sequence substantially identical thereto (e.g., an amino acid sequence at least 80%, 85%, 90% or 95% identical thereto).

In another embodiment, the antibody molecule includes a VL wherein the VL CDR1, CDR2, and CDR3 comprise the amino acids of SEQ ID NOs: 14, 15, and 16, respectively, or an amino acid sequence substantially identical thereto (e.g., an amino acid sequence at least 80%, 85%, 90% or 95% identical thereto).

In another embodiment, the antibody molecule includes a VH wherein the VL CDR1, CDR2, and CDR3 comprise the amino acids of SEQ ID NOs: 10, 11, and 12, respectively, or an amino acid sequence substantially identical thereto (e.g., an amino acid sequence at least 80%, 85%, 90% or 95% identical thereto).

In one embodiment, the antibody molecule includes a VH wherein the VH CDR1, CDR2, and CDR3 comprise the amino acids of SEQ ID NOs: 6, 7, and 8, respectively; and a VL wherein the VL CDR1, CDR2, and CDR3 comprise the amino acids of SEQ ID NOs: 14, 15, and 16, respectively; or an amino acid sequence substantially identical thereto (e.g., an amino acid sequence at least 80%, 85%, 90% or 95% identical thereto).

In one embodiment, the antibody molecule includes a VH wherein the VH CDR1, CDR2, and CDR3 comprise the amino acids of SEQ ID NOs: 2, 3, and 30, respectively; and a VL wherein the VL CDR1, CDR2, and CDR3 comprise the amino acids of SEQ ID NOs: 10, 11, and 12, respectively; or an amino acid sequence substantially identical thereto (e.g., an amino acid sequence at least 80%, 85%, 90% or 95% identical thereto).

In one embodiment, the antibody molecule includes a VH that includes the amino acid sequence of SEQ ID NO: 5, or an amino acid sequence substantially identical thereto (e.g., an amino acid sequence at least 80%, 85%, 90% or 95% identical to said SEQ ID NO: 5).

In one embodiment, the antibody molecule includes a VH that includes the amino acid sequence of SEQ ID NO:66, or an amino acid sequence substantially identical thereto (e.g., an amino acid sequence at least 80%, 85%, 90% or 95% identical to said SEQ ID NO: 66).

In one embodiment, the antibody molecule includes a VL that includes the amino acid sequence of SEQ ID NO:13, or an amino acid sequence substantially identical thereto (e.g., an amino acid sequence at least 80%, 85%, 90% or 95% identical to said SEQ ID NO: 13).

In one embodiment, the antibody molecule includes a VL that includes the amino acid sequence of SEQ ID NO:9, or an amino acid sequence substantially identical thereto (e.g., an amino acid sequence at least 80%, 85%, 90% or 95% identical to said SEQ ID NO: 9).

In one embodiment, the antibody molecule includes a VH that includes the amino acid sequence of SEQ ID NO:5, or an amino acid sequence substantially identical thereto (e.g., an amino acid sequence at least 80%, 85%, 90% or 95% identical to said SEQ ID NO: 5); and a VL that includes the amino acid sequence of SEQ ID NO: 13, or an amino acid sequence substantially identical thereto (e.g., an amino acid sequence at least 80%, 85%, 90% or 95% identical to said SEQ ID NO: 13).

In one embodiment, the antibody molecule includes a VH that includes the amino acid sequence of SEQ ID NO:66, or an amino acid sequence substantially identical thereto (e.g., an amino acid sequence at least 80%, 85%, 90% or 95% identical to said SEQ ID NO: 66); and a VL that includes the amino acid sequence of SEQ ID NO: 9, or an amino acid sequence substantially identical thereto (e.g., an amino acid sequence at least 80%, 85%, 90% or 95% identical to said SEQ ID NO: 9).

In another embodiment, the antibody molecule includes a heavy chain as shown below, comprising the amino acid sequence of SEQ ID NO: 275, or a sequence substantially identical thereto (e.g., an amino acid sequence at least 80%, 85%, 90% or 95% identical thereto), as follows:

```
                                            (SEQ ID NO: 275)
EVQLLESGGG LVQPGGSLRL SCAASGFTFS AYEMKWVRQA

PGKGLEWVSV IGPSGGFTFY ADSVKGRFTI SRDNSKNTLY

LQMNSLRAED TAVYYCATEG DNDAFDIWGQ GTTVTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKKVEPKS CDKTHTCPPC PAPELLGGPS

VFLFPPKPKD TLMISRTPEV TCVVVDVSHE DPEVKFNWYV

DGVEVHNAKT KPREEQYNSA YRVVSVLTVL HQDWLNGKEY

KCKVSNKALP APIEKTISKA KGQPREPQVY TLPPSRDELT
```

```
KNQVSLTCLV KGFYPSDIAV EWESNGQPEN NYKTTPPVLD

SDGSFFLYSK LTVDKSRWQQ GNVFSCSVMH EALHNHYTQK

SLSLSPG.
```

In other embodiments, the antibody molecule includes a light chain as shown below comprising the amino acid sequence of SEQ ID NO: 276, or a sequence substantially identical thereto (e.g., an amino acid sequence at least 80%, 85%, 90% or 95% identical thereto), as follows:

```
                                    (SEQ ID NO: 276)
DIQMTQSPAT LSLSPGERAT LSCRASQSVS SYLAWYQQKP

GQAPRLLIYD ASNRATGIPA RFSGSGSGTD FTLTISSLEP

EDFAVYYCQQ RSNWPMYTFG QGTKLEIKRT VAAPSVFIFP

PSDEQLKSGT ASVVCLLNNF YPREAKVQWK VDNALQSGNS

QESVTEQDSK DSTYSLSSTL TLSKADYEKH KVYACEVTHQ

GLSSPVTKSF NRGEC.
```

Any of the polypeptides described above may further include additional polypeptides, e.g., a signal peptide to direct secretion of the encoded polypeptide, antibody constant regions as described herein, or other heterologous polypeptides as described herein. Additionally, polypeptides of the invention include polypeptide fragments as described elsewhere. Additionally polypeptides of the invention include fusion polypeptide, Fab fragments, and other derivatives, as described herein.

Also, as described in more detail elsewhere herein, the present invention includes compositions comprising the polypeptides described above.

It will also be understood by one of ordinary skill in the art that LINGO-1 antibody polypeptides as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, or 95% identical to the starting sequence.

Furthermore, nucleotide or amino acid substitutions, deletions, or insertions leading to conservative substitutions or changes at "non-essential" amino acid regions may be made. For example, a polypeptide or amino acid sequence derived from a designated protein may be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. In certain embodiments, a polypeptide or amino acid sequence derived from a designated protein has one to five, one to ten, one to fifteen, or one to twenty individual amino acid substitutions, insertions, or deletions relative to the starting sequence.

Soluble LINGO Antagonists and Fusion Proteins

In another embodiment, the reparative agent, e.g., the antagonist of LINGO-1, is a soluble LINGO molecule, e.g., a LINGO-1 molecule (e.g., a fragment of LINGO-1), or a soluble form of a component of the LINGO-1 complex (e.g., a soluble form of NgR1, p75, or TAJ (TROY)).

In certain embodiments, a soluble LINGO molecule or a LINGO-1 antibody molecule comprises an amino acid sequence or one or more moieties not normally associated with an antibody. Exemplary modifications are described in more detail below. For example, a single-chain fv antibody fragment of the invention may comprise a flexible linker sequence, or may be modified to add a functional moiety (e.g., PEG, a drug, a toxin, or a label).

An antibody molecule, a soluble form of LINGO-1, or a complex component, as described herein, can be used alone or functionally linked (e.g., by chemical coupling, genetic or polypeptide fusion, non-covalent association or otherwise) to a second moiety, a heterologous moiety, e.g., a heterologous polypeptide. The term "heterologous" as applied to a polynucleotide or a polypeptide, means that a portion with which it is not naturally linked in nature. For example, the polynucleotide or polypeptide is derived from a distinct entity from that of the rest of the entity to which it is being compared. For instance, as used herein, a "heterologous polypeptide" to be fused to a LINGO-1 antibody molecule is derived from a non-immunoglobulin polypeptide of the same species, or an immunoglobulin or non-immunoglobulin polypeptide of a different species.

Exemplary heterologous moieties include, but are not limited to, an immunoglobulin Fc domain, serum albumin, pegylation, a GST, Lex-A and an MBP polypeptide sequence. The fusion proteins may additionally include a linker sequence joining the first moiety, e.g., the antibody molecule, the soluble form of LINGO-1 or the complex component, to the second moiety. In other embodiments, additional amino acid sequences can be added to the N- or C-terminus of the fusion protein to facilitate expression, steric flexibility, detection and/or isolation or purification. For example, a soluble form of LINGO-1 or a complex component can be fused to a heavy chain constant region of the various isotypes, including: IgG1, IgG2, IgG3, IgG4, IgM, IgA1, IgA2, IgD, and IgE.

It shall be understood that the antibody molecules and soluble or fusion proteins described herein can be functionally linked (e.g., by chemical coupling, genetic fusion, non-covalent association or otherwise) to one or more other molecular entities, such as an antibody (e.g., a bispecific or a multispecific antibody), among others.

In one embodiment, the fusion protein includes the extracellular domain of LINGO or the complex component (or a sequence homologous thereto), and, e.g., fused to, a human immunoglobulin Fc chain, e.g., human IgG (e.g., human IgG1 or human IgG2, or a mutated form thereof). The Fc sequence can be mutated at one or more amino acids to reduce effector cell function, Fc receptor binding and/or complement activity.

In certain embodiments, an anti-LINGO-1 antibody molecule can comprise, consist essentially of, or consist of, a fusion protein. Fusion proteins in this context are chimeric molecules which comprise, for example, an immunoglobulin antigen-binding domain with at least one target binding site, and at least one heterologous portion. The amino acid sequences can normally exist in separate proteins that are brought together in the fusion polypeptide or they may normally exist in the same protein, but are placed in a new arrangement in the fusion polypeptide. Fusion proteins can be created, for example, by chemical synthesis, or by creating and translating a polynucleotide in which the peptide regions are encoded in the desired relationship.

Nucleic Acid Molecule/Recombinant Expression

Nucleic acid molecules, host cells and vectors that include a nucleotide sequence encoding any of the polypeptides, e.g., reparative agents and immunomodulators, described herein, are also encompassed by the invention.

In one exemplary embodiment, an isolated polynucleotide comprising, consisting essentially of, or consisting of a nucleic acid encoding an immunoglobulin heavy chain variable region (VH) of an anti-LINGO-1 antibody molecule, where at least one of the CDRs of the heavy chain variable region or at least two of the CDRs of the heavy chain variable region are at least 80%, 85%, 90% or 95% identical to reference heavy chain CDR1, CDR2, or CDR3 amino acid sequences of Li62 or Li81 or variants thereof as described in Table 3 is provided. Alternatively, the CDR1, CDR2, and CDR3 regions of the VH are at least 80%, 85%, 90% or 95% identical to reference heavy chain CDR1, CDR2, and CDR3 amino acid sequences of Li62 or Li81 or variants thereof as described in Table 3. Thus, according to this embodiment, a heavy chain variable region of the invention has CDR1, CDR2, or CDR3 polypeptide sequences related to the polypeptide sequences shown in Table 3.

In another exemplary embodiment, an isolated polynucleotide comprising, consisting essentially of, or consisting of a nucleic acid encoding an immunoglobulin light chain variable region (VL) of an anti-LINGO-1 antibody molecule, where at least one of the CDRs of the light chain variable region or at least two of the CDRs of the light chain variable region are at least 80%, 85%, 90% or 95% identical to reference light chain CDR1, CDR2, or CDR3 amino acid sequences from monoclonal LINGO-1 antibodies disclosed herein is provided. Alternatively, the CDR1, CDR2, and CDR3 regions of the VL are at least 80%, 85%, 90% or 95% identical to reference light chain CDR1, CDR2, and CDR3 amino acid sequences from monoclonal LINGO-1 antibodies disclosed herein. Thus, according to one embodiment, a light chain variable region of the invention has CDR1, CDR2, or CDR3 polypeptide sequences related to the polypeptide sequences shown in Table 4.

Any of the polynucleotides described above may further include additional nucleic acids, encoding, e.g., a signal peptide to direct secretion of the encoded polypeptide, antibody constant regions as described herein, or other heterologous polypeptides as described herein.

Compositions comprising the polynucleotides comprising one or more of the polynucleotides described above are also disclosed. In one embodiment, the compositions comprising a first polynucleotide and second polynucleotide wherein said first polynucleotide encodes a VH polypeptide as described herein and wherein said second polynucleotide encodes a VL polypeptide as described herein.

Also disclosed are fragments of the polynucleotides of the invention, as described elsewhere. Additionally polynucleotides which encode fusion polynucleotides, Fab fragments, and other derivatives, as described herein, are also contemplated by the invention.

The polynucleotides can be produced or manufactured by any method known in the art. For example, if the nucleotide sequence of the antibody is known, a polynucleotide encoding the antibody may be assembled from chemically synthesized oligonucleotides (e.g., as described in Kutmeier et al., *BioTechniques* 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Recombinant expression of a polypeptide described herein, e.g., an antibody molecule that binds to LINGO-1, requires construction of an expression vector containing the polynucleotide that encodes the polypeptide, e.g., the antibody molecule. Once a polynucleotide encoding the antibody molecule or a heavy or light chain of an antibody, or portion thereof (preferably containing the heavy or light chain variable domain), has been obtained, the vector for the production of the antibody molecule may be produced by recombinant DNA technology using techniques known in the art. Thus, methods for preparing a protein by expressing a polynucleotide containing a polypeptide encoding nucleotide sequence are described herein and in U.S. Pat. No. 8,058,406, the contents of which are incorporated by reference in their entirety.

Methods known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. Replicable vectors comprising a nucleotide sequence encoding a polypeptide described herein (e.g., an anti-LINGO-1 antibody molecule, or a heavy or light chain thereof, or a heavy or light chain variable domain) operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The host cell may be co-transfected with two expression vectors, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain (Proudfoot, *Nature* 322:52 (1986); Kohler, *Proc. Natl. Acad. Sci. USA* 77:2197 (1980)). The coding sequences for the heavy and light chains may comprise cDNA or genomic DNA.

The term "vector" or "expression vector" is used herein to mean vectors used as a vehicle for introducing into and expressing a desired gene in a host cell. As known to those skilled in the art, such vectors can easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by co-transformation. Additional elements may also be needed for optimal synthesis of mRNA. These elements may include signal sequences, splice signals, as well as transcriptional promoters, enhancers, and termination signals.

In one embodiment, the cloned variable region genes are inserted into an expression vector along with the heavy and light chain constant region genes (preferably human) synthetic as discussed above. In one embodiment, this is effected using a proprietary expression vector of Biogen IDEC, Inc., referred to as NEOSPLA (U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in CHO cells, followed by selection in G418 containing medium and methotrexate amplification. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those which express suitably high levels if immunoglobulin heavy and light chains is routine experimentation which can be carried out, for example, by robotic systems. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed, e.g., in U.S. Pat. No. 6,413,777.

In other embodiments, the LINGO-1 antibody molecules can be expressed using polycistronic constructs such as those disclosed in United States Patent Application Publication No. 2003-0157641 A1, filed Nov. 18, 2002 and incorporated herein in its entirety. In these novel expression systems, multiple gene products of interest such as heavy and light chains of antibodies may be produced from a single polycistronic construct. These systems advantageously use an internal ribosome entry site (IRES) to provide relatively high levels of binding polypeptides in eukaryotic host cells. Compatible IRES sequences are disclosed in U.S. Pat. No. 6,193,980 which is also incorporated herein. Those skilled in the art will appreciate that such expression systems can be used to effectively produce the full range of polypeptides disclosed in the instant application.

More generally, once the vector or DNA sequence encoding a monomeric subunit of the polypeptide, e.g., the anti-LINGO-1 antibody molecule, has been prepared, the expression vector may be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Vectors, Rodriguez and Denhardt, Eds., Butterworths, Boston, Mass., Chapter 24.2, pp. 470-472 (1988). Typically, plasmid introduction into the host is via electroporation. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce a polypeptide for use in the methods described herein. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed in U.S. Pat. No. 8,058,406, the contents of which are incorporated by reference herein in its entirety.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express polypeptides, e.g., antibody molecules, for use in the methods described herein. These include, but are not limited to, microorganisms such as bacteria (e.g., *E. coli, B. subtilis*) transformed with recombinant bacteriophage DNA, plasmid DNA or cosmid DNA expression vectors containing polypeptide coding sequences; yeast (e.g., *Saccharomyces, Pichia*) transformed with recombinant yeast expression vectors containing antibody coding sequences; insect cell systems infected with recombinant virus expression vectors (e.g., baculovirus) containing polypeptide coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Typically, bacterial cells such as *Escherichia coli*, and more typically, eukaryotic cells, especially for the expression of whole recombinant antibody molecule, are used for the expression of a recombinant polypeptide or antibody molecule. For example, mammalian cells such as Chinese hamster ovary cells (CHO), in conjunction with a vector such as the major intermediate early gene promoter element from human cytomegalovirus is an effective expression system for polypeptides antibodies (Foecking et al., *Gene* 45:101 (1986); Cockett et al., *Bio/Technology* 8:2 (1990)).

The host cell line used for protein expression is often of mammalian origin; those skilled in the art are credited with ability to preferentially determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, W138, R1610 (Chinese hamster fibroblast) BALBC/3T3 (mouse fibroblast), HAK (hamster kidney line), SP2/O (mouse myeloma), P3.times0.63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

CHO cells are particularly preferred. In certain embodiment, the antibody molecules are expressed in CHO cells stably transfected with expression vectors containing the $IgG_1$-agly heavy light chain structural genes specific to the human LINGO-1 protein. A native human kappa light chain signal peptide and a human heavy chain signal peptide, which are post-translationally removed by endoplasmic reticulum-associated signal peptidase, can be used to direct secretion of the anti-LINGO-1 antibody molecule. The antibody molecule can be purified from the media and formulated as a liquid. The antibody molecule can consists of 2 heavy and 2 light chains connected by inter-chain disulfide bonds. In one embodiment, the mass of the intact antibody molecule is approximately 144.4 kDa.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 1980) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); TIB TECH 11(5):155-215 (May, 1993); and hygro, which confers resistance to hygromycin (Santerre et al., Gene 30:147 (1984). Methods commonly known in the art of recombinant DNA technology which can be used are described in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

Additional methods and host systems expression, production and/or purification of the polypeptides, e.g., antibodies, are disclosed in U.S. Pat. No. 8,058,406, the contents of which are incorporated by reference herein in its entirety.

Nucleic Acid Antagonists

In certain embodiments, the LINGO-1 antagonist inhibits the expression of nucleic acid encoding a LINGO-1. Examples of such LINGO-1 antagonists include nucleic acid molecules, for example, antisense molecules, ribozymes, RNAi double stranded molecules, triple helix molecules, microRNA molecules that hybridize to a nucleic acid encoding a LINGO-1, or a transcription regulatory region, and block or reduce mRNA expression of LINGO-1.

An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire LINGO-1 coding strand, or to only a portion thereof. In another embodiment, the antisense nucleic acid molecule is antisense to a "noncoding region" of the coding strand of a nucleotide sequence encoding LINGO-1 (e.g., the 5' and 3' untranslated regions). Antisense agents can include, for example, from about 8 to about 80 nucleobases (i.e. from about 8 to about 80 nucleotides), e.g., about 8 to about 50 nucleobases, or about 12 to about 30 nucleobases. Anti-sense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted. Exemplary antisense compounds include DNA or RNA sequences that specifically hybridize to the target nucleic acid, e.g., the mRNA encoding LINGO-1. The complementary region can extend for between about 8 to about 80 nucleobases. The compounds can include one or more modified nucleobases, which are known in the art. Descriptions of nucleic acid agents are available. See, e.g., U.S. Pat. Nos. 4,987,071; 5,116,742; and 5,093,246; Woolf et al.

(1992) *Proc Natl Acad Sci USA; Antisense RNA and DNA*, D. A. Melton, Ed., Cold Spring Harbor Laboratory, Cold Spring Harbor, N.Y. (1988); 89:7305-9; Haselhoff and Gerlach (1988) *Nature* 334:585-59; Helene, C. (1991) *Anticancer Drug Des.* 6:569-84; Helene (1992) *Ann. N.Y. Acad. Sci.* 660:27-36; and Maher (1992) *Bioassays* 14:807-15.

siRNAs are small double stranded RNAs (dsRNAs) that optionally include overhangs. For example, the duplex region of an siRNA is about 18 to 25 nucleotides in length, e.g., about 19, 20, 21, 22, 23, or 24 nucleotides in length. Typically, the siRNA sequences are exactly complementary to the target mRNA. dsRNAs and siRNAs in particular can be used to silence gene expression in mammalian cells (e.g., human cells). siRNAs also include short hairpin RNAs (shRNAs) with 29-base-pair stems and 2-nucleotide 3' overhangs. See, e.g., Clemens et al. (2000) *Proc. Natl. Acad. Sci. USA* 97:6499-6503; Billy et al. (2001) *Proc. Natl. Sci. USA* 98:14428-14433; Elbashir et al. (2001) *Nature.* 411:494-8; Yang et al. (2002) *Proc. Natl. Acad. Sci. USA* 99:9942-9947; Siolas et al. (2005), *Nat. Biotechnol.* 23(2):227-31; 20040086884; U.S. 20030166282; 20030143204; 20040038278; and 20030224432.

In still another embodiment, the nucleic acid molecule is a ribozyme. A ribozyme having specificity for a LINGO-1-encoding nucleic acid can include one or more sequences complementary to the nucleotide sequence of a LINGO-1 mRNA, and a sequence having known catalytic sequence responsible for mRNA cleavage (see U.S. Pat. No. 5,093,246 or Haselhoff and Gerlach (1988) *Nature* 334:585-591; Cech et al. U.S. Pat. No. 4,987,071; and Cech et al. U.S. Pat. No. 5,116,742; Bartel, D. and Szostak, J. W. (1993) *Science* 261:1411-1418).

In one embodiment, the nucleic acid molecule is a microRNA molecule. A microRNA having specificity for a LINGO-1-encoding nucleic acid can include one or more sequences complementary to the nucleotide sequence of a LINGO-1 mRNA, which can result in gene silencing via translational repression or target degradation (see Bartel D P (2009) *Cell* 136 (2): 215-33; Kusenda B, et al. (2006) *Biomed Pap Med Fac Univ Palacky Olomouc Czech Repub* 150 (2): 205-15).

LINGO-1 gene expression can be inhibited by targeting nucleotide sequences complementary to the regulatory region of the LINGO-1 (e.g., the LINGO-1 promoter and/or enhancers) to form triple helical structures that prevent transcription of the LINGO-1 gene in target cells. See generally, Helene, C. (1991) *Anticancer Drug Des.* 6:569-84; Helene, C. (1992) *Ann. N.Y. Acad. Sci.* 660:27-36; and Maher, L. J. (1992) *Bioassays* 14:807-15. The potential sequences that can be targeted for triple helix formation can be increased by creating a so-called "switchback" nucleic acid molecule.

A LINGO-1 nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) *Nature Biotech.* 19:17 and Faria et al. (2001) *Nature Biotech.* 19:40-44; Hyrup B. et al. (1996) *Bioorganic & Medicinal Chemistry* 4: 5-23).

Immunomodulatory Agents

Several immunomodulatory agents are presently used to modify the course of multiple sclerosis in patients. Such agents include, but are not limited to, an IFN-β1 molecule; a polymer of glutamic acid, lysine, alanine and tyrosine, e.g., glatiramer; an antibody or fragment thereof against alpha-4 integrin, e.g., natalizumab; an anthracenedione molecule, e.g., mitoxantrone; a fingolimod, e.g., FTY720; a dimethyl fumarate, e.g., an oral dimethyl fumarate; an antibody to the alpha subunit of the IL-2 receptor of T cells (CD25), e.g., daclizumab; an antibody against CD52, e.g., alemtuzumab; an inhibitor of a dihydroorotate dehydrogenase, e.g., teriflunomide; an antibody to CD20, e.g., ocrelizumab; and a corticosteroid. The reparative agents disclosed herein can be used in combination with any of these agents.

Exemplary immunomodulatory agents are described in more detail as follows.

IFNβ Agents (Beta Interferons)

One known therapy for MS includes treatment with interferon beta. Interferons (IFNs) are natural proteins produced by the cells of the immune systems of most animals in response to challenges by foreign agents such as viruses, bacteria, parasites and tumor cells. Interferons belong to the large class of glycoproteins known as cytokines. Interferon beta has 165 amino acids. Interferons alpha and beta are produced by many cell types, including T-cells and B-cells, macrophages, fibroblasts, endothelial cells, osteoblasts and others, and stimulate both macrophages and NK cells. Interferon gamma is involved in the regulation of immune and inflammatory responses. It is produced by activated T-cells and Th1 cells.

Several different types of interferon are now approved for use in humans. Interferon alpha (including forms interferon alpha-2a, interferon alpha-2b, and interferon alfacon-1) was approved by the United States Food and Drug Administration (FDA) as a treatment for Hepatitis C. There are two currently FDA-approved types of interferon beta. Interferon beta 1a (Avonex®) is identical to interferon beta found naturally in humans, and interferon beta 1b (Betaseron®) differs in certain ways from interferon beta 1a found naturally in humans, including that it contains a serine residue in place of a cysteine residue at position 17. Other uses of interferon beta have included treatment of AIDS, cutaneous T-cell lymphoma, Acute Hepatitis C (non-A, non-B), Kaposi's sarcoma, malignant melanoma, hairy cell leukemia, and metastatic renal cell carcinoma.

IFNβ agents can be administered to the subject by any method known in the art, including systemically (e.g., orally, parenterally, subcutaneously, intravenously, rectally, intramuscularly, intravitreally, intraperitoneally, intranasally, transdermally, or by inhalation or intracavitary installation). Typically, the IFNβ agents are administered subcutaneously, or intramuscularly.

IFNβ agents can be used to treat those subjects determined to be "responders" using the methods described herein. In one embodiment, the IFNβ agents are used as a monotherapy (i.e., as a single "disease modifying therapy") although the treatment regimen can further comprise the use of "symptom management therapies" such as antidepressants, analgesics, anti-tremor agents, etc. In one embodiment, the IFNβ agent is an IFNβ-1A agent (e.g., Avonex®, Rebif®). In another embodiment, the INFβ agent is an INFβ-1B agent (e.g., Betaseron®, Betaferon®, Extavia®).

Avonex®, an Interferon β-1a, is indicated for the treatment of patients with relapsing forms of MS that are determined to be responders using the methods described herein to slow the accumulation of physical disability and decrease the frequency of clinical exacerbations. Avonex® (Interferon beta-1a) is a 166 amino acid glycoprotein with a predicted molecular weight of approximately 22,500 daltons. It is produced by recombinant DNA technology using genetically engineered Chinese Hamster Ovary cells into which the human interferon beta gene has been introduced. The amino acid sequence of Avonex® is identical to that of natural human interferon beta. The recommended dosage of Avonex® (Interferon beta-1a) is 30 mcg injected intramuscularly once a week. Avonex® is commercially available as a 30 mcg lyophilized powder vial or as a 30 mcg prefilled syringe.

Interferon beta 1a (Avonex®) is identical to interferon beta found naturally in humans (AVONEX®, i.e., Interferon beta Ia (SwissProt Accession No. P01574 and gi:50593016). The sequence of interferon beta is:

```
                                          (SEQ ID NO: 277)
MTNKCLLQIALLLCFSTTALSMSYNLLGFLQRSSNFQCQKLLWQLNGRLE

YCLKDRMNFDIPEEIKQLQQFQKEDAALTIYEMLQNIFAIFRQDSSSTGW

NETIVENLLANVYHQINHLKTVLEEKLEKEDFTRGKLMSSLHLKRYYGRI

LHYLKAKEYSHCAWTIVRVEILRNFYFINRLTGYLRN.
```

Methods for making Avonex® are known in the art.

Treatment of responders identified using the methods described herein further contemplates that compositions (e.g., IFN beta 1 a molecules) having biological activity that is substantially similar to that of AVONEX® will permit successful treatment similar to treatment with AVONEX® when administered in a similar manner. Such other compositions include, e.g., other interferons and fragments, analogues, homologues, derivatives, and natural variants thereof with substantially similar biological activity. In one embodiment, the INFβ agent is modified to increase one or more pharmacokinetic properties. For example, the INFβ agent can be a modified form of interferon 1a to include a pegylated moiety. PEGylated forms of interferon beta 1a are described in, e.g., Baker, D. P. et al. (2006) *Bioconjug Chem* 17(1):179-88; Arduini, R M et al. (2004) *Protein Expr Purif* 34(2):229-42; Pepinsky, R B et al. (2001) *J. Pharmacol. Exp. Ther.* 297(3):1059-66; Baker, D. P. et al. (2010) *J Interferon Cytokine Res* 30(10):777-85 (all of which are incorporated herein by reference in their entirety, and describe a human interferon beta 1a modified at its N-terminal alpha amino acid to include a PEG moiety, e.g., a 20 kDa mPEG-O-2-methylpropionaldehyde moiety). Pegylated forms of IFN beta 1a can be administered by, e.g., injectable routes of administration (e.g., subcutaneously).

Rebif® is also an Interferon β-1a agent, while Betaseron®, Betaferon®, and Extavia® are Interferon β-1b agents. Both Rebif® and Betaseron® are formulated for administration by subcutaneous injection.

Dosages of IFNβ agents to administer can be determined by one of skill in the art, and include clinically acceptable amounts to administer based on the specific interferon-beta agent used. For example, AVONEX® is typically administered at 30 microgram once a week via intramuscular injection. Other forms of interferon beta 1a, specifically REBIF®, is administered, for example, at 22 microgram three times a week or 44 micrograms once a week, via subcutaneous injection. Interferon beta-1A can be administered, e.g., intramuscularly, in an amount of between 10 and 50 μg. For example, AVONEX® can be administered every five to ten days, e.g., once a week, while Rebif® can be administered three times a week.

Anti-VLA4 Antibody (e.g., Natalizumab (Tysabri®))

Anti-VLA4 antibodies (e.g., Natalizumab) inhibit the migration of leukocytes from the blood to the central nervous system. These antibodies bind to VLA-4 (also called α4β1) on the surface of activated T-cells and other mononuclear leukocytes. They can disrupt adhesion between the T-cell and endothelial cells, and thus prevent migration of mononuclear leukocytes across the endothelium and into the parenchyma. As a result, the levels of pro-inflammatory cytokines can also be reduced. Natalizumab can decrease the number of brain lesions and clinical relapses and accumulation of disability in patients with relapse remitting multiple sclerosis and relapsing secondary-progressive multiple sclerosis.

Natalizumab and related VLA-4 binding antibodies are described, e.g., in U.S. Pat. No. 5,840,299. Monoclonal antibodies 21.6 and HP1/2 are exemplary murine monoclonal antibodies that bind VLA-4. Natalizumab is a humanized version of murine monoclonal antibody 21.6 (see, e.g., U.S. Pat. No. 5,840,299). A humanized version of HP 1/2 has also been described (see, e.g., U.S. Pat. No. 6,602,503). Several additional VLA-4 binding monoclonal antibodies, such as HP2/1, HP2/4, L25 and P4C2, are described, e.g., in U.S. Pat. No. 6,602,503; Sanchez-Madrid et al, (1986) *Eur. J. Immunol* 16:1343-1349; Hemler et al, (1987) *J Biol. Chem.* 2:11478-11485; Issekutz et al. (1991) *J Immunol* 147: 109 (TA-2 mab); Pulido et al. (1991) *J Biol. Chem.* 266: 10241-10245; and U.S. Pat. No. 5,888,507). The contents of the aforesaid publications (including the antibody compositions, dosages, methods of administration and production) are incorporated herein by reference in their entirety.

Dimethyl Fumarate (Tecfidera®)

Dimethyl fumarate, DMF, (Tecfidera®) is a fumaric acid ester. DMF is thought to decrease leukocyte passage through the blood brain barrier and exert neuroprotective effects by the activation of antioxidative pathways, specifically through activation of the Nrf-2 pathway (Lee et al. (2008) *Int MS Journal* 15: 12-18). Research also suggests that BG-12® has the potential to reduce the activity and impact of inflammatory cells on the CNS and induce direct cytoprotective responses in CNS cells. These effects may enhance the CNS cells' ability to mitigate the toxic inflammatory and oxidative stress that plays a role in MS pathophysiology.

Glatiramer Acetate (Copaxone®)

Copaxone® (glatiramer acetate) consists of the acetate salts of synthetic polypeptides, specifically the four naturally occurring amino acids: L-glutamic acid, L-alanine, L-tyrosine, and L-lysine (Bornstein et al. (1987) *N Engl J Med.* 317: 408-414). Copaxone® exhibits structural similarity to myelin basic protein and is thought to function as an immune modulator by shifting the T helper cell type 1 response towards a T helper cell type 2 response (Duda et al. (2000) *J Clin Invest* 105: 967-976; Nicholas et al. (2011) *Drug Design, Development, and Therapy* 5: 255-274).

Mitoxantrone (Novantrone®, an Anthracenedione Molecule)

Mitoxantrone is an anthracenedione molecule (1,4-dihydroxy-5,8-bis[2-(2-hydroxyethylamino) ethylamino]-anthracene-9,10-dione) and a type II topoisomerase inhibitor that disrupts DNA synthesis and repair of cells. It is used to treat cancers and MS. Mitoxantrone is used to treat several forms of advancing MS, including secondary progressive MS, progressive relapsing MS, and advanced relapsing-remitting MS. For example, mitoxantrone is effective in slowing the progression of secondary progressive MS and extending the time between relapses in relapsing-remitting MS and progressive relapsing MS (Fox E (2006) Clin Ther 28 (4): 461-74).

Fingolimod (Gilenya®; Sphingosine 1-Phosphate Receptor Modulator)

Fingolimod is an immunomodulating drug, approved for treating MS. It has reduced the rate of relapses in relapsing-remitting multiple sclerosis by over half, but may have serious adverse effects. Fingolimod is a sphingosine 1-phosphate receptor modulator, which sequesters lymphocytes in lymph nodes, preventing them from moving to the central nervous system for autoimmune responses in MS.

Antibodies to the Alpha Subunit of the IL-2 Receptor of T Cells (CD25) (e.g., Daclizumab HYP; ZINBRYTA®)

An antibody to the alpha subunit of the IL-2 receptor of T cells (CD25), e.g., daclizumab HYP, can be used in the methods and compositions disclosed herein. Daclizumab HYP is a therapeutic humanized monoclonal antibody to the alpha subunit of the IL-2 receptor of T cells (CD25). Daclizumab HYP showed efficacy in reducing lesions and annualized relapse rate in patients with relapsing-remitting multiple sclerosis (Kappos et al. (2015). *N. Engl. J. Med.* 373 (15): 1418-28).

Antibody Against CD52, e.g., Alemtuzumab

Antibodies against CD52, e.g., alemtuzumab (currently under further development as Lemtrada®), bind to CD52, which is a protein present on the surface of mature lymphocytes, but not on stem cells. Phase III studies reported positive results comparing alemtuzumab with Rebif® (high-dose subcutaneous interferon beta-1a) in the treatment of patients with relapsing-remitting MS (RRMS). Alemtuzumab has been approved in Europe.

Antibody to CD20, e.g., Ocrelizumab

Antibodies against CD20, e.g., ocrelizumab, rituximab, ofatumumab, target mature B lymphocytes. Phase 2 clinical studies of rituximab and ocrelizumab in relapse remitting MS have demonstrated a statistically significant reduction in disease activity measured by brain lesions (e.g., measured by MRI scans) and relapse rate compared to placebo. Phase 3 studies of ocrelizumab showed both reduction in relapse rate and disability compared to interferon beta-1a (e.g., Rebif®).

Inhibitors of Dihydroorotate Dehydrogenase, e.g., Teriflunomide

Inhibitors of dihydroorotate dehydrogenase, e.g., teriflunomide, inhibit pyrimidine synthesis. Teriflunomide (also known as A77 1726 or) is an active metabolite of leflunomide. Teriflunomide inhibits rapidly dividing cells, including activated T cells, which are thought to drive the disease process in MS. Teriflunomide was investigated in clinical trials as a medication for treating MS. (Vollmer *EMS News* (May 28, 2009)).

Steroids

Steroids, e.g., corticosteroid, and ACTH agents can be used to treat acute relapses in relapsing-remitting MS or secondary progressive MS. Such agents include, but are not limited to, Depo-Medrol®, Solu-Medrol®, Deltasone®, Delta-Cortef®, Medrol®, Decadron®, and Acthar®.

One or more of the aforesaid immunomodulatory agents can be used in combination with the reparative agents disclosed herein, as described in more detail below and exemplified by the combination of IFN-b and anti-LINGO-1 Antibody Therapy.

Therapeutic Methods

Reparative agents, such as LINGO-1 antagonists, can relieve NgR1-mediated inhibition of axonal regeneration and dendritic arborization that normally takes place in CNS neurons. This is beneficial in situations where axonal repair or neurite sprouting is needed in the brain or spinal cord following CNS injury. Spinal cord injury, including partial or complete crush or severance, exemplifies a situation in which axonal repair is needed, but is normally inhibited through operation of the NgR1 pathway.

In addition, LINGO-1 is expressed in oligodendrocytes, and contributes to oligodendrocyte biology. Soluble derivatives of LINGO-1, polynucleotides (e.g. RNAi), as well as certain antibodies which specifically bind to LINGO-1 can act as antagonists to LINGO-1 function in oligodendrocytes, enhancing differentiation and survival of oligodendrocytes and promoting myelination of neurons in vitro and in vivo. This can be beneficial for treating or preventing disorders or conditions involving demyelination and dysmyelination.

Examples of diseases or disorders in which axonal extension and/or neurite sprouting in the brain, and/or oligodendrocyte proliferation, differentiation and survival, and/or myelination or remyelination, can be beneficial include, but are not limited to, CNS demyelinating diseases, CNS injury, stroke, multiple sclerosis (MS), optic neuritis (e.g., acute optic neuritis), idiopathic inflammatory demyelinating disease, transverse myelitis, neuromyelitis optica (NMO), vitamin B12 deficiency, progressive multifocal leukoencephalopathy (PML), encephalomyelitis (EPL), acute disseminated encephalomyelitis (ADEM), central pontine myelolysis (CPM), Wallerian Degeneration, adrenoleukodystrophy, Alexander's disease, Pelizaeus Merzbacher disease (PMZ), leukodystrophies, traumatic glaucoma, periventricular leukomalatia (PVL), essential tremor, white matter stroke, stroke, or radiation or toxic induced white matter injury and other neurodegenerative diseases or disorders such as multiple sclerosis, adrenoleukodystrophy, periventricular leukomalatia (PVL), Globoid cell Leucodystrophy (Krabbe's disease) and Wallerian Degenerationamylotrophic lateral sclerosis (ALS), Huntington's disease, Alzheimer's disease, Parkinson's disease, spinal cord injury, traumatic brain injury, post radiation injury, neurologic complications of chemotherapy, neuropathy (e.g., diabetic neuropathy), acute ischemic optic neuropathy, isolated vitamin E deficiency syndrome, AR, Bassen-Kornzweig syndrome, Marchiafava-Bignami syndrome, metachromatic leukodystrophy, trigeminal neuralgia, Bell's palsy, spinal cord injury, traumatic glaucoma, essential tremor, osmotic hyponatremia, and neurological diseases related to neuronal cell death. A CNS demyelinating disease can be chosen from one or more of the aforesaid disorders. In one embodiment, the CNS demyelinating disease is multiple sclerosis. In other embodiments, the CNS demyelinating disease is optic neuritis, e.g., acute optic neuritis.

Accordingly, methods for treating spinal cord injury, diseases or disorders associated with inhibition of neuronal growth in the CNS, diseases or disorders associated with inhibition of oligodendrocyte growth or differentiation, and diseases involving demyelination or dysmyelination of CNS neurons in a subject suffering from such injury or disease or predisposed to contract such disease, are disclosed. The method includes administering to the subject an effective amount of a reparative agent, e.g., a LINGO-1 antagonist, alone or in combination with an immunomodulatory agent.

"Treat," "treatment," and other forms of this word refer to the administration of a combination therapy, alone or in combination with one or more symptom management agents, to a subject, e.g., an MS patient or optic neuritis (e.g., acute optic neuritis) patient, to impede disease progression, to induce remission, to extend the expected survival time of the subject and or reduce the need for medical interventions (e.g., hospitalizations). In those subjects, treatment can include, but is not limited to, inhibiting or reducing one or more symptoms such as numbness, tingling, muscle weakness and/or other symptoms described herein for optic neuritis; reducing relapse rate or severity, reducing size or number of sclerotic lesions; inhibiting or retarding the development of new lesions; prolonging survival, or prolonging progression-free survival, and/or enhanced quality of life.

As used herein, unless otherwise specified, the terms "prevent," "preventing" and "prevention" contemplate an action that occurs before a subject begins to suffer from a relapse and/or which inhibits or reduces the severity of the disease.

As used herein, and unless otherwise specified, the terms "manage," "managing" and "management" encompass preventing the progression of disease symptoms in a subject who has already suffered from the disease, and/or lengthening the time that the subject who has suffered from the disease remains in remission. The terms encompass modulating the threshold, development and/or duration of the disease, or changing the way that a patient responds to the disease.

As used herein, and unless otherwise specified, a "therapeutically effective amount" of a compound is an amount sufficient to provide a therapeutic benefit in the treatment or management of the disease, or to delay or minimize one or more symptoms associated with the disease. A therapeutically effective amount of a compound means an amount of therapeutic agent, alone or in combination with other therapeutic agents, which provides a therapeutic benefit in the treatment or management of the disease. The term "therapeutically effective amount" can encompass an amount that improves overall therapy, reduces or avoids symptoms or causes of the disease, or enhances the therapeutic efficacy of another therapeutic agent.

As used herein, and unless otherwise specified, a "prophylactically effective amount" of a compound is an amount sufficient to prevent relapse of the disease, or one or more symptoms associated with the disease, or prevent its recurrence. A prophylactically effective amount of a compound means an amount of the compound, alone or in combination with other therapeutic agents, which provides a prophylactic benefit in the prevention of disease relapse. The term "prophylactically effective amount" can encompass an amount that improves overall prophylaxis or enhances the prophylactic efficacy of another prophylactic agent.

As used herein, the term "patient" or "subject" typically refers to a human (i.e., a male or female of any age group, e.g., a pediatric patient (e.g., infant, child, adolescent) or adult patient (e.g., young adult, middle-aged adult or senior adult) or other mammal, such as a primate (e.g., cynomolgus monkey, rhesus monkey); commercially relevant mammals such as cattle, pigs, horses, sheep, goats, cats, and/or dogs; that will be or has been the object of treatment, observation, and/or experiment. When the term is used in conjunction with administration of a compound or drug, then the patient has been the object of treatment, observation, and/or administration of the compound or drug.

In one embodiment, treatment with a LINGO-1 antagonist, alone or in combination with an immunomodulatory agent, begins as soon as a subject is diagnosed with a disorder affecting myelination or is diagnosed as being at risk for a disorder affecting myelination. For example, in one embodiment, a subject having AON in one eye is treated to enhance myelination/prevent demyelination in the visual pathway that serves the fellow eye. In another embodiment, a subject with AON is treated with a LINGO-1 antagonist, alone or in combination with an immunomodulatory agent to slow or prevent progression to MS.

In one embodiment, a subject to be treated according to the methods herein has minor symptoms at the time of initiation of treatment. In another embodiment, a subject to be treated according to the methods herein has marked impairment at the time of initiation of treatment. For example, in one embodiment, a subject with AON may have marked visual impairment in one eye at the time of treatment.

Subject to be treated according the methods described herein can be of any age when they are affected by demyelination or dismyelination or are at risk thereof. In one embodiment, a subject selected for treatment with a LINGO-1 antagonist is at least about 25 years of age. In another embodiment, a subject selected for treatment with a LINGO-1 antagonist is at least about 30 years of age. In still another embodiment, a subject selected for treatment with a LINGO-1 antagonist is at least about 30 years of age. In yet another embodiment, a subject selected for treatment with a LINGO-1 antagonist is at least about 35 years of age. In yet another embodiment, a subject selected for treatment with a LINGO-1 antagonist is at least about 40 years of age.

Acute Optic Neuritis

In one embodiment, the reparative agent, alone or in combination, reduces one or more symptoms of an inflammatory condition of the optic nerve (e.g., optic neuritis, e.g., acute optic neuritis (AON)). AON is an inflammatory disease of the optic nerve that often occurs in multiple sclerosis. AON is caused by inflammatory injury to the optic nerve and presents with visual loss due to edema, inflammation, and damage to the myelin sheath covering the optic nerve and axons. There is significant loss of the retinal nerve fiber layer and retinalganglion cell layer as a result of AON. Current treatment of AON is limited to intravenous treatment with high dose corticosteroids which fasten the resolution of edema, but do not promote central nervous system (CNS) remyelination or provide neuroaxonal protection from CNS inflammatory demyelination. Thus the reparative agents disclosed herein can be used, alone or in combination, to treat such inflammation of the optic nerve.

Treatment of MS

Multiple sclerosis (MS) is a central nervous system disease that is characterized by inflammation and loss of axons and myelin sheaths.

Subjects having MS can be identified by clinical criteria establishing a diagnosis of clinically definite MS as defined by Poser et al. (1983) *Ann. Neurol.* 13:227. Briefly, an individual with clinically definite MS has had two attacks and clinical evidence of either two lesions or clinical evidence of one lesion and paraclinical evidence of another, separate lesion. Definite MS may also be diagnosed by evidence of two attacks and oligoclonal bands of IgG in cerebrospinal fluid or by combination of an attack, clinical evidence of two lesions and oligoclonal band of IgG in cerebrospinal fluid. The McDonald criteria can also be used to diagnose MS. (McDonald et al. (2001) *Recommended diagnostic criteria for Multiple sclerosis: guidelines from the International Panel on the Diagnosis of Multiple Sclerosis, Ann Neurol* 50:121-127); Polman, C H et al. (2005 December). *Diagnostic criteria for multiple sclerosis:* 2005 revisions to the "McDonald Criteria" Annals of Neurology 58 (6): 840-6; Polman, C. H. et al. (2011) *Ann. Neurol.* 69(2):292-302). The McDonald criteria include the use of MRI evidence of CNS impairment over time to be used in diagnosis of MS, in the absence of multiple clinical attacks. Further updates to the McDonald criteria (Polman et al, Annals of Neurology 2011) allow the diagnosis of MS at the time of first CNS demyelinating episode based on the finding of pre-existing characteristic MRI lesions. Effective treatment of multiple sclerosis may be evaluated in several different ways. The following parameters can be used to gauge effectiveness of treatment. Two exemplary criteria include: EDSS (extended disability status scale as determined by an examining neurologists), and appearance of new lesions with or without clinical manifestations on MRI (magnetic resonance imaging) scans.

Exacerbations are defined as the appearance of one or more new neurological symptoms that are attributable to MS and accompanied by an appropriate new neurologic abnormality on examination. In addition, the exacerbation must last at least 24 hours and be preceded by stability or improvement for at least 30 days, and should not have alternative explanations (such as infection, drug toxicity, primary psychiatric disorders). Briefly, patients are given a standard neurological examination by clinicians. Exacerbations are mild, moderate, or severe according to changes in a Neurological Rating Scale like, for example, the Scripps Neurological Rating Scale (Sipe et al. (1984) *Neurology* 34:1368); the EDSS; or by patient reported outcomes (e.g., MSWS-12). An annual exacerbation rate and proportion of exacerbation-free patients are determined to monitor effectiveness of anti-inflammatory treatments.

Anti-inflammatory therapy can be deemed to be effective using a clinical measure if there is a statistically significant difference in the rate or proportion of exacerbation-free or relapse-free patients between the treated group and the placebo group for either of these measurements. In addition, time to first exacerbation and exacerbation duration and severity may also be measured. A measure of effectiveness as therapy in this regard is a statistically significant difference in the time to first exacerbation or duration and severity in the treated group compared to control group. An exacerbation-free or relapse-free period of greater than one year, 18 months, 20, or 24 months is particularly noteworthy. Clinical measurements include the relapse rate in one and two-year intervals, and a change in EDSS, including time to worsening from baseline of 1.0 unit on the EDSS that persists for three or six months. On a Kaplan-Meier curve, a delay in sustained progression of disability shows efficacy. Other criteria include a change in area and volume of T2 images on MRI, and the number and volume of lesions determined by gadolinium enhanced images.

MRI can be used to measure active inflammatory lesions using gadolinium-DTPA-enhanced imaging (McDonald et al., *Ann. Neurol.* 36:14, 1994) or the location and extent of lesions using T2-weighted techniques. Briefly, baseline MRIs are obtained. The same imaging plane and patient position are used for each subsequent study. Positioning and imaging sequences can be chosen to maximize lesion detection and facilitate lesion tracing. The same positioning and imaging sequences can be used on subsequent studies. The presence, location and extent of MS lesions can be determined by radiologists. Areas of lesions can be outlined and summed slice by slice for total lesion area. Three analyses may be done: evidence of new lesions, rate of appearance of active lesions, and percentage change in lesion area (Paty et al., (1993) *Neurology* 43:665). Improvement due to therapy can be established by a statistically significant improvement in an individual patient compared to baseline or in a treated group versus a placebo group.

The effects of remyelinating and/or neuroaxonal protective therapies can be evaluated using one or more of Magnetization Transfer Ratio (MTR), Diffusion Tensor Imaging (DTI), and brain volume changes, and Magnetic Resonance Spectroscopy (MRS). Each of the aforesaid techniques is described in more detail herein.

Magnetization Transfer Ratio (MTR) is based on application of off-resonance radio-frequency pulses and observing their effects on MR images, as well as measuring the signal intensity with and without application of the pulses. MTR has been shown to detect microscopic white matter pathology in MS not detectable on a standard MRI. (Siger-Zajdel M. et al., J Neurol Neurosurg Psychiatry 2001 71:752-756).

Diffusion Tensor Imaging (DTI) is a magnetic resonance imaging technique that enables the measurement of the restricted diffusion of molecules in tissue in order to produce neural tract images. This allows, for example, for visualization of neurons and white matter, which have an internal fibrous structure. Molecules diffuse more rapidly in the direction aligned with the internal structure, and more slowly perpendicular to the preferred direction. DTI can reveal abnormalities in white matter fiber structure in MS.

MRI can be used to measure changes in brain volume. Brain volume loss has been correlated with disability progression and cognitive impairment in MS, with the loss of grey matter volume more closely correlated with clinical measures than loss of white matter volume. (De Stefano N. et al., CNS Drugs. 2014 February; 28(2):147-56)

In Magnetic Resonance Spectroscopy (MRS), relative concentrations of target metabolites are determined. In the context of MS, MRS can quantify specific neurometabolites representing specific MS-related events, such as demyelination, inflammation, and axonal/neuronal dysfunction.

Exemplary symptoms associated with multiple sclerosis, which can be treated with the methods described herein or managed using symptom management therapies, include: optic neuritis, decreased visual acuity, diplopia, nystagmus, ocular dysmetria, internuclear ophthalmoplegia, movement and sound phosphenes, afferent pupillary defect, paresis, monoparesis, paraparesis, hemiparesis, quadraparesis, plegia, paraplegia, hemiplegia, tetraplegia, quadraplegia, spasticity, dysarthria, muscle atrophy, spasms, cramps, hypotonia, clonus, myoclonus, myokymia, restless leg syndrome, footdrop, dysfunctional reflexes, paraesthesia, anaesthesia, neuralgia, neuropathic and neurogenic pain, L'hermitte's, proprioceptive dysfunction, trigeminal neuralgia, ataxia, intention tremor, dysmetria, vestibular ataxia, vertigo, speech ataxia, dystonia, dysdiadochokinesia, frequent micturation, bladder spasticity, flaccid bladder, detrusor-sphincter dyssynergia, erectile dysfunction, anorgasmy, frigidity, constipation, fecal urgency, fecal incontinence, depression, cognitive dysfunction, dementia, mood swings, emotional lability, euphoria, bipolar syndrome, anxiety, aphasia, dysphasia, fatigue, Uhthoff's symptom, gastroesophageal reflux, and sleeping disorders.

Each case of MS displays one of several patterns of presentation and subsequent course. Most commonly, MS first manifests itself as a series of attacks followed by complete or partial remissions as symptoms improve, only to return later after a period of stability. This is called relapsing-remitting MS (RRMS). Primary-progressive MS (PPMS) is characterized by a gradual clinical decline with no distinct remissions, although there may be temporary plateaus or minor relief from symptoms. Secondary-progressive MS (SPMS) begins with a relapsing-remitting course followed by a later progressive course independently of relapses. PPMS, SPMS, and PRMS are sometimes lumped together and called chronic progressive MS.

A few patients experience malignant MS, defined as a swift and relentless decline resulting in significant disability or even death shortly after disease onset. This decline may be arrested or decelerated by determining the likelihood of the patient to respond to a therapy early in the therapeutic regime and switching the patient to an agent that they have the highest likelihood of responding to.

Combination Therapy

The invention discloses combined administration of an immunomodulatory agent, e.g., an IFN-β agent, e.g., Avonex®; and a reparative agent, e.g., an anti-LINGO-1 antibody, for treatment of a demyelinating disorder, e.g., MS.

The agents, e.g., pharmaceutical compositions including the agents, can be administered concurrently with, prior to, or subsequent to, one or more other additional therapies or therapeutic agents. In general, each agent can be administered at a dose and/or on a time schedule determined for that agent. In will further be appreciated that the additional therapeutic agent utilized in this combination can be administered together in a single composition or administered separately in different compositions. The particular combination to employ in a regimen will take into account compatibility of the pharmaceutical composition with the additional therapeutically active agent and/or the desired therapeutic effect to be achieved. In general, it is expected that additional therapeutic agents utilized in combination be utilized at levels that do not exceed the levels at which they are utilized individually. In some embodiments, the levels utilized in combination will be lower than those utilized individually.

Treatment of a subject with a disease with a reparative agent can be combined with one or more immunomodulatory agents. Exemplary immunomodulatory agents are described herein and include, but are not limited to, an IFN-β1 molecule; a polymer of glutamic acid, lysine, alanine and tyrosine, e.g., glatiramer; an antibody or fragment thereof against alpha-4 integrin, e.g., natalizumab; an anthracenedione molecule, e.g., mitoxantrone; a fingolimod, e.g., FTY720 or other S1P1 modulators, such as BAF312 or ozanimod; a dimethyl fumarate, e.g., an oral dimethyl fumarate; an antibody to the alpha subunit of the IL-2 receptor of T cells (CD25), e.g., daclizumab; an antibody against CD52, e.g., alemtuzumab; an inhibitor of a dihydroorotate dehydrogenase, e.g., teriflunomide; a corticosteroid; and an anti-CD20 antibody, e.g., ocrelizumab.

In one embodiment, a combination of Avonex® and anti-LINGO-1 antibody therapy is administered. In certain embodiments, an anti-LINGO-1 antibody can be administered once about every 4 weeks (plus or minus about 5 days) by intravenous (IV) infusion in addition to once weekly Avonex® intramuscular (IM) injections. Anti-LINGO-1 antibody treatment doses can include: IV infusions of: 3 mg/kg; or 10 mg/kg; or 30 mg/kg; or 50 mg/kg or 100 mg/kg; concurrent with once-weekly Avonex® IM injections.

In one embodiment, 3 mg/kg IV infusion once every 4 weeks of an anti-LINGO-1 antibody was selected. This regimen is expected to yield a mean average serum concentration similar to rat serum EC50 in the spinal cord lysolecithin model (adjusted for ~0.1% CNS penetration). Additional dosing regimens, 10 mg/kg and 30 mg/kg can also be administered. These 2 dosing regimens are expected to yield mean average serum concentrations approximately 1.2-fold and 3.7-fold higher than the rat serum EC90 (adjusted for ~0.1% brain penetration), respectively.

In certain embodiments, the immunomodulatory agent is an IFN-β1 molecule and is administered intravenously, subcutaneously or intramuscularly. For example, the IFN-β1 molecule can be administered at one or more of:

(i) at 20-45 microgram (e.g., 30 microgram), e.g., once a week via intramuscular injection;

(ii) at 20-30 microgram (e.g., 22 microgram), e.g., three times a week, or at 40-50 micrograms (e.g., 44 micrograms), e.g., three times a week, via subcutaneous injection; or (iii) in an amount of between 10 and 50 μg intramuscularly, e.g., three times a week, or every five to ten days, e.g., once a week.

In one embodiment, Avonex® is administered at 30 microgram once a week via intramuscular injection. Following titration when applicable, Avonex® can be administered by IM injection following dosage and administration schedules known in the art.

In one embodiment, the IFN-β agent, e.g., Avonex®, is administered by an injection device, e.g., an autoinjection device or pen.

In one embodiment, the anti-LINGO-1 antibody molecule is supplied as a liquid drug product containing 50 mg/mL opicinumab (BIIB033) (also referred to herein as an antibody molecule having a VH that includes the amino acid sequence of SEQ ID NO: 275 and a VL that includes the amino acid sequence of SEQ ID NO: 276), 10 mM sodium citrate, 160 mM L-arginine hydrochloride (pH 6.5), and 0.03% (weight per volume) polysorbate 80. The anti-LINGO-1 antibody molecule can be administered by IV infusion following saline dilution.

In one embodiment, the immunomodulatory agent is Avonex®, which is is formulated as a sterile clear liquid for IM injection. Each 0.5 mL of Avonex in a prefilled glass syringe contains 30 mcg of interferon β-1a. Other ingredients include sodium acetate trihydrate, glacial acetic acid, arginine hydrochloride, and polysorbate 20 in Water for Injection at a pH of approximately 4.8. The immunomodulatory agent, e.g., Avonex®, can be administered by any suitable means, e.g., a pen or other device.

Symptom Management

Treatment of a subject with a combination therapy described herein can be combined with one or more of the following therapies often used in symptom management of subjects having MS: Tegretol® (carbamazepine), Epitol® (carbamazepine), Atretol® (carbamazepine), Carbatrol® (carbamazepine), Neurontin® (gabapentin), Topamax® (topiramate), Zonegran® (zonisamide), Dilantin® (phenytoin), Norpramin® (desipramine), Elavil® (amitriptyline), Tofranil® (imipramine), Imavate® (imipramine), Janimine® (imipramine), Sinequan® (doxepine), Adapin® (doxepine), Triadapin® (doxepine), Zonalon® (doxepine), Vivactil® (protriptyline), Marinol® (synthetic cannabinoids), Trental® (pentoxifylline), Neurofen® (ibuprofen), aspirin, acetaminophen, Atarax® (hydroxyzine), Prozac® (fluoxetine), Zoloft® (sertraline), Lustral® (sertraline), Effexor XR® (venlafaxine), Celexa® (citalopram), Paxil®, Seroxat®, Desyrel® (trazodone), Trialodine® (trazodone), Pamelor® (nortriptyline), Aventyl® (imipramine), Prothiaden® (dothiepin), Gamanil® (lofepramine), Parnate® (tranylcypromine), Manerix® (moclobemide), Aurorix® (moclobemide), Wellbutrin SR® (bupropion), Amfebutamone® (bupropion), Serzone® (nefazodone), Remeron® (mirtazapine), Ambien® (zolpidem), Xanax® (alprazolam), Restoril® (temazepam), Valium® (diazepam), BuSpar® (buspirone), Symmetrel® (amantadine), Cylert® (pemoline), Provigil® (modafinil), Ditropan XL® (oxybutynin), DDAVP® (desmopressin, vasopressin), Detrol® (tolterodine), Urecholine® (bethane), Dibenzyline® (phenoxybenzamine), Hytrin® (terazosin), Pro-Banthine® (propantheline), Urispas® (hyoscyamine), Cystopas® (hyoscyamine), Lioresal® (baclofen), Hiprex® (methenamine), Mandelamine® (metheneamine), Macrodantin® (nitrofurantoin), Pyridium® (phenazopyridine), Cipro®

(ciprofloxacin), Dulcolax® (bisacodyl), Bisacolax® (bisacodyl), Sani-Supp® (glycerin), Metamucil® (psyllium hydrophilic mucilloid), Fleet Enema® (sodium phosphate), Colace® (docusate), Therevac Plus®, Klonopin® (clonazepam), Rivotril® (clonazepam), Dantrium® (dantrolen sodium), Catapres® (clonidine), Botox® (botulinum toxin), Neurobloc® (botulinum toxin), Zanaflex® (tizanidine), Sirdalud® (tizanidine), Mysoline® (primidone), Diamox® (acetozolamide), Sinemet® (levodopa, carbidopa), Laniazid® (isoniazid), Nydrazid® (isoniazid), Antivert® (meclizine), Bonamine® (meclizine), Dramamine® (dimenhydrinate), Compazine® (prochlorperazine), Transderm® (scopolamine), Benadryl® (diphenhydramine), Antegren® (natalizumab), Campath-1H® (alemtuzumab), Fampridine® (4-aminopyridine), Gammagard® (IV immunoglobulin), Gammar-IV® (IV immunoglobulin), Gamimune N® (IV immunoglobulin), Iveegam® (IV immunoglobulin), Panglobulin® (IV immunoglobulin), Sandoglobulin® (IV immunoglobulin), Venoblogulin® (IV immunoglobulin), pregabalin, ziconotide, Baclofen and AnergiX-MS®.

Clinical Tests/Assessments for the Evaluation of Combination Avonex® and Anti-LINGO-1 Antibody Therapy Efficacy endpoints of the therapy in any subject can be evaluated using tests and assessments known in the art. For example, for an RRMS patient, the subject can be evaluated by acquiring the subject's status using EDSS. In other embodiments where the subject has a progressive form of MS, e.g., SPMS or PPMS, the subject can be evaluated by obtaining a measure of upper and/or lower extremity function, and/or a measure of ambulatory function, e.g., short distance ambulatory function, in addition to acquiring the subject's status using EDSS. In certain embodiments, an assessment of lower extremity ambulatory function (e.g., Timed Walk of 25 Feet (T25FW)), and/or an assessment of upper extremity function (e.g., 9 Hole Peg Test (9HP)) can be performed.

Additional exemplary efficacy endpoints that can be evaluated include one or more of the following.

Efficacy Endpoints

Exemplary Primary Endpoints

Subjects can be evaluated for confirmed improvement of neurophysical and/or cognitive function over treatment as measured by a composite endpoint comprising the Expanded Disability Status Scale (EDSS), Timed 25-Foot Walk (T25FW), 9-Hole Peg Test (9HPT), and (3-Second) Paced Auditory Serial Addition Test (PASAT). Improvement on neurophysical and/or cognitive function can be defined as at least 1 of the following:

a) A ≥1.0 point decrease in EDSS from a baseline score of ≤6.0 (decrease sustained for 3 months or greater);

b) A ≥15% improvement from baseline in T25FW (improvement sustained for 3 months or greater);

c) A ≥15% improvement from baseline in SHPT (improvement sustained for 3 months or greater); and d) A ≥10% (e.g., 10%, 12%, 20%, 30%) improvement from baseline in PASAT (improvement sustained for 3 months or greater). Alternatively, the improvement can be detected using the Symbol Digit Modalities Test (SDMT).

In one embodiment, an exemplary end point for measuring the status of a patient with AON is measurement of the recovery of latency of the VEP (e.g., time for a signal to travel from the retina to the visual cortex). Latency is a measure of how well neurons can conduct, e.g., their conduction timing. Neurons that have intact myelin can conduct better (transmit a signal faster) than neurons that have lost or damaged myelin. The amplitude as measured by VEP is a measure of the number of functioning neurons (e.g., that contain axons capable of transmitting information) and the number of inactive (e.g., dead/damaged) neurons, with a higher amplitude indicative of a greater number of normally functioning neurons. Such measurement can be made using methods known in the art, e.g., using full field visual evoked potential (FF-VEP). Visual evoked potential (VEP) can be measured by methods known in the art, including the traditional method (referred to as full-field VEP) or with a multifocal VEP (mfVEP) that measures a larger sample of visual pathway and with better precision. These methods can be applied to increase the sensitivity of detection. For example, the fellow eye in AON can show amplitude changes (in nanovolts) with the mfVEP as the FF-VEP which measures amplitude changes in microvolts may not be sufficiently sensitive FF-VEP measures the latency and amplitude of the central visual field, e.g., sum of the latencies or amplitudes of the visual pathway representing about 5 degrees of the central vision (macular vision). mfVEP measures the latency and amplitude of up to 56 segments covering up to 60 degrees of the visual field for each individual eye. (Hood et al. Trans. Am. Ophthalmol. Soc. 104(2006):71-77). mfVEP permits the mapping of individual segments of the visual pathway, which may have different amplitudes and latencies depending on the degree of injury and repair.

In embodiments, an improvement in latency delay (e.g., reduced FF-VEP and/or mfVEP latency delay in milliseconds) is an indication of remyelination of lesions along the visual pathway, including optic nerves, optic radiations, or visual cortex. In embodiments, preserved amplitude (e.g., preserved FF-VEP or mfVEP amplitude) is an indication of neuroaxonal protection and/or repair along the visual pathway anywhere between the ganglion cell neurons in the retina and the cerebral visual cortical neurons.

Exemplary Secondary Endpoints

Subjects can be evaluated for confirmed worsening of neurophysical and/or cognitive function and/or disability treatment as measured by a composite endpoint of the EDSS, T25FW, SHPT, and PASAT. Progression of disability or worsening of neuro-physical and/or cognitive function is defined as at least 1 of the following:

a) A ≥1.0 point increase in EDSS from a baseline score of ≤5.5 or a ≥0.5 point increase from a baseline score equal to 6.0 (increase sustained for 3 months or greater);

b) A ≥15% worsening from baseline in T25FW (worsening sustained for 3 months or greater);

c) A ≥15% worsening from baseline in SHPT (worsening sustained for 3 months or greater); and d) A ≥10% (e.g., 10%, 12%, 20%, 30%) worsening from baseline in PASAT (worsening sustained for 3 months or greater). Alternatively, the worsening from baseline can be measured by SDMT.

In one embodiment, exemplary secondary endpoints to measure the status of a patient with AON include measuring the change in thickness of the retinal layers (retinal ganglion cells neurons and unmyelinated axonal segment) and/or measurement of retinal structure and function. Retinal structure can be measured using known methods, e.g., spectral domain optical coherence tomography (SD-OCT) while clinical visual function can be measured using visual acuity, e.g. low contrast letter acuity (1.25% and 2.5%), and/or high contrast visual acuity.

Exemplary techniques described herein for primary and secondary efficacy biomarker endpoint analysis can be further described as follows:

Latency recovery as measured by Full Field Visual evoked potential (FF-VEP) or Multifocal visual evoked potential (mfVEP) which measure whether remaining (live) axons can be repaired via remyelination following AON.

In embodiments, the FF-VEP and/or mfVEP amplitude is a different but equally important measure of visual pathway damage for each eye. In embodiments, an amplitude of at least 40 nanovolts (e.g., at least 40, 50, 60, 70, 80, 90, 100 nanovolts or more) lower than a control amplitude on mfVEP indicates the presence of visual pathway damage serving each of the two eye(s) of the subject. In embodiments, an amplitude that is at least 20% (e.g., at least 20%, 30%, 40%, 50%, 60%, 70%, 80%, 90%, or more) lower than a control amplitude indicates the presence of optic nerve damage in the eye(s) of the subject. In embodiments, an mfVEP amplitude that is about 180 nanovolts or lower (e.g., about 180, 170, 160, 150, 140, 130, 120, 110, 100, 90 nanovolts or lower) indicates the presence of optic nerve damage in the eye(s) of the subject. In embodiments, a control amplitude is the average VEP amplitude (e.g., FF-VEP in microvolts or mfVEP amplitude in microvolts) of a normal eye, e.g., an eye of a subject not having one or more symptoms of an optic nerve disorder or condition (e.g., acute optic neuritis); or the fellow eye of the subject where the fellow eye does not exhibit one or more symptoms of an optic nerve disorder or condition (e.g., acute optic neuritis) but the visual pathway can become affected over time as a results of new lesion development anywhere along the pathway. In embodiments, a control amplitude is the baseline VEP amplitude (e.g., FF-VEP or mfVEP amplitude) of a fellow normal eye.

In embodiments, the FF-VEP and/or mfVEP latency is a measure of optic nerve conductance. In embodiments, a latency that is at least 3 milliseconds higher (e.g., at least 3, 4, 5, 6, 7, 8, 9, 10, or more milliseconds higher) than a control latency indicates a delay in optic nerve conductance in the eye(s) of the subject. In embodiments, a latency that is at least 3% (e.g., at least 3%, 4%, 5%, 6%, 7%, 8%, 9%, 10%, 12%, 15%, 20%, 30%, 40%, 60%, 80%, or more) higher than a control latency indicates a delay in optic nerve conductance in the eye(s) of the subject. In embodiments, a FF-VEP latency that is at least about 110 milliseconds (e.g., at least about 110, 120, 130, 140, 150, 160, 170, 180 milliseconds or more) indicates a delay in optic nerve conductance in the eye(s) of the subject. In embodiments, an mfVEP latency can be at least about 155 msec (e.g., at least about 155, 165, 175, 185 milliseconds or more). In embodiments, a control latency is the average VEP latency (e.g., FF-VEP or mfVEP latency) of a normal eye, e.g., an eye of a subject not having one or more symptoms of an optic nerve disorder or condition (e.g., acute optic neuritis); or the fellow eye of the subject where the fellow eye does not exhibit one or more symptoms of an optic nerve disorder or condition (e.g., acute optic neuritis). In embodiments, a control latency is the baseline VEP latency (e.g., FF-VEP or mfVEP latency) of a fellow normal eye.

In embodiments, latency recovery is indicated by a FF-VEP and/or mfVEP latency of an affected eye after treatment that is within 15% (e.g., within 15%, 12%, 10%, 8%, 6%, 4%, or less) of the FF-VEP and/or mfVEP latency of a control latency, e.g., the baseline latency of the fellow normal eye or the unaffected eyes of healthy adults of similar age, sex, and head circumference (normative data). In embodiments, latency recovery is indicated by a FF-VEP and/or mfVEP latency of an affected eye after treatment that is within 15 milliseconds (e.g., within 15, 14, 13, 12, 11, 10, 9, 8, 7, 6, 5, 4, 3, or 2 milliseconds) of the FF-VEP and/or mfVEP latency of a control latency, e.g., the baseline latency of the fellow normal eye. In embodiments, latency recovery is indicated by a FF-VEP latency of an affected eye after treatment that is about 120 milliseconds or less (e.g., about 120, 110, 100, 90, 80 nanovolts, or less). Without being bound by theory, it is believed that the presence of latency recovery, e.g., as measured by FF-VEP and/or mfVEP, in one or both eyes after treatment is an indicator of remyelination of the optic nerve(s).

Spectral Domain Optical Coherence Tomography (SD-OCT) (secondary endpoint) is different, and measures the thickness of the retinal nerve fiber layer (RNFL—unmyelinated portion of the optic nerve within the retina) and the retinal ganglion cell layer (RGCL—neuron cell body for optic nerve axons within the retina). The reduction of thickness in RNFL and RGCL following AON are considered evidence of axonal and neuronal loss (death). In embodiments, reduced loss of RNFL and/or RGCL thickness, e.g., a less than 12% (e.g., less than 12%, 11%, 10%, 9%, 8%, 6%, 4%, or less) reduction in thickness compared to the thickness of RNFL and/or RGCL in a normal eye (e.g., normal fellow eye), is evidence of neuroaxonal protection and/or repair.

In embodiments, visual function is measured by visual acuity, e.g., low-contrast (e.g., 1.25 or 2.5%) letter acuity (LCLA) or high-contrast (e.g., 100%) visual acuity (HCVA). Low Contrast Letter Acuity (secondary endpoint) is a measure of the ability of a patient to distinguish between degrees of low contrast (faint grey letters on white background). High contrast visual acuity is a measure of the ability to distinguish between degrees of high contrast (black letters on white background). In embodiments, the visual acuity is reported in number of letters that a subject is able to correctly read. In embodiments, an increase in visual acuity (e.g., by at least 6 letters, e.g., at least 6, 7, 8, 9, 10, 12, 14, 16, 18, 20, 30, 40, or more letters), e.g., LCLA and/or HCVA, is evidence of improvement or preservation of visual function in an AON-affected eye.

In embodiments, visual quality of life is an endpoint used in accordance with the methods described herein. In embodiments, visual quality of life is measured as described herein, e.g., in Example 6. For example, visual quality of life is measured by a patient reported outcome test. Exemplary patient reported outcome tests include but are not limited to a NIH-NEI visual functional questionnaire (NEI-VFQ) (see, e.g., Mangione et al. Arch. Opthalmol. 116.11(1998):1496-1504) and a neuro-ophthalmic supplement (NOS-10) (see, e.g., Raphael et al. Am. J. Ophthalmol. 142.6(2006):1026-35.e2). In embodiments, an increase of at least 4 points (e.g., at least 4, 5, 6, 7, 8, 9, 10, 11, 12, 13, 14, 15, 16, 17, 18, 19, 20, or more points) in a patient reported outcome test described herein, e.g., NEI-VFQ and/or NOS-10, is evidence of improvement of visual related quality of life.

Additional Clinical Efficacy Endpoints

In certain embodiments, subjects can be evaluated using additional clinical measures, including:

a) A change from baseline in cognitive function as measured by an MS cognitive composite endpoint comprising 2 tests of processing speed (the PASAT and the Symbol-Digit Modalities Test [SDMT]) and 2 tests of memory and learning (the Selective Reminding Test [SRT] for verbal memory and the Brief Visuospatial Memory Test-Revised [BVMT-R] for visual memory);

b) Severity of clinical relapses as determined by the Scripps Neurological Rating Scale (SNRS) or EDSS examination; and/or c) A ≥10% (e.g., ≥15%, ≥20%, ≥30%) worsening from baseline in Six Minute Walk (6MW) walking time (worsening sustained for 3 months or greater).

Exemplary MRI Efficacy Endpoints

Analysis of brain MRI focused on measures of repair at the focal and diffuse levels with both new and preexisting lesions can include one or more of:

(i) Analysis of new brain lesions:

a) Percentage Gd lesion volume with increased and decreased magnetization transfer ratio (MTR);

b) A change from onset in new Gd lesion mean MTR relative to the normal appearing white matter (NAWM) with lesions per subject as the unit of measure;

c) A change from onset in MTR signal for voxels per scan whose MTR drops below the normal value (new MTR lesions) with subject as the unit of measure;

d) A change from onset in new Gd lesion radial diffusivity with subject as the unit of measure;

e) A change from onset in radial diffusivity for voxels per scan whose MTR drops below the normal value (new MTR lesions) with subject as the unit of measure; or f) Percentage conversion from new Gd brain lesions to chronic black hole with chronic black holes defined as T1 hypointensity still visible after at least 6 months from onset.

(ii) Analysis of pre-existing brain lesions (lesions that are present at baseline scan):

a. A change in MTR from baseline for abnormal Ti volume;

b. A change in MTR from baseline for abnormal T2 volume;

c. A change in MTR from baseline for abnormal T2 volume not associated with T1 hypointensity;

d. A change in diffusion tensor imaging (DTI) from baseline for abnormal T1 volume;

e. A change in DTI from baseline for abnormal T2 volume; or f. A change in DTI from baseline for abnormal T2 volume not associated with T1 hypointensity.

(iii) Analysis of diffuse brain MRI metrics:

a) Percentage brain volume change;

b) A change from baseline in cerebral cortical brain volume;

c) A change from baseline in thalamic volume; or d) A change from baseline in whole brain radial diffusivity.

e) A chance from baseline in whole brain MTR.

Exemplary Patient-Reported Outcomes (PROs) Efficacy Endpoints

In certain embodiments, subjects can be evaluated by patient reported outcomes, including one or more of:

a) 12-Item Multiple Sclerosis Walking Scale (MSWS-12).

b) ABILHAND 56-Item Questionnaire.

c) 29-Item Multiple Sclerosis Impact Scale (MSIS-29).

d) The Short Form (36) Health Survey (SF-36).

e) MSNQ-informant and MSNQ-patient

Efficacy Endpoint Analysis

General Methods of Analysis

Summary statistics may be presented. For continuous endpoints, the summary statistics may generally include: the number of subjects randomized or dosed; or the number of subjects with data, mean, SD, median, and range. For categorical endpoints, the summary statistics may generally include: the number of subjects randomized or dosed; the number of subjects with data, or the percent of subjects with data in each category.

Exemplary Primary Endpoint Analyses

Exemplary primary efficacy endpoints can include the percentage of subjects with confirmed clinical improvement in 1 or more of the components of the composite endpoint (EDSS, T25FW, 9HPT, or PASAT). The percentage of confirmed improvers can be presented by treatment groups, and the data analyzed by a logistic regression model. Time to confirmed improvement may be analyzed using the Cox proportional hazards model. Baseline EDSS, T25FW, SHPT (both dominant and non-dominant hands), PASAT, and stratification factors may be included in both logistic regression and Cox models as covariates. If 2 baseline EDSS assessments are performed, the higher EDSS score can be used for analysis. MRI activity may be explored as potential covariates as well.

Exemplary Secondary Endpoint Analyses

The secondary efficacy endpoint may include the percentage of subjects with confirmed clinical worsening in 1 or more of the components of the composite endpoint (EDSS, T25FW, 9HPT, or PASAT). The percentage of confirmed worseners can be presented by treatment groups, and the data analyzed by a logistic regression model. Time to confirmed worsening may be analyzed using the Cox proportional hazards model. Baseline EDSS, T25FW, SHPT (both dominant and non-dominant hands), PASAT, and stratification factors may be included in both logistic regression and Cox models as covariates. If 2 baseline EDSS assessments are performed, the higher EDSS score can be used for analysis. MRI activity may be explored as potential covariates as well.

Exploratory Endpoint Analyses

The exploratory endpoints may include clinical metrics, MRI metrics, and PRO variables. They can be summarized by presenting summary statistics for continuous variables or frequency distributions for categorical variables. The statistical methods used will depend on the nature of the variables. Binary variables can be analyzed by using a logistic regression model; continuous variables can be analyzed by using the analysis of covariance model, adjusting for the corresponding baselines and stratification factors. Time-to-event variables can be analyzed using the Cox proportional hazards regression model, by adjusting for the corresponding baselines and stratification factors. Count variables can be analyzed by a Negative Binomial regression model or a Wilcoxon rank-sum test.

Ambulatory Assessments

T25FW

The T25FW is a timed walk of 25 feet. The T25W is a measure of quantitative ambulatory capacity over a short distance that is responsive to deterioration mostly for subjects who are very disabled, e.g., EDSS steps 6-6.5. It can be used as quantitative measure of lower extremity function. Broadly, the patient is directed to one end of a clearly labeled 25-foot course and is instructed to walk 25 feet as quickly as possible, but safely. The task can be immediately administered again by having the patient walk back the same distance. Patients may use assistive devices when completing the T25W. A time limit of 3 minutes to complete the test is usually used. The test is discontinued if the patient cannot complete Trial 2 of the T25W after a 5 minute rest period, or if the patient cannot complete a trial in 3 minutes.

9HPT

The 9HPT is a 9-hole peg test. It is a quantitative measure that captures a clinically important aspect of upper extremity (e.g., arm and hand) function that is not measured by the EDSS or the T25FW. Unlike the EDSS and the T25FW, the 9HPT is responsive across a wide EDSS range. Broadly, a patient is asked to pick up 9 pegs one at a time, using their hands only, and put the pegs into the holes on a peg board as quickly as possible until all of the holes are filled. The patient must then, without pausing, remove the pegs one at a time and return them to the container as quickly as possible. Both the dominant and non-dominant hands are tested twice (two consecutive trials of the dominant hand, followed immediately by two consecutive trials of the non-dominant hand). A time limit of 5 minutes to complete the test is usually used. The test is discontinued if the patient cannot complete one trial of the 9HPT test in 5 minutes; if the patient cannot complete a trial with his or her dominant hand within 5 minutes, the patient is usually instructed to move onto the trials with the non-dominant hand.

6MW

The 6 minute walking test (6MW) is used to assess walking distance. Broadly, the patient is asked to walk the fastest speed possible without physical assistance for 6 minutes and the distance is measured. Assistive devices can be used but should be kept consistent and documented from test to test. The patient should walk continuously if possible, but the patient can slow down to stop or rest during the test.

SNRS

The Scripps Neurological Rating Scale (SNRS) measures several parameters, including, mentation and mood; eyes and related cranial nerves, e.g., visual acuity, visual fields, eye movements, nystagmus; lower cranial nerves; motor function in each extremity, e.g., right upper, left upper, right lower, left lower; deep tendon reflexes, e.g., upper extremities, lower extremities; Babinski sign, e.g., left side, right side; sensory function in each extremity, e.g., right upper, left upper, right lower, left lower; cerebellar signs, e.g., upper extremities, lower extremities; and gait trunk balance, e.g., special category for autonomic dysfunction, e.g., bladder dysfunction, sexual dysfunction.

EDSS

As described above, the EDSS is based on a standardized neurological examination, focusing on the symptoms that occur frequently in MS. The EDSS assess the seven functional systems: visual, brainstem, pyramidal, cerebellar, sensory, bowel/bladder and cerebral; through neurological examination. In addition the EDSS also includes an assessment of walking range. Based on the functional system scores and the walking range, an EDSS step is determined. The range of the EDSS includes 19 steps from 0 to 10, with EDSS step 0 corresponding to a completely normal examination and EDSS step 10 to death due to MS. For EDSS ratings between 0 and 4, the scale relies mainly on the scores of the individual FS. For ratings over 4, the EDSS is primarily determined by the ability and range of walking.

Patient Reported Outcome Assessments

MSWS-12

The Multiple Sclerosis Walking Scale-12 (MSWS-12) test is a self rated measure of walking ability. The test contains 12 questions with Likert-type responses, describing the impact of MS on walking. The questions were generated from 30 MS patient interviews, expert opinions, and literature reviews.

ABILHAND 56-Item Questionnaire

The ABILHAND 56-Item Questionnaire is a measure of manual ability designed to measure a patient's experience of problems in performing everyday tasks such as feeding, dressing, or managing tasks. The ABILHAND contains 56 unbiased and bimanual activities, which the patients are asked to judge on a four-level scale: 0=impossible, 1=very difficult, 2=difficult, 3=easy.

MSIS-29

The Multiple Sclerosis Impact Scale 29 (MSIS-29) is a 29 item self report rating scale which measures physical and psychological parameters of MS. Three of the items deal with limited abilities, and the remaining 26 items are related to being impacted by symptoms or consequences of disease. Twenty of the items refer to physical function. Responses use a 5 point Likert scale range from 1 to 5.

SF-36

The short form 36 (SF-36) test measures overall health related quality of life. The SF-36 is a structured, self report questionnaire that the patient can generally complete with little to no intervention from a physician. There is no single overall score for the SF-36, instead it generates 8 subscales and two summary scores. The 8 subscales include physical functioning, role limitations due to physical problems, bodily pain, general health perceptions, vitality, social functioning, role limitations due to emotional problems, and mental health. The two summary scores include a physical component summary and a mental health component summary.

Cognitive Test Assessments

Several cognitive test instruments can be used to determine the value of the composite parameter, as follows.

Symbol Digit Modalities Test (SDMT)

The SDMT is a test that evaluates processing speed and working memory in which the subject is given 90 seconds to pair specific numbers with given geometric figures based on a reference key. It is modeled after the Digit Symbol or Coding Tasks tests, which have been included in the Wechsler intelligence scales for many years (e.g., Wechsler et al. (1974) *Manual for the Wechsler Intelligence Scale for Children-Revised*. New York: Psychological Corporation; Wechsler et al. (1981) *WAIS-R Manual*. New York: Psychological Corporation). Recognizing the limitations some patients have with manual dexterity, Rao and colleagues modified the SDMT to include only an oral response (Rao et al. (1991) *Neurology* 41: 685-691). In this oral SDMT selected in the present invention, participants are presented with an 8.5×11 inch sheet that contains the numbers and symbols to be processed. The top row of stimuli includes nine symbols, each of which is paired with a single digit in the key. The remainder of the page has a pseudo-randomized sequence of these symbols, and the participant's task is to respond orally with the digit associated with each of the symbols as quickly as possible. The score is the total number of correct matches (out of 110) made by the subject within the 90 second time frame.

Good test-retest reliability ($r=0.93-0.97$, $p<0.001$) has been established in MS subjects (Benedict et al. (2006) *Journal of the International Neuropsychological Society* 12: 549-558; Benedict et al. (2008) *Multiple Sclerosis* 14: 940-946). Good discriminative validity for distinguishing between MS patients and normal controls ($d=1.0-1.5$, $p<0.001$) (see e.g., Deloire et al. (2005) *Journal of Neurology, Neurosurgery & Psychiatry* 76: 519-526; Benedict et al. (2006) *Journal of the International Neuropsychological Society* 12: 549-558; Houtchens et al. (2007) *Neurology* 69: 113-123; Strober et al. (2009) *Multiple Sclerosis* 15: 1077-1084; Parmenter et al. (2010) *J Int Neuropsychol Soc* 16: 6-16) and for distinguishing between RRMS and SPMS patients ($d=0.8$, $p<0.001$) (see Benedict et al. (2006) *Archives of Neurology* 63: 1301-1306) has also been confirmed. In addition, correlations between performance and brain MRI have also been documented (see e.g., Benedict et al. (2007) *Multiple Sclerosis* 13: 722-730; Houtchens et al. (2007) *Neurology* 69: 113-123; Tekok-Kilic et al. (2007) *Neurolmage* 36: 1294-1300).

Paced Serial Addition Test (PASAT)

First developed by Gronwall et al. to assess patients recovering from concussion, the PASAT requires patients to monitor a series of 61 audiotaped digits while adding each consecutive digit to the one immediately preceding it (Gronwall et al. (1977) *Perceptual and Motor Skills* 44: 367-373). The PASAT requires both rapid information processing and simultaneous allocation of attention to two tasks, as well as reasonably intact calculation ability. In its original format, the PASAT was administered at four inter-stimulus intervals (2.4 seconds, 2.0 seconds, 1.6 seconds, and 1.2 seconds). The number of inter-stimulus intervals and presentation rates were subsequently modified by Rao and colleagues for use with MS patients to 3.0 seconds and 2.0 seconds (Rao et al. (1991) A Manual for the Brief, Repeatable Battery of Neuropsychological Tests in Multiple Sclerosis: National Multiple Sclerosis Society; Rao et al. (1991) Neuropsychological Screening Battery for Multiple Sclerosis: National Multiple Sclerosis Society; Rao et al. (1991) *Neurology* 41: 685-691; Rao et al. (1991) *Neurology* 41: 692-696).

This latter version of the test was selected to be a component of the MS Functional Composite (MSFC) and the MACFIMS battery (Benedict et al. (2002) *Clinical Neuropsychologist* 16: 381-397). Test-retest reliability in MS populations ranges from r=0.78 to 0.93 (Benedict et al. (2006) *Journal of the International Neuropsychological Society* 16: 228-237; Drake et al. (2010) *Multiple Sclerosis* 16: 228-237). Good discriminative validity for distinguishing between MS patients and normal controls (d=0.5-0.7, p<0.001 to 0.34) (Deloire et al. (2005) *Journal of Neurology, Neurosurgery & Psychiatry* 76: 519-526; Benedict et al. (2006) *Journal of the International Neuropsychological Society* 12: 549-558; Houtchens et al. (2007) *Neurology* 69: 113-123; Strober et al. (2009) *Multiple Sclerosis* 15: 1077-1084; Parmenter et al. (2010) *J Int Neuropsychol Soc* 16: 6-16; Drake et al. (2010) *Multiple Sclerosis* 16: 228-237) and for distinguishing between RRMS and SPMS patients (d=0.5, p<0.002) (Benedict et al. (2006) *Archives of Neurology* 63: 1301-1306) has been confirmed. The PASAT score of interest is the total number of correct responses at each presentation rate. Two alternate forms of the Rao version of the PASAT are available (PASAT 3" and PASAT 2") and were selected in the current invention. In the PASAT 3", the stimulus is presented every 3 seconds, where as in the PASAT 2", the stimulus is presented every 2 seconds.

Selective Reminding Test (SRT)

The SRT was first developed by Buschke et al. (see Buschke et al. (1974) *Neurology* 24: 1019-1025) who conducted research in the area of anterograde amnesia. Rather than ask patients to recall an entire word list on each successive learning trial, the experimenter only repeated words not recalled on each successive learning trial. Subsequently, several memory investigators developed normative data for the test, and alternate forms. Note, the original versions were based on a form of the test using 15 words and 12 learning trials. Such an administration is arduous and time consuming, and therefore there has been much interest in shorter forms of the SRT. The administration procedure widely used in MS research is a six-trial form developed by Rao et al. (see e.g., Rao et al. (1991) A Manual for the Brief, Repeatable Battery of Neuropsychological Tests in Multiple Sclerosis: National Multiple Sclerosis Society; Rao et al. (1991) Neuropsychological Screening Battery for Multiple Sclerosis: National Multiple Sclerosis Society; Rao et al. (1991) *Neurology* 41: 685-691; Rao et al. (1991) *Neurology* 41: 692-696). This six-trial format is utilized in the current invention. A number of different versions of SRT word lists exist. Hannay and Levin's word lists for adults, test forms 1 and 3, are utilized in the current invention (Hannay et al. (1985) *J Clin Exp Neuropsychol.* 7: 251-263). Discriminative validity of the SRT has been established in several studies, with SRT discriminating between MS subjects and normal controls d=0.6 to d=1.0 (see e.g., Rao et al. (1991) A Manual for the Brief, Repeatable Battery of Neuropsychological Tests in Multiple Sclerosis: National Multiple Sclerosis Society; Deloire et al. (2005) *Journal of Neurology, Neurosurgery & Psychiatry* 76: 519-526; Strober et al. (2009) *Multiple Sclerosis* 15: 1077-1084). It has also been shown that SRT findings can be associated with ventricular enlargement as seen on brain MRI ($R^2$=0.14; p=0.05) (Christodoulou et al. (2003) *Neurology* 60: 1793-1798).

Brief Visuospatial Memory Test-Revised (BVMT-R)

The BVMT-R is based on an initial effort to develop an equivalent alternate form visual memory test along the lines of the visual reproduction subtest from the Wechsler Memory Scale (Benedict et al. (1993) *Neuropsychological Rehabilitation* 3: 37-51; Benedict et al. (1995) *Clinical Neuropsychologist* 9: 11-16; Wechsler et al. (1987) *Wechsler Memory Scale-Revised Manual.* New York: Psychological Corporation). Initially, the BVMT included just a single exposure to a one-page presentation of six visual designs. The revised version includes three 10-second exposures to the stimulus (Benedict et al. (1997) Brief Visuospatial Memory Test—Revised: Professional Manual. Odessa, Fla.: Psychological Assessment Resources, Inc.; Benedict et al. (1996) *Psychological Assessment* 8: 145-153). After each exposure, the subject is asked to reproduce the matrix using a pencil on a blank sheet of paper. There are rigid scoring criteria for accuracy and location. After a 25 minute delay, the patient is asked to reproduce the information again without another exposure. Finally a yes/no recognition task is presented. The BVMT-R has excellent reproducibility, with test-retest reliability ranging from r=0.85 to r=0.91 (Benedict et al. (1996) *Psychological Assessment* 8: 145-153; Benedict et al. (2005) *Journal of the International Neuropsychological Society* 11: 727-736); as well as good discriminative validity between MS and normal control subjects (d=0.9, p<0.) (Strober et al. (2009) *Multiple Sclerosis* 15: 1077-1084; Parmenter et al. (2010) *J Int Neuropsychol Soc* 16: 6-16) and RRMS and SPMS patients (d=0.6, p<0.001) (Benedict et al. (2006) *Archives of Neurology* 63: 1301-1306). Predictive validity, in the form of correlation between BVMT-R performance and brain MRI findings, has also been established. Further, there is extensive research showing that all 6 forms of the test are of equivalent difficulty. Variables of interest in the current invention are the Total Learning and Delayed Recall scores.

This invention is further illustrated by the following examples which should not be construed as limiting. The contents of all references, figures, sequence listing, patents and published patent applications cited throughout this application are hereby incorporated by reference.

EXEMPLIFICATION

Example 1. LINGO-1 Antagonism Reduces Morbidity and Mortality from MOG-EAE in Mice and Promotes Axonal Protection in the Inflamed Optic Nerve Acute optic neuritis (AON) is an inflammatory disease of the optic nerve that often occurs in multiple sclerosis. AON is caused by inflammatory injury to the optic nerve and presents with visual loss due to edema, inflammation, and damage to the myelin sheath covering the optic nerve and axons. As a result of AON, there is often a significant loss of the retinal nerve fiber layer and retinal ganglion cell layer. Current treatment of AON is limited to intravenous treatment with high dose corticosteroids which fasten the resolution of edema but do not promote central nervous system (CNS) remyelination or provide neuroaxonal protection from CNS inflammatory demyelination.

Animal models for the study of optic neuritis include the rat and mouse experimental autoimmune encephalomyelitis (EAE) models; in which EAE induction results in the development of optic nerve neuritis. In the present example, the effects of LINGO-1 antagonism were analyzed using an EAE mouse model. Briefly, EAE was induced in C57BL/6 male and female mice at 8-12 weeks of age by subcutaneous injection of 250 µl into both flanks at the tail base with 125 µg of MOG 35-55 emulsified in complete Freund's adjuvant (CFA) followed by intravenous injection of 300 ng $pertussis$ toxin in phosphate buffered saline (PBS) immediately afterwards and three days later. Efficacy on motor system impairment was measured using EAE severity scores on a range from 0-7.

Two separate cohorts of 14 mice each were blindly treated with intraperitoneal injections of 10 mg/kg of an antagonistic anti-LINGO-1 mouse antibody or a control monoclonal antibody (N=7 per treatment group per cohort). Mice were treated on 4 different occasions every three days starting on day six post EAE induction and prior to the onset of clinical disease (days 6, 9, 12, and 15). Mice were sacrificed at EAE-disease peak.

The optic nerve was imaged once at EAE-disease peak using diffusion tensor imaging (DTI) on a Bruker 4,7T MRI system. MRI images were acquired with the following parameters: TR of 1 s, TE of 30 ms, A of 10 ms, 8 NEX, slice thickness 0.5 mm, field of view 2×2 cm$^2$, data matrix 256×128. B values of 0s/mm$^2$ (non-diffusion weighted image) and 700 s/mm$^2$ for one parallel and one perpendicular diffusion sensitizing gradient directions (Wu, Butzkueven et al. (2007) $Neuroimage$ 37: 13138-1147) were employed.

Immediately following MRI analysis, mice were euthanized with pentobarbital, perfused with PBS, fixed with 4% paraformaldhyde (PFA) in 0.1M PBS, and the optic nerves removed and post fixed in 4% PFA solution containing 2.5% glutaraldhyde and 0.1M sodium cacodylate buffer and processed for electron microscopy. Whole pre-chiasmal cross-sectional optic nerve images were taken at 10× and 100× magnification and merged on Photoshop CS3 software (Adobe Systems Incorporated, San Jose, Calif., USA). Five pre-chiasmal cross-sectional optic nerve ROIs (regions of interest) were chosen for analysis, four peripheral and one central, each measuring approximately 3600 µm$^2$ (FIG. 1). Analysis was conducted using image Pro Plus software (Media Cybernetics, Inc., Rockville, Md., USA) to assess axonal number, axonal area, and axoplasmal area of each identified axon on each ROI. The periphery of the nerve contained the majority of the inflammatory infiltrate. The heavily infiltrated peripheral area and the central nerve areas were assessed separately for each nerve.

Figure 2A:
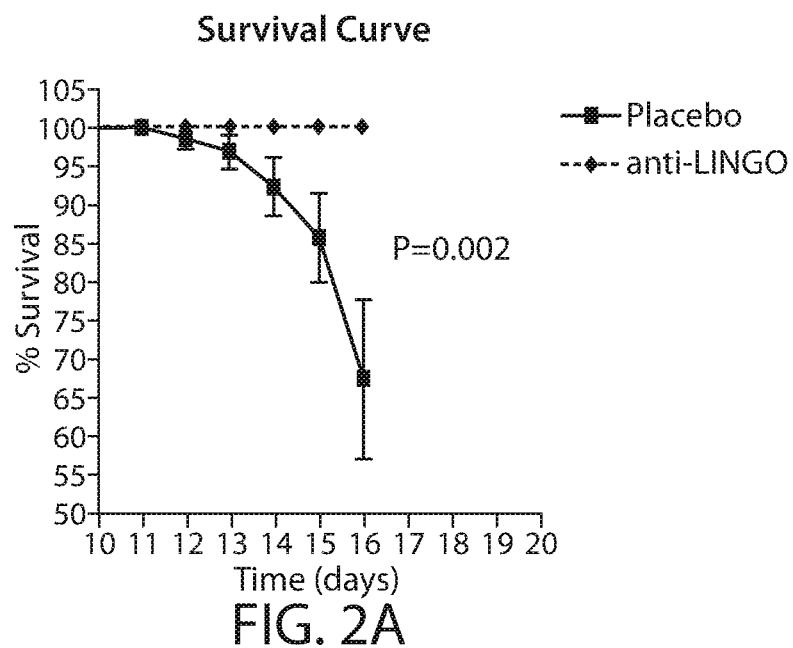
FIG. 2A is a line graph showing the survival curve of EAE mice treated with vehicle or anti-LINGO-1 antibody.
Figure 2B:
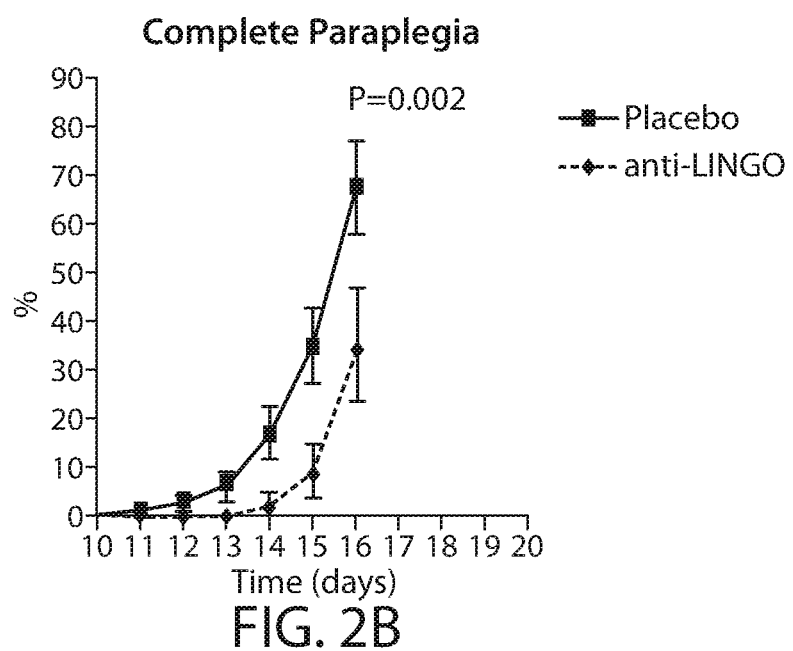
FIG. 2B is a line graph showing the development of complete paraplegia in EAE mice treated with vehicle or anti-LINGO-1 antagonist.
Figure 3A:
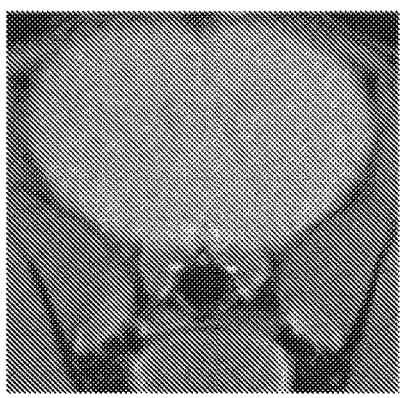
FIGS. 3A-3F contain images of the coronal optic nerve diffusion imaging in mouse EAE. Diffusion direction is indicated by the small arrows. The right optic nerve location is indicated by the large arrows.
Figure 3B:
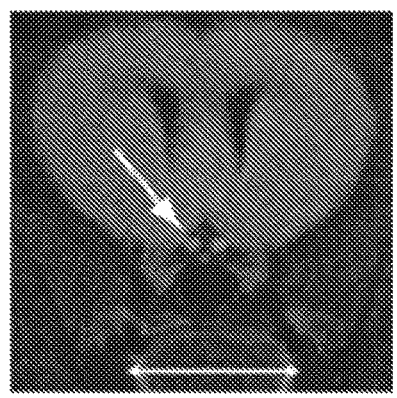
Figure 3E:
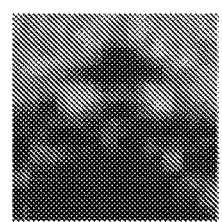
Figure 3C:
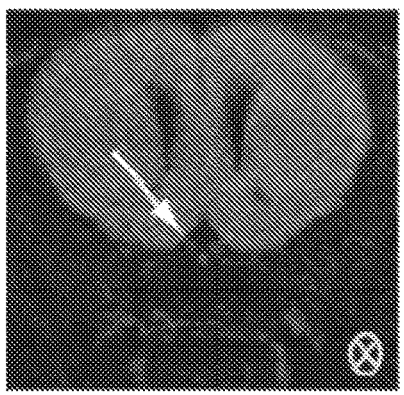
Figure 3D:
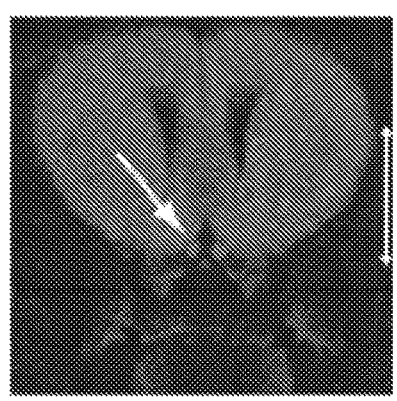
Figure 3F:
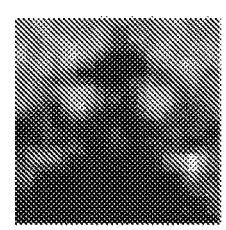

There was no EAE mortality observed in the anti-LINGO antibody treated mice, whereas 5/14 placebo treated mice had to be euthanized due to EAE severity (FIG. 2A). In addition, a significantly lower proportion of anti-LINGO-1 antibody treated mice reached complete hindlimb paralysis (paraplegia) (grade 5 disease severity) (4/14 mice) compared to placebo-treated mice (7/14 mice) (FIG. 2B).

Figure 4:
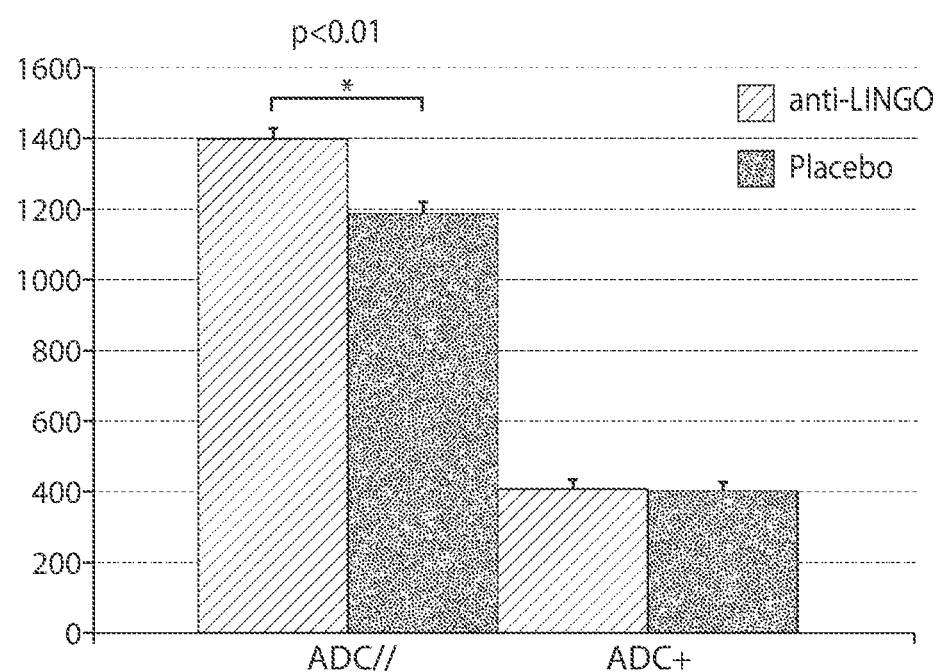
FIG. 4 is a bar graph depicting the optic nerve integrity analyzed by diffusion tensor imaging (DTI) in mouse EAE.

Optic nerve diffusion MRI scans were conducted on 16 surviving control-treated mice and 18 surviving anti-LINGO-1 antibody treated mice at peak EAE severity on days 16-17 post induction. The optic nerve ROI images comprised 10 voxels in the center of the optic nerves at the prechiasmal level. Diffusion tensor imaging (DTI) showed significantly higher apparent diffusion coefficient (ADC) values parallel to the long axis (longitudinal, axial, or parallel diffusivity or λII) in anti-LINGO-1 antibody treated mice (mean 1,400, SD 27 msec) than in control-treated mice (mean 1,183, SD 36 msec) (FIG. 3, FIG. 4). In contrast, there was no difference by treatment group in ADC values perpendicular to the optic nerve long axis (radial or perpendicular diffusivity or k) (415±19 msec in anti-LINGO-1 antagonist treated mice versus 403±25 msec in control treated mice) (FIG. 3, FIG. 4).

Figure 5:
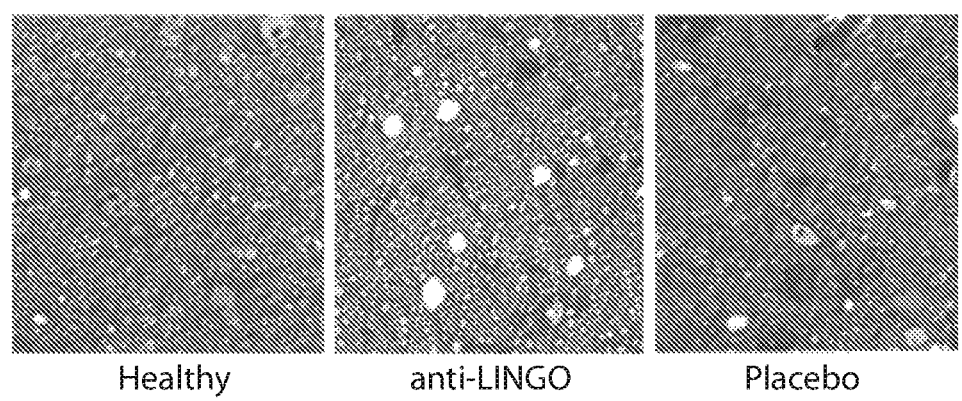
FIG. 5 depicts the histological analysis of the optic nerve in EAE mice treated with vehicle or anti-LINGO-1 antibody or healthy mice.

Assessment of central and peripheral axonal areas, axonal counts, and axo-plasmal cross sectional areas in the 5 ROIs for each optic nerve examined were tabulated for comparison (FIG. 5; FIG. 6). Nineteen EAE nerves per condition and 5 healthy nerves were analyzed. The results showed there was no difference in the total optic nerve area or the number of axons in the ROIs with the central or peripheral (FIG. 5; FIG. 6). However, the individual axonal area (a measure of axonal health) in the central optic nerve ROI was 13% lower in the control-treated mice relative to the anti-LINGO-1 antibody treated mice (FIG. 5; FIG. 6). Overall, LINGO-1 antagonism reduced the morbidity and mortality from MOG-EAE in mice; and promoted axonal protection in the inflamed optic nerve by reducing the loss of axonal area and reducing the loss of axial diffusivity. In summary, damage to the optic nerve was seen in MOG-EAE histologically and by MRI, and it appeared to be reduced by LINGO-1 blockade.

Example 2. LINGO-1 Antagonism in Combination with Corticosteroid Treatment Provides Increased Axonal Protection Compared to LINGO-1 Antagonism Alone in the Rat EAE Model Acute optic neuritis (AON) is an inflammatory disease of the optic nerve that often occurs in multiple sclerosis. AON is caused by inflammatory injury to the optic nerve and presents with visual loss due to edema, inflammation, and damage to the myelin sheath covering the optic nerve and axons. There is significant loss of the retinal nerve fiber layer and retinalganglion cell layer as a result of AON. Current treatment of AON is limited to intravenous treatment with high dose corticosteroids which fasten the resolution of edema, but do not promote central nervous system (CNS) remyelination or provide neuroaxonal protection from CNS inflammatory demyelination.

Animal models for the study of optic neuritis include the rat and mouse experimental autoimmune encephalomyelitis (EAE) models; in which EAE induction results in the development of optic nerve neuritis. In the present example, the effects of LINGO-1 antagonism alone and in combination with corticosteroid treatment were analyzed using the EAE rat model. Briefly, female Brown Norway (BN) rats 8 to 10 weeks of age were anesthetized by inhalation of isoflurane and injected intradermally at the base of the tail with a total volume of 200 µl of inoculums, containing 100 µg rMOG1-125 in saline emulsified (1:1) with complete Freud's adjuvant containing 400 µg heat inactivated $Mycobacterium\ tuberculosis$.

After the onset of clinical symptoms (15-16 days post EAE induction), rats were treated with 30 mg/kg/day of methylprednisolone (MP) in saline solution or saline solution alone (Veh) intravenously for three consecutive days. On the second day of MP injection, rats were given either 6 mg/kg of the anti-LINGO-1 monoclonal antibody or control antibody, administered intrapetitoneally once a week for three weeks. There were a total of four different treatment groups: (1) control treatment group (Veh+control Antibody (Ab)); (2) MP treatment group (MP+control antibody); (3) anti-LINGO-1 monoclonal antibody treatment group (Veh+ anti-LINGO-1 monoclonal antibody); and (4) combination treatment group (MP+anti-LINGO-1 monoclonal antibody).

One week post the last treatment (4 weeks post the onset of symptoms and 6 weeks post EAE induction), the rats were perfused with 4% paraformaldehyde (PFA) in PBS and cryostat microtome sections of optic nerves (ONs) were stained with anti-βIII tubulin antibody to analyze axonal pathology using DAPI and visualized by fluorescence microscopy at 40× magnification. For axonal quantification, 3 different sections per optic nerve were analyzed, and 3-5 animals were counted per treatment group.

Figure 7:
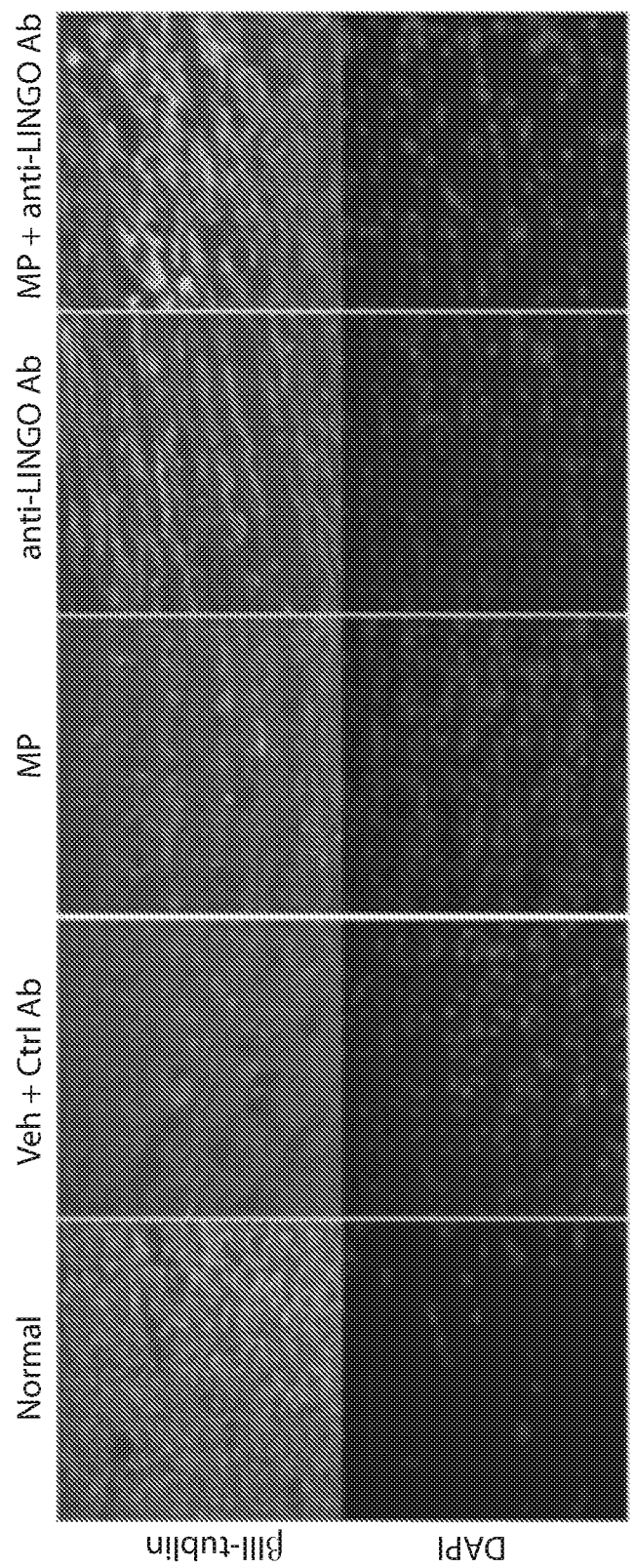
FIG. 7 depicts histological analysis of sections of optic nerve detected by anti-βIII tubulin staining and DAPI, respectively, after the following treatments: treatment group (Veh+control Antibody), methylprednisolone (MP), anti-LINGO-1 antibody, and MP+anti-LINGO-1 antibody.
Figure 8:
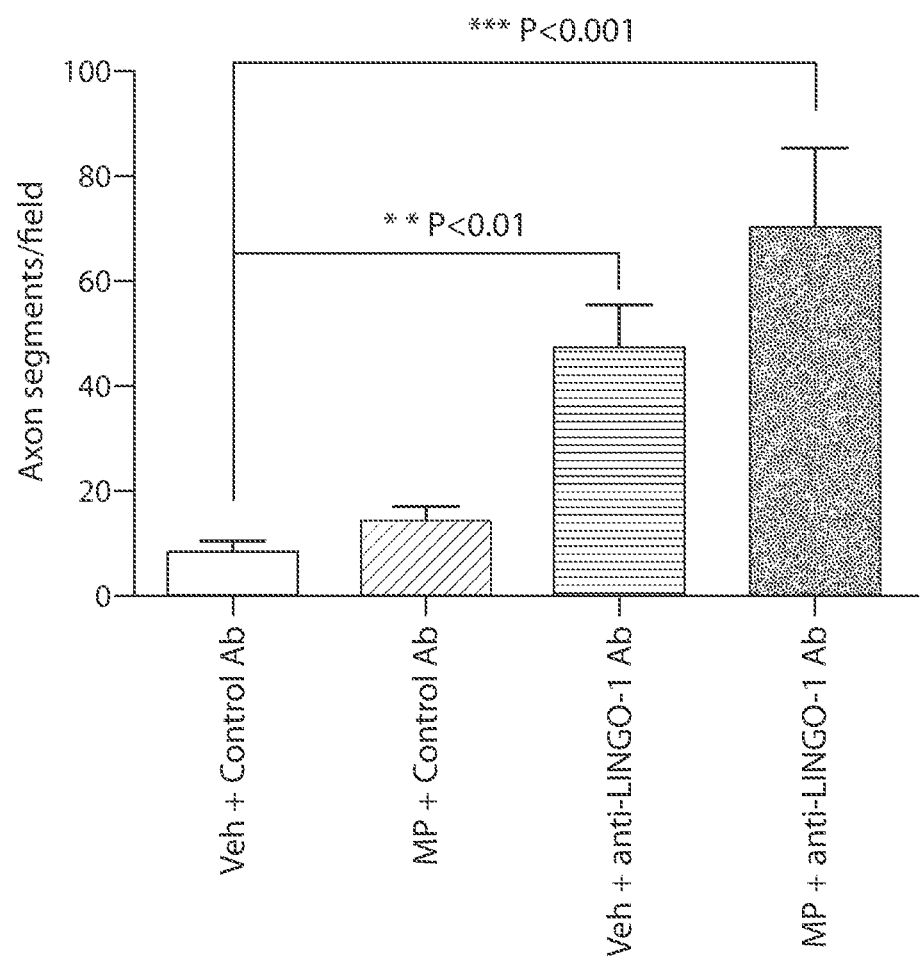
FIG. 8 is a bar graph reflecting the axonal segment count/field in the treatment groups indicated. The anti-LINGO-1 monoclonal antibody treatment group (Veh+anti-LINGO-1 monoclonal antibody) showed 5-fold higher axonal numbers, suggesting that anti-LINGO-1 monoclonal antibody treatment prevented axonal loss (FIG. 8). The combination treatment group (MP+anti-LINGO-1 monoclonal antibody) showed an 8-fold increase in axonal numbers compared with the control treatment group (Veh+control Antibody.

As shown in FIG. (FIG. 7), axonal loss was detected in the sections of optic nerves of the control treatment group (Veh+control Antibody) by anti-βIII tubulin staining, suggesting severe axonal loss. Inflammatory infiltration was also observed ion these areas as shown by DAPI staining (FIG. 7). The number of axons was slightly higher in the MP treatment group (MP+control antibody) (p value=non significant) (FIG. 8). The anti-LINGO-1 monoclonal antibody treatment group (Veh+anti-LINGO-1 monoclonal antibody) showed 5-fold higher axonal numbers, suggesting that anti-LINGO-1 monoclonal antibody treatment prevented axonal loss (FIG. 8). The combination treatment group (MP+anti-LINGO-1 monoclonal antibody) showed an 8-fold increase in axonal numbers compared with the control treatment group (Veh+control Antibody; suggesting that combination treatment of anti-LINGO-1 antagonist such as an anti-LINGO-1 monoclonal antibody with high dose corticosteroids can have a synergistic effect (FIG. 8).

Overall, LINGO-1 antagonism reduced axonal loss in the optic nerve in rat EAE. While axonal protection was not seen with daily treatment for three days with high dose intravenous methylprednisolone, anti-LINGO-1 monoclonal antibody treatment resulted in axonal protection in inflammatory demyelination; and combination treatment of the anti-LINGO-1 monoclonal antibody with high dose IV methylprednisolone resulted in even greater axonal protection.

In summary, LINGO-1 blockade with the monoclonal anti-LINGO-1 antibody reduced axonal loss in rat MOG-EAE; and the neuroprotective effects of LINGO-1 blockade in rat MOG-EAE were seen in the presence or absence of anti-inflammatory treatment with high-dose steroids.

Example 3. Efficacy of Anti-LINGO-1 Antibodies in a Clinical Study

AON damages the optic nerve, causing loss of the myelin sheath and axonal injury, and may result in loss of visual function, e.g., result in permanent structural and functional visual deficits. AON is one of the initial manifestations of MS. There are commonalities in the pathology of MS and AON lesions (e.g., demyelination, axonal loss, inflammation). Current treatment is limited to high-dose intravenous (IV) corticosteroids that decrease inflammation in the acute phase but do not affect long-term visual outcome. Hence, there is an unmet need for therapies that can support repair and protection in AON and more generally in the central nervous system (CNS) during acute injury.

AON is considered a good clinical model to measure the mechanisms of action of anti-LINGO-1: remyelination and neuroprotection. Anti-LINGO-1 is a first-in-class human monoclonal antibody directed against LINGO-1 (leucine-rich repeat and immunoglobulin domain-containing neurite outgrowth inhibitor receptor-interacting protein-1), a CNS-specific cell surface glycoprotein and inhibitor of oligodendrocyte differentiation, myelination and remyelination. Anti-LINGO-1 has shown efficacy in preclinical models of remyelination and neuroprotection, and was well tolerated in Phase 1 clinical studies. See, e.g., Mi et al. *CNS Drugs* 27.7(2013):493-503; and Tran et al. *Neurol. Neuroimmunol. Neuroinflamm.* 1.2(2014):e18.

The randomized, double-blind, placebo-controlled, parallel-group Phase 2 (RENEW) trial (ClinicalTrials.gov Identifier: NCT01721161) was aimed to determine the efficacy and safety of anti-LINGO-1, e.g., BIIB033, e.g., opicinumab, for CNS remyelination following the onset of a first episode of AON and establish proof of biology. In the RENEW trial, two distinct mechanisms of action (MOA) of anti-LINGO-1 were studied: (i) remyelination via latency recovery as measured by visual evoked potentials (VEP); and (ii) neuroprotection via reduction of retinal nerve fiber layer (RNFL) and retinal ganglion cell layer (RGCL) thinning as measured by spectral-domain optical coherence tomography (SD-OCT).

Methods

A group of 82 patients receiving a total of 6 intravenous infusions of 100 mg/kg of anti-LINGO-1 antibody or placebo every four weeks was treated to evaluate the effect of an anti-LINGO-1 antibody in patients treated following a first episode of AON according to the RENEW) trial ClinicalTrials.gov Identifier: NCT01721161.

Eligible subjects were 18-55 years of age, had no history of multiple sclerosis (MS), and were experiencing a first unilateral AON episode. A diagnosis AON was based on the presence of at least two of the following: reduced visual acuity; afferent pupillary defect; color vision loss; visual field abnormality; and pain on eye movement. Enrollment was permitted irrespective of whether demyelinating lesions were present on brain magnetic resonance imaging. AON as onset of multiple sclerosis (MS; newly diagnosed) was acceptable. Participants were excluded if they had: a prior episode of optic neuritis/previous central nervous system demyelinating event indicative of MS; an established diagnosis of MS; refractive errors of ±6 diopters or more in either eye; loss of vision not due to AON; a history or evidence of severe disc edema or haemorrhage; an abnormal full-field visual evoked potential (FF-VEP) in the fellow eye at screening; a concomitant ophthalmologic disorder, e.g., diabetic retinopathy, macular degeneration, macular exudate, macular edema, glaucoma, severe astigmatism, ocular trauma, neuromyelitis optica, ischemic optic neuropathy, congenital nystagmus, or other ophthalmologic conditions that could confound the assessment of functional and anatomic endpoint; a history of any clinically significant cardiac, endocrinologic, hematologic, hepatic, immunologic, metabolic, urologic, pulmonary, neurologic, dermatologic, psychiatric, oncologic, renal, severe allergic or anaphylactic reactions, or other major disease; a history of HIV, hepatitis C infection, or hepatitis B infection; a history of drug or alcohol abuse in the last 2 years; been enrolled in another study within the last 3 months or participated in a previous study with anti-leucine-rich repeat and immunoglobulin domain-containing neurite outgrowth inhibitor receptor-interacting protein-1 (anti-LINGO-1); or an inability to comply with study requirements. Participants also were excluded if the investigator felt there were other reasons making participation unsuitable or, if female participants were currently pregnant, were breastfeeding or were planning to conceive during the study.

Figure 9:
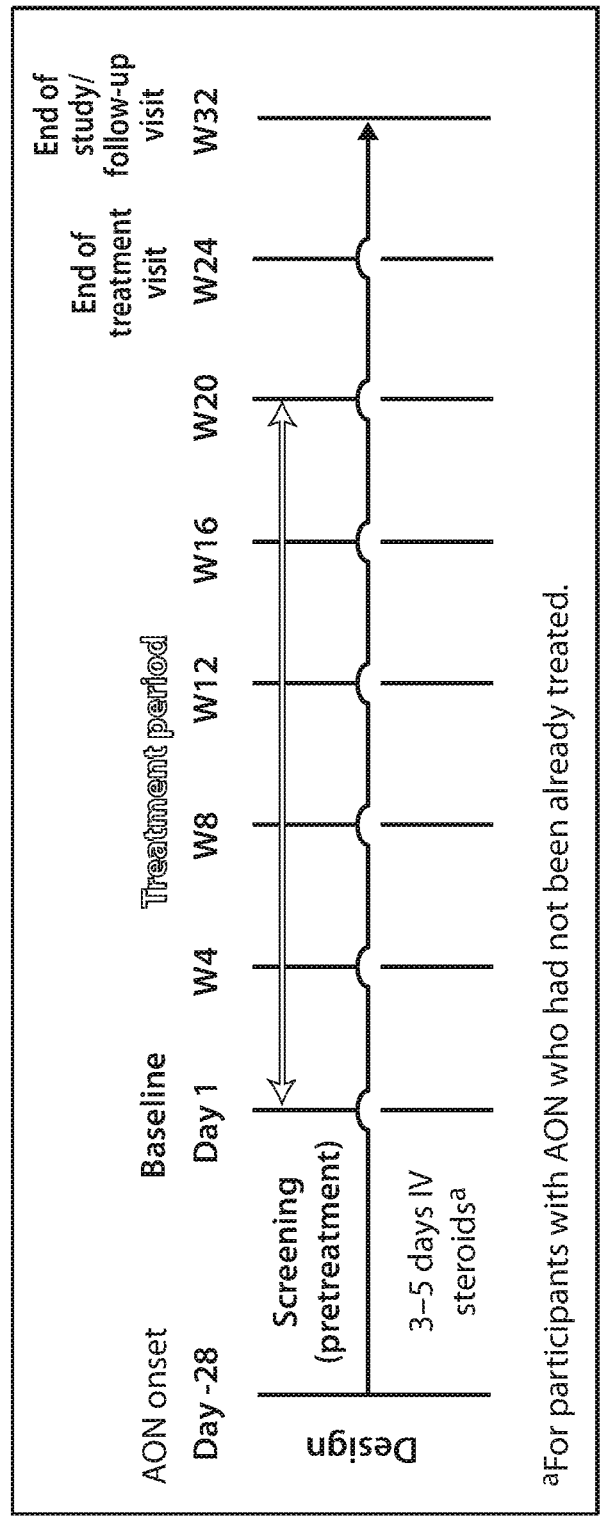
FIG. 9 is a schematic showing a clinical trial design (RENEW trial ClinicalTrials.gov Identifier: NCT01721161).

All participants received treatment with 1 g methylprednisolone/day IV for 3-5 days before randomization. Following treatment with high-dose methylprednisolone, participants were randomized 1:1 to placebo or anti-LINGO-1 100 mg/kg IV every 4 weeks from baseline to week 20 (6 treatments) and followed to week 32 (FIG. 9). Only the pharmacists preparing treatments/pharmacy monitors were unblinded. Participants were randomized by the permuted block method using a centralized interactive voice and web response system. The block size was four and the number of blocks was 50. An independent biostatistician was responsible for overseeing the randomization.

Full-field VEP (FF-VEP), spectral-domain optical coherence tomography (SD-OCT), and low-contrast letter acuity (LCLA) were assessed at screening, baseline, and every 4-8 weeks to study end (week 32) to assess efficacy. The primary endpoint was optic nerve conduction latency at week 24 in the affected eye compared with the unaffected fellow eye at baseline, as measured using full-field VEP (FF-VEP). Recovery of optic nerve conduction latency using FF-VEP compared with the unaffected fellow eye at baseline was a way to evaluate remyelination. A final latency assessment was performed at study end (week 32).

A number of additional analyses, based on FF-VEP latency, were performed, including evaluating the number of participants with FF-VEP latency recovery, defined as affected eye FF-VEP latency ≤10% worse than the fellow eye, at week 24 (prespecified). A post hoc sensitivity analysis around this recovery threshold was performed. The change in FF-VEP latency at week 24 in the intent-to-treat (ITT) population between treatment groups for participants who received ≥4 infusions (post hoc) was also determined.

Secondary efficacy endpoints included change in the following at week 24: (i) RNFL thickness in the affected eye compared with the unaffected eye at baseline; (ii) RGCL/inner plexiform retinal layer (IPL) thickness in the affected eye compared with the unaffected eye at baseline; (iii) change in low-contrast letter acuity (LCLA) from baseline measured using 1.25% and 2.5% Sloan letter charts; the affected eye's own baseline value was used. Thickness of the retinal nerve fiber layer and ganglion cell layer (measured using spectral-domain optical coherence tomography (SD-OCT)) and change in low-contract letter acuity (LCLA) were methods used to evaluate neuroprotection.

Between-treatment comparisons were evaluated by analysis of covariance (ANCOVA) and mixed-effect model repeated measure (MMRM) in the following subject populations: (i) per-protocol (PP; subjects who completed the study, did not miss >1 dose of treatment, and did not receive MS modifying therapy) and (ii) intent-to-treat (ITT; all randomized subjects who received ≥1 dose of study treatment).

For the efficacy endpoints, adjusted mean change was calculated and between-treatment comparisons evaluated by analysis of covariance (ANCOVA) at week 24 and mixed-effect model repeated measure (MMRM) through week 32. Week 32 data were used as a supportive analysis to check whether treatment effect was sustained between end of treatment (week 24) and end of study (week 32).

A more detailed description of these patient populations is as follows:

Intent-to-Treat Population (ITT)

All randomized patients who received at least 1 dose of anti-LINGO-1 or placebo (regardless of their compliance with the protocol), but did not necessarily complete the study. It carries forward the last observed data point per patient who discontinued, until end of study. The ITT population received fewer doses and last observation data was carried forward, potentially impacting the treatment effect observed.

Per-Protocol Population

The per-protocol population is defined as subjects from the ITT population who complete the study, did not miss more than one dose of anti-LINGO-1 or placebo, and did not receive MS modifying therapies during the study period. Last observation carried forward was used for imputation in the ANCOVA analyses.

The subgroups of patients with vs. without FF-VEP latency recovery, defined as affected eye FF-VEP latency ≤10% worse than the fellow eye at week 24, also were compared (post hoc analysis) between treatment groups using a chi-squared test; the sensitivity analyses surrounding the 10% cutoff for these analyses used both chi-squared and Fisher's exact tests. The baseline of the unaffected fellow eye was used as the baseline covariate in ANCOVA and MMRM.

Measurement of FF-VEP

All centers were required to perform all FF-VEP studies using a standard protocol which complied with both the International Society for Clinical Electrophysiology of Vision and American Clinical Neurophysiology Society guidelines. Each VEP study was interpreted independently by two masked clinical electrophysiologists. If the data agreement was not within specified parameters, a third masked, independent clinical electrophysiologist arbitrated the data by reconciling the reader disagreements according to his/her best judgment and expertise, and providing the final interpretation. Each VEP was interpreted without reference to any of the participant's other VEP data. Central readers were not involved in data collection or analysis.

Measurement of RGCL/IPL and RNFL by SD-OCT

SD-OCT scans were obtained according to a standardized study protocol. Images were obtained at each site from a Spectralis (Heidelberg Engineering, Heidelberg Germany) or Cirrus (Carl Zeiss Meditec, Dublin, Calif.) system.

For each participant for whom images were obtained on the Spectralis System, the following scan patterns were obtained on each eye: a dense 97-line preset scan covering a $20°\times20°$ area of the macula centered on the foveal center point in high-speed mode with an ART setting of 16 was used to image the neurosensory retinal layers and vitreoretinal interface; a seven-line preset scan pattern covering a $30°\times5°$ area centered on the foveal center point in high-resolution mode with an ART setting of 25 was used to assess the central macula; an optic nerve head 73-line preset scan covering a $15°\times15°$ area centered on the optic nerve in high-speed mode with an ART setting of 9 was used to image the optic nerve, peripapillary area, and corresponding vitreoretinal interface; an RNFL preset optic nerve $12°$ diameter circle scan centered on the optic nerve was used to measure the RNFL thickness.

For each participant for whom images were obtained on the Cirrus System, the following scan patterns were obtained on each eye: a 512×128 macular cube covering a 6 mm×6 mm area of the macula centered on the foveal center point was used to image the neurosensory retinal layers and vitreoretinal interface; a five-line raster (HD) preset raster scan pattern centered on the foveal center point was used to assess the central macula; a 200×200 optic nerve cube preset scan centered on the optic nerve was used to image the optic nerve, peripapillary area, and corresponding vitreoretinal interface, and to measure RNFL thickness.

Two certified readers in a masked and independent manner determined macular and RNFL thickness and made morphological assessments on coded scans for each participant. A data specialist entered all concordant values from the two readers into the trial database and flagged discrepant values. A third certified senior reader arbitrated the discrepant values. The senior reader reconciled all reader disagreements according to his/her best judgment and expertise, recording his/her decision as the final arbitrated value that the data specialist entered into the trial database. Each SD-OCT categorical variable was graded as present, absent, or unreadable (due to poor quality or centration of the scan), according to either the agreed decision between masked readers or the arbitrated decision when the readers disagreed. For ganglion cell complex measurement, two independent readers assessed segmentation line placement, and the two readers adjudicated discrepancies. After finishing arbitration, adjudication, and data entry, another masked data specialist verified the accuracy of all values entered into the trial database.

Figure 10:
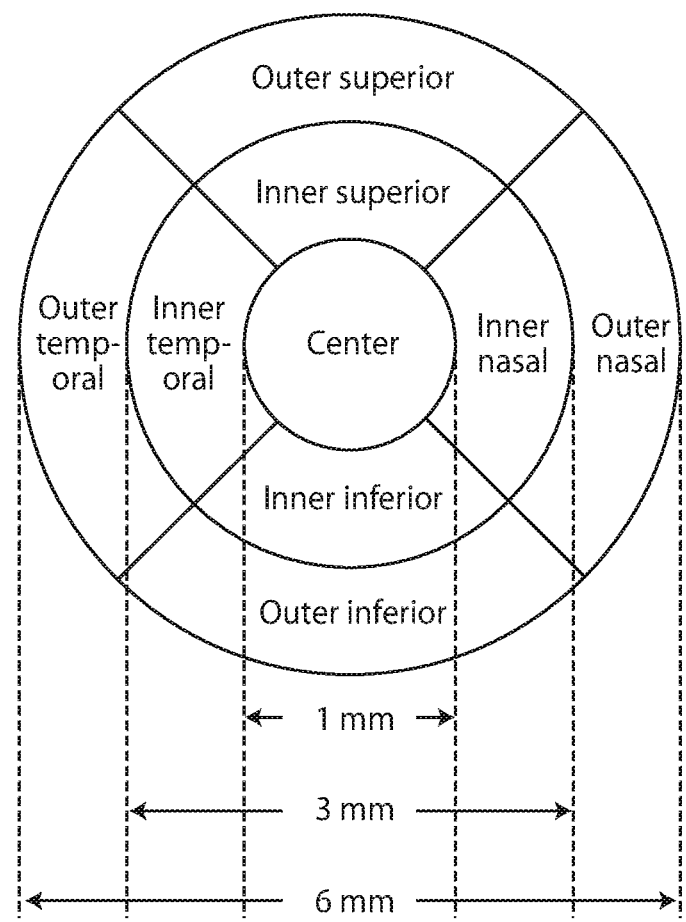
FIG. 10 is a diagram depicting the nine sectors (corresponding to the early treatment diabetic retinopathy grid) used to calculate average retinal ganglion cell layer thickness.

Central subfield and RNFL thickness were measured on macular and RNFL Spectralis and Cirrus scans using Heyex software (Heidelberg Engineering), and Cirrus software (Zeiss Meditech), respectively. Spectralis macular and RNFL segmentation line artifacts were corrected manually. Cirrus macular segmentation line artifacts were also corrected manually. It was not possible to correct Cirrus RNFL segmentation artifacts manually because of software limitations. Ganglion cell complex that comprised the RGCL/IPL thickness was measured using customized semiautomated software (DOCTRAP). The average RGCL thickness was calculated in each of nine sectors corresponding to the Early Treatment Diabetic Retinopathy grid as shown in FIG. 10. In addition, a global average thickness across all nine sectors was determined.

Results

Figure 11:
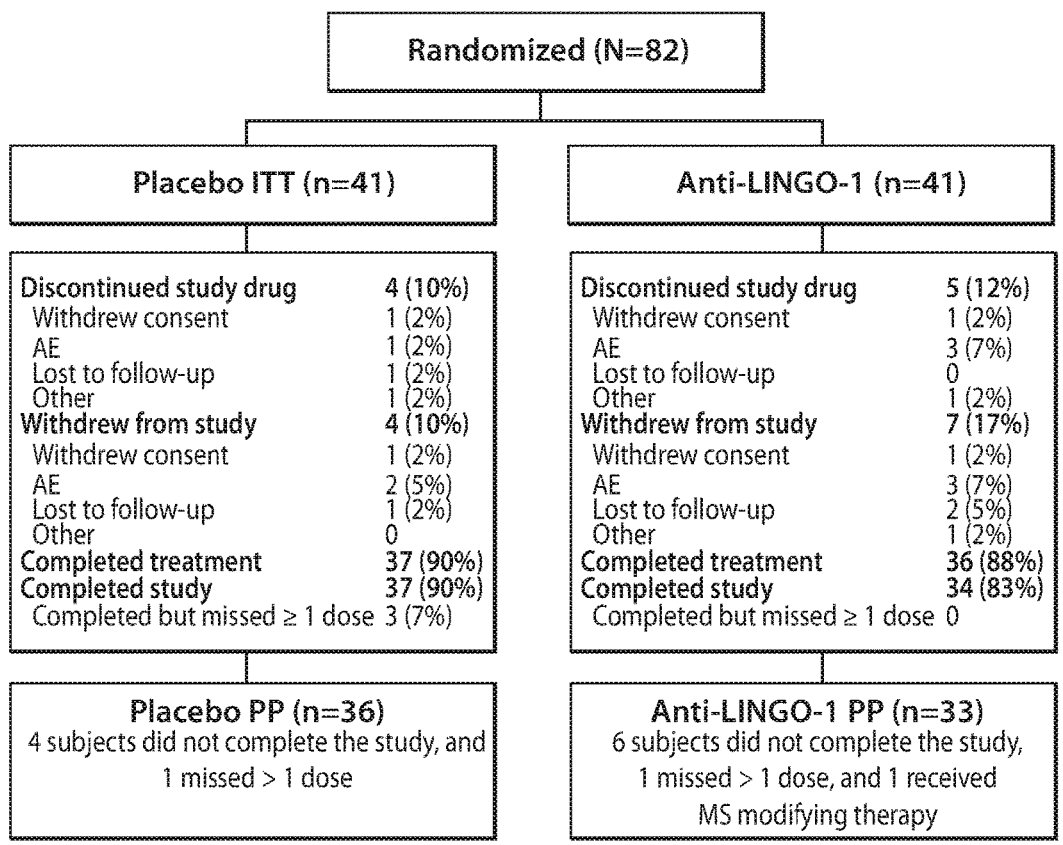
FIG. 11 is a chart showing rates of withdrawal and treatment discontinuation in the clinical trial.

Eighty-two subjects were randomized to placebo or anti-LINGO-1 at 33 sites across Europe, Australia, and Canada. All subjects were included in the ITT analyses (n=41 in each group). The PP population comprised 36 subjects in the placebo group and 33 treated with anti-LINGO-1 (FIG. 11). The groups were similar in baseline demographics (Table 5) and rates of study withdrawal and treatment discontinuation (FIG. 11).

TABLE 5

Subject demographic characteristics at baseline

| | ITT | | | PP | | |
|---|---|---|---|---|---|---|
| Characteristic | Placebo n = 41 | Anti-LINGO-1 n = 41 | All subjects N = 82 | Placebo n = 36 | Anti-LINGO-1 n = 33 | All subjects N = 69 |
| Female, % | 76 | 66 | 71 | 75 | 64 | 70 |
| White, % | 95 | 98 | 96 | 97 | 97 | 97 |
| Mean ± SD age, y | 32.4 ± 8.85 | 31.8 ± 7.17 | 32.1 ± 8.01 | 32.2 ± 8.80 | 31.2 ± 7.12 | 31.7 ± 8.00 |
| Median (range) weight, kg | 75 (47-119) | 71.2 (46-106) | 72.2 (46-119) | 73.8 (50-119) | 72.2 (46-106) | 72.5 (46-119) |
| Median (range) height, cm | 169.0a (155-194) | 170.0a (158-188) | 170.0a (155-194) | 169.5b (155-194) | 170.0b (158-188) | 170.0b (155-194) | a n = 39 in each group; total N = 78.
b Placebo, n = 34; anti-LINGO-1, n = 31; total N = 65.

However, more severe cases of AON were randomized more frequently to anti-LINGO-1 than placebo as shown by the prevalence of conduction block (lack of any FF-VEP response; 2:1 for the anti-LINGO-1 vs. placebo groups) and severity of AON signs and symptoms post steroid treatment (Table 6).

TABLE 6

Subject clinical characteristics

| | ITT | | | PP | | |
|---|---|---|---|---|---|---|
| Characteristic | Placebo n = 41 | Anti-LINGO-1 n = 41 | All subjects N = 82 | Placebo n = 36 | Anti-LINGO-1 n = 33 | All subjects N = 69 |
| Mean ± SD days from first AON symptom to first dose$^a$ | 24.6 ± 3.44 | 23.6 ± 3.98 | 24.1 ± 3.73 | 24.3 ± 3.49 | 24.0 ± 3.75 | 24.2 ± 3.59 |
| Mean ± SD days from confirmed AON diagnosis to first dose | 19.2 ± 4.85 | 18.7 ± 4.73 | 19.0 ± 4.77 | 19.1 ± 4.97 | 19.2 ± 4.55 | 19.1 ± 4.74 |
| No. with affected right eye (%) | 19 (46) | 25 (61) | 44 (54) | 16 (44) | 20 (61) | 36 (52) |
| Criteria for AON diagnosis, n (%) | 36 (88) | 41 (100) | 77 (94) | 31 (86) | 33 (100) | 64 (93) |
| | 30 (73) | 33 (80) | 63 (77) | 27 (75) | 26 (79) | 53 (77) |
| Decreased visual acuity | 34 (83) | 31 (76) | 65 (79) | 29 (81) | 23 (70) | 52 (75) |
| Decreased color vision | 32 (78) | 37 (90) | 69 (84) | 27 (75) | 30 (91) | 57 (83) |

TABLE 6-continued

Subject clinical characteristics

|  | ITT | | | PP | | |
|---|---|---|---|---|---|---|
| Characteristic | Placebo n = 41 | Anti-LINGO-1 n = 41 | All subjects N = 82 | Placebo n = 36 | Anti-LINGO-1 n = 33 | All subjects N = 69 |
| Relative afferent pupillary defect | 31 (76) | 36 (88) | 67 (82) | 27 (75) | 28 (85) | 55 (80) |
| Visual field defect | 5 (12) | 4 (10) | 9 (11) | 5 (14) | 4 (12) | 9 (13) |
| Ocular pain |  |  |  |  |  |  |
| Other |  |  |  |  |  |  |
| AON signs and symptoms[b] | 29 (71) | 34 (83) | 63 (77) | 25 (69) | 27 (82) | 52 (75) |
| at Screening or Baseline, n (%) | 33 (80) | 32 (78) | 65 (79) | 28 (78) | 25 (76) | 53 (77) |
|  | 8 (20) | 18 (44) | 26 (32) | 6 (17) | 16 (48) | 22 (32) |
| Visual field defect | 8 (20) | 12 (29) | 20 (24) | 6 (17) | 11 (33) | 17 (25) |
| Color desaturation | 33 (80) | 30 (73) | 63 (77) | 28 (78) | 24 (73) | 52 (75) |
| Uhthoff's symptom |  |  |  |  |  |  |
| Swollen optic disc |  |  |  |  |  |  |
| Relative afferent pupillary defect |  |  |  |  |  |  |
| FF-VEP conduction block in the affected eye at Baseline, n (%) | 5 (12) | 10 (24) | 15 (18) | 5 (14) | 6 (18) | 11 (16) |
| Mean ± SD FF-VEP latency in the fellow eye at Baseline, ms | 101.66 ± 5.248 | 102.66 ± 6.353 | 102.16 ± 5.812 | 101.00 ± 4.905 | 102.62 ± 6.074 | 101.78 ± 5.514 |
| Mean ± SD brain Gd+ lesions before first dose[c] | 0.5 ± 1.61 | 0.2 ± 1.02 | 0.4 ± 1.35 | 0.2 ± 0.65 | 0.1 ± 0.35 | 0.1 ± 0.53 |
| Mean ± SD RGCL/IPL thickness in the affected eye at baseline—μm§ | 66.0 ± 6.9 | 63.8 ± 7.4 | 64.8 ± 7.2 | 65.9 ± 7.2 | 63.6 ± 8.1 | 64.8 ± 7.7 |
| Mean ± SD volume of brain T2 lesions before first dose,[a] mL | 1.0895 ± 1.31543 | 1.0900 ± 1.90443 | 1.0898 ± 1.62570 | 0.9461 ± 1.03425 | 0.8419 ± 1.54836 | 0.8948 ± 1.30383 |

Gd+ = gadolinium-enhancing.
[a]First dose given on average 2 weeks after completion of high-dose IV methylprednisolone treatment (1 g daily for 3-5 days).
[b]Symptoms were not uniformly tested in accordance with a predefined protocol.
[c]ITT population: n = 38 in each group; total N = 76.
§n = 38 in the placebo group and n = 40 in the opicinumab group, total = 78 for the ITT population; n = 34 in the placebo group and n = 32 in the opicinumab group, total = 66 for the per protocol (PP) population. PP population: placebo, n = 34; anti-LINGO-1, n = 33; total N = 67.

Figure 12:
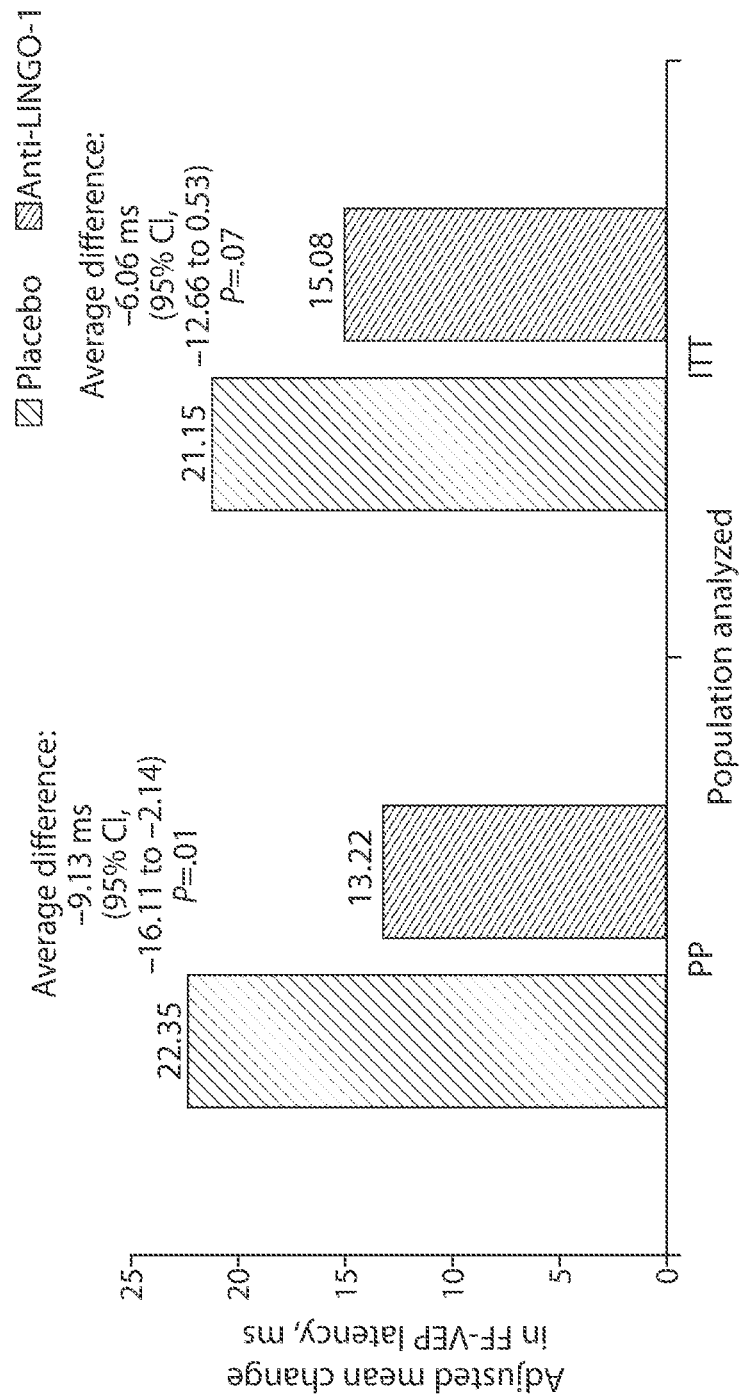
FIG. 12 is a bar graph showing the adjusted mean change in optic nerve conduction latency (measured by FF-VEP) in the affected eye compared with the unaffected fellow eye at baseline in the PP and ITT populations at week 32 (by MMRM) in the RENEW trial. The left bar of each set of bars refers to the placebo group, and the right bar of each set of bars refers to the anti-LINGO-1 group.
Figures 18A, 18B:
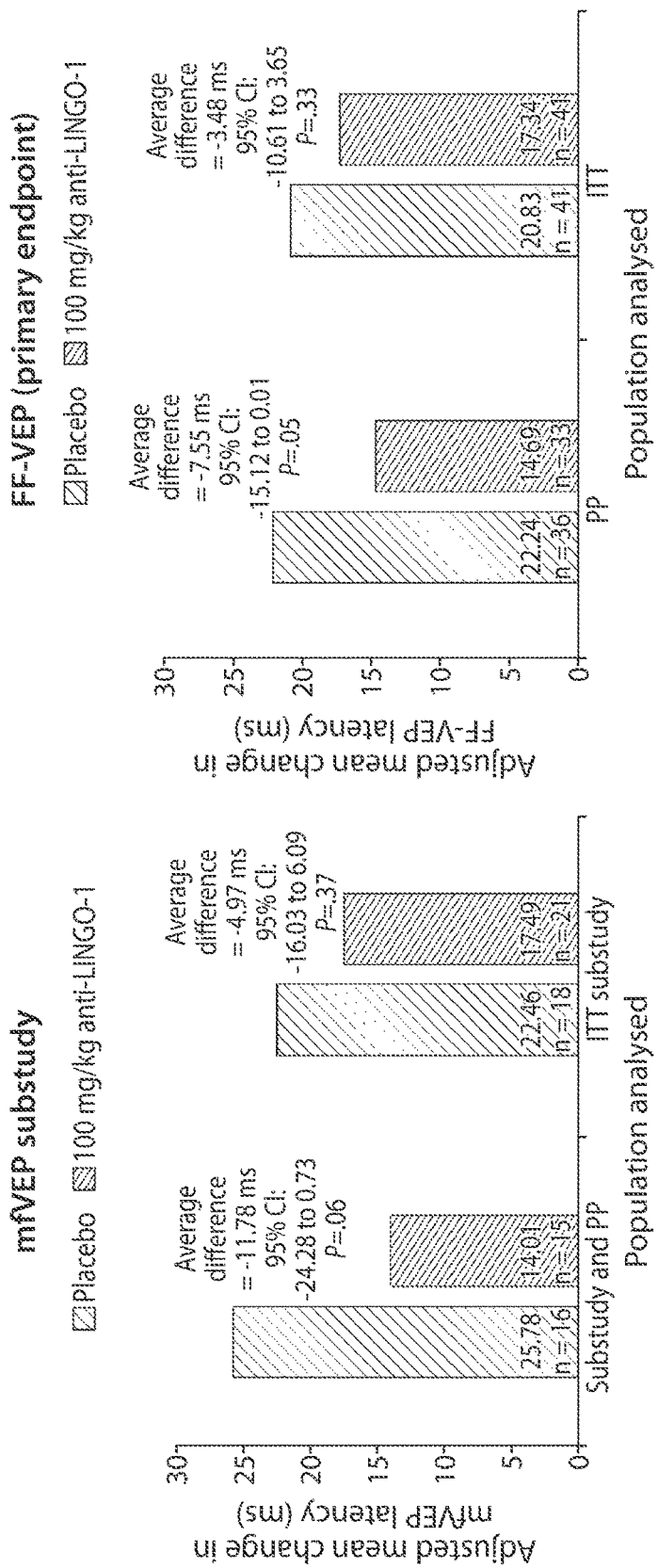
FIGS. 18A and 18B are bar graphs showing the adjusted mean change in mfVEP latency compared with FF-VEP latency at week 24 in the affected eye compared with the unaffected fellow eye at baseline (by ANCOVA). CI=confidence interval; FF-VEP=full-field visual evoked potentials; ITT=intent-to-treat; mfVEP=multifocal visual evoked potentials; PP=per-protocol in the RENEW trial. The left bar of each set of bars refers to the placebo group, and the right bar of each set of bars refers to the anti-LINGO-1 group. mfVEP latency is shown in 18A and FF-VEP latency is shown in 18B.

The average time on treatment was 23.0±4.12 weeks in the placebo group and 22.5±5.01 weeks in the anti-LINGO-1 group. In the PP and ITT populations, the anti-LINGO-1 group showed improved optic nerve conduction latency vs. placebo at week 24 (Table 7) and week 32. In the PP population, anti-LINGO-1-treated patients showed a significantly improved average difference in latency recovery vs placebo: 7.55 msec at 24 wks (95% CI, −15.1 to 0.0, ANCOVA p=0.05) (FIG. 12) and 9.13 msec (95% CI, −16.1 to −2.1, MMRM p=0.01) at 32 wks (FIG. 18B). Corresponding differences in the ITT population were 3.48 msec (95% CI, −10.6 to 3.7, p=0.33) at 24 wks (FIG. 12) and 6.06 msec (95% CI, −12.7 to 0.5, p=0.07) at 32 wks (FIG. 18B). In participants from the ITT population who received ≥4 infusions, improvement in FF-VEP latency at week 24 was similar to the PP population analysis: adjusted mean change of 22.0 (placebo; n=38) versus 15.8 (anti-LINGO-1; n=37), a treatment difference versus placebo of −6.1 ms (95% CI, −13.3 to 1.1; P=0.10) using ANCOVA.

Figure 13:
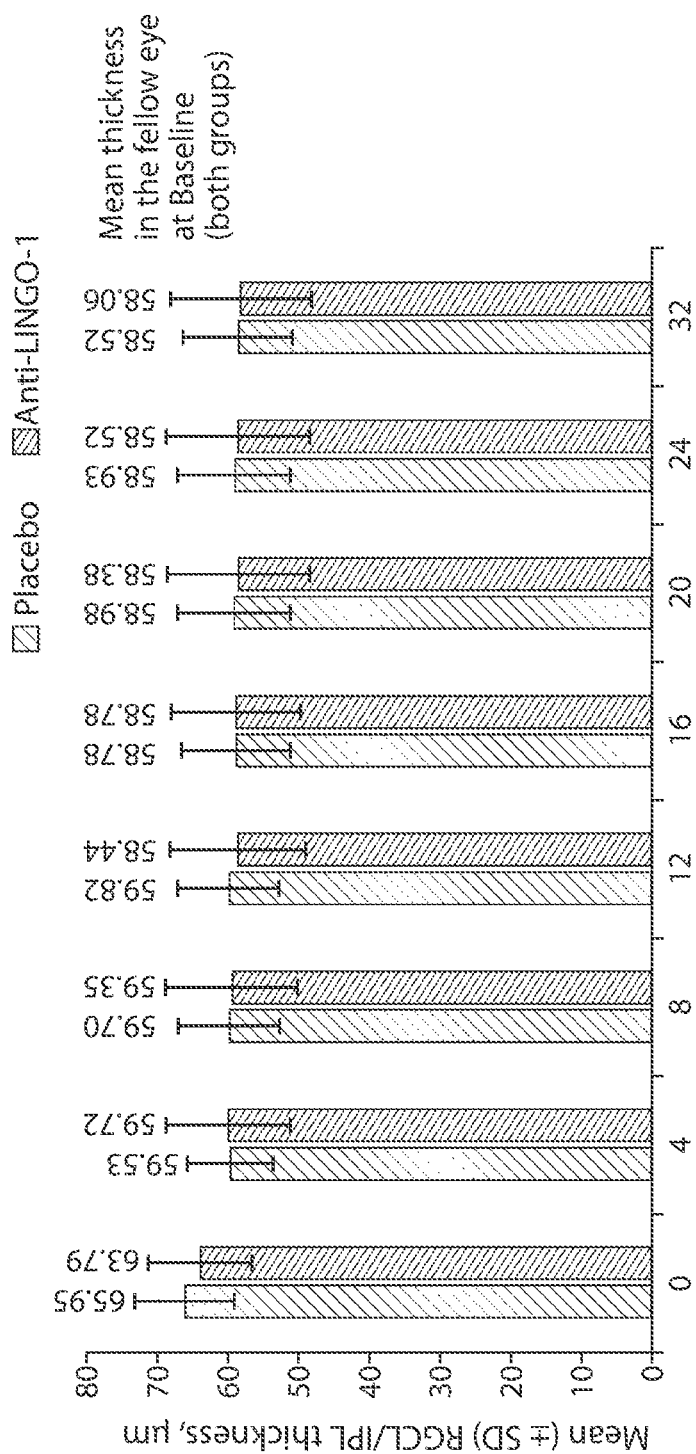
FIG. 13 is a bar graph showing the mean RGCL/IPL thickness at each visit (measured by SD-OCT) in the affected eye in the ITT population up to week 32 in the RENEW trial. The left bar of each set of bars refers to the placebo group, and the right bar of each set of bars refers to the anti-LINGO-1 group.
Figure 14:
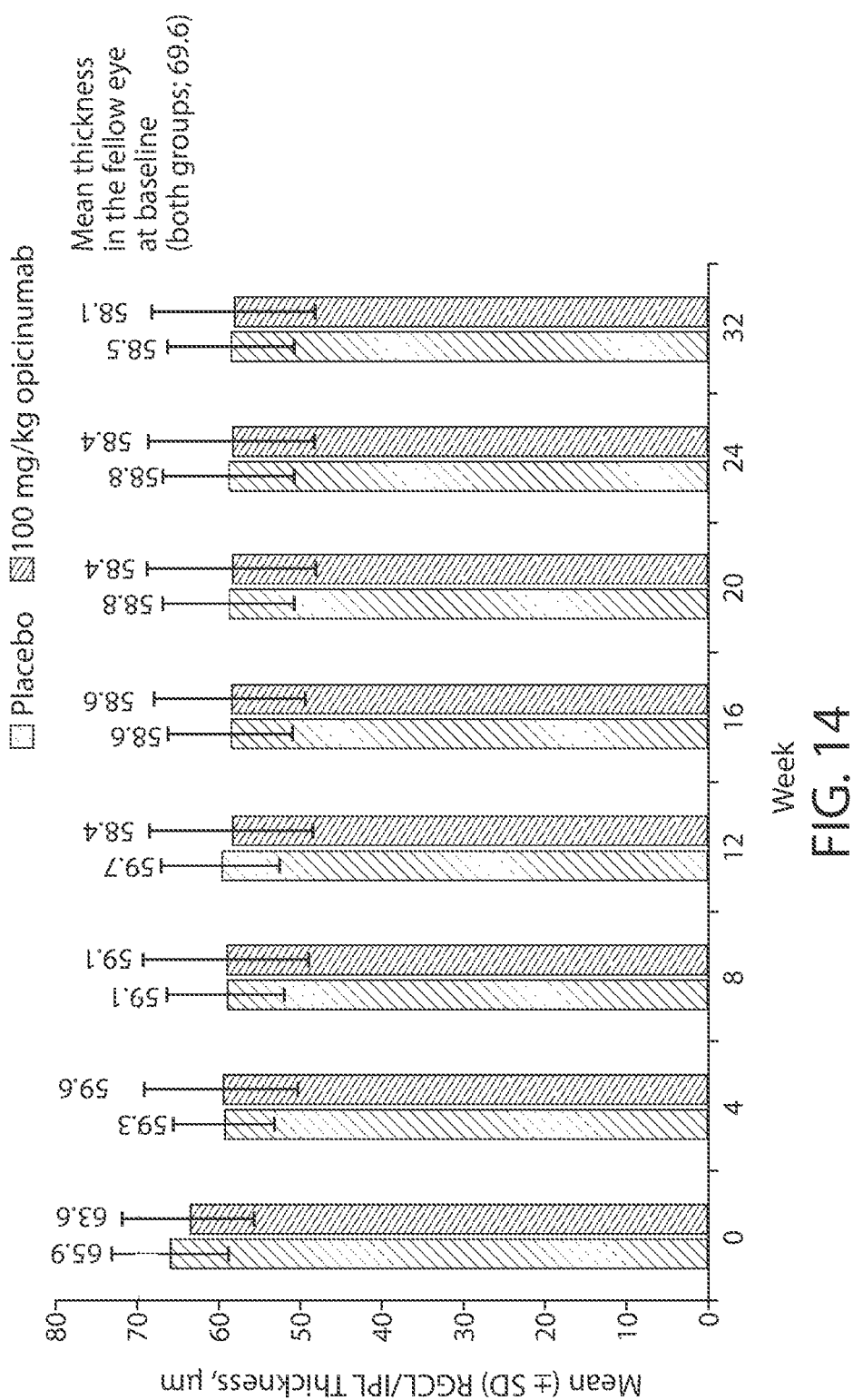
FIG. 14 is a bar graph showing the mean RGCL/IPL thickness at each visit (measured by SD-OCT) in the affected eye in the PP population up to week 32 in the RENEW trial. The left bar of each set of bars refers to the placebo group, and the right bar of each set of bars refers to the anti-LINGO-1 group.

During the 32 week period, no differences were observed in secondary efficacy endpoints, SD-OCT and LCLA. (Table 7 and FIGS. 13 and 14). Overall incidence and severity of adverse events (AEs) were comparable across treatment arms. Treatment-related serious AEs were infusion-related hypersensitivity reactions (N=2) and asymptomatic transient elevation in liver transaminases (N=1).

TABLE 7

Summary of primary and secondary efficacy outcomes at week 24

| Endpoint | ITT | | PP | |
|---|---|---|---|---|
|  | Change for placebo and anti-LINGO-1, plus difference vs. placebo (95% CI) | P value | Change for placebo and anti-LINGO-1, plus difference vs. placebo (95% CI) | P value |
| Mean change in optic nerve latency (FF- | 20.83 ms; 17.34 ms −3.48 ms (−10.61 to 3.65) | .33 | 22.24 ms; 14.69 ms −7.55 ms (−15.12 to 0.01) | .05 |

TABLE 7-continued

Summary of primary and secondary efficacy outcomes at week 24

|  | ITT | | PP | |
|---|---|---|---|---|
| Endpoint | Change for placebo and anti-LINGO-1, plus difference vs. placebo (95% CI) | P value | Change for placebo and anti-LINGO-1, plus difference vs. placebo (95% CI) | P value |
| VEP) Mean percentage change in RNFL thickness (SD-OCT) | −11.77%; −15.66% −3.89% (−9.70 to 1.92) | .19 | −12.22%; −16.98% −4.76%(−11.26 to 1.74) | .15 |
| Mean change in RGCL/IPL thickness | −9.90 μm; −11.05 μm −1.15 μm (−4.51 to 2.21) | .50 | −10.17 μm; −11.93 μm −1.76 μm (−5.50 to 1.98) | .35 |
| Change in LCLA; affected eye, 1.25% Sloan letter chart | 8.1; 6.5 −1.6 (−6.9 to 3.6) | .54 | 7.2; 6.0 −1.2 (−6.6 to 4.3) | .66 |
| Change in LCLA; affected eye, 2.5% Sloan letter chart | 11.9; 11.0 −0.8 (−6.5 to 4.9) | .77 | 11.6; 10.8 −0.8(−6.7 to 5.2) | .80 |

CI = confidence interval.

Among participants in the ITT population whose FF-VEP latency was impaired in the affected eye at baseline (defined as >3% worse than fellow eye or with conduction block), 53% of patients (16/30) in the anti-LINGO-1 group had FF-VEP latency recovery at week 24 (defined as affected eye FF-VEP latency ≤10% worse than the fellow eye) compared with 26% (9/34) of the placebo group (P=0.0279). At week 12, 29% (10/35) of the anti-LINGO-1 group and 12% (4/33) of the placebo group had normal/mildly prolonged FF-VEP latency (P=0.09). Similar results were observed in the PP population with 54% (15/28) of the anti-LINGO-1 and 27% (9/33) of the placebo groups having normal/mildly prolonged FF-VEP latency at week 24 (P=0.04) and 30% (9/30) of the anti-LINGO-1 and 13% (4/31) of the placebo groups at week 12 (P=0.10). Post hoc sensitivity analyses performed in the PP population demonstrated that 10% was an appropriate cutoff to indicate latency recovery (see Table 8).

TABLE 8

Full-Field Visual Evoked Potential Latency Recovery Sensitivity Analyses in the Per-Protocol Population.

|  | Baseline | | Week 12 | | Week 24 | |
|---|---|---|---|---|---|---|
|  | Placebo | Anti-LINGO-1 | Placebo | Anti-LINGO-1 | Placebo | Anti-LINGO-1 |
| No. with >3% prolonged latency or conduction failure | 34 (n = 36) | 30 (n = 33) | | | | |
| ≤5% worse than fellow eye | 1/34 (3) | 2/30 (7) | 0/31 | 4/30 (13) | 5/33 (15) | 9/28 (32) |
| >5% worse than fellow eye or conduction block - no. (%) | 33/34 (97) | 28/30 (93) | 31/31 (100) | 26/30 (87) | 28/33 (85) | 19/28 (68) |
| Difference* | | 4 | | 13 | | 17 |
| Chi-squared P value | | 0.48 | | 0.04 | | 0.12 |
| Fisher exact P value | | 0.60 | | 0.05 | | 0.14 |
| ≤8% worse than fellow eye | 1/34 (3) | 2/30 (7) | 2/31 (6) | 7/30 (23) | 8/33 (24) | 14/28 (50) |
| >8% worse than fellow eye or conduction block - no. (%) | 33/34 (97) | 28/30 (93) | 29/31 (94) | 23/30 (77) | 25/33 (76) | 14/28 (50) |
| Difference* | | 4 | | 17 | | 26 |
| Chi-squared P value | | 0.48 | | 0.06 | | 0.04 |
| Fisher exact P value | | 0.60 | | 0.08 | | 0.06 |
| ≤10% worse than fellow eye | 1/34 (3) | 2/30 (7) | 4/31 (13) | 9/30 (30) | 9/33 (27) | 15/28 (54) |
| >10% worse than fellow eye or | 33/34 (97) | 28/30 (93) | 27/31 (87) | 21/30 (70) | 24/33 (73) | 13/28 (46) |

TABLE 8-continued

Full-Field Visual Evoked Potential Latency Recovery Sensitivity Analyses in the Per-Protocol Population.

| | Baseline | | Week 12 | | Week 24 | |
|---|---|---|---|---|---|---|
| | Placebo | Anti-LINGO-1 | Placebo | Anti-LINGO-1 | Placebo | Anti-LINGO-1 |
| conduction block - no. (%) | | | | | | |
| Difference* | 4 | | 17 | | 27 | |
| Chi-squared P value | 0.48 | | 0.10 | | 0.04 | |
| Fisher exact P value | 0.60 | | 0.13 | | 0.06 | |
| ≤12% worse than fellow eye - no. (%) | 3/34 (9) | 4/30 (13) | 7/31 (23) | 13/30 (43) | 9/33 (27) | 15/28 (54) |
| >12% worse than fellow eye or conduction block - no. (%) | 31/34 (91) | 26/30 (87) | 24/31 (77) | 17/30 (57) | 24/33 (73) | 13/28 (46) |
| Difference* | 4 | | 20 | | 27 | |
| Chi-squared P value | 0.56 | | 0.08 | | 0.04 | |
| Fisher exact P value | 0.70 | | 0.11 | | 0.06 | |
| ≤15% worse than fellow eye - no. (%) | 3/34 (9) | 10/30 (33) | 11/31 (35) | 16/30 (53) | 11/33 (33) | 16/28 (57) |
| >15% worse than fellow eye or conduction block - no. (%) | 31/34 (91) | 20/30 (67) | 20/31 (65) | 14/30 (47) | 22/33 (67) | 12/28 (43) |
| Difference* | 24 | | 18 | | 24 | |
| Chi-squared P value | 0.02 | | 0.16 | | 0.06 | |
| Fisher exact P value | 0.03 | | 0.20 | | 0.08 | |

*Difference was calculated as percentage of anti-LINGO-1 minus percentage of placebo.

No treatment effect was observed for the secondary efficacy endpoints of RNFL and RGCL/IPL thickness by SD-OCT or change in LCLA for placebo versus anti-LINGO-1 at week 24 (see Table 9 for PP population). However, the majority of RGCL/IPL thinning in the PP population occurred before the first study dose administration and all had occurred before the second dose was given on week 4 (Table 6, FIG. 14; corresponding fellow eye data given in Table 10). The results for the secondary endpoints were similar for the ITT population (Table 11, FIG. 13).

TABLE 9

Secondary Efficacy Outcomes at Week 24 (Analysis of Covariance) for the Per-Protocol Population.

| Endpoint | Placebo (N = 36) | Opicinumab (N = 33) |
|---|---|---|
| Mean percentage change in RNFL thickness - SD-OCT*; affected eye at week 24 vs. baseline fellow eye | −12.2 | −17.0 |
| Treatment difference at week 24 vs. placebo (95% CI)* | −4.8 (−11.3 to 1.7) | |
| P value | 0.15 | |
| Mean change in RGCL/IPL thickness - μm*; affected eye at week 24 vs. baseline fellow eye | −10.2 | −11.9 |
| Treatment difference at week 24 vs. placebo (95% CI)* | −1.8 (−5.5 to 2.0) | |
| P value | 0.35 | |
| Change in LCLA - 1.25% Sloan chart†; affected eye at week 24 vs. baseline | 7.2 | 6.0 |
| Treatment difference at week 24 vs. placebo (95% CI)† | −1.2 (−6.6 to 4.3) | |
| P value | 0.66 | |
| Change in LCLA - 2.5% Sloan chart†; affected eye at week 24 vs. baseline | 11.6 | 10.8 |

TABLE 9-continued

Secondary Efficacy Outcomes at Week 24 (Analysis of Covariance) for the Per-Protocol Population.

| Endpoint | Placebo (N = 36) | Opicinumab (N = 33) |
|---|---|---|
| Treatment difference at week 24 vs. placebo (95% CI)† | −0.8 (−6.7 to 5.2) | |
| P value | 0.80 | |

CI denotes confidence interval, RGCL/IPL retinal ganglion cell layer/inner plexiform retinal layer, RNFL retinal nerve fiber layer, and SD-OCT spectral-domain optical coherence tomography.

*A decrease (negative value) represents loss of retinal layers; the difference vs. placebo represents the more severe acute optic neuritis evident pretreatment initiation in the opicinumab group (Table 6).

†An increase in low-contrast letter acuity (LCLA) from baseline represents recovery; a negative difference vs. placebo indicates a lack of treatment effect.

TABLE 10

Mean Retinal Ganglion Cell Layer/Inner Plexiform Layer (RGCL/IPL) Thickness (Measured by Spectral-Domain Optical Coherence Tomography) in the Fellow Eye in the Intent-to-Treat (ITT) and Per-Protocol (PP) Populations over the Course of the Study.

| Mean ± SD | ITT | | PP | |
|---|---|---|---|---|
| GCL/IPL thickness - μm | Placebo (N = 41) | Anti-LINGO-1 (N = 41) | Placeb (N = 36) | Anti-LINGO-1 (N = 33) |
| Baseline | 69.2 ± 5.7 | 69.8 ± 5.5 | 68.9 ± 5.8 | 70.5 ± 5.7 |
| Week 12 | 69.0 ± 6.1 | 69.8 ± 5.9 | 68.7 ± 5.9 | 70.4 ± 6.0 |
| Week 24 | 69.1 ± 5.8 | 69.9 ± 6.5 | 68.8 ± 5.7 | 70.2 ± 6.5 |
| Week 32 | 68.7 ± 5.7 | 69.9 ± 6.5 | 68.7 ± 5.7 | 69.9 ± 6.4 |

TABLE 11

Secondary Efficacy Outcomes at Week 24 (Analysis of Covariance) for the Intent-to-Treat Population.

| Endpoint | Placebo (N = 41) | Anti-LINGO-1 (N = 41) |
|---|---|---|
| Mean percentage change in RNFL thickness - SD-OCT*; affected eye at week 24 vs. baseline fellow eye | −11.8 | −15.7 |
| Treatment difference at week 24 vs. placebo (95% CI)* | −3.9 (−9.7 to 1.9) | |
| P value | 0.19 | |
| Mean change in RGCL/IPL thickness - μm*; affected eye at week 24 vs. baseline fellow eye | −9.9 | −11.1 |
| Treatment difference at week 24 vs. placebo (95% CI)* | −1.2 (−4.5 to 2.2) | |
| P value | 0.50 | |
| Change in LCLA - 1.25% Sloan chart†; affected eye at week 24 vs. baseline | 8.1 | 6.5 |
| Treatment difference at week 24 vs. placebo (95% CI)† | −1.6 (−6.9 to 3.6) | |
| P value | 0.54 | |
| Change in LCLA - 2.5% Sloan chart†; affected eye at week 24 vs. baseline | 11.9 | 11.0 |
| Treatment difference at week 24 vs. placebo (95% CI)† | −0.8 (−6.5 to 4.9) | |
| P value | 0.77 | |

CI denotes confidence interval,
RGCL/IPL retinal ganglion cell layer/inner plexiform retinal layer,
RNFL retinal nerve fiber layer, and
SD-OCT spectral-domain optical coherence tomography.
*A decrease (negative value) represents loss of retinal layers; as retinal thinning occurred very rapidly (≥half before the first dose and all by the second dose), the difference versus placebo represents the more severe acute optic neuritis evident in the anti-LINGO-1 treatment group.
†An increase in low-contrast letter acuity (LCLA) from baseline represents recovery; a negative difference versus placebo indicates a lack of treatment effect.

Figures 15A, 15B:
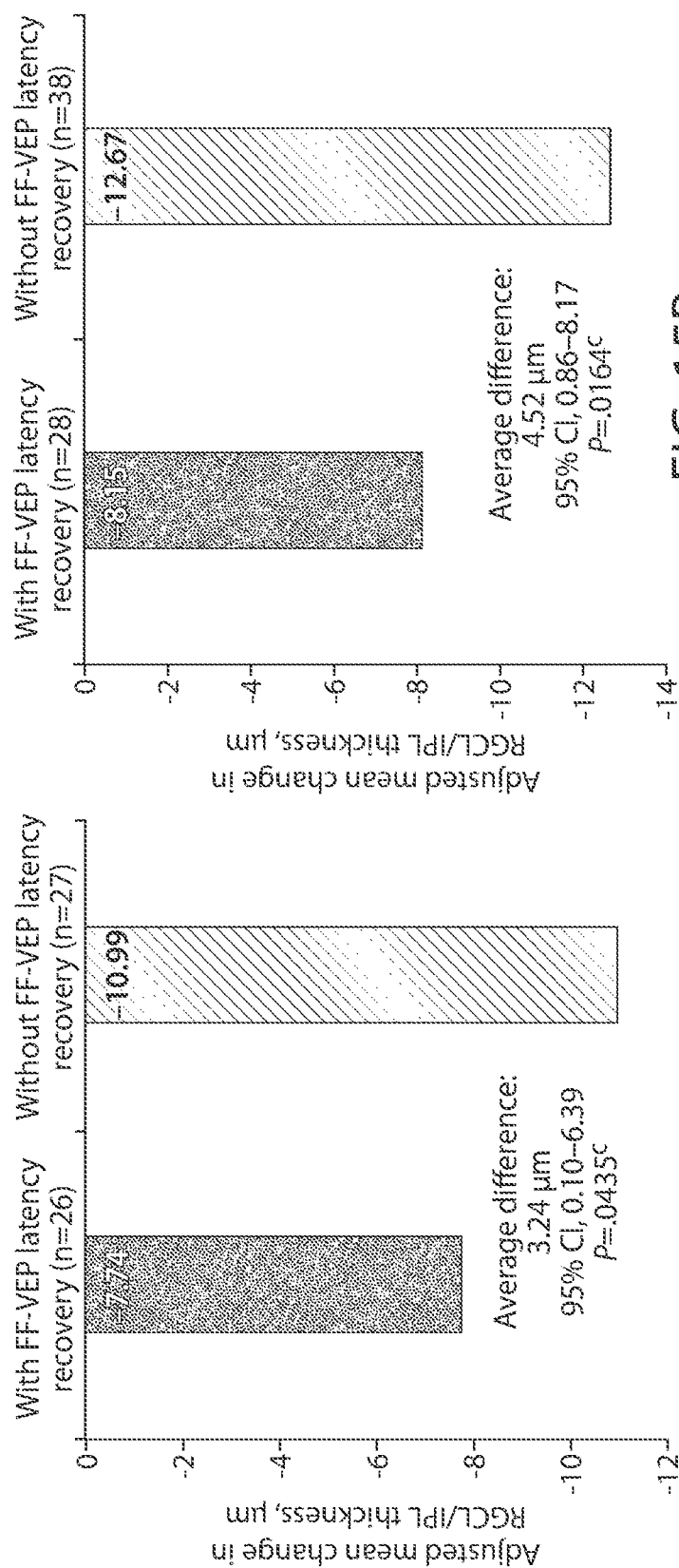
FIGS. 15A and 15B are bar graphs showing the adjusted mean change in RGCL/IPL thickness in the affected eye in the PP population at 4 weeks (A) and 24 weeks (B). The left bar of each set of bars refers to the group with FF-VEP latency recovery, and the right bar of each set of bars refers to the group without FF-VEP latency recovery.

Mean RGCL thinning (as measured by SD-OCT; post hoc analysis) at week 24 was significantly lower in subjects in the ITT population with FF-VEP latency recovery than without. Average difference was 4.92 μm (95% CI, 1.39-8.46; P=0.0071). Adjusted mean change in RGCL/IPL thickness was −7.83 μm in 29 subjects with FF-VEP latency recovery (placebo, n=10; anti-LINGO-1, n=19) and −12.75 μm in 40 subjects without (placebo, n=26; anti-LINGO-1, n=14). In the PP population, at week 4, the average difference was 3.24 μm (95% CI, 0.10-6.39 P=0.0435 by ANCOVA) in subjects having FF-VEP latency recovery relative to those without FF-VEP latency recovery. At week 24, the average difference was 4.52 μm (95% CI, 0.86-8.17 P=0.0164 by ANCOVA). The results for the PP population are shown in FIG. 15.

Change in FF-VEP latency was stratified in subgroups by baseline characteristics (post hoc). The results are shown in Table 12. The median value was used as the cutoff for each characteristic (except for brain T2 lesion volume).

TABLE 12

Change in FF-VEP latency stratified in subgroups.

| Characteristic | | FF-VEP treatment difference at Week 24 vs. placebo, ms$^a$ | P value$^a$ |
|---|---|---|---|
| Age | <33 years | −0.89 | .87 |
| | ≥33 years | −14.17 | .01 |
| Treated | <25 days from AON onset | −9.01 | .12 |
| | ≥25 days from AON onset | −6.68 | .19 |
| Treated | <15 days after steroids | −8.21 | .14 |
| | ≥15 days after steroids | −7.16 | .20 |
| Low-Contrast Letter Acuity (LCLA) score | 0, 2.5% Sloan chart | −6.46 | .27 |
| | >2.5% Sloan chart | −3.79 | .48 |

TABLE 12-continued

Change in FF-VEP latency stratified in subgroups.

| Characteristic | | FF-VEP treatment difference at Week 24 vs. placebo, ms$^a$ | P value$^a$ |
|---|---|---|---|
| High-Contrast Visual Acuity (HCVA) score | <49 | −10.92 | .08 |
| | ≥49 | −4.14 | .41 |
| Brain T2 lesion volume = | 0$^b$ | −10.48 | .25 |
| | >0$^c$ | −5.13 | .23 |

$^a$Based on ANCOVA.
$^b$n = 5, n = 8, anti-LINGO-1.
$^c$n = 29, placebo; n = 25, anti-LINGO-1

Treatment effects of anti-LINGO-1 were age-related in the PP population. Younger subjects had a smaller effect of anti-LINGO-1 on FF-VEP latency than older subjects, as shown in Table 13. The change in FF-VEP latency at week 24, according to age is shown in FIG. 16. Subjects ≤33 years of age in the treated group showed a 16.93 millisecond delay, amounting to a difference of −0.89 msec relative to untreated subjects (95% CI −11.43 to 9.65; P=0.87 based on ANCOVA). However, subjects >33 years of age showed a 12.15 millisecond delay, amounting to a difference of −14.17 msec relative to untreated subjects (95% CI=95% CI −24.83 to −3.52, P=0.01 based on ANCOVA).

TABLE 13

| Age | Placebo latency in ms | Anti-LINGO-1 latency in ms | p-value |
|---|---|---|---|
| <33 | 116.9 (10.8)* | 118.8 (15.9) | 0.86 |
| ≥33 | 127.9 (18.1) | 116.9 (17.4) | 0.0099** |

*Data are mean (SD) msec
**p-value for the treatment by age interaction = 0.081

The effects of anti-LINGO-1 were affected by time of first dose in the PP population. For patients in which the first dose was administered <25 days from AON onset, the placebo-treated group showed a 20.2 msec delay in latency and the anti-LINGO-1 treated group showed a 11.19 msec delay in latency, amounting to a difference of −9.01 msec [95% CI −20.44 to 2.42; p=0.12]. For patients in which the first dose was administered ≥25 days after AON onset, the placebo-treated group showed a 23.91 msec delay in latency and the anti-LINGO-1 treated group showed a 17.23 msec delay in latency, amounting to a difference of −6.68 msec [95% CI −16.75 to 3.39; p=0.19]. Thus, administration of anti-LINGO-1 shortly after AON onset (e.g., less than 25 days after AON onset) led to a greater reduction in latency delay when compared to placebo.

Additionally, the treatment effect of anti-LINGO-1 was more pronounced in patients with more severe baseline visual acuity impairment as determined by high contrast visual acuity (HCVA). In particular, subjects having a HCVA of less than 49 letters at baseline (more severely visually impaired at baseline) showed a latency recovery of −10.92 milliseconds [95% CI −23 to 1.2; p=0.076]. Subjects having a HCVA of 49 or more letters at baseline (less severely visually impaired at baseline) showed a latency recovery of −4.14 milliseconds [−14.1 to 5.86; p=0.41].

A summary of the efficacy of anti-LINGO-1 on FF-VEP latency is shown in Table 14.

TABLE 14

|  | Wk 24 ANCOVA (LOCF) | Wk 24 MMRM | Wk 32 MMRM |
|---|---|---|---|
| ITT | −3.48 | −4.11 | −6.06 |
| Δ diff (p-value) | (0.3337) | (0.2546) | (0.0711) |
| Improvement over placebo | 16.8% | 19.8% | 28.7% |
| Per-Protocol | −7.55 | −7.67 | −9.13 |
| Δ diff (p-value) | (0.0504) | (0.0514) | (0.0112) |
| Improvement over placebo | 33.9% | 34.6% | 40.9% |

Baseline fellow eye reading: around 100 msec (normal average latency)
Wk 24 placebo affected eye reading: around 123 msec (~20% worse than normal)

There were three categories of FF-VEP responders based on impairments at baseline and week 24. The three categories were:

(1) subjects with non-recordable baseline latency for the affected eye (indicating a severe initial latency delay) and a first recordable latency >3% worse than the baseline of the unaffected fellow eye, in whom the week 24 latency for the affected eye returned to within 10% of the week 24 latency of the unaffected eye (indicating a mild improvement);

(2) subjects with measurable latency of the affected eye that was ≥10% worse than the baseline latency for the unaffected fellow eye, in whom (a) the week 24 latency for the affected eye returned to within 10% of the week 24 latency of the unaffected fellow eye (indicating a mild improvement), or (b) the week 24 latency for the affected eye was ≥15% improved from baseline (indicating a substantial improvement); and (3) subjects with abnormal measurable baseline latency for the affected eye that was within 10% of the baseline latency for the unaffected fellow eye (indicating mild or moderate latency impairment), in whom the week 24 latency for the affected eye returned to normal (within 3% of the week 24 latency of the unaffected eye).

Also, MRI was used to measure the burden of disease by detecting lesions (e.g., GD-enhancing or T2 lesions) in the anti-LINGO-1 or placebo groups. Table 10 shows the size of T2 lesions in the brain of subjects, the placebo latency, and the anti-LINGO-1 treated latency. Lower anti-LINGO-1 latency appeared to correlate with smaller T2 lesions.

TABLE 15

| T2 burden of disease (BOD) in ml | Placebo subjects | Placebo latency (msec) | Anti LINGO subjects | Anti LINGO latency (msec) | Treatment difference (p value) |
|---|---|---|---|---|---|
| 0 | 4 | 17.72 | 8 | 7.35 | −10.37 (0.24) |
| >0 but <0.78 | 14 | 20.13 | 15 | 13.08 | −7.05 (0.207) |
| ≥0.78 | 13 | 24.43 | 9 | 24.31 | −0.1 (0.59) |

Example 4. Efficacy by Multifocal Visual Evoked Potentials in Subjects Treated with the Anti-LINGO-1 Monoclonal Antibody BIIB033 in AON Increased latency of cortical responses to monocular stimulation, indicative of demyelinating events in the optic nerve, is a hallmark of AON and has been demonstrated using full-field (FF) visual evoked potentials (VEP) and multifocal VEP (mfVEP). With mfVEP, visual stimuli are provided simultaneously to multiple regions of the visual field to provide stimulation to a wider visual field and more precise analysis. See Klistorner A, et al. Invest Ophthalmol Vis Sci. 2010; 51(5):2770-2777.

As described in Example 3, the RENEW trial was aimed at determining the efficacy and safety of anti-LINGO-1 antibody for CNS remyelination following the onset of a first episode of AON. In the RENEW trial described in Example 3, a mfVEP substudy was also conducted to explore the use of mfVEP as a potentially improved measure of treatment efficacy in AON trials than traditional FF-VEP (the pre-specified primary endpoint for the study). The mfVEP substudy is described in this example.

Methods

Figure 17:
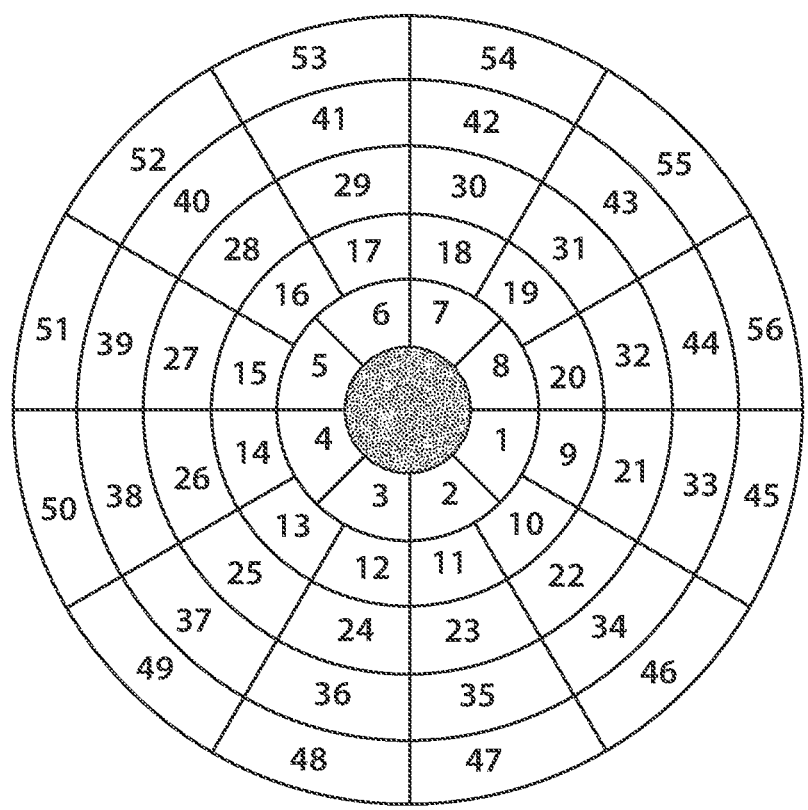
FIG. 17 is a diagram depicting exemplary individual segments assessed using multifocal visual evoked potentials (mfVEP).

The protocols for the RENEW trial are described in detail in Example 3. In the mfVEP substudy, visual evoked potential latency measured by mfVEP was included as an exploratory endpoint at selected study sites. The individual segments assessed using mfVEP are shown in FIG. 17. mfVEP was performed at 4-week intervals from randomization to week 24 (primary efficacy analysis) and week 32 (end-of-study follow-up). Change in mfVEP latency from its own baseline in the fellow eye and affected eyes to weeks 24 and 32 were determined using progression analysis by a blind examiner. A central reading center was used for training, qualification, quality control, and data analysis of the mfVEP substudy (Duke Reading Center in cooperation with Vision Search, Sydney Australia).

Between-treatment comparisons were evaluated by ANCOVA and MMRM. Correlations with FF-VEP and retinal ganglion cell layer/inner plexiform layer thickness were assessed using pairwise correlation and the Pearson correlation coefficient. Subject groups analyzed (ITT, PP, those with or without FF-VEP latency recovery) are described in detail in Example 3.

Results

The mfVEP substudy comprised 48% of the subjects participating in the RENEW trial (N=39/82); 18 were treated with placebo and 21 with anti-LINGO-1. The groups were similar in baseline demographics (Table 16). Sixteen participants treated with placebo and 15 treated with anti-LINGO-1 were part of the PP population in the RENEW trial.

TABLE 16

Demographic characteristics of the subjects in the mfVEP substudy at baseline

| Characteristic | All patients (n = 39) | Placebo (n = 18) | 100 mg/kg anti-LINGO-1 (n = 21) |
|---|---|---|---|
| Sex, % female | 72 | 78 | 67 |
| Race, % white | 97 | 94 | 100 |
| Mean age (years ± SD) | 32.3 ± 8.78 | 31.8 ± 9.93 | 32.7 ± 7.90 |
| Weight, kg (median, range) | 75.0 (47-119) | 75.0 (47-119) | 72.2 (57-106) |
| Height, cm (median, range) | 170.0 (155-194)* | 170.0 (155-194) | 171.0 (158-185)* |
| Mean ± SD latency of the fellow eye, ms | | 144.4 ± 6.2 | 147.7 ± 5.3 |
| Mean ± SD amplitude of the affected eye, nV | | 87.2 ± 48.6 | 78.4 ± 57.6 |
| Mean ± SD amplitude of the fellow eye, nV | | 156.8 ± 57.3 | 167.4 ± 34.6 |
| Subjects with < 60% measurable segments, n (%) | 13 (34) | 4 (22) | 9 (45) | mfVEP = multifocal visual evoked potentials;
SD = standard deviation
*n = 20; total = 38.

In subjects from the mfVEP substudy as a whole (ITT) and included in the PP population, the anti-LINGO-1-treated group showed improved VEP latency vs placebo at week 24 (difference of −4.97 ms [P=0.37] in the ITT substudy population and −11.78 ms [P=0.06] in the substudy PP population; FIG. 18). An improvement vs placebo of −3.82 ms (P=0.50) was seen at week 32 in the ITT substudy and of −9.38 ms (P=0.15) in the PP population substudy (by MMRM).

Figures 19A, 19B:
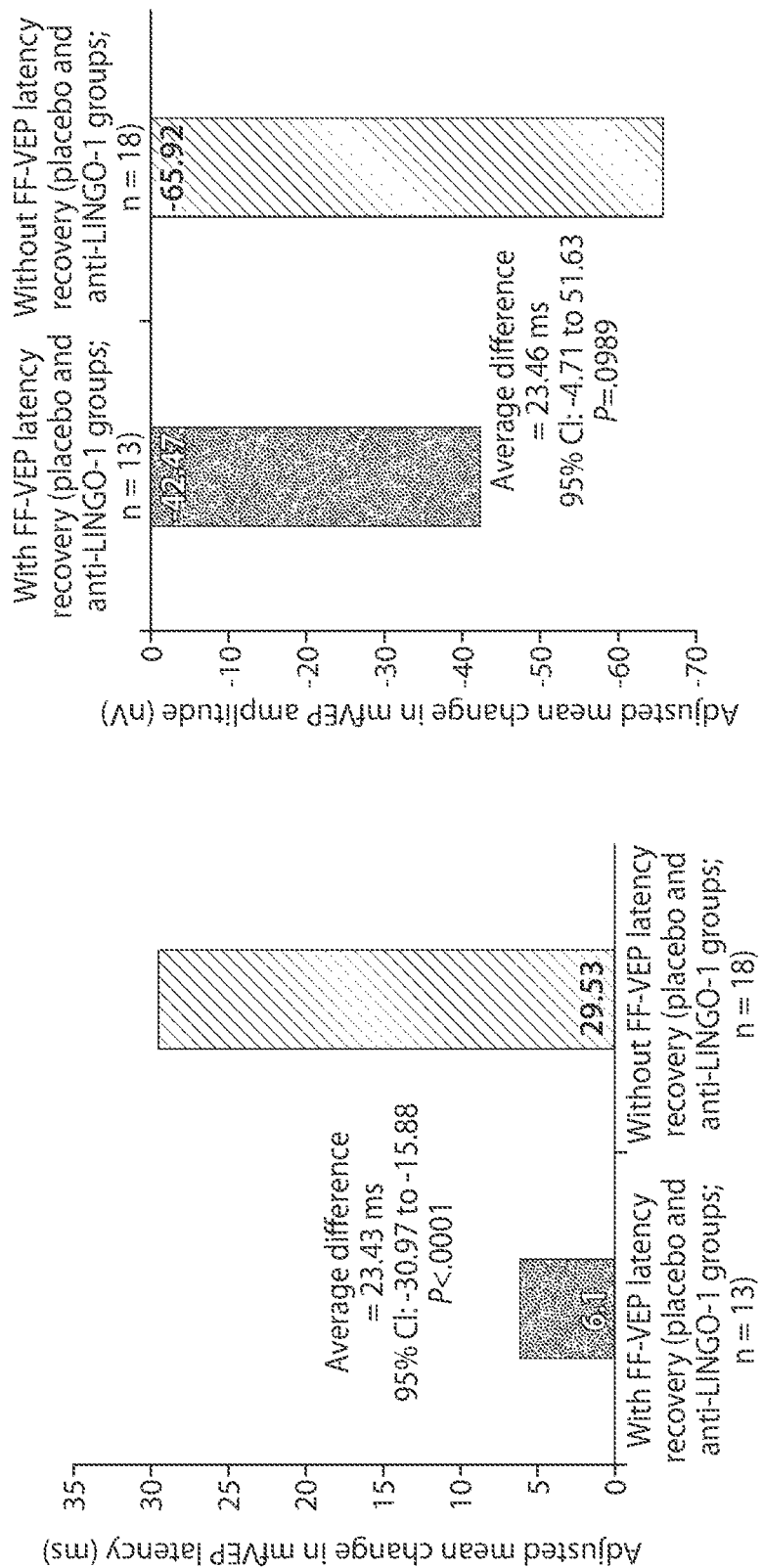
FIGS. 19A and 19B are bar graphs showing the adjusted mean differences in mfVEP latency and amplitude at week 24 in subjects classified as having latency recovery using the primary endpoint measure, FF-VEP*. CI=confidence interval; FF-VEP=full-field visual evoked potentials; mfVEP=multifocal visual evoked potentials; *FF-VEP latency recovery was defined as affected eye FF-VEP latency ≤10% worse than the fellow eye; FF-VEP latency was the primary endpoint in the RENEW trial. The adjusted mean difference in mfVEP latency is shown in 19A and the adjusted mean difference in mfVEP amplitude is shown in 19B.

A total of 13 subjects (4 assigned to placebo and 9 to anti-LINGO-1) participating in the substudy had been identified as having latency recovery using FF-VEP (latency of the affected eye at 24 weeks returning to within 10% of the fellow eye baseline latency), compared with 18 without (11 placebo; 7 anti-LINGO-1). The extent of latency recovery by mfVEP was compared in these subjects. There was significantly less mfVEP latency delay at week 24 in those with FF-VEP latency recovery (FIG. 19). There was also a trend toward a significant difference in recovery of mfVEP amplitude (FIG. 19) in those with FF-VEP latency recovery that was not apparent using FF-VEP.

A summary of the efficacy of anti-LINGO-1 on mfVEP latency is shown in Table 17.

TABLE 17

| | Wk 24 ANCOVA (LOCF) | Wk 24 MMRM | Wk 32 MMRM |
|---|---|---|---|
| ITT population | −4.970 | −5.636 | −3.592 |
| Δ diff (p-value) | (0.3680) | (0.3127) | (0.5543) |
| Improvement over placebo | 22.1% | 25% | 18.5% |
| Per-Protocol | −11.78 | −10.720 | −9.379 |
| Δ diff (p-value) | (0.0638) | (0.0962) | (0.1456) |
| Improvement over placebo | 47.5% | 44.9% | 42.2% |

RENEW baseline fellow eye average = 146 msec
RENEW placebo affected eye wk 24 average = 169 msec Comparing the substudy mfVEP latency or amplitude changes with other efficacy endpoints in the RENEW trial PP and ITT populations revealed several correlations (Table 18).

TABLE 18

High correlations identified for change at week 24 for the affected eye from baseline of the unaffected fellow eye*

| | Substudy and PP (n = 31) | | | Total substudy (n = 39) | | |
|---|---|---|---|---|---|---|
| | Placebo n = 16 | 100 mg/kg anti-LINGO-1 n = 15 | Total | Placebo n = 18 | 100 mg/kg anti-LINGO-1 n = 21 | Total |
| Mean mfVEP latency and FF-VEP latency | r = 0.98 | r = 0.93 | r = 0.96 | r = 0.98 | r = 0.91 | r = 0.95 |
| Mean mfVEP latency and mean | | r = −0.50 | | | r = −0.50 | |

TABLE 18-continued

High correlations identified for change at week 24 for the
affected eye from baseline of the unaffected fellow eye*

| | Substudy and PP (n = 31) | | | Total substudy (n = 39) | | |
|---|---|---|---|---|---|---|
| | Placebo n = 16 | 100 mg/kg anti-LINGO-1 n = 15 | Total | Placebo n = 18 | 100 mg/kg anti-LINGO-1 n = 21 | Total |
| RGCL/IPL thickness | | | | | | |
| Mean mfVEP latency and mean mfVEP amplitude | r = −0.54 | | | r = −0.54 | | |
| Mean mfVEP amplitude and FF-VEP latency | | r = −0.52 | | | r = −0.58 | |
| Mean mfVEP amplitude and FF-VEP amplitude | r = 0.63 | | | r = 0.63 | | |
| Mean mfVEP amplitude and mean RGCL/IPL thickness | | r = 0.51 | | | r = 0.51 | |

FF-VEP = full-field visual evoked potentials;
ITT = intent-to-treat;
mfVEP = multifocal visual evoked potentials;
PP = per-protocol;
RGCL/IPL = retinal ganglion cell layer/inner plexiform layer
*Subgroup mfVEP latency or amplitude results were compared with other efficacy endpoints in the RENEW trial PP and ITT populations.

Additionally, the condition of the fellow eye was observed over time during the study by mfVEP latency and amplitude. The mfVEP amplitude of the fellow eye over time is shown in Table 19.

TABLE 19

| Visit | Placebo (N = 18) nanovolts | Anti-LINGO-1 (N = 21) nanovolts | p-value |
|---|---|---|---|
| baseline | 180.927 (72.75) | 196.237 (55.89) | |
| Week 4 | 161.802 (54.83) | 183.7 (52.55) | 0.236 |
| Week 8 | 165.581 (58.5) | 179.5 (52.36) | 0.78 |
| Week 12 | 159.456 (57.28) | 182.16 (45.28) | 0.18 |
| Week 16 | 165.748 (58.34) | 186.14 (49.15) | 0.18 |
| Week 20 | 153.78 (55.74) | 191.54 (49.4) | 0.0019 |
| Week 24 | 162.726 (58.81) | 182.875 (61.89) | 0.048 |
| Week 32 | 146.142 (51.14) | 186.218 (55.57) | 0.0006 |

Figure 20:
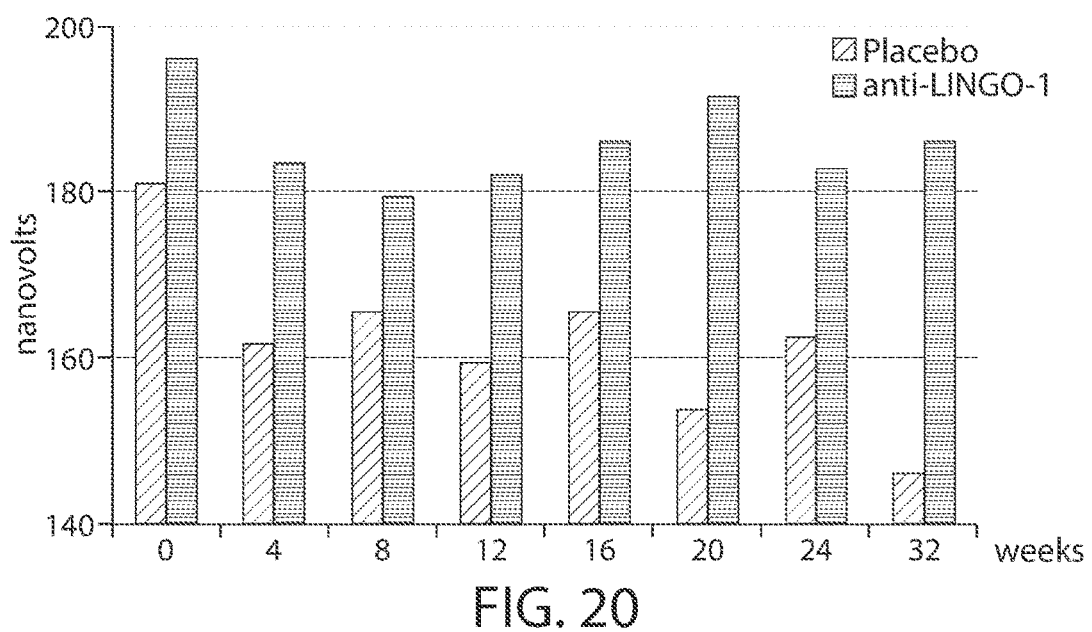
FIG. 20 is a bar graph showing mfVEP data for the unaffected fellow eye (mfVEP fellow eye average amplitude by treatment group-ITT analysis), demonstrating preservation of amplitude with anti-LINGO-1 treatment. The left bar of each set of bars refers to the placebo group, and the right bar of each set of bars refers to the anti-LINGO-1 group.

A strong treatment effect was observed by mfVEP on preventing amplitude loss and preserving amplitude in the fellow eye. See FIG. 20. As shown in FIG. 20, the mfVEP amplitude dropped in fellow eye in the placebo treated group as early as week 20, which indicates the presence of damage to the fellow eye. In groups treated with anti-LINGO-1, the mfVEP amplitude was preserved through the 32 week study. Thus, anti-LINGO-1 prevented damage from becoming established in the fellow eye of subjects following a first episode of AON.

Figure 21:
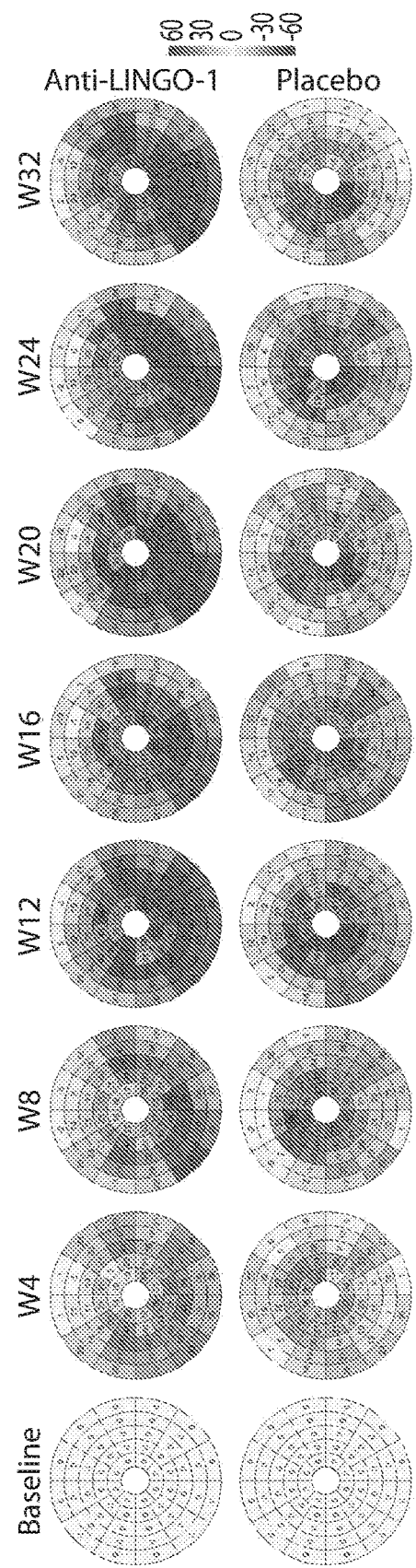
FIG. 21 is a series of heatmaps depicting the mean change in MF-VEP amplitude (nV) in the affected eye from baseline of the affected eye during treatment with anti-LINGO-1 antibody over 32 weeks.

For both the affected and unaffected eye, the change in MF-VEP Amplitude from baseline in the same eye over 32 weeks was determined. The mean change in MF-VEP amplitude by treatment in the affected eye from baseline in the affected eye (nV) is shown in Table 20 and FIG. 21.

TABLE 20

Mean change in MF-VEP amplitude by treatment in the affected eye from baseline in the affected eye over 32 weeks.

| | Average amplitude, nV; 56 segments | | Difference vs. placebo | | |
|---|---|---|---|---|---|
| Affected eye[a] | Placebo | Anti-LINGO-1 | Estimated difference | 95% CI | P value |
| Change at Week 4 | 23.548 | 25.210 | 1.662 | −18.462 to 21.786 | .8678 |
| Change at Week 8 | 30.743 | 30.335 | −0.408 | −21.083 to 20.267 | .9683 |
| Change at Week 12 | 29.920 | 41.556 | 11.636 | −13.257 to 36.528 | .3491 |
| Change at Week 16 | 34.443 | 43.119 | 8.677 | −15.225 to 32.578 | .4662 |
| Change at Week 20 | 29.547 | 50.178 | 20.631 | −3.621 to 44.883 | .0930 |
| Change at Week 24 | 29.864 | 43.516 | 13.652 | −11.658 to 38.962 | .2808 |
| Change at Week 32 | 25.882 | 48.198 | 22.316 | −1.261 to 45.893 | .0628 |

Figure 22:
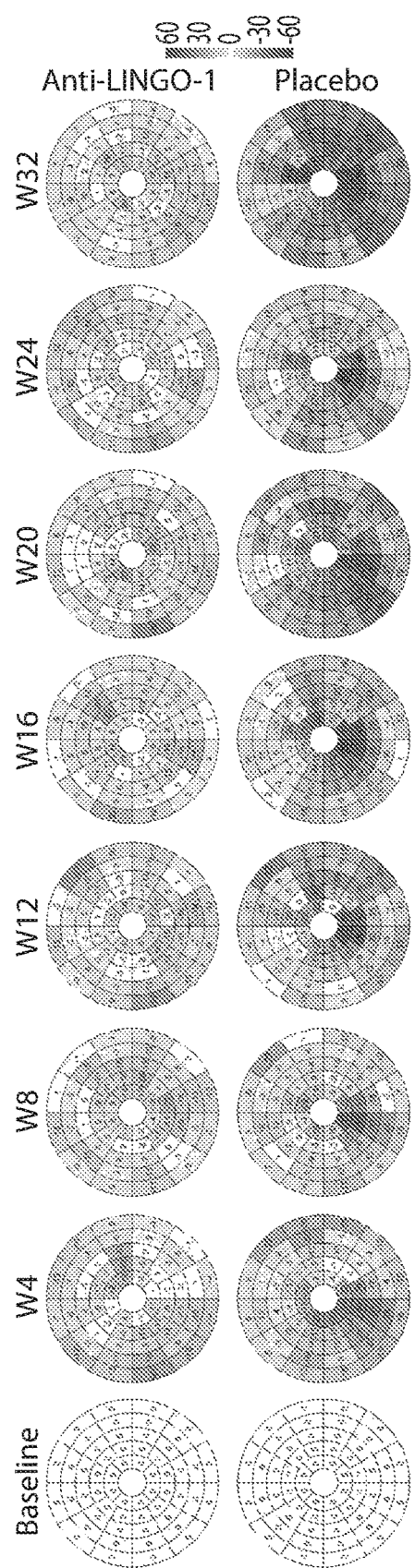
FIG. 22 is a series of heatmaps depicting the mean change in MF-VEP amplitude (nV) in the unaffected eye from baseline of the unaffected eye during treatment with anti-LINGO-1 antibody over 32 weeks.

The mean change in MF-VEP Amplitude by Treatment in the unaffected eye from baseline in the unaffected eye over 32 weeks (nV) is shown in Table 21 and FIG. 22.

TABLE 21

Mean change in MF-VEP amplitude by treatment in the unaffected eye from baseline in the unaffected eye over 32 weeks.

| Fellow eye | Average amplitude, nV; 56 segments | | Difference vs. placebo | | |
|---|---|---|---|---|---|
| | Placebo | Anti-LINGO-1 | Estimated difference | 95% CI | P value |
| Change at Week 4 | −14.017 | −6.126 | 7.891 | −5.926 to 21.708 | .2543 |
| Change at Week 8 | −12.361 | −4.814 | 7.547 | −9.399 to 24.493 | .3723 |
| Change at Week 12 | −18.452 | −2.628 | 15.824 | −0.608 to 32.256 | .0585 |
| Change at Week 16 | −17.522 | −2.845 | 14.677 | −1.456 to 30.809 | .0731 |
| Change at Week 20 | −24.336 | 1.120 | 25.456 | 8.150 to 42.762 | .0053 |
| Change at Week 24 | −17.565 | −0.588 | 16.977 | −0.225 to 34.178 | .0529 |
| Change at Week 32 | −31.407 | 1.926 | 33.333 | 16.408 to 50.258 | .0004 |

Also, the change in latency (msec) of the fellow eye was measured by mfVEP over time during the study. A MMRM-ITT analysis was performed using all timepoints and shown in Table 22. There was no significant difference in latency measured by mfVEP over time in the fellow eye when treated with placebo versus anti-LINGO-1.

TABLE 22

| Visit | Placebo msec | Anti-LINGO-1 msec | Difference | p-value |
|---|---|---|---|---|
| baseline | 144.45 (6.2) | 147.68 (5.33) | | |
| Week 4 | 145.35 (6.8) | 148.68 (4.78) | 0.623 | 0.43 |
| Week 8 | 145.405 (6.4) | 148.37 (4.8) | −0.442 | 0.63 |
| Week 12 | 146.65 (5.8) | 149.110 (4.7) | −0.772 | 0.41 |
| Week 16 | 145.83 (6.18) | 149.56 (4.3) | −0.487 | 0.59 |
| Week 20 | 146.55 (6.5) | 148.7 (5.1) | −1.885 | 0.09 |
| Week 24 | 146.95 (5.1) | 148.18 (5.28) | −1.749 | 0.11 |
| Week 32 | 145.94 (5.29) | 149.14 (4.68) | −0.771 | 0.39 |

A comparison of the efficacy outcome measures in FF-VEP latency recoverers versus non-recoverers is shown in Table 23 (the numbers indicate the change at 24 weeks versus baseline (ITT)).

TABLE 23

| Efficacy measures | Recoverer on anti-LINGO-1 or placebo | Non-recoverer on anti-LINGO-1 or placebo | P value |
|---|---|---|---|
| FF-VEP latency (msec)* | 4.51 (N = 29) | 29.33 (N = 37) | <0.0001 |
| FF-VEP amplitude (uV)* | −3.22 (N = 29) | −2.64 (N = 37) | 0.587 |
| mfVEP latency (msec)* | 6.10 (N = 13) | 29.53 (N = 16) | <0.0001 |
| mfVEP amplitude (nV)* | −42.47 (N = 13) | −65.92 (N = 16) | 0.098 |
| RGCL thickness (microns)* | −7.83 (N = 29) | −12.75 (N = 40) | 0.0071 |
| 1.25% LCLA(# of letters)** | 9.8 (N = 27) | 6.09 (40) | 0.206 |
| 2.5% LCLA (# of letters)** | 13.47 (N = 27) | 11.44 (N = 40) | 0.512 |
| HCVA (# of letters)** | 10.78 (N = 28) | 12.40 (N = 40) | 0.528 |
| 39 items VFQ | 14.87 (N = 28) | 15.24 (N = 39) | 0.828 |
| 10 item NOS | 17.65 (N = 27) | 16.78 (N = 38) | 0.780 |

*Adjusted mean vs baseline of fellow eye;
**Adjusted mean vs baseline of affected eye Conclusions for RENEW Trial The results described in Example 3 show improved latency recovery (a greater shortening of latency delay) measured by FF-VEP in the anti-LINGO-1 group compared with placebo. Analysis in the PP population was statistically significant; analysis in the ITT population showed a positive trend (MMRM; Week 32). At the individual level, FF-VEP latency recovery analysis showed that latency in the affected eye recovered to normal or close to normal in twice as many subjects treated with anti-LINGO-1 (53%) than placebo (26%). Subjects whose FF-VEP latency recovered to normal or close to normal had experienced significantly less RGCL thinning (average, −7.83 μm) than those that did not (average, −12.75 μm). The magnitude of the treatment effect (about 40-50% improvement in conduction delay or about 8-10 msec reduction in P100 latency) is consistent with optic nerve remyelination by anti-LINGO-1 following AON.

No detectable treatment effect was observed on the secondary endpoints of SD-OCT thinning, LCLA, and high contrast visual acuity that measured the neuroprotective effects. However, the results revealed that retinal thinning occurred very rapidly, at least half before the first dose and the remainder before the second dose.

Also, the treatment effect by anti-LINGO-1 was better in the higher age group, in patients with greater baseline acuity impairment, and in patients with earlier treatment initiation.

The anti-LINGO-1 antibody, opicinumab, demonstrated an improvement in the study's primary endpoint, recovery of latency (time for a signal to travel from the retina to the visual cortex), as measured by full field visual evoked potential (FF-VEP), relative to placebo. The study showed no detectable effect on secondary endpoints, including change in thickness of the retinal layers (optic nerve neurons and axons) and visual function, as measured by spectral domain optical coherence tomography (SD-OCT) and low contrast letter acuity, respectively, as herein. The primary and secondary endpoints were measuring two different aspects of the potential drug's impact of the visual system (remyelination and neuroprotection). The lack of treatment effects in both secondary endpoints, low contrast visual acuity and OCT, are consistent. No neuroprotective effect on the retina was detected in the AON lesion in this study. However, a protective treatment effect of anti LINGO-1 treatment was seen for the amplitude of the mfVEP in both the affected and the fellow eye visual pathways over 32 weeks, which was highly statistically significant at 32 weeks for the fellow eye mfVEP amplitude.

NCT01721161 was designed to study anti-LINGO-1's ability to enable repair of an optic nerve lesion via axonal remyelination following the onset of a first episode of AON. It characterized the effects on remyelination by measuring the latency of nerve conduction between the retina and the visual cortex in the brain using FF-VEP. The primary endpoint measured FF-VEP latency for the affected eye at week 24 compared to the unaffected fellow eye at baseline. Results demonstrated a 34 percent improvement (p=0.0504) in the recovery of optic nerve latency compared to placebo in the per-protocol population at 24 weeks, and even higher at 32 weeks.

The analysis of the intent-to-treat (ITT) population, which includes patients in both arms who did not complete the study, showed a positive trend but did not reach statistical significance.

The results herein show that anti-LINGO-1 was effective in causing optic nerve remyelination in patients who experienced a first episode of AON, but who did not yet have diagnosable MS. Furthermore, it showed clearly protective effects on the amplitude of the mfVEP in both the affected and fellow eye visual pathways over 32 weeks. Thus, administering anti-LINGO-1 early on, soon after a first episode of AON and before development of diagnosable MS, may prevent the worsening of AON and/or prevent the development of MS.

RENEW is the first clinical trial demonstrating the clinical efficacy of anti-LINGO-1 with the observed shortening of FF-VEP latency consistent with optic nerve remyelination following a first episode of AON. Consistent results were observed in a substudy that measured latency using multifocal VEP (mfVEP) and are described in Example 4. Protective effects of the amplitude were seen by mfVEP for both the affected and fellow eyes, and by FF-VEP amplitude for the affected eye (data not shown). Results from the safety analyses show that anti-LINGO-1 was well tolerated, with an overall incidence and severity of AEs similar to placebo-treated subjects. Safety and tolerability analyses from the trial are described in Example 5, and patient reported outcomes from the trial are described in Example 6.

A second ongoing Phase 2 dose-range finding study (SYNERGY) that investigates anti-LINGO-1 in participants with relapsing forms of MS is described, e.g., at Clinical Trials Identifier No. ClinicalTrials.gov Identifier: NCT01864148.

The per-protocol population is defined as subjects from the ITT population who complete the study, did not miss more than one dose of anti-LINGO-1 or placebo, and did not receive MS modifying therapies during the study period.

Example 4 describes the first reported use of mfVEP in the context of a randomized clinical trial. Results from the mfVEP substudy showed improved mfVEP latency (a greater shortening of latency delay) in the anti-LINGO-1 group compared with placebo at both week 24 and week 32. Differences between the placebo and anti-LINGO-1 arms were greater when comparing substudy subjects included in the PP population rather than all substudy participants. Subjects whose FF-VEP latency (RENEW study primary endpoint) recovered to normal or close to normal experienced significantly less delay in mfVEP latency from baseline to week 24 (average 6.1 ms) and a trend towards better amplitude recovery (P<0.10) than those who did not (average 29.53 ms). mfVEP latency changes were highly correlated with FF-VEP latency changes (r≥0.91), while the correlation between amplitude changes was lower (r=0.63).

Results from the mfVEP substudy are consistent with the overall efficacy results for the primary endpoint (FF-VEP), as described in Example 3. This suggests that mfVEP could be a powerful efficacy endpoint in clinical trials investigating the efficacy of candidate CNS remyelinating and neuroprotective agents. Furthermore, by generating reliable and informative results in a multicenter international substudy, the feasibility of this technique has been established.

The treatment effects from the RENEW study (including the mfVEP substudy) occurred within several months (3-6 months) and was of a magnitude (about 8-10 msec) consistent with a CNS remyelination mechanism of action by anti-LINGO-1. Due to the significantly reduced loss of mfVEP amplitude on the fellow eye over time in the anti-LINGO-1 treated group, anti-LINGO-1 likely has neuroprotective effects as well. These results suggest that anti-LINGO-1 may be neuroprotective in MS when used prophylactically. These results also suggest that mfVEP of healthy eyes could be a way to diagnose MS early on, before the development of diagnosable MS symptoms and/or before the onset of AON. Though the reduced loss of amplitude was not observed in the FF-VEP study, this was likely due to the lack of sensitivity of the FF-VEP measurement for amplitude changes. No retinal neuroaxonal protection was observed in the RENEW study, likely because much of the thinning had already taken place by the time of the first dose. However, cerebral neuroprotection in the visual pathway was likely observed with anti LINGO-1 treatment during the longitudinal 32 week follow up of the RENEW subjects enrolled in the mfVEP substudy.

Example 5. Safety and Tolerability of Anti-LINGO1 Antibody in AON

The safety and tolerability of anti-LINGO-1 antibody in participants of the RENEW trial (NCT01721161) described herein (e.g., in Examples 3 and 4) were assessed. The RENEW trial protocol is described in detail in the examples above. Safety and tolerability assessments included adverse events (AEs) and severe AEs, clinical laboratory results (hematology, blood chemistry, urinalysis), physical exam findings, clinically-relevant vital sign abnormalities, brain magnetic resonance imaging results, 12-lead electrocardiogram readings, measurement of anti-LINGO-1 antibody in blood, and AON signs and symptoms. All subjects who received ≥1 dose of study treatment were included in the safety population.

Results

Eighty-two subjects received placebo (n=41) or anti-LINGO-1 (n=41) and were largely similar in baseline characteristics (Table 5). The number of subjects with an AE and the severity of the AEs were similar between the placebo and anti-LINGO-1 groups (Tables 24 and 25). The number of subjects with a serious AE and discontinuing treatment were higher in the anti-LINGO-1 group than the placebo group (Table 24).

TABLE 24

Summary of AEs

| AE, n (%) | Placebo n = 41 | Anti-LINGO-1 n = 41 | All subjects N = 82 |
|---|---|---|---|
| Any AE | 34 (83) | 34 (83) | 68 (83) |
| Serious AE | 2 (5) | 5 (12) | 7 (9) |
| Treatment-related serious AE | 0 | 3 (7) | 3 (4) |
| Discontinued treatment due to AE | 1 (2) | 3 (7) | 4 (5) |
| Withdrew from study due to AE | 2 (5) | 3 (7) | 5 (6) |

TABLE 25

Severity of AEs

| AE, n (%) | Placebo n = 41 | Anti-LINGO-1 n = 41 | All subjects N = 82 |
|---|---|---|---|
| Any AE | 34 (83) | 34 (83) | 68 (83) |
| Mild AE | 12 (29) | 13 (32) | 25 (30) |
| Moderate AE | 20 (49) | 18 (44) | 38 (46) |
| Severe AE | 2 (5) | 3 (7) | 5 (6) |

Four subjects discontinued treatment due to an AE. In the placebo group, one patient discontinued treatment (due to MS). In the anti-LINGO-1 treated group, 3 patients discontinued treatment due to treatment-related serious AEs. Two of the three patients had hypersensitivity, and in both patients, reactions occurred shortly after the start of the second infusion and fully resolved shortly after discontinuation of infusion. The third patient had an asymptomatic case of increased alanine and aspartate aminotransferases that was reported as hepatopathy, first observed after the second infusion, and resolved following treatment discontinuation.

Serious AEs occurred in 7 subjects. Two subjects in the placebo group experienced serious AEs. In addition to the subject who discontinued treatment, a second subject had viral pericarditis and tested positive for cytomegalovirus. Five subjects had serious AEs in the anti-LINGO-1 group; 3 resulted in treatment discontinuation (see above), 1 suffered an MS relapse, and 1 had optic neuritis in the fellow eye.

The incidence of AEs by System Organ Class (SOC) was generally similar between groups (Table 26). However, gastrointestinal disorders occurred more frequently in those treated with anti-LINGO-1 than placebo. The most commonly reported gastrointestinal symptoms were nausea (anti-LINGO-1, 12% vs. placebo, 7%) and dyspepsia (anti-LINGO-1, 5% vs. placebo, 2%). Six AEs occurred in ≥10% of all subjects, regardless of treatment group (Table 27). Of these, 3 occurred more frequently with anti-LINGO-1 than placebo: (i) fatigue (15% vs. 12%), (ii) nausea (12% vs. 7%), and (iii) paresthesia (10% vs. 0). The remainder occurred at a similar frequency between groups or more frequently in the placebo group (Uhthoff's phenomenon). AEs occurring ≤4 hours after the start of infusion were higher in the anti-LINGO-1 group than the placebo group (Table 28). The same event did not occur with every infusion and the events were most frequent after the second and third infusions. The most common infusion-related events were headache (7%) and nausea (7%). Both events of hypersensitivity occurred during the second infusion.

TABLE 26

Incidence of AEs by System Organ Class

| AE, n (%) | Placebo n = 41 | Anti-LINGO-1 n = 41 |
|---|---|---|
| Infections and infestations | 22 (54) | 19 (46) |
| Nervous system disorders | 22 (54) | 22 (54) |
| General disorders and administration site conditions | 10 (24) | 9 (22) |
| Eye disorders | 7 (17) | 8 (20) |
| Musculoskeletal and connective tissue disorders | 7 (17) | 8 (20) |
| Skin and subcutaneous tissue disorders | 7 (17) | 6 (15) |
| Gastrointestinal disorders | 5 (12) | 12 (29) |
| Respiratory, thoracic, and mediastinal disorders | 4 (10) | 4 (10) |
| Injury, poisoning, and procedural complications | 3 (7) | 2 (5) |
| Investigations | 3 (7) | 6 (15) |
| Psychiatric disorders | 3 (7) | 3 (7) |
| Renal and urinary disorders | 2 (5) | 2 (5) |
| Reproductive system and breast disorders | 2 (5) | 1 (2) |

TABLE 27

Incidence of AEs occurring in ≥10% of subjects

| AE, n (%) | Placebo n = 41 | Anti-LINGO-1 n = 41 |
|---|---|---|
| Nasopharyngitis | 13 (32) | 12 (29) |
| Headache | 11 (27) | 11 (27) |
| Fatigue | 5 (12) | 6 (15) |
| Nausea | 3 (7) | 5 (12) |
| Paresthesia | 0 | 4 (10) |
| Uhthoff's phenomenon | 6 (15) | 3 (7) |

TABLE 28

No. of subjects with AEs occurring ≤4 hours after infusion

| | Dose 1 (Baseline) | Dose 2 (Week 4) | Dose 3 (Week 8) | Dose 4 (Week 12) | Dose 5 (Week 16) | Dose 6 (Week 20) |
|---|---|---|---|---|---|---|
| Placebo | | | | | | |
| No. dosed | 41 | 39 | 40 | 37 | 37 | 37 |
| No. with AE | 1 | 0 | 0 | 0 | 0 | 0 |
| Anti-LINGO-1 | | | | | | |
| No. dosed | 41 | 40 | 38 | 37 | 35 | 36 |
| No. with AE | 3 | 8[a] | 6 | 4 | 5 | 2 |

[a]Includes 2 cases of hypersensitivity leading to treatment discontinuation.

Seventeen subjects had weight gain >7% from Baseline. Placebo, n=4 (10%) vs. anti-LINGO-1, n=13 (32%). Subgroup analyses showed that subjects who gained >7% during the study had worse baseline disease (including higher frequency of conduction block, high contrast visual acuity impairment, and visual evoked potential latency delay). Three participants had weight decrease >7% (placebo, n=2; anti-LINGO-1, n=1). Other safety and tolerability investigations were similar between groups.

Conclusions for Safety and Tolerability

The results show that anti-LINGO-1 at the dose of 100 mg/kg was generally well tolerated, and the overall incidence and severity of AEs was comparable with that of placebo-treated subjects. In the study, few treatment-related serious AEs were observed, and they all resolved on discontinuation of treatment. The incidence of serious AEs not related to treatment also was low, and the majority were MS related.

The most common AEs regardless of treatment were nasopharyngitis, headache, fatigue, Uhthoff phenomenon, and nausea. The most common AEs occurring at a higher rate on anti-LINGO-1 than placebo were fatigue, nausea, and paresthesia. No deaths occurred during the trial. The incidence of serious adverse effects (SAEs) were higher in the anti-LINGO-1 treated group (12%) than the placebo treated group (5%). Two patients treated with anti-LINGO-1 had SAEs of hypersensitivity reactions occurring around the time of infusion. One patient had a SAE of asymptomatic elevation in liver transaminases, which was resolved after drug discontinuation.

No immunogenicity was observed. Increased numbers of asymptomatic elevation in serum transaminases >3×ULN were seen in the anti-LINGO-1 treated group than in the placebo treated group (anti-LINGO-17% versus placebo 0). An increased incidence of post-baseline weight changes of greater than 7% (increase at any post-baseline timepoint) were seen in the anti-LINGO-1 treated subjects (anti-LINGO-1 32% versus placebo 10%). The safety and tolerability of anti-LINGO-1 in the treatment of AON support the use and ongoing clinical development of anti-LINGO-1 for CNS demyelinating diseases.

Example 6. Effects of Anti-LINGO-1 Antibody on Vision-Related Quality of Life in Subjects with AON The RENEW clinical trial is described in detail in the above examples. There are currently no established patient reported outcomes (PROs) for AON or to measure remyelination. Thus, in the RENEW trial, a further exploratory endpoint was assessed. In particular, a PRO measure for vision-related quality of life (QoL), the National Eye Institute Visual Functioning Questionnaire-25 (NEI VFQ-25) (Mangione C M, et al. Arch Ophthalmol. 1998; 116(11): 1496-1504), was performed to evaluate the treatment benefit of anti-LINGO-1. This analysis evaluated the self-reported visual functioning of patients with AON randomized to anti-LINGO-1 or placebo in RENEW.

The protocol of the RENEW trial is described in detail in the above examples. The NEI-VFQ-25, including 13 addendum items, and the 10-Item Neuro-Ophthalmic Supplement (NOS-10 (Raphael B A. et al. Am J Ophthalmol. 2006; 142(6):1026-1035.e2); exploratory endpoints), ranged from 0 (high impairment) to 100 (no impairment). A change of 4 points was considered clinically meaningful (Suner I J, et al. Invest Ophthalmol Vis Sci. 2009; 50(8):3629-3635), The NEI VFQ-25 was administered at baseline and at weeks 4, 8, 12, 16, 20, 24, and 32. Results of the NEI VFQ-25 and the NOS-10 are presented separately and combined.

Statistical Analyses

The PP population was defined as subjects who completed the study, did not miss >1 dose of treatment, and did not receive multiple sclerosis modifying therapy. Data from the PP population are presented in this example. Between-treatment differences in mean change in score from baseline for each of the vision-related QoL assessments were analyzed by mixed-effect model repeated measure (MMRM) and analysis of covariance (ANCOVA). MMRM and ANCOVA models were adjusted for baseline vision-related QoL assessment value and treatment group. Last observation carried forward (LOCF) was used for imputation in ANCOVA analyses.

Results

Figure 23A:
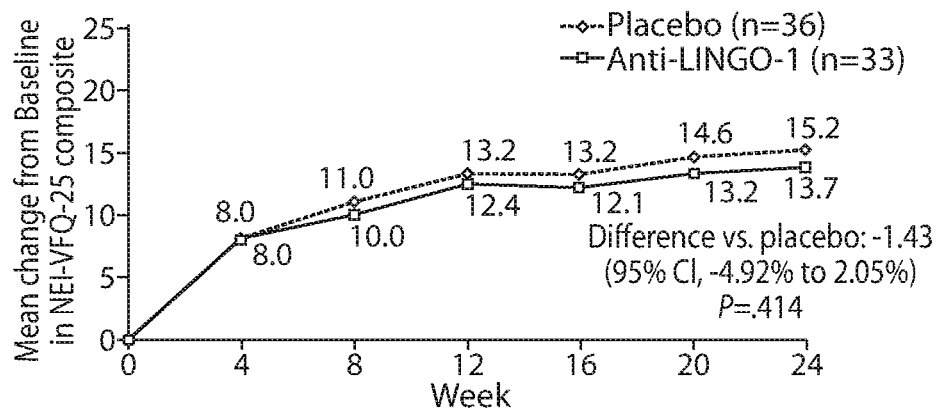
FIGS. 23A, 23B, and 23C are graphs showing the change from baseline in mean (A) NEI VFQ-25 composite; (B) NOS-10; and (C) combined NEI VFQ-25 and NOS-10 composite scores to week 24 as analyzed by MMRM in the RENEW trial.
Figure 23B:
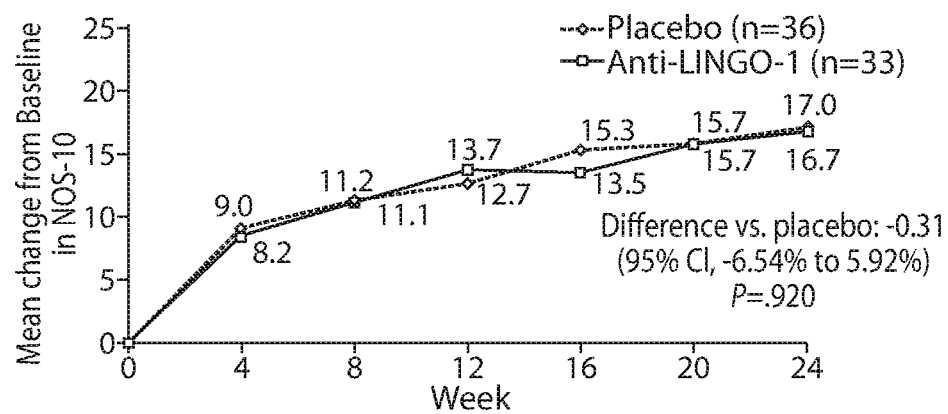
Figure 23C:
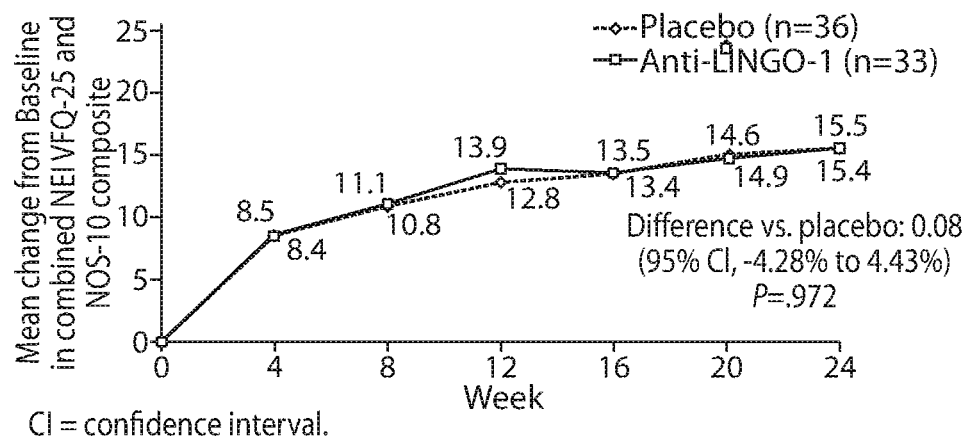

A total of 69 patients were included in the PP population of RENEW and received either placebo (n=36) or anti-LINGO-1 (n=33). Demographic characteristics were similar at baseline (Table 5). Patient scores reflected considerable impairment at baseline on the NEE VFQ-25 composite (Table 29). Patients in the placebo group had slightly higher mean scores at baseline compared with the anti-LINGO-1 group (Table 29). Both groups experienced substantial improvements from baseline in adjusted mean NEI VFQ-25 composite, NOS-10, and combined NEI VFQ-25 and NOS-10 composite scores through week 24 (FIG. 23). Between-treatment differences in mean change in score from baseline for each of the vision-related QoL assessments were not significantly different at any time point (FIG. 23).

Figure 24:
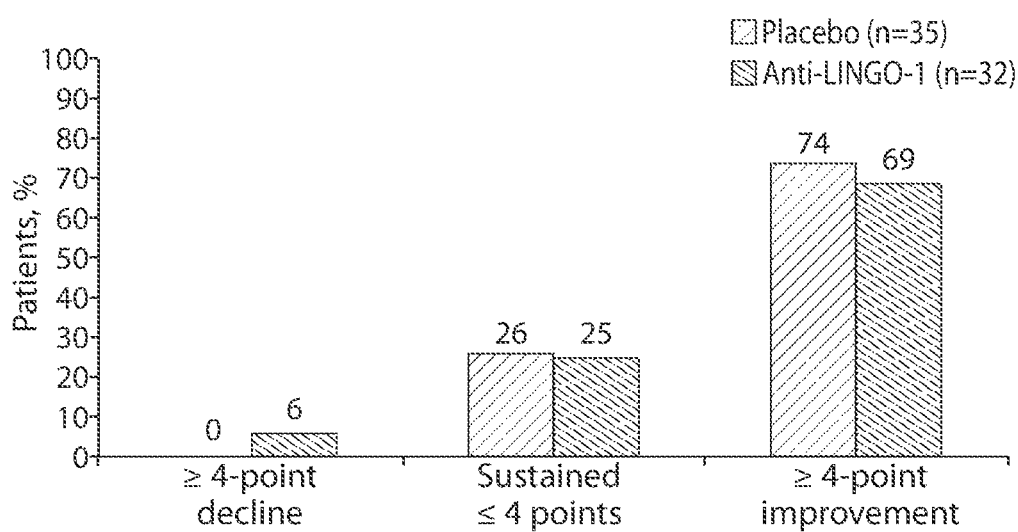
FIG. 24 is a bar graph showing the percentage of patients with change in NEI VFQ-25 composite score who declined by ≥4 points, sustained ≤4 points, or improved ≥4 points from baseline at week 24 in the RENEW trial. The left bar of each set of bars refers to the placebo group, and the right bar of each set of bars refers to the anti-LINGO-1 group.

At Week 24, the majority of patients in both groups had ≥4-point improvement in NEI VFQ-25 composite score, while few patients experienced ≥4-point decline (FIG. 24). Mean change from baseline for NEI VFQ-25 composite, NOS-10, and combined NEI VFQ-25 and NOS-10 composite scores did not differ between treatment groups based on ANCOVA models (Table 30).

TABLE 29

Demographic characteristics and baseline vision-related QoL (PP population)

| Parameter | Placebo n = 36 | Anti-LINGO-1 n = 33 | All subjects N = 69 |
|---|---|---|---|
| Female, % | 75 | 64 | 70 |
| White, % | 97 | 97 | 97 |
| Mean ± SD age, y | 32.2 ± 8.80 | 31.2 ± 7.12 | 31.7 ± 8.00 |
| Median (range) weight, kg | 73.8 (50-119) | 72.2 (46-106) | 72.5 (46-119) |
| Median (range) height, cm[a] | 169.5 (155-194) | 170.0 (158-188) | 170.0 (155-194) |
| Mean ± SD NEI VFQ-25 composite score[b] | 79.0 ± 16.6 | 75.5 ± 17.6 | 77.3 ± 17.02d |
| Mean ± SD NOS-10 score[a] | 69.8 ± 21.2 | 63.6 ± 19.8 | 66.9 ± 20.6 |
| Mean ± SD combined NEI VFQ-25 and NOS-10 composite score[a] | 77.2 ± 16.9 | 70.4 ± 18.3 | 74.0 ± 17.8 |

[a]Placebo, n = 34; anti-LINGO-1, n = 31; total N = 65.
[b]Placebo, n = 35; anti-LINGO-1, n = 32; total N = 67.

TABLE 30

Change from Baseline in mean in NEI VFQ-25 composite, NOS-10, and combined NEI VFQ-25 and NOS-10 composite scores at Week 24 analyzed by ANCOVA[a] (PP population)

| Parameter | Placebo n = 36 | Anti-LINGO-1 n = 33 |
|---|---|---|
| NEI VFQ-25 composite score | | |
| Mean change from Baseline | 15.17 | 13.51 |
| Difference vs. placebo (95% CI) | — | −1.66 (−5.11% to 1.78%) |
| P value | — | .3374 |

TABLE 30-continued

Change from Baseline in mean in NEI VFQ-25 composite, NOS-10, and combined NEI VFQ-25 and NOS-10 composite scores at Week 24 analyzed by ANCOVA[a] (PP population)

| Parameter | Placebo n = 36 | Anti-LINGO-1 n = 33 |
|---|---|---|
| NOS-10 score | | |
| Mean change from Baseline | 17.40 | 16.04 |
| Difference vs. placebo (95% CI) | — | −1.35 |
| | | (−7.38% to 4.67%) |
| P value | — | .6550 |
| Combined NEI VFQ-25 and NOS-10 composite score | | |
| Mean change from Baseline | 15.83 | 14.88 |
| Difference vs. placebo (95% CI) | — | −0.95 |
| | | (−5.08% to 3.19%) |
| P value | — | .6487 |

[a]Adjusted for baseline vision-related QoL assessment value and treatment group.

Conclusions for Patient Reported Outcomes

The RENEW trial evaluated patient-reported visual functioning in an AON episode with an intervention. Baseline NEI VFQ-25 composite and NOS-10 scores indicated that all patients had visual functioning impairment at the start of the study. Regardless of initial injury or treatment group, patients demonstrated notable improvements in vision-related QoL scores from Baseline to week 24. Despite improvements, mean NEI VFQ-25 composite score by week 24 for each group remained below the maximum possible score of 100 (no visual impairment). The residual PRO visual functioning impairment is consistent with the permanent loss of neurons that occurred early on (see Example 3) and likely prevented treatment effect on neuroprotection and visual-related QoL assessments. It is unclear whether any of the 49 items included in the NEI VFQ-25 and NOS-10 are sensitive to demyelination or remyelination in the optic nerve. The NOS-10 may be more sensitive, as it showed more visual function impairment at baseline and was more sensitive to change over time.

Incorporation by Reference

The contents of all references, figures, sequence listing, patents and published patent applications cited throughout this application are hereby incorporated by reference. All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the worldwide web at tigr.org and/or the National Center for Biotechnology Information (NCBI) on the worldwide web at ncbi.nlm.nih.gov.

Equivalents

Those skilled in the art will recognize, or be able to ascertain using no more than routine experimentation, many equivalents to the specific embodiments of the invention described herein. Such equivalents are intended to be encompassed.

What is claimed is:

1. A method of treating or preventing a CNS demyelinating disorder chosen from one or both of multiple sclerosis (MS) or an inflammatory condition of the optic nerve, said method comprising administering to a human subject in need thereof, an anti-LINGO-1 antibody, wherein the anti-LINGO-1 antibody is administered in an amount to treat or prevent the CNS demyelinating disorder at a selected time interval chosen from one, two, or all of:

(i) prior to the onset or relapse of one or more symptoms of the CNS demyelinating disorder;

(ii) within 7 days after the onset or relapse of one or more symptoms of the CNS demyelinating disorder; or (iii) within 30 days after the onset or relapse of one or more symptoms of the CNS demyelinating disorder, and wherein the anti-LINGO-1 antibody comprises an immunoglobulin heavy chain variable domain (VH) comprising VH complementarity determining region (CDR)1, VH CDR2, and VH CDR3, wherein:

the VH CDR1 comprises the amino acid sequence set forth in SEQ ID NO:6;

the VH CDR2 comprises the amino acid sequence set forth in SEQ ID NO:7; and the VH CDR3 comprises the amino acid sequence set forth in SEQ ID NO:8; and wherein the anti-LINGO-1 antibody comprises an immunoglobulin light chain variable domain (VL) comprising VL CDR1, VL CDR2, and VL CDR3, wherein:

the VL CDR1 comprises the amino acid sequence set forth in SEQ ID NO:14;

the VL CDR2 comprises the amino acid sequence set forth in SEQ ID NO:15; and the VL CDR3 comprises the amino acid sequence set forth in SEQ ID NO:16.

2. The method of claim 1, wherein administration of the anti-LINGO antibody is initiated before the onset or relapse of one or more symptoms of the inflammatory condition of the optic nerve in one or both eyes of the subject.

3. The method of claim 1, wherein the anti-LINGO antibody is administered prophylactically or chronically.

4. The method of claim 1, wherein administration of the anti-LINGO antibody is initiated less than 13 days after an acute lesion in MS, an MS relapse, or an optic nerve lesion.

5. The method of claim 4, wherein the anti-LINGO antibody is administered, as a monotherapy or as a combination therapy, at about 1, 3, 10, 30, 60, 100 or 150 mg/kg once every one, two, three, four or five weeks by intravenous, subcutaneous, or intramuscular injection.

6. The method of claim 1, wherein the subject is asymptomatic at the time of treatment.

7. The method of claim 1, wherein the subject is diagnosed with the inflammatory condition of the optic nerve in one or both eyes, but does not show an MS symptom.

8. The method of claim 7, wherein the VH of the anti-LINGO-1 antibody comprises the amino acid sequence of SEQ ID NO:5 and the VL of the anti-LINGO-1 antibody comprises the amino acid sequence of SEQ ID NO:13.

9. The method of claim 7, wherein the anti-LINGO-1 antibody comprises a heavy chain comprising the amino acid sequence of SEQ ID NO:275 and a light chain comprising the amino acid sequence of SEQ ID NO:276.

10. The method of claim 1, wherein the anti-LINGO antibody is administered as a monotherapy in an amount ranging from about 10 to 300 mg/kg.

11. The method of claim 1, wherein the anti-LINGO antibody is administered as a combination therapy in an amount ranging from about 1 to 150 mg/kg.

12. The method of claim 1, wherein the anti-LINGO-1 antibody is administered in combination with an IFN-β 1 molecule.

13. The method of claim 12, wherein the VH of the anti-LINGO-1 antibody comprises the amino acid sequence of SEQ ID NO: 5 and the VL of the anti-LINGO-1 antibody comprises the amino acid sequence of SEQ ID NO: 13 and the immunosuppressive agent is Avonex®.

14. The method of claim 12, wherein:
the anti-LINGO-1 antibody is administered once every four weeks by intravenous infusion dosed at about 3 mg/kg, about 10 mg/kg, about 30 mg/kg, about 50 mg/kg, or about 100 mg/kg; and
IFN-β 1 is administered at one or more of:
(i) at 20-45 micrograms once a week via intramuscular injection;
(ii) at 20-30 micrograms once or three times a week, or at 40-50 micrograms once or three times a week, via subcutaneous injection; or
(iii) in an amount of between 10 and 50 micrograms μg intramuscularly.

15. The method of claim 12, wherein the VH of the anti-LINGO-1 antibody comprises the amino acid sequence of SEQ ID NO:5 and the VL of the anti-LINGO-1 antibody comprises the amino acid sequence of SEQ ID NO:13.

16. The method of claim 12, wherein the anti-LINGO-1 antibody comprises a heavy chain comprising the amino acid sequence of SEQ ID NO:275 and a light chain comprising the amino acid sequence of SEQ ID NO:276.

17. The method of claim 1, wherein the anti-LINGO-1 antibody is modified to reduce effector cell and complement function compared to wild-type IgG1.

18. The method of claim 1, wherein the anti-LINGO-1 antibody comprises a heavy chain comprising the amino acid sequence of SEQ ID NO: 275 and a light chain comprising the amino acid sequence of SEQ ID NO: 276.

19. The method of claim 1, wherein the subject has been, or is being evaluated by one or more of:
performing a neurological examination;
acquiring the subject's status on the Expanded Disability Status Scale (EDSS);
acquiring the subject's status on the Multiple Sclerosis Functional Composite (MSFC);
detecting the subject's lesion status;
acquiring a measure of upper and/or lower extremity function;
acquiring a measure of short distance ambulatory function;
acquiring a measure of long distance ambulatory function;
acquiring a measure of cognitive function; or
acquiring a measure of visual function.

20. The method of claim 19, wherein an improvement in the subject is defined by one or more of:
a. ≥1.0 point decrease in EDSS from a baseline score of <6.0;
b. ≥15% improvement from baseline in T25FW;
c. ≥15% improvement from baseline in 9HPT; or
d. ≥15% improvement from baseline in PASAT or SDMT.

21. The method of claim 1, further comprising one or more of:
acquiring the subject's status on the MSFC;
performing a neurological examination;
acquiring the subject's status on the Expanded Disability Status Scale (EDSS);
detecting the subject's lesion status;
acquiring a measure of upper and/or lower extremity function;
acquiring a measure of short distance ambulatory function;
acquiring a measure of long distance ambulatory function;
acquiring a measure of cognitive function; or
acquiring a measure of visual function.

22. The method of claim 1, wherein the VH of the anti-LINGO-1 antibody comprises the amino acid sequence of SEQ ID NO:5 and the VL of the anti-LINGO-1 antibody comprises the amino acid sequence of SEQ ID NO:13.

23. A kit comprising an anti-LINGO-1 antibody with instructions for use in treating multiple sclerosis or an inflammatory condition of the optic nerve, wherein the antibody is instructed to be administered at a selected time interval chosen from one, two, or all of:
(i) prior to the onset or relapse of one or more symptoms of the CNS demyelinating disorder;
(ii) within 7 days after the onset or relapse of one or more symptoms of the CNS demyelinating disorder; or
(iii) within 30 days after the onset or relapse of one or more symptoms of the CNS demyelinating disorder,
wherein the anti-LINGO-1 antibody comprises an immunoglobulin heavy chain variable domain (VH) comprising VH complementarity determining region (CDR)1, VH CDR2, and VH CDR3, wherein:
the VH CDR1 comprises the amino acid sequence set forth in SEQ ID NO:6,
the VH CDR2 comprises the amino acid sequence set forth in SEQ ID NO:7; and
the VH CDR3 comprises the amino acid sequence set forth in SEQ ID NO:8; and
wherein the anti-LINGO-1 antibody comprises an immunoglobulin light chain variable domain (VL) comprising VL CDR1, VL CDR2, and VL CDR3, wherein:
the VL CDR1 comprises the amino acid sequence set forth in SEQ ID NO:14;
the VL CDR2 comprises the amino acid sequence set forth in SEQ ID NO:15; and
the VL CDR3 comprises the amino acid sequence set forth in SEQ ID NO:16.

24. The kit of claim 23, wherein the VH of the anti-LINGO-1 antibody comprises the amino acid sequence of SEQ ID NO:5 and the VL of the anti-LINGO-1 antibody comprises the amino acid sequence of SEQ ID NO:13.

25. The kit of claim 23, wherein the anti-LINGO-1 antibody comprises a heavy chain comprising the amino acid sequence of SEQ ID NO:275 and a light chain comprising the amino acid sequence of SEQ ID NO:276.

* * * * *

UNITED STATES PATENT AND TRADEMARK OFFICE
CERTIFICATE OF CORRECTION

PATENT NO. : 10,435,467 B2  
APPLICATION NO. : 15/541944  
DATED : October 8, 2019  
INVENTOR(S) : Diego Cadavid et al.

Page 1 of 1

It is certified that error appears in the above-identified patent and that said Letters Patent is hereby corrected as shown below:

In the Claims

Column 339
Claim 14, Line 34, after "micrograms" delete "μg".

Column 340
Claim 23, Line 43, delete "NO:6," and insert -- NO:6; --.

Signed and Sealed this
Tenth Day of December, 2019

Andrei Iancu
*Director of the United States Patent and Trademark Office*

SEQUENCE LISTING

```
<160> NUMBER OF SEQ ID NOS: 277

<210> SEQ ID NO 1
<211> LENGTH: 119
<212> TYPE: PRT
<213> ORGANISM: Artificial
<220> FEATURE:
<223> OTHER INFORMATION: VH sequence of Li62 antibody

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
        115
```

```
<210> SEQ ID NO 2
<211> LENGTH: 5
<212> TYPE: PRT
<213> ORGANISM: Artificial
<220> FEATURE:
<223> OTHER INFORMATION: VH CDR1 sequence of Li62 antibody

<400> SEQUENCE: 2

Ile Tyr Pro Met Phe
1               5

<210> SEQ ID NO 3
<211> LENGTH: 17
<212> TYPE: PRT
<213> ORGANISM: Artificial
<220> FEATURE:
<223> OTHER INFORMATION: VH CDR2 sequence of Li62 antibody

<400> SEQUENCE: 3

Trp Ile Gly Pro Ser Gly Gly Ile Thr Lys Tyr Ala Asp Ser Val Lys
1               5                   10                  15

Gly

<210> SEQ ID NO 4
<211> LENGTH: 10
<212> TYPE: PRT
<213> ORGANISM: Artificial
<220> FEATURE:
<223> OTHER INFORMATION: VH CDR3 sequence of Li62 antibody

<400> SEQUENCE: 4

Glu Gly His Asn Asp Trp Tyr Phe Asp Leu
1               5                   10

<210> SEQ ID NO 5
<211> LENGTH: 118
<212> TYPE: PRT
<213> ORGANISM: Artificial
<220> FEATURE:
<223> OTHER INFORMATION: VH sequence of Li81 antibody

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Ala Phe Asp Ile Trp Gly Gln Gly Thr
            100                 105                 110

Thr Val Thr Val Ser Ser
            115

<210> SEQ ID NO 6
<211> LENGTH: 5
<212> TYPE: PRT
```

```
<213> ORGANISM: Artificial
<220> FEATURE:
<223> OTHER INFORMATION: VH CDR1 sequence of Li81 antibody

<400> SEQUENCE: 6

Ala Tyr Glu Met Lys
1               5

<210> SEQ ID NO 7
<211> LENGTH: 17
<212> TYPE: PRT
<213> ORGANISM: Artificial
<220> FEATURE:
<223> OTHER INFORMATION: VH CDR2 sequence of Li81 antibody

<400> SEQUENCE: 7

Val Ile Gly Pro Ser Gly Gly Phe Thr Phe Tyr Ala Asp Ser Val Lys
1               5                   10                  15

Gly

<210> SEQ ID NO 8
<211> LENGTH: 9
<212> TYPE: PRT
<213> ORGANISM: Artificial
<220> FEATURE:
<223> OTHER INFORMATION: VH CDR3 sequence of Li81 antibody

<400> SEQUENCE: 8

Glu Gly Asp Asn Asp Ala Phe Asp Ile
1               5

<210> SEQ ID NO 9
<211> LENGTH: 107
<212> TYPE: PRT
<213> ORGANISM: Artificial
<220> FEATURE:
<223> OTHER INFORMATION: VL sequence of Li62 antibody

<400> SEQUENCE: 9

Asp Ile Gln Met Thr Gln Ser Pro Ser Phe Leu Ser Ala Ser Val Gly
1               5                   10                  15

Asp Ser Val Ala Ile Thr Cys Arg Ala Ser Gln Asp Ile Ser Arg Tyr
            20                  25                  30

Leu Ala Trp Tyr Gln Gln Arg Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Phe Thr Ile Thr Ser Leu Gln Pro
65                  70                  75                  80

Glu Asp Phe Gly Thr Tyr Tyr Cys Gln Gln Tyr Asp Thr Leu His Pro
                85                  90                  95

Ser Phe Gly Pro Gly Thr Thr Val Asp Ile Lys
            100                 105

<210> SEQ ID NO 10
<211> LENGTH: 11
<212> TYPE: PRT
<213> ORGANISM: Artificial
<220> FEATURE:
<223> OTHER INFORMATION: VL CDR1 sequence of Li62 antibody

<400> SEQUENCE: 10

Arg Ala Ser Gln Asp Ile Ser Arg Tyr Leu Ala
```

-continued

```
<210> SEQ ID NO 11
<211> LENGTH: 7
<212> TYPE: PRT
<213> ORGANISM: Artificial
<220> FEATURE:
<223> OTHER INFORMATION: VL CDR2 sequence of Li62 antibody

<400> SEQUENCE: 11

Asp Ala Ser Asn Leu Gln Thr
1               5

<210> SEQ ID NO 12
<211> LENGTH: 9
<212> TYPE: PRT
<213> ORGANISM: Artificial
<220> FEATURE:
<223> OTHER INFORMATION: VL CDR3 sequence of Li62 antibody

<400> SEQUENCE: 12

Gln Gln Tyr Asp Thr Leu His Pro Ser
1               5

<210> SEQ ID NO 13
<211> LENGTH: 108
<212> TYPE: PRT
<213> ORGANISM: Artificial
<220> FEATURE:
<223> OTHER INFORMATION: VL sequence of Li81 antibody

<400> SEQUENCE: 13

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Met
                85                  90                  95

Tyr Thr Phe Gly Gln Gly Thr Lys Leu Glu Ile Lys
            100                 105

<210> SEQ ID NO 14
<211> LENGTH: 11
<212> TYPE: PRT
<213> ORGANISM: Artificial
<220> FEATURE:
<223> OTHER INFORMATION: VL CDR1 sequence of Li81 antibody

<400> SEQUENCE: 14

Arg Ala Ser Gln Ser Val Ser Ser Tyr Leu Ala
1               5                   10

<210> SEQ ID NO 15
<211> LENGTH: 7
<212> TYPE: PRT
<213> ORGANISM: Artificial
<220> FEATURE:
<223> OTHER INFORMATION: VL CDR2 sequence of Li81 antibody
```

```
<400> SEQUENCE: 15

Asp Ala Ser Asn Arg Ala Thr
1               5

<210> SEQ ID NO 16
<211> LENGTH: 10
<212> TYPE: PRT
<213> ORGANISM: Artificial
<220> FEATURE:
<223> OTHER INFORMATION: VL CDR3 sequence of Li81 antibody

<400> SEQUENCE: 16

Gln Gln Arg Ser Asn Trp Pro Met Tyr Thr
1               5                   10

<210> SEQ ID NO 17
<211> LENGTH: 10
<212> TYPE: PRT
<213> ORGANISM: Artificial
<220> FEATURE:
<223> OTHER INFORMATION: VH CDR3 sequence of Li62 variant B06 antibody

<400> SEQUENCE: 17

Glu Gly Tyr Tyr Asp Trp Tyr Phe Asp Gln
1               5                   10

<210> SEQ ID NO 18
<211> LENGTH: 10
<212> TYPE: PRT
<213> ORGANISM: Artificial
<220> FEATURE:
<223> OTHER INFORMATION: VH CDR3 sequence of Li62 variant B12 antibody

<400> SEQUENCE: 18

Glu Gly Gln Tyr Asp Trp Tyr Phe Asp Val
1               5                   10

<210> SEQ ID NO 19
<211> LENGTH: 10
<212> TYPE: PRT
<213> ORGANISM: Artificial
<220> FEATURE:
<223> OTHER INFORMATION: VH CDR3 sequence of Li62 variant F06 antibody

<400> SEQUENCE: 19

Glu Gly Asp Tyr Asp Trp Tyr Phe Asp Leu
1               5                   10

<210> SEQ ID NO 20
<211> LENGTH: 10
<212> TYPE: PRT
<213> ORGANISM: Artificial
<220> FEATURE:
<223> OTHER INFORMATION: VH CDR3 sequence of Li62 variant B01 antibody

<400> SEQUENCE: 20

Glu Gly Gln Tyr Asp Trp Tyr Phe Glu Leu
1               5                   10

<210> SEQ ID NO 21
<211> LENGTH: 10
<212> TYPE: PRT
<213> ORGANISM: Artificial
<220> FEATURE:
<223> OTHER INFORMATION: VH CDR3 sequence of Li62 variant D09 antibody
```

```
<400> SEQUENCE: 21

Glu Ala Asp Ile Asp Trp Phe Phe Asp Leu
1               5                   10

<210> SEQ ID NO 22
<211> LENGTH: 10
<212> TYPE: PRT
<213> ORGANISM: Artificial
<220> FEATURE:
<223> OTHER INFORMATION: VH CDR3 sequence of Li62 variant D12 antibody

<400> SEQUENCE: 22

Glu Gly His Tyr Asp Trp Tyr Phe Asp Leu
1               5                   10

<210> SEQ ID NO 23
<211> LENGTH: 10
<212> TYPE: PRT
<213> ORGANISM: Artificial
<220> FEATURE:
<223> OTHER INFORMATION: VH CDR3 sequence of Li62 variant F01 antibody

<400> SEQUENCE: 23

Glu Gly Arg Tyr Asp Trp Tyr Phe Asp Pro
1               5                   10

<210> SEQ ID NO 24
<211> LENGTH: 10
<212> TYPE: PRT
<213> ORGANISM: Artificial
<220> FEATURE:
<223> OTHER INFORMATION: VH CDR3 sequence of Li62 variant F02 antibody

<400> SEQUENCE: 24

Glu Gly Asp Tyr Asp Trp Tyr Phe Gly Leu
1               5                   10

<210> SEQ ID NO 25
<211> LENGTH: 10
<212> TYPE: PRT
<213> ORGANISM: Artificial
<220> FEATURE:
<223> OTHER INFORMATION: VH CDR3 sequence of Li62 variant F06 antibody

<400> SEQUENCE: 25

Glu Gly Arg Tyr Asp Trp Tyr Phe Asp Leu
1               5                   10

<210> SEQ ID NO 26
<211> LENGTH: 10
<212> TYPE: PRT
<213> ORGANISM: Artificial
<220> FEATURE:
<223> OTHER INFORMATION: VH CDR3 sequence of Li62 variant F10 antibody

<400> SEQUENCE: 26

Glu Ser His Ile Asp Arg Tyr Phe Asp Leu
1               5                   10

<210> SEQ ID NO 27
<211> LENGTH: 10
<212> TYPE: PRT
<213> ORGANISM: Artificial
<220> FEATURE:
<223> OTHER INFORMATION: VH CDR3 sequence of Li62 variant G08 antibody

<400> SEQUENCE: 27
```

```
Glu Gly Gln Tyr Asp Trp Tyr Phe Asp Val
1               5                   10

<210> SEQ ID NO 28
<211> LENGTH: 10
<212> TYPE: PRT
<213> ORGANISM: Artificial
<220> FEATURE:
<223> OTHER INFORMATION: VH CDR3 sequence of Li62 variant H08 antibody

<400> SEQUENCE: 28

Glu Gly His Tyr Asn Gly Tyr Phe Asp Leu
1               5                   10

<210> SEQ ID NO 29
<211> LENGTH: 10
<212> TYPE: PRT
<213> ORGANISM: Artificial
<220> FEATURE:
<223> OTHER INFORMATION: VH CDR3 sequence of Li62 variant C10 antibody

<400> SEQUENCE: 29

Glu Gly Tyr Tyr Asp Trp Tyr Phe Asp Leu
1               5                   10

<210> SEQ ID NO 30
<211> LENGTH: 10
<212> TYPE: PRT
<213> ORGANISM: Artificial
<220> FEATURE:
<223> OTHER INFORMATION: VH CDR3 sequence of Li62 variant C02 antibody

<400> SEQUENCE: 30

Glu Gly Thr Tyr Asp Trp Tyr Leu Asp Leu
1               5                   10

<210> SEQ ID NO 31
<211> LENGTH: 10
<212> TYPE: PRT
<213> ORGANISM: Artificial
<220> FEATURE:
<223> OTHER INFORMATION: VH CDR3 sequence of Li62 variant D05 antibody

<400> SEQUENCE: 31

Glu Gly Tyr Tyr Asp Trp Tyr Phe Glu Leu
1               5                   10

<210> SEQ ID NO 32
<211> LENGTH: 10
<212> TYPE: PRT
<213> ORGANISM: Artificial
<220> FEATURE:
<223> OTHER INFORMATION: VH CDR3 sequence of Li62 variant F02 antibody

<400> SEQUENCE: 32

Glu Gly Leu Ile Asp Trp Phe Phe Asp Gln
1               5                   10

<210> SEQ ID NO 33
<211> LENGTH: 10
<212> TYPE: PRT
<213> ORGANISM: Artificial
<220> FEATURE:
<223> OTHER INFORMATION: VH CDR3 sequence of Li62 variant C10 antibody

<400> SEQUENCE: 33
```

```
Glu Gly Gln Phe Asp Trp Tyr Phe Asp Leu
1               5                   10
```

<210> SEQ ID NO 34
<211> LENGTH: 10
<212> TYPE: PRT
<213> ORGANISM: Artificial
<220> FEATURE:
<223> OTHER INFORMATION: VH CDR3 sequence of Li62 variant H08 antibody

<400> SEQUENCE: 34

```
Glu Gly Thr Tyr Asp Trp Tyr Phe Asp Leu
1               5                   10
```

<210> SEQ ID NO 35
<211> LENGTH: 9
<212> TYPE: PRT
<213> ORGANISM: Artificial
<220> FEATURE:
<223> OTHER INFORMATION: VH CDR3 sequence of Li81 variant F09 antibody

<400> SEQUENCE: 35

```
Glu Gly Glu Asn Asp Ala Phe Asp Val
1               5
```

<210> SEQ ID NO 36
<211> LENGTH: 9
<212> TYPE: PRT
<213> ORGANISM: Artificial
<220> FEATURE:
<223> OTHER INFORMATION: VH CDR3 sequence of Li81 variant G02 antibody

<400> SEQUENCE: 36

```
Glu Gly Asp Asn Asp Ala Tyr Asp Thr
1               5
```

<210> SEQ ID NO 37
<211> LENGTH: 9
<212> TYPE: PRT
<213> ORGANISM: Artificial
<220> FEATURE:
<223> OTHER INFORMATION: VH CDR3 sequence of Li81 variant H03 antibody

<400> SEQUENCE: 37

```
Glu Gly Thr Asn Asp Ala Phe Asp Ile
1               5
```

<210> SEQ ID NO 38
<211> LENGTH: 9
<212> TYPE: PRT
<213> ORGANISM: Artificial
<220> FEATURE:
<223> OTHER INFORMATION: VH CDR3 sequence of Li81 variant A12 antibody

<400> SEQUENCE: 38

```
Glu Gly Asp Asn Asp Ala Phe Asp Ser
1               5
```

<210> SEQ ID NO 39
<211> LENGTH: 9
<212> TYPE: PRT
<213> ORGANISM: Artificial
<220> FEATURE:
<223> OTHER INFORMATION: VH CDR3 sequence of Li81 variant C02 antibody

<400> SEQUENCE: 39

```
Glu Gly Asp Asn Asp Ala Phe Asp Thr
```

```
<210> SEQ ID NO 40
<211> LENGTH: 9
<212> TYPE: PRT
<213> ORGANISM: Artificial
<220> FEATURE:
<223> OTHER INFORMATION: VH CDR3 sequence of Li81 variant C11 antibody

<400> SEQUENCE: 40

Glu Gly Asp Asn Asp Ala Tyr Asp Arg
1               5

<210> SEQ ID NO 41
<211> LENGTH: 9
<212> TYPE: PRT
<213> ORGANISM: Artificial
<220> FEATURE:
<223> OTHER INFORMATION: VH CDR3 sequence of Li81 variant D11 antibody

<400> SEQUENCE: 41

Glu Gly Asp Asn Asp Val Phe Asp Ser
1               5

<210> SEQ ID NO 42
<211> LENGTH: 9
<212> TYPE: PRT
<213> ORGANISM: Artificial
<220> FEATURE:
<223> OTHER INFORMATION: VH CDR3 sequence of Li81 variant E05 antibody

<400> SEQUENCE: 42

Glu Gly Asp Asp Asp Val Phe Asp Met
1               5

<210> SEQ ID NO 43
<211> LENGTH: 9
<212> TYPE: PRT
<213> ORGANISM: Artificial
<220> FEATURE:
<223> OTHER INFORMATION: VH CDR3 sequence of Li81 variant H04 antibody

<400> SEQUENCE: 43

Glu Gly Tyr Asn Asp Ala Phe Asp Phe
1               5

<210> SEQ ID NO 44
<211> LENGTH: 9
<212> TYPE: PRT
<213> ORGANISM: Artificial
<220> FEATURE:
<223> OTHER INFORMATION: VH CDR3 sequence of Li81 variant B04 antibody

<400> SEQUENCE: 44

Glu Gly Asp Asp Asp Ala Tyr Asp Met
1               5

<210> SEQ ID NO 45
<211> LENGTH: 9
<212> TYPE: PRT
<213> ORGANISM: Artificial
<220> FEATURE:
<223> OTHER INFORMATION: VH CDR3 sequence of Li81 variant A02 antibody

<400> SEQUENCE: 45

Glu Gln Asp Tyr Asp Thr Tyr Asp Leu
1               5
```

<210> SEQ ID NO 46
<211> LENGTH: 9
<212> TYPE: PRT
<213> ORGANISM: Artificial
<220> FEATURE:
<223> OTHER INFORMATION: VH CDR3 sequence of Li81 variant B12 antibody

<400> SEQUENCE: 46

Glu Gly Asp Asp Asp Ala Phe Asp Thr
1               5

<210> SEQ ID NO 47
<211> LENGTH: 9
<212> TYPE: PRT
<213> ORGANISM: Artificial
<220> FEATURE:
<223> OTHER INFORMATION: VH CDR3 sequence of Li81 variant H06 antibody

<400> SEQUENCE: 47

Glu Ala Asp Asp Asp Ala Phe Asp Ile
1               5

<210> SEQ ID NO 48
<211> LENGTH: 9
<212> TYPE: PRT
<213> ORGANISM: Artificial
<220> FEATURE:
<223> OTHER INFORMATION: VH CDR3 sequence of Li81 variant H08 antibody

<400> SEQUENCE: 48

Glu Gly Glu Asn Asp Ala Phe Asp Met
1               5

<210> SEQ ID NO 49
<211> LENGTH: 9
<212> TYPE: PRT
<213> ORGANISM: Artificial
<220> FEATURE:
<223> OTHER INFORMATION: VH CDR3 sequence of Li81 variant E07 antibody

<400> SEQUENCE: 49

Glu Gly Glu Tyr Asp Thr Tyr Asp Ile
1               5

<210> SEQ ID NO 50
<211> LENGTH: 447
<212> TYPE: PRT
<213> ORGANISM: Artificial
<220> FEATURE:
<223> OTHER INFORMATION: Aglycosylated Li81 heavy chain

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                         85                  90                  95
Ala Thr Glu Gly Asp Asn Asp Ala Phe Asp Ile Trp Gly Gln Gly Thr
                    100                 105                 110

Thr Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Ala Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 51
<211> LENGTH: 614
<212> TYPE: PRT
<213> ORGANISM: Homo sapiens

<400> SEQUENCE: 51

Met Leu Ala Gly Gly Val Arg Ser Met Pro Ser Pro Leu Leu Ala Cys
1               5                   10                  15
```

```
Trp Gln Pro Ile Leu Leu Leu Val Leu Gly Ser Val Leu Gly Ser
                20                  25                  30

Ala Thr Gly Cys Pro Pro Arg Cys Glu Cys Ser Ala Gln Asp Arg Ala
            35                  40                  45

Val Leu Cys His Arg Lys Arg Phe Val Ala Val Pro Glu Gly Ile Pro
50                  55                  60

Thr Glu Thr Arg Leu Leu Asp Leu Gly Lys Asn Arg Ile Lys Thr Leu
65                  70                  75                  80

Asn Gln Asp Glu Phe Ala Ser Phe Pro His Leu Glu Glu Leu Glu Leu
                85                  90                  95

Asn Glu Asn Ile Val Ser Ala Val Glu Pro Gly Ala Phe Asn Asn Leu
            100                 105                 110

Phe Asn Leu Arg Thr Leu Gly Leu Arg Ser Asn Arg Leu Lys Leu Ile
        115                 120                 125

Pro Leu Gly Val Phe Thr Gly Leu Ser Asn Leu Thr Lys Leu Asp Ile
    130                 135                 140

Ser Glu Asn Lys Ile Val Ile Leu Leu Asp Tyr Met Phe Gln Asp Leu
145                 150                 155                 160

Tyr Asn Leu Lys Ser Leu Glu Val Gly Asp Asn Asp Leu Val Tyr Ile
                165                 170                 175

Ser His Arg Ala Phe Ser Gly Leu Asn Ser Leu Glu Gln Leu Thr Leu
            180                 185                 190

Glu Lys Cys Asn Leu Thr Ser Ile Pro Thr Glu Ala Leu Ser His Leu
        195                 200                 205

His Gly Leu Ile Val Leu Arg Leu Arg His Leu Asn Ile Asn Ala Ile
    210                 215                 220

Arg Asp Tyr Ser Phe Lys Arg Leu Tyr Arg Leu Lys Val Leu Glu Ile
225                 230                 235                 240

Ser His Trp Pro Tyr Leu Asp Thr Met Thr Pro Asn Cys Leu Tyr Gly
                245                 250                 255

Leu Asn Leu Thr Ser Leu Ser Ile Thr His Cys Asn Leu Thr Ala Val
            260                 265                 270

Pro Tyr Leu Ala Val Arg His Leu Val Tyr Leu Arg Phe Leu Asn Leu
        275                 280                 285

Ser Tyr Asn Pro Ile Ser Thr Ile Glu Gly Ser Met Leu His Glu Leu
    290                 295                 300

Leu Arg Leu Gln Glu Ile Gln Leu Val Gly Gly Gln Leu Ala Val Val
305                 310                 315                 320

Glu Pro Tyr Ala Phe Arg Gly Leu Asn Tyr Leu Arg Val Leu Asn Val
                325                 330                 335

Ser Gly Asn Gln Leu Thr Thr Leu Glu Glu Ser Val Phe His Ser Val
            340                 345                 350

Gly Asn Leu Glu Thr Leu Ile Leu Asp Ser Asn Pro Leu Ala Cys Asp
        355                 360                 365

Cys Arg Leu Leu Trp Val Phe Arg Arg Arg Trp Arg Leu Asn Phe Asn
    370                 375                 380

Arg Gln Gln Pro Thr Cys Ala Thr Pro Glu Phe Val Gln Gly Lys Glu
385                 390                 395                 400

Phe Lys Asp Phe Pro Asp Val Leu Leu Pro Asn Tyr Phe Thr Cys Arg
                405                 410                 415

Arg Ala Arg Ile Arg Asp Arg Lys Ala Gln Gln Val Phe Val Asp Glu
            420                 425                 430

Gly His Thr Val Gln Phe Val Cys Arg Ala Asp Gly Asp Pro Pro Pro
```

```
                435                 440                 445
Ala Ile Leu Trp Leu Ser Pro Arg Lys His Leu Val Ser Ala Lys Ser
    450                 455                 460

Asn Gly Arg Leu Thr Val Phe Pro Asp Gly Thr Leu Glu Val Arg Tyr
465                 470                 475                 480

Ala Gln Val Gln Asp Asn Gly Thr Tyr Leu Cys Ile Ala Ala Asn Ala
                485                 490                 495

Gly Gly Asn Asp Ser Met Pro Ala His Leu His Val Arg Ser Tyr Ser
            500                 505                 510

Pro Asp Trp Pro His Gln Pro Asn Lys Thr Phe Ala Phe Ile Ser Asn
        515                 520                 525

Gln Pro Gly Glu Gly Glu Ala Asn Ser Thr Arg Ala Thr Val Pro Phe
    530                 535                 540

Pro Phe Asp Ile Lys Thr Leu Ile Ile Ala Thr Thr Met Gly Phe Ile
545                 550                 555                 560

Ser Phe Leu Gly Val Val Leu Phe Cys Leu Val Leu Leu Phe Leu Trp
                565                 570                 575

Ser Arg Gly Lys Gly Asn Thr Lys His Asn Ile Glu Ile Glu Tyr Val
            580                 585                 590

Pro Arg Lys Ser Asp Ala Gly Ile Ser Ser Ala Asp Ala Pro Arg Lys
        595                 600                 605

Phe Asn Met Lys Met Ile
    610

<210> SEQ ID NO 52
<211> LENGTH: 1845
<212> TYPE: DNA
<213> ORGANISM: Homo sapiens

<400> SEQUENCE: 52
atgctggcgg ggggcgtgag gagcatgccc agccccctcc tggcctgctg gcagcccatc    60
ctcctgctgg tgctgggctc agtgctgtca ggctcggcca cgggctgccc gccccgctgc   120
gagtgctccg cccaggaccg cgctgtgctg tgccaccgca gcgctttgt ggcagtcccc    180 gagggcatcc ccaccgagac gcgcctgctg acctaggca agaaccgcat caaaacgctc    240
aaccaggacg agttcgccag cttcccgcac ctggaggagc tggagctcaa cgagaacatc   300
gtgagcgccc tggagcccgg cgccttcaac aacctcttca acctccggac gctgggtctc   360
cgcagcaacc gcctgaagct catcccgcta ggcgtcttca ctggcctcag caacctgacc   420
aagctggaca tcagcgagaa caagattgtt atcctgctgg actacatgtt tcaggacctg   480
tacaacctca gtcactgga ggttggcgac aatgacctcg tctacatctc tcaccgcgcc    540
ttcagcggcc tcaacagcct ggagcagctg acgctggaga atgcaacct gacctccatc    600 cccaccgagg cgctgtccca cctgcacggc tcatcgtcc tgaggctccg gcacctcaac   660
atcaatgcca tccgggacta ctccttcaag aggctctacc gactcaaggt cttggagatc   720
tcccactggc cctacttgga caccatgaca cccaactgcc tctacggcct caacctgacg   780
tccctgtcca tcacacactg caatctgacc gctgtgccct acctggccgt ccgccaccta   840
gtctatctcc gcttcctcaa cctctcctac aaccccatca gcaccattga gggctccatg   900
ttgcatgagc tgctccggct gcaggagatc cagctggtgg gcgggcagct ggccgtggtg   960
gagccctatg cctccgcgg cctcaactac ctgcgcgtgc tcaatgtctc tggcaaccag   1020
ctgaccacac tggaggaatc agtcttccac tcggtgggca acctggagac actcatcctg  1080
```

```
gactccaacc cgctggcctg cgactgtcgg ctcctgtggg tgttccggcg ccgctggcgg      1140
ctcaacttca accggcagca gcccacgtgc gccacgcccg agtttgtcca gggcaaggag      1200
ttcaaggact tccctgatgt gctactgccc aactacttca cctgccgccg cgcccgcatc      1260
cgggaccgca aggcccagca ggtgtttgtg gacgagggcc acacggtgca gtttgtgtgc      1320
cgggccgatg gcgacccgcc gccgccatc ctctggctct caccccgaaa gcacctggtc       1380
tcagccaaga gcaatgggcg gctcacagtc ttccctgatg gcacgctgga ggtgcgctac      1440
gcccaggtac aggacaacgg cacgtacctg tgcatcgcgg ccaacgcggg cggcaacgac      1500
tccatgcccg cccacctgca tgtgcgcagc tactcgcccg actggcccca tcagcccaac      1560
aagaccttcg ctttcatctc caaccagccg ggcgagggag aggccaacag cacccgcgcc      1620
actgtgcctt tccccttcga catcaagacc ctcatcatcg ccaccaccat gggcttcatc      1680
tctttcctgg gcgtcgtcct cttctgcctg gtgctgctgt ttctctggag ccggggcaag      1740
ggcaacacaa agcacaacat cgagatcgag tatgtgcccc gaaagtcgga cgcaggcatc      1800
agctccgccg acgcgccccg caagttcaac atgaagatga tatga                     1845
```

<210> SEQ ID NO 53
<211> LENGTH: 119
<212> TYPE: PRT
<213> ORGANISM: Artificial
<220> FEATURE:
<223> OTHER INFORMATION: VH sequence of Li62 variant B06 antibody

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Tyr Tyr Asp Trp Tyr Phe Asp Gln Trp Gly Arg Gly
            100                 105                 110

Thr Leu Val Thr Val Ser Ser
        115

<210> SEQ ID NO 54
<211> LENGTH: 119
<212> TYPE: PRT
<213> ORGANISM: Artificial
<220> FEATURE:
<223> OTHER INFORMATION: VH sequence of Li62 variant B12 antibody

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly Gln Tyr Asp Trp Tyr Phe Asp Val Trp Gly Arg Gly
             100                 105                 110

Thr Leu Val Thr Val Ser Ser
            115

<210> SEQ ID NO 55
<211> LENGTH: 119
<212> TYPE: PRT
<213> ORGANISM: Artificial
<220> FEATURE:
<223> OTHER INFORMATION: VH sequence of Li62 variant F06 antibody

<400> SEQUENCE: 55

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ile Tyr
                 20                  25                  30

Pro Met Phe Trp Val Arg Gln Ala Pro Gly Lys Gly Leu Glu Trp Val
             35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly Asp Tyr Asp Trp Tyr Phe Asp Leu Trp Gly Arg Gly
             100                 105                 110

Thr Leu Val Thr Val Ser Ser
            115

<210> SEQ ID NO 56
<211> LENGTH: 119
<212> TYPE: PRT
<213> ORGANISM: Artificial
<220> FEATURE:
<223> OTHER INFORMATION: VH sequence of Li62 variant B01 antibody

<400> SEQUENCE: 56

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ile Tyr
                 20                  25                  30

Pro Met Phe Trp Val Arg Gln Ala Pro Gly Lys Gly Leu Glu Trp Val
             35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly Gln Tyr Asp Trp Tyr Phe Glu Leu Trp Gly Arg Gly
             100                 105                 110

```
Thr Leu Val Thr Val Ser Ser
        115

<210> SEQ ID NO 57
<211> LENGTH: 119
<212> TYPE: PRT
<213> ORGANISM: Artificial
<220> FEATURE:
<223> OTHER INFORMATION: VH sequence of Li62 variant D09 antibody

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Ala Asp Ile Asp Trp Phe Phe Asp Leu Trp Gly Arg Gly
            100                 105                 110

Thr Leu Val Thr Val Ser Ser
        115

<210> SEQ ID NO 58
<211> LENGTH: 119
<212> TYPE: PRT
<213> ORGANISM: Artificial
<220> FEATURE:
<223> OTHER INFORMATION: VH sequence of Li62 variant D12 antibody

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Tyr Asp Trp Tyr Phe Asp Leu Trp Gly Arg Gly
            100                 105                 110

Thr Leu Val Thr Val Ser Ser
        115

<210> SEQ ID NO 59
<211> LENGTH: 119
<212> TYPE: PRT
<213> ORGANISM: Artificial
<220> FEATURE:
<223> OTHER INFORMATION: VH sequence of Li62 variant F01 antibody
```

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Arg Tyr Asp Trp Tyr Phe Asp Pro Trp Gly Arg Gly
            100                 105                 110

Thr Leu Val Thr Val Ser Ser
            115

<210> SEQ ID NO 60
<211> LENGTH: 119
<212> TYPE: PRT
<213> ORGANISM: Artificial
<220> FEATURE:
<223> OTHER INFORMATION: VH sequence of Li62 variant F02 antibody

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Asp Tyr Asp Trp Tyr Phe Gly Leu Trp Gly Arg Gly
            100                 105                 110

Thr Leu Val Thr Val Ser Ser
            115

<210> SEQ ID NO 61
<211> LENGTH: 119
<212> TYPE: PRT
<213> ORGANISM: Artificial
<220> FEATURE:
<223> OTHER INFORMATION: VH sequence of Li62 variant F06 antibody

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                85                  90                  95

Ala Arg Glu Gly Arg Tyr Asp Trp Tyr Phe Asp Leu Trp Gly Arg Gly
            100                 105                 110

Thr Leu Val Thr Val Ser Ser
            115

<210> SEQ ID NO 62
<211> LENGTH: 119
<212> TYPE: PRT
<213> ORGANISM: Artificial
<220> FEATURE:
<223> OTHER INFORMATION: VH sequence of Li62 variant F10 antibody

<400> SEQUENCE: 62

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
            35                  40                  45

Ser Trp Ile Gly Pro Ser Gly Gly Ile Thr Lys Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                85                  90                  95

Ala Arg Glu Ser His Ile Asp Arg Tyr Phe Asp Leu Trp Gly Arg Gly
            100                 105                 110

Thr Leu Val Thr Val Ser Ser
            115

<210> SEQ ID NO 63
<211> LENGTH: 119
<212> TYPE: PRT
<213> ORGANISM: Artificial
<220> FEATURE:
<223> OTHER INFORMATION: VH sequence of Li62 variant G08 antibody

<400> SEQUENCE: 63

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
            35                  40                  45

Ser Trp Ile Gly Pro Ser Gly Gly Ile Thr Lys Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                85                  90                  95

Ala Arg Glu Gly Gln Tyr Asp Trp Tyr Phe Asp Val Trp Gly Arg Gly

Thr Leu Val Thr Val Ser Ser
        115

<210> SEQ ID NO 64
<211> LENGTH: 119
<212> TYPE: PRT
<213> ORGANISM: Artificial
<220> FEATURE:
<223> OTHER INFORMATION: VH sequence of Li62 variant H08 antibody

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Tyr Asn Gly Tyr Phe Asp Leu Trp Gly Arg Gly
            100                 105                 110

Thr Leu Val Thr Val Ser Ser
        115

<210> SEQ ID NO 65
<211> LENGTH: 119
<212> TYPE: PRT
<213> ORGANISM: Artificial
<220> FEATURE:
<223> OTHER INFORMATION: VH sequence of Li62 variant C10 antibody

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Tyr Tyr Asp Trp Tyr Phe Asp Leu Trp Gly Arg Gly
            100                 105                 110

Thr Leu Val Thr Val Ser Ser
        115

<210> SEQ ID NO 66
<211> LENGTH: 119
<212> TYPE: PRT
<213> ORGANISM: Artificial
<220> FEATURE:

<223> OTHER INFORMATION: VH sequence of Li62 variant C02 antibody

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 67
<211> LENGTH: 119
<212> TYPE: PRT
<213> ORGANISM: Artificial
<220> FEATURE:
<223> OTHER INFORMATION: VH sequence of Li62 variant D05 antibody

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Tyr Tyr Asp Trp Tyr Phe Glu Leu Trp Gly Arg Gly
            100                 105                 110

Thr Leu Val Thr Val Ser Ser
        115

<210> SEQ ID NO 68
<211> LENGTH: 119
<212> TYPE: PRT
<213> ORGANISM: Artificial
<220> FEATURE:
<223> OTHER INFORMATION: VH sequence of Li62 variant F02 antibody

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val

```
                35                  40                  45

Ser Trp Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly Leu Ile Asp Trp Phe Phe Asp Gln Trp Gly Arg Gly
            100                 105                 110

Thr Leu Val Thr Val Ser Ser
            115

<210> SEQ ID NO 69
<211> LENGTH: 119
<212> TYPE: PRT
<213> ORGANISM: Artificial
<220> FEATURE:
<223> OTHER INFORMATION: VH sequence of Li62 variant C10 antibody

<400> SEQUENCE: 69

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Ile Tyr
                 20                  25                  30

Pro Met Phe Trp Val Arg Gln Ala Pro Gly Lys Gly Leu Glu Trp Val
                 35                  40                  45

Ser Trp Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly Gln Phe Asp Trp Tyr Phe Asp Leu Trp Gly Arg Gly
            100                 105                 110

Thr Leu Val Thr Val Ser Ser
            115

<210> SEQ ID NO 70
<211> LENGTH: 119
<212> TYPE: PRT
<213> ORGANISM: Artificial
<220> FEATURE:
<223> OTHER INFORMATION: VH sequence of Li62 variant H08 antibody

<400> SEQUENCE: 70

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Ile Tyr
                 20                  25                  30

Pro Met Phe Trp Val Arg Gln Ala Pro Gly Lys Gly Leu Glu Trp Val
                 35                  40                  45

Ser Trp Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95
```

Ala Arg Glu Gly Thr Tyr Asp Trp Tyr Phe Asp Leu Trp Gly Arg Gly
            100                 105                 110

Thr Leu Val Thr Val Ser Ser
        115

<210> SEQ ID NO 71
<211> LENGTH: 118
<212> TYPE: PRT
<213> ORGANISM: Artificial
<220> FEATURE:
<223> OTHER INFORMATION: VH sequence of Li81 variant F09 antibody

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Glu Asn Asp Ala Phe Asp Val Trp Gly Gln Gly Thr
            100                 105                 110

Thr Val Thr Val Ser Ser
        115

<210> SEQ ID NO 72
<211> LENGTH: 118
<212> TYPE: PRT
<213> ORGANISM: Artificial
<220> FEATURE:
<223> OTHER INFORMATION: VH sequence of Li81 variant G02 antibody

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Ala Tyr Asp Thr Trp Gly Gln Gly Thr
            100                 105                 110

Thr Val Thr Val Ser Ser
        115

<210> SEQ ID NO 73
<211> LENGTH: 118
<212> TYPE: PRT
<213> ORGANISM: Artificial

```
<220> FEATURE:
<223> OTHER INFORMATION: VH sequence of Li81 variant H03 antibody

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Thr Asn Asp Ala Phe Asp Ile Trp Gly Gln Gly Thr
            100                 105                 110

Thr Val Thr Val Ser Ser
        115

<210> SEQ ID NO 74
<211> LENGTH: 118
<212> TYPE: PRT
<213> ORGANISM: Artificial
<220> FEATURE:
<223> OTHER INFORMATION: VH sequence of Li81 variant A12 antibody

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Ala Phe Asp Ser Trp Gly Gln Gly Thr
            100                 105                 110

Thr Val Thr Val Ser Ser
        115

<210> SEQ ID NO 75
<211> LENGTH: 118
<212> TYPE: PRT
<213> ORGANISM: Artificial
<220> FEATURE:
<223> OTHER INFORMATION: VH sequence of Li81 variant C02 antibody

<400> SEQUENCE: 75

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30
```

Glu Met Lys Trp Val Arg Gln Ala Pro Gly Lys Gly Leu Glu Trp Val
            35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Ala Phe Asp Thr Trp Gly Gln Gly Thr
            100                 105                 110

Thr Val Thr Val Ser Ser
            115

<210> SEQ ID NO 76
<211> LENGTH: 118
<212> TYPE: PRT
<213> ORGANISM: Artificial
<220> FEATURE:
<223> OTHER INFORMATION: VH sequence of Li81 variant C11 antibody

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
            35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Ala Tyr Asp Arg Trp Gly Gln Gly Thr
            100                 105                 110

Thr Val Thr Val Ser Ser
            115

<210> SEQ ID NO 77
<211> LENGTH: 118
<212> TYPE: PRT
<213> ORGANISM: Artificial
<220> FEATURE:
<223> OTHER INFORMATION: VH sequence of Li81 variant D11 antibody

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
            35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Val Phe Asp Ser Trp Gly Gln Gly Thr
                100                 105                 110

Thr Val Thr Val Ser Ser
        115

<210> SEQ ID NO 78
<211> LENGTH: 118
<212> TYPE: PRT
<213> ORGANISM: Artificial
<220> FEATURE:
<223> OTHER INFORMATION: VH sequence of Li81 variant E05 antibody

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asp Asp Val Phe Asp Met Trp Gly Gln Gly Thr
                100                 105                 110

Thr Val Thr Val Ser Ser
        115

<210> SEQ ID NO 79
<211> LENGTH: 118
<212> TYPE: PRT
<213> ORGANISM: Artificial
<220> FEATURE:
<223> OTHER INFORMATION: VH sequence of Li81 variant H04 antibody

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Tyr Asn Asp Ala Phe Asp Phe Trp Gly Gln Gly Thr
                100                 105                 110

Thr Val Thr Val Ser Ser
        115

<210> SEQ ID NO 80
<211> LENGTH: 118
<212> TYPE: PRT

```
<213> ORGANISM: Artificial
<220> FEATURE:
<223> OTHER INFORMATION: VH sequence of Li81 variant B04 antibody

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asp Asp Ala Tyr Asp Met Trp Gly Gln Gly Thr
            100                 105                 110

Thr Val Thr Val Ser Ser
        115

<210> SEQ ID NO 81
<211> LENGTH: 118
<212> TYPE: PRT
<213> ORGANISM: Artificial
<220> FEATURE:
<223> OTHER INFORMATION: VH sequence of Li81 variant A02 antibody

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gln Asp Tyr Asp Thr Tyr Asp Leu Trp Gly Gln Gly Thr
            100                 105                 110

Thr Val Thr Val Ser Ser
        115

<210> SEQ ID NO 82
<211> LENGTH: 118
<212> TYPE: PRT
<213> ORGANISM: Artificial
<220> FEATURE:
<223> OTHER INFORMATION: VH sequence of Li81 variant B12 antibody

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30
```

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                85                  90                  95

Ala Thr Glu Gly Asp Asp Asp Ala Phe Asp Thr Trp Gly Gln Gly Thr
            100                 105                 110

Thr Val Thr Val Ser Ser
        115

<210> SEQ ID NO 83
<211> LENGTH: 118
<212> TYPE: PRT
<213> ORGANISM: Artificial
<220> FEATURE:
<223> OTHER INFORMATION: VH sequence of Li81 variant H06 antibody

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                85                  90                  95

Ala Thr Glu Ala Asp Asp Asp Ala Phe Asp Ile Trp Gly Gln Gly Thr
            100                 105                 110

Thr Val Thr Val Ser Ser
        115

<210> SEQ ID NO 84
<211> LENGTH: 118
<212> TYPE: PRT
<213> ORGANISM: Artificial
<220> FEATURE:
<223> OTHER INFORMATION: VH sequence of Li81 variant H08 antibody

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys

Ala Thr Glu Gly Glu Asn Asp Ala Phe Asp Met Trp Gly Gln Gly Thr
            100                 105                 110

Thr Val Thr Val Ser Ser
        115

<210> SEQ ID NO 85
<211> LENGTH: 118
<212> TYPE: PRT
<213> ORGANISM: Artificial
<220> FEATURE:
<223> OTHER INFORMATION: VH sequence of Li81 variant E07 antibody

<400> SEQUENCE: 85

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Glu Tyr Asp Thr Tyr Asp Ile Trp Gly Gln Gly Thr
            100                 105                 110

Thr Val Thr Val Ser Ser
        115

<210> SEQ ID NO 86
<211> LENGTH: 447
<212> TYPE: PRT
<213> ORGANISM: Artificial
<220> FEATURE:
<223> OTHER INFORMATION: Li81 heavy chain

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Ala Phe Asp Ile Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

-continued

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445
```

<210> SEQ ID NO 87
<211> LENGTH: 6
<212> TYPE: PRT
<213> ORGANISM: Artificial
<220> FEATURE:
<223> OTHER INFORMATION: N-terminus of LINGO-1 polypeptide

<400> SEQUENCE: 87

```
Met Gln Val Ser Lys Arg
1               5
```

<210> SEQ ID NO 88
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: MISC_FEATURE

```
<222> LOCATION: (3)..(5)
<223> OTHER INFORMATION: X can be lysine, arginine, histidine,
      glutamine, asparagine

<400> SEQUENCE: 88

Ile Thr Xaa Xaa Xaa
1               5

<210> SEQ ID NO 89
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: MISC_FEATURE
<222> LOCATION: (3)..(5)
<223> OTHER INFORMATION: X can be lysine, arginine, histidine,
      glutamine, asparagine

<400> SEQUENCE: 89

Ala Cys Xaa Xaa Xaa
1               5

<210> SEQ ID NO 90
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: MISC_FEATURE
<222> LOCATION: (3)..(5)
<223> OTHER INFORMATION: X can be lysine, arginine, histidine,
      glutamine, asparagine

<400> SEQUENCE: 90

Val Cys Xaa Xaa Xaa
1               5

<210> SEQ ID NO 91
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: MISC_FEATURE
<222> LOCATION: (3)..(5)
<223> OTHER INFORMATION: X can be lysine, arginine, histidine,
      glutamine, asparagine

<400> SEQUENCE: 91

Ser Pro Xaa Xaa Xaa
1               5

<210> SEQ ID NO 92
<211> LENGTH: 5
<212> TYPE: PRT
<213> ORGANISM: Artificial
<220> FEATURE:
<223> OTHER INFORMATION: LINGO-1 polypeptide

<400> SEQUENCE: 92

Ser Pro Arg Lys His
1               5

<210> SEQ ID NO 93
<211> LENGTH: 5
```

```
<212> TYPE: PRT
<213> ORGANISM: Artificial
<220> FEATURE:
<223> OTHER INFORMATION: LINGO-1 polypeptide

<400> SEQUENCE: 93

Ser Pro Arg Lys Lys
1               5

<210> SEQ ID NO 94
<211> LENGTH: 5
<212> TYPE: PRT
<213> ORGANISM: Artificial
<220> FEATURE:
<223> OTHER INFORMATION: LINGO-1 polypeptide

<400> SEQUENCE: 94

Ser Pro Arg Lys Arg
1               5

<210> SEQ ID NO 95
<211> LENGTH: 5
<212> TYPE: PRT
<213> ORGANISM: Artificial
<220> FEATURE:
<223> OTHER INFORMATION: LINGO-1 polypeptide

<400> SEQUENCE: 95

Ser Pro Lys Lys His
1               5

<210> SEQ ID NO 96
<211> LENGTH: 5
<212> TYPE: PRT
<213> ORGANISM: Artificial
<220> FEATURE:
<223> OTHER INFORMATION: LINGO-1 polypeptide

<400> SEQUENCE: 96

Ser Pro His Lys His
1               5

<210> SEQ ID NO 97
<211> LENGTH: 5
<212> TYPE: PRT
<213> ORGANISM: Artificial
<220> FEATURE:
<223> OTHER INFORMATION: LINGO-1 polypeptide

<400> SEQUENCE: 97

Ser Pro Arg Arg His
1               5

<210> SEQ ID NO 98
<211> LENGTH: 5
<212> TYPE: PRT
<213> ORGANISM: Artificial
<220> FEATURE:
<223> OTHER INFORMATION: LINGO-1 polypeptide

<400> SEQUENCE: 98

Ser Pro Arg His His
1               5

<210> SEQ ID NO 99
<211> LENGTH: 5
<212> TYPE: PRT
```

```
<213> ORGANISM: Artificial
<220> FEATURE:
<223> OTHER INFORMATION: LINGO-1 polypeptide

<400> SEQUENCE: 99

Ser Pro Arg Arg Arg
1               5

<210> SEQ ID NO 100
<211> LENGTH: 5
<212> TYPE: PRT
<213> ORGANISM: Artificial
<220> FEATURE:
<223> OTHER INFORMATION: LINGO-1 polypeptide

<400> SEQUENCE: 100

Ser Pro His His His
1               5

<210> SEQ ID NO 101
<211> LENGTH: 5
<212> TYPE: PRT
<213> ORGANISM: Artificial
<220> FEATURE:
<223> OTHER INFORMATION: LINGO-1 polypeptide

<400> SEQUENCE: 101

Ser Pro Lys Lys Lys
1               5

<210> SEQ ID NO 102
<211> LENGTH: 6
<212> TYPE: PRT
<213> ORGANISM: Artificial
<220> FEATURE:
<223> OTHER INFORMATION: LINGO-1 polypeptide

<400> SEQUENCE: 102

Leu Ser Pro Arg Lys His
1               5

<210> SEQ ID NO 103
<211> LENGTH: 6
<212> TYPE: PRT
<213> ORGANISM: Artificial
<220> FEATURE:
<223> OTHER INFORMATION: LINGO-1 polypeptide

<400> SEQUENCE: 103

Leu Ser Pro Arg Lys Lys
1               5

<210> SEQ ID NO 104
<211> LENGTH: 6
<212> TYPE: PRT
<213> ORGANISM: Artificial
<220> FEATURE:
<223> OTHER INFORMATION: LINGO-1 polypeptide

<400> SEQUENCE: 104

Leu Ser Pro Arg Lys Arg
1               5

<210> SEQ ID NO 105
<211> LENGTH: 6
<212> TYPE: PRT
<213> ORGANISM: Artificial
```

```
<220> FEATURE:
<223> OTHER INFORMATION: LINGO-1 polypeptide

<400> SEQUENCE: 105

Leu Ser Pro Lys Lys His
1               5

<210> SEQ ID NO 106
<211> LENGTH: 6
<212> TYPE: PRT
<213> ORGANISM: Artificial
<220> FEATURE:
<223> OTHER INFORMATION: LINGO-1 polypeptide

<400> SEQUENCE: 106

Leu Ser Pro His Lys His
1               5

<210> SEQ ID NO 107
<211> LENGTH: 6
<212> TYPE: PRT
<213> ORGANISM: Artificial
<220> FEATURE:
<223> OTHER INFORMATION: LINGO-1 polypeptide

<400> SEQUENCE: 107

Leu Ser Pro Arg Arg His
1               5

<210> SEQ ID NO 108
<211> LENGTH: 6
<212> TYPE: PRT
<213> ORGANISM: Artificial
<220> FEATURE:
<223> OTHER INFORMATION: LINGO-1 polypeptide

<400> SEQUENCE: 108

Leu Ser Pro Arg His His
1               5

<210> SEQ ID NO 109
<211> LENGTH: 6
<212> TYPE: PRT
<213> ORGANISM: Artificial
<220> FEATURE:
<223> OTHER INFORMATION: LINGO-1 polypeptide

<400> SEQUENCE: 109

Leu Ser Pro Arg Arg Arg
1               5

<210> SEQ ID NO 110
<211> LENGTH: 6
<212> TYPE: PRT
<213> ORGANISM: Artificial
<220> FEATURE:
<223> OTHER INFORMATION: LINGO-1 polypeptide

<400> SEQUENCE: 110

Leu Ser Pro His His His
1               5

<210> SEQ ID NO 111
<211> LENGTH: 6
<212> TYPE: PRT
<213> ORGANISM: Artificial
<220> FEATURE:
```

```
<223> OTHER INFORMATION: LINGO-1 polypeptide

<400> SEQUENCE: 111

Leu Ser Pro Lys Lys Lys
1               5

<210> SEQ ID NO 112
<211> LENGTH: 7
<212> TYPE: PRT
<213> ORGANISM: Artificial
<220> FEATURE:
<223> OTHER INFORMATION: LINGO-1 polypeptide

<400> SEQUENCE: 112

Trp Leu Ser Pro Arg Lys His
1               5

<210> SEQ ID NO 113
<211> LENGTH: 7
<212> TYPE: PRT
<213> ORGANISM: Artificial
<220> FEATURE:
<223> OTHER INFORMATION: LINGO-1 polypeptide

<400> SEQUENCE: 113

Trp Leu Ser Pro Arg Lys Lys
1               5

<210> SEQ ID NO 114
<211> LENGTH: 7
<212> TYPE: PRT
<213> ORGANISM: Artificial
<220> FEATURE:
<223> OTHER INFORMATION: LINGO-1 polypeptide

<400> SEQUENCE: 114

Trp Leu Ser Pro Arg Lys Arg
1               5

<210> SEQ ID NO 115
<211> LENGTH: 7
<212> TYPE: PRT
<213> ORGANISM: Artificial
<220> FEATURE:
<223> OTHER INFORMATION: LINGO-1 polypeptide

<400> SEQUENCE: 115

Trp Leu Ser Pro Lys Lys His
1               5

<210> SEQ ID NO 116
<211> LENGTH: 7
<212> TYPE: PRT
<213> ORGANISM: Artificial
<220> FEATURE:
<223> OTHER INFORMATION: LINGO-1 polypeptide

<400> SEQUENCE: 116

Trp Leu Ser Pro His Lys His
1               5

<210> SEQ ID NO 117
<211> LENGTH: 7
<212> TYPE: PRT
<213> ORGANISM: Artificial
<220> FEATURE:
<223> OTHER INFORMATION: LINGO-1 polypeptide
```

```
<400> SEQUENCE: 117

Trp Leu Ser Pro Arg Arg His
1               5

<210> SEQ ID NO 118
<211> LENGTH: 7
<212> TYPE: PRT
<213> ORGANISM: Artificial
<220> FEATURE:
<223> OTHER INFORMATION: LINGO-1 polypeptide

<400> SEQUENCE: 118

Trp Leu Ser Pro Arg His His
1               5

<210> SEQ ID NO 119
<211> LENGTH: 7
<212> TYPE: PRT
<213> ORGANISM: Artificial
<220> FEATURE:
<223> OTHER INFORMATION: LINGO-1 polypeptide

<400> SEQUENCE: 119

Trp Leu Ser Pro Arg Arg Arg
1               5

<210> SEQ ID NO 120
<211> LENGTH: 7
<212> TYPE: PRT
<213> ORGANISM: Artificial
<220> FEATURE:
<223> OTHER INFORMATION: LINGO-1 polypeptide

<400> SEQUENCE: 120

Trp Leu Ser Pro His His His
1               5

<210> SEQ ID NO 121
<211> LENGTH: 7
<212> TYPE: PRT
<213> ORGANISM: Artificial
<220> FEATURE:
<223> OTHER INFORMATION: LINGO-1 polypeptide

<400> SEQUENCE: 121

Trp Leu Ser Pro Lys Lys Lys
1               5

<210> SEQ ID NO 122
<211> LENGTH: 6
<212> TYPE: PRT
<213> ORGANISM: Artificial
<220> FEATURE:
<223> OTHER INFORMATION: LINGO-1 polypeptide

<400> SEQUENCE: 122

Ile Thr Pro Lys Arg Arg
1               5

<210> SEQ ID NO 123
<211> LENGTH: 5
<212> TYPE: PRT
<213> ORGANISM: Artificial
<220> FEATURE:
<223> OTHER INFORMATION: LINGO-1 polypeptide
```

```
<400> SEQUENCE: 123

Ala Cys His His Lys
1               5

<210> SEQ ID NO 124
<211> LENGTH: 5
<212> TYPE: PRT
<213> ORGANISM: Artificial
<220> FEATURE:
<223> OTHER INFORMATION: LINGO-1 polypeptide

<400> SEQUENCE: 124

Val Cys His His Lys
1               5

<210> SEQ ID NO 125
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 125

Xaa Xaa Arg Lys His
1               5

<210> SEQ ID NO 126
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 126

Xaa Xaa Arg Arg Arg
1               5

<210> SEQ ID NO 127
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 127

Xaa Xaa Lys Lys Lys
1               5

<210> SEQ ID NO 128
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
```

-continued

```
<223> OTHER INFORMATION: Xaa can be any naturally occurring amino acid

<400> SEQUENCE: 128

Xaa Xaa His His His
1               5

<210> SEQ ID NO 129
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 129

Xaa Xaa Arg Lys Lys
1               5

<210> SEQ ID NO 130
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 130

Xaa Xaa Arg Lys Arg
1               5

<210> SEQ ID NO 131
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 131

Xaa Xaa Lys Lys His
1               5

<210> SEQ ID NO 132
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 132

Xaa Xaa His Lys His
1               5

<210> SEQ ID NO 133
<211> LENGTH: 5
<212> TYPE: PRT
```

```
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 133

Xaa Xaa Arg Arg His
1               5

<210> SEQ ID NO 134
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 134

Xaa Xaa Arg His His
1               5

<210> SEQ ID NO 135
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: MISC_FEATURE
<222> LOCATION: (3)..(3)
<223> OTHER INFORMATION: X can be lysine, arginine, histidine,
      glutamine, asparagine
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: X can be lysine, arginine, histidine,
      glutamine, asparagine

<400> SEQUENCE: 135

Ile Thr Xaa Xaa Xaa
1               5

<210> SEQ ID NO 136
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: MISC_FEATURE
<222> LOCATION: (3)..(3)
<223> OTHER INFORMATION: X can be lysine, arginine, histidine,
      glutamine, asparagine
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: X can be lysine, arginine, histidine,
      glutamine, asparagine
```

```
<400> SEQUENCE: 136

Ala Cys Xaa Xaa Xaa
1               5

<210> SEQ ID NO 137
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: MISC_FEATURE
<222> LOCATION: (3)..(3)
<223> OTHER INFORMATION: X can be lysine, arginine, histidine,
      glutamine, asparagine
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: X can be lysine, arginine, histidine,
      glutamine, asparagine

<400> SEQUENCE: 137

Val Cys Xaa Xaa Xaa
1               5

<210> SEQ ID NO 138
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: MISC_FEATURE
<222> LOCATION: (3)..(3)
<223> OTHER INFORMATION: X can be lysine, arginine, histidine,
      glutamine, asparagine
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: X can be lysine, arginine, histidine,
      glutamine, asparagine

<400> SEQUENCE: 138

Ser Pro Xaa Xaa Xaa
1               5

<210> SEQ ID NO 139
<211> LENGTH: 5
<212> TYPE: PRT
<213> ORGANISM: Artificial
<220> FEATURE:
<223> OTHER INFORMATION: LINGO-1 polypeptide

<400> SEQUENCE: 139

Ser Pro Arg Leu His
1               5

<210> SEQ ID NO 140
<211> LENGTH: 9
<212> TYPE: PRT
<213> ORGANISM: Artificial
<220> FEATURE:
<223> OTHER INFORMATION: LINGO-1 polypeptide
```

<400> SEQUENCE: 140

Arg Arg Ala Arg Ile Arg Asp Arg Lys
1               5

<210> SEQ ID NO 141
<211> LENGTH: 9
<212> TYPE: PRT
<213> ORGANISM: Artificial
<220> FEATURE:
<223> OTHER INFORMATION: LINGO-1 polypeptide

<400> SEQUENCE: 141

Lys Lys Val Lys Val Lys Glu Lys Arg
1               5

<210> SEQ ID NO 142
<211> LENGTH: 9
<212> TYPE: PRT
<213> ORGANISM: Artificial
<220> FEATURE:
<223> OTHER INFORMATION: LINGO-1 polypeptide

<400> SEQUENCE: 142

Arg Arg Leu Arg Leu Arg Asp Arg Lys
1               5

<210> SEQ ID NO 143
<211> LENGTH: 9
<212> TYPE: PRT
<213> ORGANISM: Artificial
<220> FEATURE:
<223> OTHER INFORMATION: LINGO-1 polypeptide

<400> SEQUENCE: 143

Arg Arg Gly Arg Gly Arg Asp Arg Lys
1               5

<210> SEQ ID NO 144
<211> LENGTH: 9
<212> TYPE: PRT
<213> ORGANISM: Artificial
<220> FEATURE:
<223> OTHER INFORMATION: LINGO-1 polypeptide

<400> SEQUENCE: 144

Arg Arg Ile Arg Ala Arg Asp Arg Lys
1               5

<210> SEQ ID NO 145
<211> LENGTH: 214
<212> TYPE: PRT
<213> ORGANISM: Artificial
<220> FEATURE:
<223> OTHER INFORMATION: Li33 Fab' light chain

<400> SEQUENCE: 145

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 146
<211> LENGTH: 230
<212> TYPE: PRT
<213> ORGANISM: Artificial
<220> FEATURE:
<223> OTHER INFORMATION: Li33 Fab' heavy chain

<400> SEQUENCE: 146

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Trp Ile Gly Pro Ser Gly Gly Ile Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro
225                 230

<210> SEQ ID NO 147
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
            35                  40                  45

Ser His Ile Gly Pro Ser Gly Gly Ile Thr Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 148
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val

```
            35                  40                  45
Ser Phe Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Trp Tyr Phe Asp Leu Trp Gly Arg Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 149
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 149

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
             20                  25                  30

Pro Met Phe Trp Val Arg Gln Ala Pro Gly Lys Gly Leu Glu Trp Val
         35                  40                  45

Ser Leu Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Trp Tyr Phe Asp Leu Trp Gly Arg Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro
225             230

<210> SEQ ID NO 150
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 150

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Met Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225             230

<210> SEQ ID NO 151
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 151

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Trp Ile Gly Leu Ser Gly Gly Ile Thr Lys Tyr Ala Asp Ser Val
50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro
225                 230

<210> SEQ ID NO 152
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 152

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Trp Ile Gly Ser Ser Gly Gly Ile Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
                100                 105                 110

Thr Leu Val Thr Val Ser Ser Ala Ser Thr Lys Gly Pro Ser Val Phe
            115                 120                 125

```
Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro
225                 230

<210> SEQ ID NO 153
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 153

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Thr Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro
225                 230

<210> SEQ ID NO 154
<211> LENGTH: 230
```

<212> TYPE: PRT
<213> ORGANISM: Artificial
<220> FEATURE:
<223> OTHER INFORMATION: Li33 Heavy Chain Variant

<400> SEQUENCE: 154

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Trp Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 155
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 155

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Val Tyr Phe Asp Leu Trp Gly Arg Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro
225                 230

<210> SEQ ID NO 156
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 156

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp His Tyr Phe Asp Leu Trp Gly Arg Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro
225                 230

<210> SEQ ID NO 157
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 157

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Ser Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 158
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 158

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                     85                  90                  95

Ala Arg Glu Gly His Asn Asp Gln Tyr Phe Asp Leu Trp Gly Arg Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
210                 215                 220

Thr His Thr Cys Pro Pro
225                 230

<210> SEQ ID NO 159
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 159

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
                 20                  25                  30

Pro Met Phe Trp Val Arg Gln Ala Pro Gly Lys Gly Leu Glu Trp Val
                 35                  40                  45

Ser Trp Ile Gly Pro Ser Gly Gly Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                     85                  90                  95

Ala Arg Glu Gly His Asn Asp Trp Tyr Phe Asp Leu Trp Gly Arg Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
                180             185             190
Ser Ser Leu Gly Thr Gln Thr Tyr Ile Cys Asn Val Asn His Lys Pro
            195             200             205
Ser Asn Thr Lys Val Asp Lys Lys Val Glu Pro Lys Ser Cys Asp Lys
            210             215             220
Thr His Thr Cys Pro Pro
225             230

<210> SEQ ID NO 160
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 160

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Trp Ile Gly Pro Ser Gly Gly Met Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
            85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro
225             230

<210> SEQ ID NO 161
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 161

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Asn Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 162
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly His Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225             230

<210> SEQ ID NO 163
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Leu Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225             230

<210> SEQ ID NO 164
<211> LENGTH: 230
<212> TYPE: PRT
<213> ORGANISM: Artificial
<220> FEATURE:

<223> OTHER INFORMATION: Li33 Heavy Chain Variant

<400> SEQUENCE: 164

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Phe Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230
```

<210> SEQ ID NO 165
<211> LENGTH: 214
<212> TYPE: PRT
<213> ORGANISM: Artificial
<220> FEATURE:
<223> OTHER INFORMATION: Li33 Light Chain Variant

<400> SEQUENCE: 165

```
Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Ala Pro Leu
                85                  90                  95

Thr Phe Gly Gly Gly Thr Lys Val Glu Ile Lys Arg Thr Val Ala Ala
            100                 105                 110
```

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 166
<211> LENGTH: 214
<212> TYPE: PRT
<213> ORGANISM: Artificial
<220> FEATURE:
<223> OTHER INFORMATION: Li33 Light Chain Variant

<400> SEQUENCE: 166

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Asp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 167
<211> LENGTH: 214
<212> TYPE: PRT
<213> ORGANISM: Artificial
<220> FEATURE:
<223> OTHER INFORMATION: Li33 Light Chain Variant

<400> SEQUENCE: 167

```
Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Leu Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 168
<211> LENGTH: 214
<212> TYPE: PRT
<213> ORGANISM: Artificial
<220> FEATURE:
<223> OTHER INFORMATION: Li33 Light Chain Variant

<400> SEQUENCE: 168

```
Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Asn Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
                115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
                195                 200                 205
Phe Asn Arg Gly Glu Cys
    210

<210> SEQ ID NO 169
<211> LENGTH: 214
<212> TYPE: PRT
<213> ORGANISM: Artificial
<220> FEATURE:
<223> OTHER INFORMATION: Li33 Light Chain Variant

<400> SEQUENCE: 169

Asp Ile Gln Met Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Asp Lys Gly Pro Leu
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
                195                 200                 205
Phe Asn Arg Gly Glu Cys
    210

<210> SEQ ID NO 170
<211> LENGTH: 214
<212> TYPE: PRT
<213> ORGANISM: Artificial
<220> FEATURE:
<223> OTHER INFORMATION: Li33 Light Chain Variant
```

<400> SEQUENCE: 170

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Gln Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 171
<211> LENGTH: 214
<212> TYPE: PRT
<213> ORGANISM: Artificial
<220> FEATURE:
<223> OTHER INFORMATION: Li33 Light Chain Variant

<400> SEQUENCE: 171

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Val Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 172
<211> LENGTH: 214
<212> TYPE: PRT
<213> ORGANISM: Artificial
<220> FEATURE:
<223> OTHER INFORMATION: Li33 Light Chain Variant

<400> SEQUENCE: 172

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 173
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 173

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Gly Ile Gly Pro Ser Gly Gly Ile Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro
225                 230

<210> SEQ ID NO 174
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 174

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Ile Ile Gly Pro Ser Gly Gly Ile Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
            115                 120                 125

```
Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
        210                 215                 220

Thr His Thr Cys Pro Pro
225             230

<210> SEQ ID NO 175
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 175

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Asp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
        210                 215                 220

Thr His Thr Cys Pro Pro
225             230

<210> SEQ ID NO 176
```

```
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 176

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Met Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 177
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 177

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
```

```
                85                  90                  95
Ala Arg Glu Gly His Asn Asp Leu Tyr Phe Asp Leu Trp Gly Arg Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro
225                 230

<210> SEQ ID NO 178
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 178

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Trp Ile Gly Pro Ser Gly Gly Ile Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Leu Tyr Phe Asp Leu Trp Gly Arg Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
```

<210> SEQ ID NO 179
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 179

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Ile Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230
```

<210> SEQ ID NO 180
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 180

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45
```

```
Ser Trp Ile Gly Gly Ser Gly Gly Ile Thr Lys Tyr Ala Asp Ser Val
    50              55                  60

Lys Gly Arg Phe Thr Ile Ser Arg Asp Asn Ser Lys Asn Thr Leu Tyr
 65              70                  75                  80

Leu Gln Met Asn Ser Leu Arg Ala Glu Asp Thr Ala Thr Tyr Tyr Cys
             85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro
225                 230

<210> SEQ ID NO 181
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 181

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
         35                  40                  45

Ser Trp Ile Gly Pro Ser Gly Gly Trp Thr Lys Tyr Ala Asp Ser Val
    50              55                  60

Lys Gly Arg Phe Thr Ile Ser Arg Asp Asn Ser Lys Asn Thr Leu Tyr
 65              70                  75                  80

Leu Gln Met Asn Ser Leu Arg Ala Glu Asp Thr Ala Thr Tyr Tyr Cys
             85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225             230

<210> SEQ ID NO 182
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 182

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Tyr Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225             230

<210> SEQ ID NO 183
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 183

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Trp Ile Gly Pro Ser Gly Ser Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
            85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
 130                 135                 140

Gly Cys Leu Val Lys Asp Tyr Phe Pro Glu Pro Val Thr Val Ser Trp
 145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
 210                 215                 220

Thr His Thr Cys Pro Pro
 225                 230

<210> SEQ ID NO 184
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 184

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Trp Ile Gly Pro Ser Gly Pro Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
            85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
 130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225             230

<210> SEQ ID NO 185
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 185

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Val Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225             230

<210> SEQ ID NO 186
<211> LENGTH: 230
<212> TYPE: PRT
<213> ORGANISM: Artificial
```

<220> FEATURE:
<223> OTHER INFORMATION: Li33 Heavy Chain Variant

<400> SEQUENCE: 186

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Thr Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 187
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 187

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Gln Tyr Phe Asp Leu Trp Gly Arg Gly

```
                      100                 105                 110
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro
225                 230

<210> SEQ ID NO 188
<211> LENGTH: 119
<212> TYPE: PRT
<213> ORGANISM: Artificial
<220> FEATURE:
<223> OTHER INFORMATION: Li62 VH Variant

<400> SEQUENCE: 188

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser His Ile Gly Pro Ser Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
            85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 189
<211> LENGTH: 119
<212> TYPE: PRT
<213> ORGANISM: Artificial
<220> FEATURE:
<223> OTHER INFORMATION: Li62 VH Variant

<400> SEQUENCE: 189

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45
```

```
Ser Phe Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Trp Tyr Phe Asp Leu Trp Gly Arg Gly
            100                 105                 110

Thr Leu Val Thr Val Ser Ser
            115

<210> SEQ ID NO 190
<211> LENGTH: 119
<212> TYPE: PRT
<213> ORGANISM: Artificial
<220> FEATURE:
<223> OTHER INFORMATION: Li62 VH Variant

<400> SEQUENCE: 190

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
                 20                  25                  30

Pro Met Phe Trp Val Arg Gln Ala Pro Gly Lys Gly Leu Glu Trp Val
             35                  40                  45

Ser Leu Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Trp Tyr Phe Asp Leu Trp Gly Arg Gly
            100                 105                 110

Thr Leu Val Thr Val Ser Ser
            115

<210> SEQ ID NO 191
<211> LENGTH: 119
<212> TYPE: PRT
<213> ORGANISM: Artificial
<220> FEATURE:
<223> OTHER INFORMATION: Li62 VH Variant

<400> SEQUENCE: 191

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
                 20                  25                  30

Pro Met Phe Trp Val Arg Gln Ala Pro Gly Lys Gly Leu Glu Trp Val
             35                  40                  45

Ser Met Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Trp Tyr Phe Asp Leu Trp Gly Arg Gly
            100                 105                 110
```

Thr Leu Val Thr Val Ser Ser
        115

<210> SEQ ID NO 192
<211> LENGTH: 119
<212> TYPE: PRT
<213> ORGANISM: Artificial
<220> FEATURE:
<223> OTHER INFORMATION: Li62 VH Variant

<400> SEQUENCE: 192

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Leu Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 193
<211> LENGTH: 119
<212> TYPE: PRT
<213> ORGANISM: Artificial
<220> FEATURE:
<223> OTHER INFORMATION: Li62 VH Variant

<400> SEQUENCE: 193

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Ser Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 194
<211> LENGTH: 119
<212> TYPE: PRT
<213> ORGANISM: Artificial
<220> FEATURE:
<223> OTHER INFORMATION: Li62 VH Variant

<400> SEQUENCE: 194

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Thr Ser Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
            115

<210> SEQ ID NO 195
<211> LENGTH: 119
<212> TYPE: PRT
<213> ORGANISM: Artificial
<220> FEATURE:
<223> OTHER INFORMATION: Li62 VH Variant

<400> SEQUENCE: 195

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Trp Ser Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
            115

<210> SEQ ID NO 196
<211> LENGTH: 119
<212> TYPE: PRT
<213> ORGANISM: Artificial
<220> FEATURE:
<223> OTHER INFORMATION: Li62 VH Variant

<400> SEQUENCE: 196

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

```
Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Val Tyr Phe Asp Leu Trp Gly Arg Gly
                100                 105                 110

Thr Leu Val Thr Val Ser Ser
            115

<210> SEQ ID NO 197
<211> LENGTH: 119
<212> TYPE: PRT
<213> ORGANISM: Artificial
<220> FEATURE:
<223> OTHER INFORMATION: Li62 VH Variant

<400> SEQUENCE: 197

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
                 20                  25                  30

Pro Met Phe Trp Val Arg Gln Ala Pro Gly Lys Gly Leu Glu Trp Val
             35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp His Tyr Phe Asp Leu Trp Gly Arg Gly
                100                 105                 110

Thr Leu Val Thr Val Ser Ser
            115

<210> SEQ ID NO 198
<211> LENGTH: 119
<212> TYPE: PRT
<213> ORGANISM: Artificial
<220> FEATURE:
<223> OTHER INFORMATION: Li62 VH Variant

<400> SEQUENCE: 198

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
                 20                  25                  30

Pro Met Phe Trp Val Arg Gln Ala Pro Gly Lys Gly Leu Glu Trp Val
             35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Ser Tyr Phe Asp Leu Trp Gly Arg Gly
```

Thr Leu Val Thr Val Ser Ser
        115

<210> SEQ ID NO 199
<211> LENGTH: 119
<212> TYPE: PRT
<213> ORGANISM: Artificial
<220> FEATURE:
<223> OTHER INFORMATION: Li62 VH Variant

<400> SEQUENCE: 199

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Gln Tyr Phe Asp Leu Trp Gly Arg Gly
            100                 105                 110

Thr Leu Val Thr Val Ser Ser
        115

<210> SEQ ID NO 200
<211> LENGTH: 119
<212> TYPE: PRT
<213> ORGANISM: Artificial
<220> FEATURE:
<223> OTHER INFORMATION: Li62 VH Variant

<400> SEQUENCE: 200

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 201
<211> LENGTH: 119
<212> TYPE: PRT
<213> ORGANISM: Artificial
<220> FEATURE:

<223> OTHER INFORMATION: Li62 VH Variant

<400> SEQUENCE: 201

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Met Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
            115

<210> SEQ ID NO 202
<211> LENGTH: 119
<212> TYPE: PRT
<213> ORGANISM: Artificial
<220> FEATURE:
<223> OTHER INFORMATION: Li62 VH Variant

<400> SEQUENCE: 202

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Asn Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
            115

<210> SEQ ID NO 203
<211> LENGTH: 119
<212> TYPE: PRT
<213> ORGANISM: Artificial
<220> FEATURE:
<223> OTHER INFORMATION: Li62 VH Variant

<400> SEQUENCE: 203

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val

```
                35                  40                  45
Ser Trp Ile Gly Pro Ser Gly Gly His Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Trp Tyr Phe Asp Leu Trp Gly Arg Gly
                100                 105                 110

Thr Leu Val Thr Val Ser Ser
            115

<210> SEQ ID NO 204
<211> LENGTH: 119
<212> TYPE: PRT
<213> ORGANISM: Artificial
<220> FEATURE:
<223> OTHER INFORMATION: Li62 VH Variant

<400> SEQUENCE: 204

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
                35                  40                  45

Ser Trp Ile Gly Pro Ser Gly Gly Leu Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Trp Tyr Phe Asp Leu Trp Gly Arg Gly
                100                 105                 110

Thr Leu Val Thr Val Ser Ser
            115

<210> SEQ ID NO 205
<211> LENGTH: 119
<212> TYPE: PRT
<213> ORGANISM: Artificial
<220> FEATURE:
<223> OTHER INFORMATION: Li62 VH Variant

<400> SEQUENCE: 205

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
                35                  40                  45

Ser Trp Ile Gly Pro Ser Gly Gly Phe Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95
```

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 206
<211> LENGTH: 119
<212> TYPE: PRT
<213> ORGANISM: Artificial
<220> FEATURE:
<223> OTHER INFORMATION: Li62 VH Variant

<400> SEQUENCE: 206

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Gly Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 207
<211> LENGTH: 119
<212> TYPE: PRT
<213> ORGANISM: Artificial
<220> FEATURE:
<223> OTHER INFORMATION: Li62 VH Variant

<400> SEQUENCE: 207

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Ile Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 208
<211> LENGTH: 119
<212> TYPE: PRT
<213> ORGANISM: Artificial
<220> FEATURE:
<223> OTHER INFORMATION: Li62 VH Variant

<400> SEQUENCE: 208

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Asp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 209
<211> LENGTH: 119
<212> TYPE: PRT
<213> ORGANISM: Artificial
<220> FEATURE:
<223> OTHER INFORMATION: Li62 VH Variant

<400> SEQUENCE: 209

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Met Tyr Phe Asp Leu Trp Gly Arg Gly
            100                 105                 110

Thr Leu Val Thr Val Ser Ser
        115

<210> SEQ ID NO 210
<211> LENGTH: 119
<212> TYPE: PRT
<213> ORGANISM: Artificial
<220> FEATURE:
<223> OTHER INFORMATION: Li62 VH Variant

<400> SEQUENCE: 210

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

```
Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Leu Tyr Phe Asp Leu Trp Gly Arg Gly
            100                 105                 110

Thr Leu Val Thr Val Ser Ser
            115

<210> SEQ ID NO 211
<211> LENGTH: 119
<212> TYPE: PRT
<213> ORGANISM: Artificial
<220> FEATURE:
<223> OTHER INFORMATION: Li62 VH Variant

<400> SEQUENCE: 211

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Thr Tyr Phe Asp Leu Trp Gly Arg Gly
            100                 105                 110

Thr Leu Val Thr Val Ser Ser
            115

<210> SEQ ID NO 212
<211> LENGTH: 119
<212> TYPE: PRT
<213> ORGANISM: Artificial
<220> FEATURE:
<223> OTHER INFORMATION: Li62 VH Variant

<400> SEQUENCE: 212

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                85                  90                  95
```

Ala Arg Glu Gly His Asn Asp Ile Tyr Phe Asp Leu Trp Gly Arg Gly
            100                 105                 110

Thr Leu Val Thr Val Ser Ser
        115

<210> SEQ ID NO 213
<211> LENGTH: 119
<212> TYPE: PRT
<213> ORGANISM: Artificial
<220> FEATURE:
<223> OTHER INFORMATION: Li62 VH Variant

<400> SEQUENCE: 213

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Gly Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 214
<211> LENGTH: 119
<212> TYPE: PRT
<213> ORGANISM: Artificial
<220> FEATURE:
<223> OTHER INFORMATION: Li62 VH Variant

<400> SEQUENCE: 214

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Trp Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 215
<211> LENGTH: 119
<212> TYPE: PRT

<213> ORGANISM: Artificial
<220> FEATURE:
<223> OTHER INFORMATION: Li62 VH Variant

<400> SEQUENCE: 215

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Tyr Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
        115
```

<210> SEQ ID NO 216
<211> LENGTH: 119
<212> TYPE: PRT
<213> ORGANISM: Artificial
<220> FEATURE:
<223> OTHER INFORMATION: Li62 VH Variant

<400> SEQUENCE: 216

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ser Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
        115
```

<210> SEQ ID NO 217
<211> LENGTH: 119
<212> TYPE: PRT
<213> ORGANISM: Artificial
<220> FEATURE:
<223> OTHER INFORMATION: Li62 VH Variant

<400> SEQUENCE: 217

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30
```

Pro Met Phe Trp Val Arg Gln Ala Pro Gly Lys Gly Leu Glu Trp Val
        35                  40                  45

Ser Trp Ile Gly Pro Ser Gly Pro Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 218
<211> LENGTH: 119
<212> TYPE: PRT
<213> ORGANISM: Artificial
<220> FEATURE:
<223> OTHER INFORMATION: Li62 VH Variant

<400> SEQUENCE: 218

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
             20                  25                  30

Pro Met Phe Trp Val Arg Gln Ala Pro Gly Lys Gly Leu Glu Trp Val
        35                  40                  45

Ser Trp Ile Gly Pro Ser Gly Gly Val Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 219
<211> LENGTH: 119
<212> TYPE: PRT
<213> ORGANISM: Artificial
<220> FEATURE:
<223> OTHER INFORMATION: Li62 VH Variant

<400> SEQUENCE: 219

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
             20                  25                  30

Pro Met Phe Trp Val Arg Gln Ala Pro Gly Lys Gly Leu Glu Trp Val
        35                  40                  45

Ser Trp Ile Gly Pro Ser Gly Gly Thr Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys 85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 220
<211> LENGTH: 119
<212> TYPE: PRT
<213> ORGANISM: Artificial
<220> FEATURE:
<223> OTHER INFORMATION: Li62 VH Variant

<400> SEQUENCE: 220

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Gln Tyr Phe Asp Leu Trp Gly Arg Gly
            100                 105                 110

Thr Leu Val Thr Val Ser Ser
        115

<210> SEQ ID NO 221
<211> LENGTH: 108
<212> TYPE: PRT
<213> ORGANISM: Artificial
<220> FEATURE:
<223> OTHER INFORMATION: Li81 VL Variant

<400> SEQUENCE: 221

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Tyr Thr Phe Gly Gln Gly Thr Lys Leu Glu Ile Lys
            100                 105

<210> SEQ ID NO 222
<211> LENGTH: 108
<212> TYPE: PRT
<213> ORGANISM: Artificial
<220> FEATURE:

<223> OTHER INFORMATION: Li81 VL Variant

<400> SEQUENCE: 222

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Tyr Thr Phe Gly Gln Gly Thr Lys Leu Glu Ile Lys
            100                 105

<210> SEQ ID NO 223
<211> LENGTH: 108
<212> TYPE: PRT
<213> ORGANISM: Artificial
<220> FEATURE:
<223> OTHER INFORMATION: Li81 VL Variant

<400> SEQUENCE: 223

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Gln
                85                  90                  95

Tyr Thr Phe Gly Gln Gly Thr Lys Leu Glu Ile Lys
            100                 105

<210> SEQ ID NO 224
<211> LENGTH: 108
<212> TYPE: PRT
<213> ORGANISM: Artificial
<220> FEATURE:
<223> OTHER INFORMATION: Li81 VL Variant

<400> SEQUENCE: 224

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro

```
                65                  70                  75                  80
Glu Asp Phe Ala Val Tyr Tyr Cys Gln Gln Arg Ser Asn Trp Pro Lys
                    85                  90                  95

Tyr Thr Phe Gly Gln Gly Thr Lys Leu Glu Ile Lys
                100                 105

<210> SEQ ID NO 225
<211> LENGTH: 108
<212> TYPE: PRT
<213> ORGANISM: Artificial
<220> FEATURE:
<223> OTHER INFORMATION: Li81 VL Variant

<400> SEQUENCE: 225

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ala
                85                  90                  95

Tyr Thr Phe Gly Gln Gly Thr Lys Leu Glu Ile Lys
                100                 105

<210> SEQ ID NO 226
<211> LENGTH: 108
<212> TYPE: PRT
<213> ORGANISM: Artificial
<220> FEATURE:
<223> OTHER INFORMATION: Li81 VL Variant

<400> SEQUENCE: 226

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Val
                85                  90                  95

Tyr Thr Phe Gly Gln Gly Thr Lys Leu Glu Ile Lys
                100                 105

<210> SEQ ID NO 227
<211> LENGTH: 108
<212> TYPE: PRT
<213> ORGANISM: Artificial
<220> FEATURE:
<223> OTHER INFORMATION: Li81 VL Variant

<400> SEQUENCE: 227
```

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65              70                  75                  80

Glu Asp Phe Ala Val Tyr Tyr Cys Gln Gln Arg Ser Asn Trp Pro Tyr
                85                  90                  95

Tyr Thr Phe Gly Gln Gly Thr Lys Leu Glu Ile Lys
            100                 105

<210> SEQ ID NO 228
<211> LENGTH: 108
<212> TYPE: PRT
<213> ORGANISM: Artificial
<220> FEATURE:
<223> OTHER INFORMATION: Li81 VL Variant

<400> SEQUENCE: 228

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65              70                  75                  80

Glu Asp Phe Ala Val Tyr Tyr Cys Gln Gln Arg Ser Asn Trp Pro Phe
                85                  90                  95

Tyr Thr Phe Gly Gln Gly Thr Lys Leu Glu Ile Lys
            100                 105

<210> SEQ ID NO 229
<211> LENGTH: 118
<212> TYPE: PRT
<213> ORGANISM: Artificial
<220> FEATURE:
<223> OTHER INFORMATION: Li81 VH Variant

<400> SEQUENCE: 229

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Leu Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys

```
                    85                  90                  95

Ala Thr Glu Gly Asp Asn Asp Ala Phe Asp Ile Trp Gly Gln Gly Thr
            100                 105                 110

Thr Val Thr Val Ser Ser
        115

<210> SEQ ID NO 230
<211> LENGTH: 118
<212> TYPE: PRT
<213> ORGANISM: Artificial
<220> FEATURE:
<223> OTHER INFORMATION: Li81 VH Variant

<400> SEQUENCE: 230

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Ser Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Ala Phe Asp Ile Trp Gly Gln Gly Thr
            100                 105                 110

Thr Val Thr Val Ser Ser
        115

<210> SEQ ID NO 231
<211> LENGTH: 118
<212> TYPE: PRT
<213> ORGANISM: Artificial
<220> FEATURE:
<223> OTHER INFORMATION: Li81 VH Variant

<400> SEQUENCE: 231

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Thr Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Ala Phe Asp Ile Trp Gly Gln Gly Thr
            100                 105                 110

Thr Val Thr Val Ser Ser
        115

<210> SEQ ID NO 232
<211> LENGTH: 118
```

```
<212> TYPE: PRT
<213> ORGANISM: Artificial
<220> FEATURE:
<223> OTHER INFORMATION: Li81 VH Variant

<400> SEQUENCE: 232

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Trp Ser Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Ala Phe Asp Ile Trp Gly Gln Gly Thr
            100                 105                 110

Thr Val Thr Val Ser Ser
        115

<210> SEQ ID NO 233
<211> LENGTH: 118
<212> TYPE: PRT
<213> ORGANISM: Artificial
<220> FEATURE:
<223> OTHER INFORMATION: Li81 VH Variant

<400> SEQUENCE: 233

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Gly Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Ala Phe Asp Ile Trp Gly Gln Gly Thr
            100                 105                 110

Thr Val Thr Val Ser Ser
        115

<210> SEQ ID NO 234
<211> LENGTH: 108
<212> TYPE: PRT
<213> ORGANISM: Artificial
<220> FEATURE:
<223> OTHER INFORMATION: Li81 VL Variant

<400> SEQUENCE: 234

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
```

```
                    20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Ala Pro Met
                85                  90                  95

Tyr Thr Phe Gly Gln Gly Thr Lys Leu Glu Ile Lys
            100                 105

<210> SEQ ID NO 235
<211> LENGTH: 108
<212> TYPE: PRT
<213> ORGANISM: Artificial
<220> FEATURE:
<223> OTHER INFORMATION: Li81 VL Variant

<400> SEQUENCE: 235

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Asp Pro Met
                85                  90                  95

Tyr Thr Phe Gly Gln Gly Thr Lys Leu Glu Ile Lys
            100                 105

<210> SEQ ID NO 236
<211> LENGTH: 108
<212> TYPE: PRT
<213> ORGANISM: Artificial
<220> FEATURE:
<223> OTHER INFORMATION: Li81 VL Variant

<400> SEQUENCE: 236

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Leu Pro Met
                85                  90                  95

Tyr Thr Phe Gly Gln Gly Thr Lys Leu Glu Ile Lys
            100                 105
```

<210> SEQ ID NO 237
<211> LENGTH: 108
<212> TYPE: PRT
<213> ORGANISM: Artificial
<220> FEATURE:
<223> OTHER INFORMATION: Li81 VL Variant

<400> SEQUENCE: 237

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Asn Pro Met
                85                  90                  95

Tyr Thr Phe Gly Gln Gly Thr Lys Leu Glu Ile Lys
            100                 105

<210> SEQ ID NO 238
<211> LENGTH: 108
<212> TYPE: PRT
<213> ORGANISM: Artificial
<220> FEATURE:
<223> OTHER INFORMATION: Li81 VL Variant

<400> SEQUENCE: 238

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Gly Pro Met
                85                  90                  95

Tyr Thr Phe Gly Gln Gly Thr Lys Leu Glu Ile Lys
            100                 105

<210> SEQ ID NO 239
<211> LENGTH: 108
<212> TYPE: PRT
<213> ORGANISM: Artificial
<220> FEATURE:
<223> OTHER INFORMATION: Li81 VL Variant

<400> SEQUENCE: 239

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile

```
                    35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Gln Pro Met
                 85                  90                  95

Tyr Thr Phe Gly Gln Gly Thr Lys Leu Glu Ile Lys
            100                 105

<210> SEQ ID NO 240
<211> LENGTH: 108
<212> TYPE: PRT
<213> ORGANISM: Artificial
<220> FEATURE:
<223> OTHER INFORMATION: Li81 VL Variant

<400> SEQUENCE: 240

Asp Ile Gln Met Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Val Pro Met
                 85                  90                  95

Tyr Thr Phe Gly Gln Gly Thr Lys Leu Glu Ile Lys
            100                 105

<210> SEQ ID NO 241
<211> LENGTH: 108
<212> TYPE: PRT
<213> ORGANISM: Artificial
<220> FEATURE:
<223> OTHER INFORMATION: Li81 VL Variant

<400> SEQUENCE: 241

Asp Ile Gln Met Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Ser Pro Met
                 85                  90                  95

Tyr Thr Phe Gly Gln Gly Thr Lys Leu Glu Ile Lys
            100                 105

<210> SEQ ID NO 242
<211> LENGTH: 119
```

```
<212> TYPE: PRT
<213> ORGANISM: Artificial
<220> FEATURE:
<223> OTHER INFORMATION: Li113 VH Variant

<400> SEQUENCE: 242

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser His Ile Gly Pro Ser Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 243
<211> LENGTH: 119
<212> TYPE: PRT
<213> ORGANISM: Artificial
<220> FEATURE:
<223> OTHER INFORMATION: Li113 VH Variant

<400> SEQUENCE: 243

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Phe Ile Gly Pro Ser Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 244
<211> LENGTH: 119
<212> TYPE: PRT
<213> ORGANISM: Artificial
<220> FEATURE:
<223> OTHER INFORMATION: Li113 VH Variant

<400> SEQUENCE: 244

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
```

```
                    20                  25                  30
Pro Met Phe Trp Val Arg Gln Ala Pro Gly Lys Gly Leu Glu Trp Val
        35                  40                  45

Ser Leu Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
                100                 105                 110

Thr Leu Val Thr Val Ser Ser
            115

<210> SEQ ID NO 245
<211> LENGTH: 119
<212> TYPE: PRT
<213> ORGANISM: Artificial
<220> FEATURE:
<223> OTHER INFORMATION: Li113 VH Variant

<400> SEQUENCE: 245

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
        35                  40                  45

Ser Met Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
                100                 105                 110

Thr Leu Val Thr Val Ser Ser
            115

<210> SEQ ID NO 246
<211> LENGTH: 119
<212> TYPE: PRT
<213> ORGANISM: Artificial
<220> FEATURE:
<223> OTHER INFORMATION: Li113 VH Variant

<400> SEQUENCE: 246

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
        35                  40                  45

Ser Trp Ile Gly Leu Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 247
<211> LENGTH: 119
<212> TYPE: PRT
<213> ORGANISM: Artificial
<220> FEATURE:
<223> OTHER INFORMATION: Li113 VH Variant

<400> SEQUENCE: 247

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Ser Ser Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 248
<211> LENGTH: 119
<212> TYPE: PRT
<213> ORGANISM: Artificial
<220> FEATURE:
<223> OTHER INFORMATION: Li113 VH Variant

<400> SEQUENCE: 248

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Thr Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 249

```
<211> LENGTH: 119
<212> TYPE: PRT
<213> ORGANISM: Artificial
<220> FEATURE:
<223> OTHER INFORMATION: Li113 VH Variant

<400> SEQUENCE: 249

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Trp Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 250
<211> LENGTH: 119
<212> TYPE: PRT
<213> ORGANISM: Artificial
<220> FEATURE:
<223> OTHER INFORMATION: Li113 VH Variant

<400> SEQUENCE: 250

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Val Tyr Leu Asp Leu Trp Gly Arg Gly
            100                 105                 110

Thr Leu Val Thr Val Ser Ser
        115

<210> SEQ ID NO 251
<211> LENGTH: 119
<212> TYPE: PRT
<213> ORGANISM: Artificial
<220> FEATURE:
<223> OTHER INFORMATION: Li113 VH Variant

<400> SEQUENCE: 251

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp His Tyr Leu Asp Leu Trp Gly Arg Gly
            100                 105                 110

Thr Leu Val Thr Val Ser Ser
        115

<210> SEQ ID NO 252
<211> LENGTH: 119
<212> TYPE: PRT
<213> ORGANISM: Artificial
<220> FEATURE:
<223> OTHER INFORMATION: Li113 VH Variant

<400> SEQUENCE: 252

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Ser Tyr Leu Asp Leu Trp Gly Arg Gly
            100                 105                 110

Thr Leu Val Thr Val Ser Ser
        115

<210> SEQ ID NO 253
<211> LENGTH: 119
<212> TYPE: PRT
<213> ORGANISM: Artificial
<220> FEATURE:
<223> OTHER INFORMATION: Li113 VH Variant

<400> SEQUENCE: 253

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Gln Tyr Leu Asp Leu Trp Gly Arg Gly
            100                 105                 110

Thr Leu Val Thr Val Ser Ser
        115

<210> SEQ ID NO 254
<211> LENGTH: 119
<212> TYPE: PRT
<213> ORGANISM: Artificial
<220> FEATURE:
<223> OTHER INFORMATION: Li113 VH Variant

<400> SEQUENCE: 254

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Trp Ile Gly Pro Ser Gly Gly Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 255
<211> LENGTH: 119
<212> TYPE: PRT
<213> ORGANISM: Artificial
<220> FEATURE:
<223> OTHER INFORMATION: Li113 VH Variant

<400> SEQUENCE: 255

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Trp Ile Gly Pro Ser Gly Gly Met Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

-continued

<210> SEQ ID NO 256
<211> LENGTH: 119
<212> TYPE: PRT
<213> ORGANISM: Artificial
<220> FEATURE:
<223> OTHER INFORMATION: Li113 VH Variant

<400> SEQUENCE: 256

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Asn Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 257
<211> LENGTH: 119
<212> TYPE: PRT
<213> ORGANISM: Artificial
<220> FEATURE:
<223> OTHER INFORMATION: Li113 VH Variant

<400> SEQUENCE: 257

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly His Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 258
<211> LENGTH: 119
<212> TYPE: PRT
<213> ORGANISM: Artificial
<220> FEATURE:
<223> OTHER INFORMATION: Li113 VH Variant

<400> SEQUENCE: 258

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Leu Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 259
<211> LENGTH: 119
<212> TYPE: PRT
<213> ORGANISM: Artificial
<220> FEATURE:
<223> OTHER INFORMATION: Li113 VH Variant

<400> SEQUENCE: 259

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Phe Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 260
<211> LENGTH: 119
<212> TYPE: PRT
<213> ORGANISM: Artificial
<220> FEATURE:
<223> OTHER INFORMATION: Li113 VH Variant

<400> SEQUENCE: 260

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Gly Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr

```
               65                  70                  75                  80
Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
            115

<210> SEQ ID NO 261
<211> LENGTH: 119
<212> TYPE: PRT
<213> ORGANISM: Artificial
<220> FEATURE:
<223> OTHER INFORMATION: Li113 VH Variant

<400> SEQUENCE: 261

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
            35                  40                  45

Ser Ile Ile Gly Pro Ser Gly Gly Ile Thr Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
            115

<210> SEQ ID NO 262
<211> LENGTH: 119
<212> TYPE: PRT
<213> ORGANISM: Artificial
<220> FEATURE:
<223> OTHER INFORMATION: Li113 VH Variant

<400> SEQUENCE: 262

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
            35                  40                  45

Ser Asp Ile Gly Pro Ser Gly Gly Ile Thr Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
            115
```

<210> SEQ ID NO 263
<211> LENGTH: 119
<212> TYPE: PRT
<213> ORGANISM: Artificial
<220> FEATURE:
<223> OTHER INFORMATION: Li113 VH Variant

<400> SEQUENCE: 263

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Met Tyr Leu Asp Leu Trp Gly Arg Gly
            100                 105                 110

Thr Leu Val Thr Val Ser Ser
        115
```

<210> SEQ ID NO 264
<211> LENGTH: 119
<212> TYPE: PRT
<213> ORGANISM: Artificial
<220> FEATURE:
<223> OTHER INFORMATION: Li113 VH Variant

<400> SEQUENCE: 264

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Leu Tyr Leu Asp Leu Trp Gly Arg Gly
            100                 105                 110

Thr Leu Val Thr Val Ser Ser
        115
```

<210> SEQ ID NO 265
<211> LENGTH: 119
<212> TYPE: PRT
<213> ORGANISM: Artificial
<220> FEATURE:
<223> OTHER INFORMATION: Li113 VH Variant

<400> SEQUENCE: 265

```
Glu Val Gln Leu Leu Glu Ser Gly Gly Gly Leu Val Gln Pro Gly Gly
```

-continued

```
                1               5                  10                  15
              Ser Leu Arg Leu Ser Cys Ala Ala Ser Gly Phe Thr Phe Ser Ile Tyr
                          20                  25                  30

Pro Met Phe Trp Val Arg Gln Ala Pro Gly Lys Gly Leu Glu Trp Val
                          35                  40                  45

Ser Trp Ile Gly Pro Ser Gly Gly Ile Thr Lys Tyr Ala Asp Ser Val
                          50                  55                  60

Lys Gly Arg Phe Thr Ile Ser Arg Asp Asn Ser Lys Asn Thr Leu Tyr
               65                  70                  75                  80

Leu Gln Met Asn Ser Leu Arg Ala Glu Asp Thr Ala Thr Tyr Tyr Cys
                          85                  90                  95

Ala Arg Glu Gly Thr Tyr Asp Thr Tyr Leu Asp Leu Trp Gly Arg Gly
                          100                 105                 110

Thr Leu Val Thr Val Ser Ser
                          115

<210> SEQ ID NO 266
<211> LENGTH: 119
<212> TYPE: PRT
<213> ORGANISM: Artificial
<220> FEATURE:
<223> OTHER INFORMATION: Li113 VH Variant

<400> SEQUENCE: 266

Glu Val Gln Leu Leu Glu Ser Gly Gly Gly Leu Val Gln Pro Gly Gly
                1               5                  10                  15

Ser Leu Arg Leu Ser Cys Ala Ala Ser Gly Phe Thr Phe Ser Ile Tyr
                          20                  25                  30

Pro Met Phe Trp Val Arg Gln Ala Pro Gly Lys Gly Leu Glu Trp Val
                          35                  40                  45

Ser Trp Ile Gly Pro Ser Gly Gly Ile Thr Lys Tyr Ala Asp Ser Val
                          50                  55                  60

Lys Gly Arg Phe Thr Ile Ser Arg Asp Asn Ser Lys Asn Thr Leu Tyr
               65                  70                  75                  80

Leu Gln Met Asn Ser Leu Arg Ala Glu Asp Thr Ala Thr Tyr Tyr Cys
                          85                  90                  95

Ala Arg Glu Gly Thr Tyr Asp Ile Tyr Leu Asp Leu Trp Gly Arg Gly
                          100                 105                 110

Thr Leu Val Thr Val Ser Ser
                          115

<210> SEQ ID NO 267
<211> LENGTH: 119
<212> TYPE: PRT
<213> ORGANISM: Artificial
<220> FEATURE:
<223> OTHER INFORMATION: Li113 VH Variant

<400> SEQUENCE: 267

Glu Val Gln Leu Leu Glu Ser Gly Gly Gly Leu Val Gln Pro Gly Gly
                1               5                  10                  15

Ser Leu Arg Leu Ser Cys Ala Ala Ser Gly Phe Thr Phe Ser Ile Tyr
                          20                  25                  30

Pro Met Phe Trp Val Arg Gln Ala Pro Gly Lys Gly Leu Glu Trp Val
                          35                  40                  45

Ser Trp Ile Gly Gly Ser Gly Ile Thr Lys Tyr Ala Asp Ser Val
                          50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly Thr Tyr Asp Trp Tyr Leu Asp Leu Trp Gly Arg Gly
            100                 105                 110

Thr Leu Val Thr Val Ser Ser
            115

<210> SEQ ID NO 268
<211> LENGTH: 119
<212> TYPE: PRT
<213> ORGANISM: Artificial
<220> FEATURE:
<223> OTHER INFORMATION: Li113 VH Variant

<400> SEQUENCE: 268

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ile Tyr
                 20                  25                  30

Pro Met Phe Trp Val Arg Gln Ala Pro Gly Lys Gly Leu Glu Trp Val
             35                  40                  45

Ser Trp Ile Gly Pro Ser Gly Gly Trp Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly Thr Tyr Asp Trp Tyr Leu Asp Leu Trp Gly Arg Gly
            100                 105                 110

Thr Leu Val Thr Val Ser Ser
            115

<210> SEQ ID NO 269
<211> LENGTH: 119
<212> TYPE: PRT
<213> ORGANISM: Artificial
<220> FEATURE:
<223> OTHER INFORMATION: Li113 VH Variant

<400> SEQUENCE: 269

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ile Tyr
                 20                  25                  30

Pro Met Phe Trp Val Arg Gln Ala Pro Gly Lys Gly Leu Glu Trp Val
             35                  40                  45

Ser Trp Ile Gly Pro Ser Gly Gly Tyr Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly Thr Tyr Asp Trp Tyr Leu Asp Leu Trp Gly Arg Gly
            100                 105                 110

Thr Leu Val Thr Val Ser Ser
            115
```

<210> SEQ ID NO 270
<211> LENGTH: 119
<212> TYPE: PRT
<213> ORGANISM: Artificial
<220> FEATURE:
<223> OTHER INFORMATION: Li113 VH Variant

<400> SEQUENCE: 270

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Ser Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 271
<211> LENGTH: 119
<212> TYPE: PRT
<213> ORGANISM: Artificial
<220> FEATURE:
<223> OTHER INFORMATION: Li113 VH Variant

<400> SEQUENCE: 271

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Pro Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 272
<211> LENGTH: 119
<212> TYPE: PRT
<213> ORGANISM: Artificial
<220> FEATURE:
<223> OTHER INFORMATION: Li113 VH Variant

<400> SEQUENCE: 272

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Val Thr Lys Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 273
<211> LENGTH: 119
<212> TYPE: PRT
<213> ORGANISM: Artificial
<220> FEATURE:
<223> OTHER INFORMATION: Li113 VH Variant

<400> SEQUENCE: 273

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Thr Thr Lys Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 274
<211> LENGTH: 119
<212> TYPE: PRT
<213> ORGANISM: Artificial
<220> FEATURE:
<223> OTHER INFORMATION: Li113 VH Variant

<400> SEQUENCE: 274

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
50                      55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly Thr Tyr Asp Gln Tyr Leu Asp Leu Trp Gly Arg Gly
            100                 105                 110

Thr Leu Val Thr Val Ser Ser
        115

<210> SEQ ID NO 275
<211> LENGTH: 447
<212> TYPE: PRT
<213> ORGANISM: Artificial Sequence
<220> FEATURE:
<223> OTHER INFORMATION: Li113 VH Variant

<400> SEQUENCE: 275

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ala Tyr
             20                  25                  30

Glu Met Lys Trp Val Arg Gln Ala Pro Gly Lys Gly Leu Glu Trp Val
         35                  40                  45

Ser Val Ile Gly Pro Ser Gly Gly Phe Thr Phe Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Glu Gly Asp Asn Asp Ala Phe Asp Ile Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Ala Tyr Arg Val Val
    290                 295                 300
```

```
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 276
<211> LENGTH: 215
<212> TYPE: PRT
<213> ORGANISM: Artificial Sequence
<220> FEATURE:
<223> OTHER INFORMATION: Li113 VH Variant

<400> SEQUENCE: 276

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Met
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

```
<210> SEQ ID NO 277
<211> LENGTH: 187
<212> TYPE: PRT
<213> ORGANISM: Homo sapiens

<400> SEQUENCE: 277

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
                180                 185
```